(12) United States Patent
Paul et al.

(10) Patent No.: US 8,980,646 B2
(45) Date of Patent: Mar. 17, 2015

(54) PROTEOLYTIC AND COVALENT ANTIBODIES

(75) Inventors: Sudhir Paul, Missouri City, TX (US); Yasuhiro Nishiyama, Houston, TX (US)

(73) Assignee: Paul, Sudhir, Missouri City, TX (US)

( * ) Notice: Subject to any disclaimer, the term of this patent is extended or adjusted under 35 U.S.C. 154(b) by 1592 days.

(21) Appl. No.: 10/581,294

(22) PCT Filed: Mar. 26, 2004

(86) PCT No.: PCT/US2004/009398
§ 371 (c)(1),
(2), (4) Date: Jun. 1, 2006

(87) PCT Pub. No.: WO2004/087735
PCT Pub. Date: Oct. 14, 2004

(65) Prior Publication Data
US 2007/0105092 A1  May 10, 2007

Related U.S. Application Data

(60) Provisional application No. 60/458,063, filed on Mar. 26, 2003, provisional application No. 60/534,689, filed on Jan. 8, 2004.

(51) Int. Cl.
| | | |
|---|---|---|
| C07K 16/00 | (2006.01) |
| C12P 21/08 | (2006.01) |
| C07K 16/28 | (2006.01) |
| C07K 16/10 | (2006.01) |
| C07K 16/44 | (2006.01) |
| C12Q 1/37 | (2006.01) |
| G01N 33/68 | (2006.01) |

(52) U.S. Cl.
CPC ......... *C07K 16/2863* (2013.01); *C07K 16/1063* (2013.01); *C07K 16/44* (2013.01); *C12Q 1/37* (2013.01); *G01N 33/6854* (2013.01); *A01K 2207/15* (2013.01); *A01K 2217/00* (2013.01); *A01K 2217/05* (2013.01); *A01K 2227/105* (2013.01); *A01K 2267/01* (2013.01); *C07K 2317/21* (2013.01); *C07K 2317/34* (2013.01); *G01N 2333/901* (2013.01)
USPC ......... 436/547; 436/548; 435/188.5; 530/403

(58) Field of Classification Search
USPC ..................................... 435/188.5
See application file for complete search history.

(56) References Cited

U.S. PATENT DOCUMENTS

| | | | |
|---|---|---|---|
| 5,445,960 A | 8/1995 | Masuho et al. |
| 5,695,927 A | 12/1997 | Masuho et al. |
| 5,783,670 A | 7/1998 | Masuho et al. |
| 5,807,715 A | 9/1998 | Morrison et al. |
| 5,811,238 A | 9/1998 | Stemmer et al. |
| 5,952,462 A | 9/1999 | Powell et al. |
| 6,156,541 A | 12/2000 | Paul et al. |
| 6,235,714 B1 | 5/2001 | Paul et al. |
| 6,406,863 B1 | 6/2002 | Zhu et al. |
| 6,407,213 B1 | 6/2002 | Carter et al. |
| 6,855,804 B2 * | 2/2005 | Paul et al. ............ 530/324 |
| 2003/0078203 A1 | 4/2003 | Paul et al. |

FOREIGN PATENT DOCUMENTS

| | | |
|---|---|---|
| WO | WO 2004/087059 | 10/2004 |
| WO | WO 2004/087735 | 10/2004 |
| WO | WO 2004/087738 | 10/2004 |

OTHER PUBLICATIONS

Mader et al. Chem Rev. 1997, 97, 1281-1301.*
Chica et al. Curr Opin Biotechnol. Aug. 2005; 16(4):378-84.*
Fahey et al. (Clin. Exp. Immunol., 1992).*
Hirsch et al. (N. Eng. J. Med., 1993).*
Haynes et al. (Ann. Med., 1996).*
The Dictionary of Immunology, Herbert et al eds, Academic Press, 1995, three pages.*
Ellis, R.W. (Chapter 29 of "Vaccines" [Plotkin, S.A. et al. (eds) published by W. B. Saunders company (Philadelphia) in 1988.*
Feb 14, 2008 Mark Henderson, Science Editor, in Boston http://www.timesonline.co.uk.*
International Search report, PCT/US04/09399, mailed Jun. 1, 2005.
Written Opinion of the International Searching Authority, PCT/US04/09399, mailed Jun. 1, 2005.
International Search report, PCT/US04/09662, mailed Jun. 28, 2006.
Written Opinion of the International Searching Authority PCT/US04/09662, mailed Jun. 28, 2006.
Mar. 28, 2003, Paul et al., Specific HIV gp 120-cleaving antibodies induced by covalently reactive analog of gp 120. J. Biol. Chem. May 30, 2003, vol. 278, No. 22, pp. 20429-20435.
Nishiyama et al., "Antibodies to the Superantigenic Site of HIV-1 gp 120: Hydrolytic and Binding Aactivities of the Light Chain Subunit" submitted with U.S. Appl. No. 60/857,764, filed Nov. 9, 2006.
"Induction of antibodies to the gp120 superantigenic site by administration of protein A" submitted with U.S. Appl. No. 60/857,764, filed Nov. 9, 2006.
Planque et al., "Naturally Occurring Catalytic IgAs: Protective Anti-HIV Mediators?" submitted with U.S. Appl. No. 60/857,764, filed Nov. 9, 2006.
Planque et al., "Ontogeny of Proteolytic Immunity; IgM Serine Proteases" submitted with U.S. Appl. No. 60/534,689, filed Jan. 8, 2004.
Karle et al., "Selective IgM-Catalyzed Hydrolysis of HIV gp120: An innate defense against gp120?" submitted with U.S. Appl. No. 60/534,689, filed Jan. 8, 2004.
Dec. 15, 2003, Nishiyama et al., "Toward selective covalent inactivation of pathogenic antibodies" J. Biol. Chem. Feb. 27, 2004, vol. 279, No. 9, pp. 7877-7883.
Planque et al., "Broadly Distributed Chemical Reactivity of Natural Antibodies Expressed in Coordination with Specific Antigen Binding Activity" submitted with application in U.S. Appl. No. 60/457,293, filed Mar. 26, 2003.

(Continued)

*Primary Examiner* — Patricia A Duffy
(74) *Attorney, Agent, or Firm* — Robert C. Netter, Jr.; Kathleen D. Rigaut; Dann, Dorfman, Herrell & Skillman

(57) ABSTRACT

Improved methods for the production, selection and inhibition of catalytic and covalent antibodies are disclosed.

15 Claims, 52 Drawing Sheets

(56) References Cited

OTHER PUBLICATIONS

Karle et al., "HIV-1 Neutralizing Antibody Fragments to a Conserved Envelope Determinant from Lupus Libraries" submitted with application in U.S. Appl. No. 60/457,570, filed Mar. 27, 2003.

Jan. 2000, Paul et al., "Natural catalytic immunity is not restricted to autoantigenetic substrates: Identification of a human immunodeficiency virus gp 120-cleaving antibody light chain" Appl. Biochem Bioteclmol. Jan.-Mar. 2000, vol. 83, No. 1-3, pp. 71-82.

Nov. 7, 1994, Pinto et al. "Panel of anti-gp 120 monoclonal antibodies reacts with same nuclear proteins in uninfected cells as those recognized by autoantibodies from patients with systemic lulus erythematosus" Aids Res. and Hum Retroviruses, 1994, vol. 10, pp. 823-828.

Nov. 6, 1996 Fraziano et al., "Epitope specificity of anti-HIV antibodies in human and murine autoimmune diseases" Aids Research and Human Retroviruses, 1996, vol. 12, No. 6, pp. 491-496.

Root-Bernstein, "Preliminary evidence for idiotype-antidiotype immune complexes cross-reactive with Lymphocyte antigenss in AIDS and lupus" Medical Hypotheses (1995) 44, 20-27.

2002, Taguchi et al. "A mechanism-based probe for gp 120-hydrolyzing antibodies" Bioorg. Med. Chem. Lett. 2002, vol. 12, pp. 3167-3170.

* cited by examiner

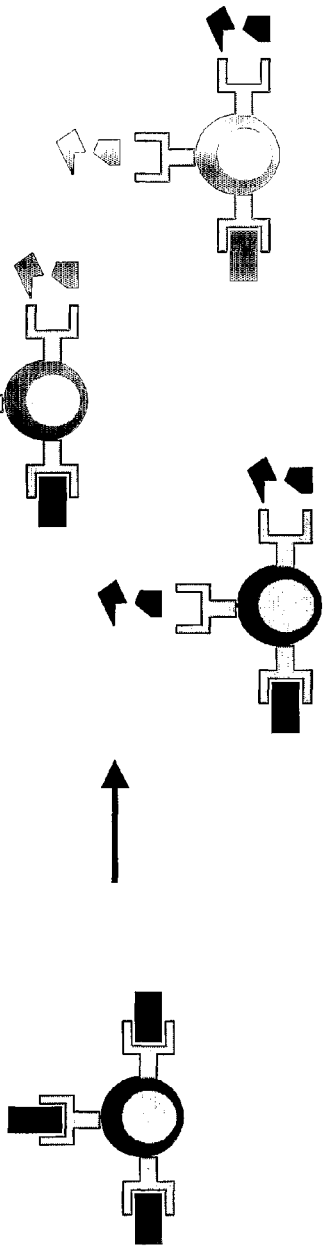
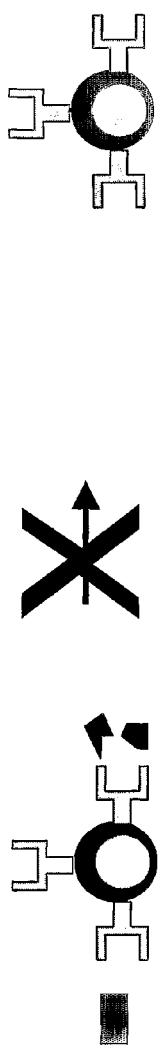
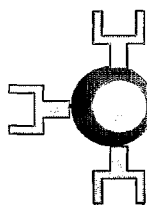
Fig 3

Fig 4

General structure of pCRA

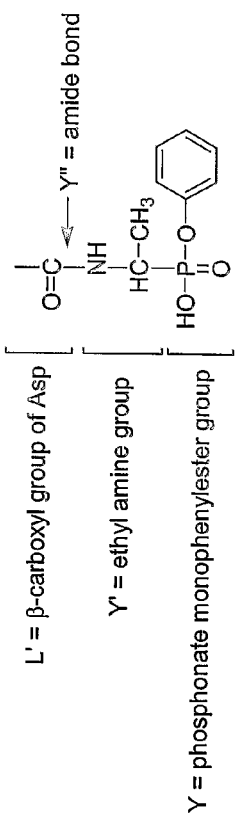

L'-Y"-Y'-Y, Example 1

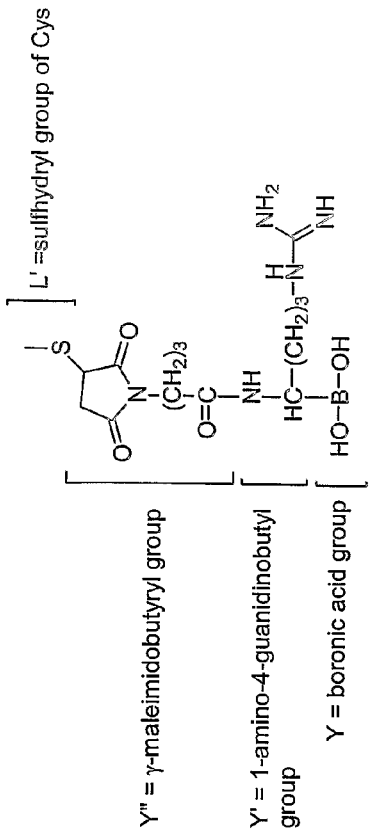

- L' = β-carboxyl group of Asp
- Y" = ethyl amine group
- Y = phosphonate monophenylester group

L'-Y"-Y'-Y, Example 3

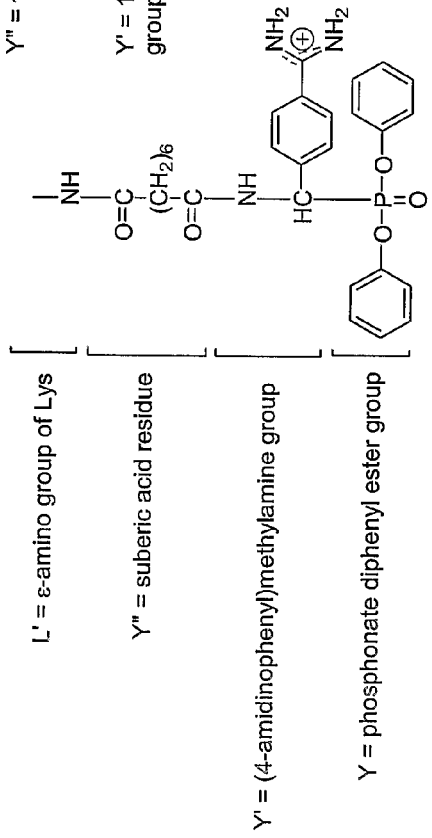

- L' = sulfhydryl group of Cys
- Y" = γ-maleimidobutyryl group
- Y' = 1-amino-4-guanidinobutyl group
- Y = boronic acid group

L'-Y"-Y'-Y, Example 2

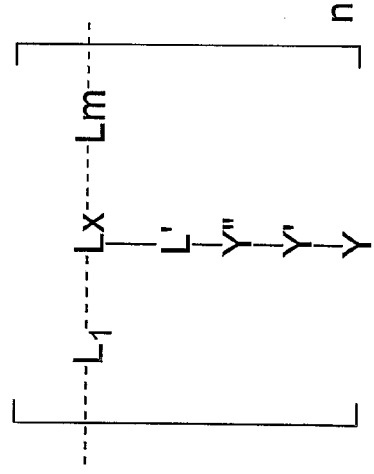

- L' = ε-amino group of Lys
- Y" = suberic acid residue
- Y' = (4-amidinophenyl)methylamine group
- Y = phosphonate diphenyl ester group

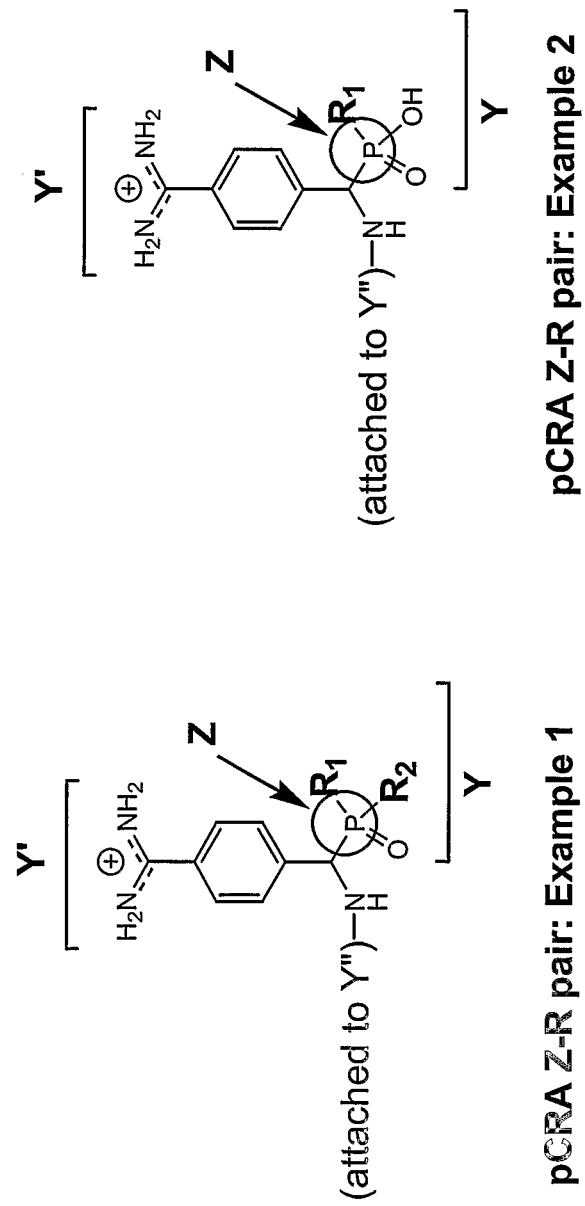

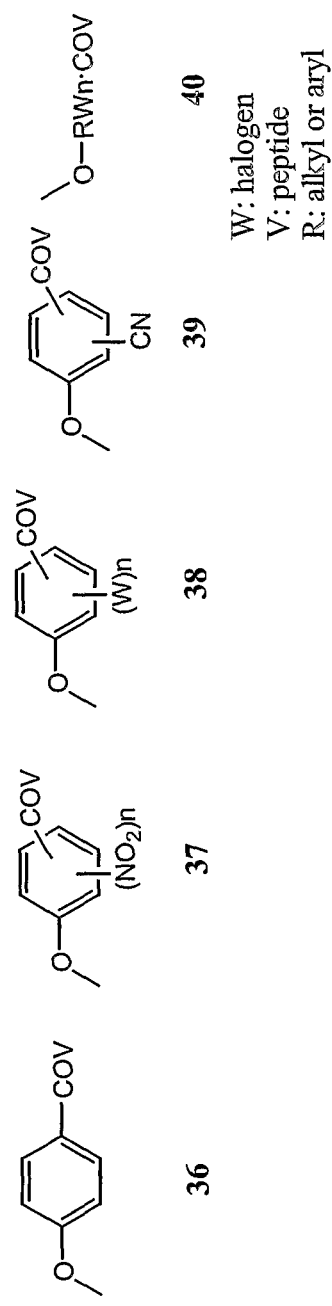
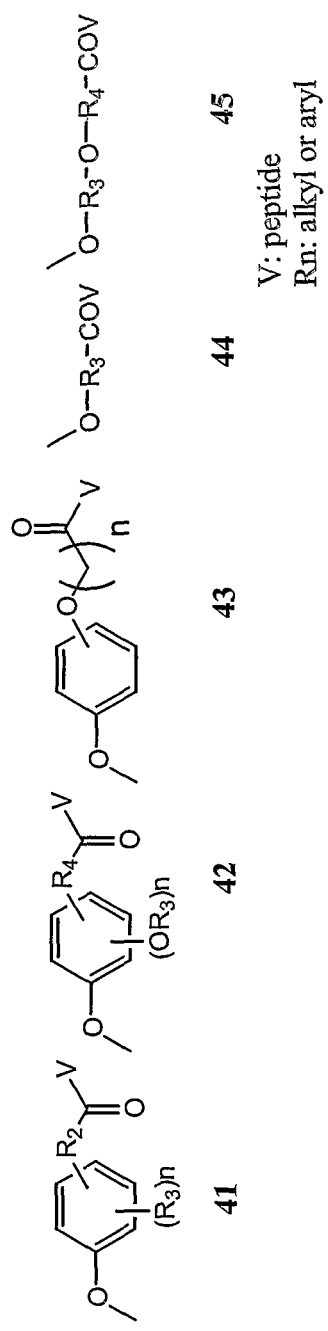
Fig 5D

Selected examples of metal binding moiety
1. (His)n
2. (Cys-Aaa-Cys-Cys): metallothionein α-domain-derived peptide
3. (Cys-Aaa-Cys): metallothionein β-domain-derived peptide
4. EDTA
5. a crown ether
6. DAMP
Example of 1: (His)₆
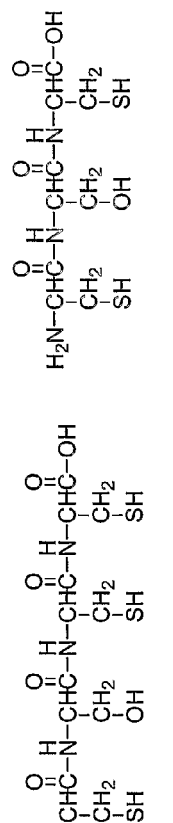
Example of 2: Cys-Ser-Cys-Cys
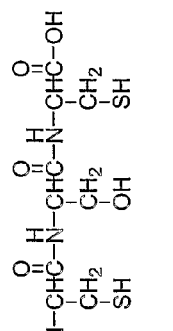
Example of 3: Cys-Ser-Cys
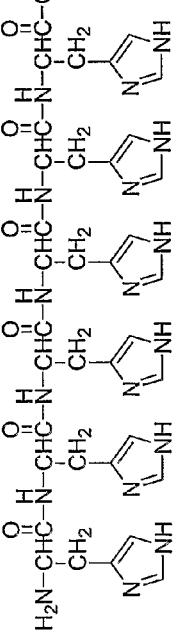
Example of 4: EDTA
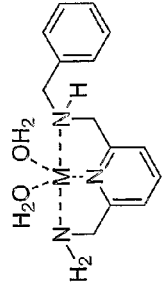
Example of 5: 4'-Carboxybenzo-18-crown-6
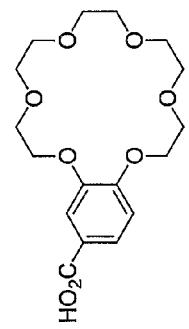
Example of 6: DAMP
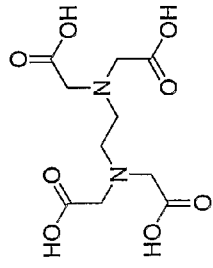
Fig 6

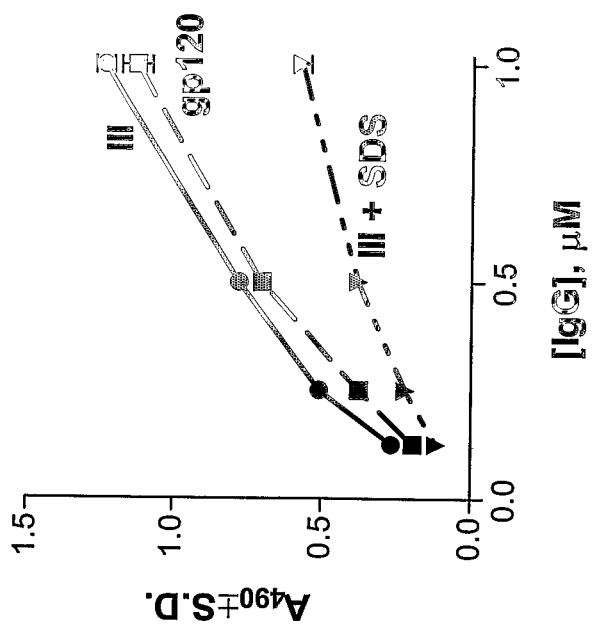
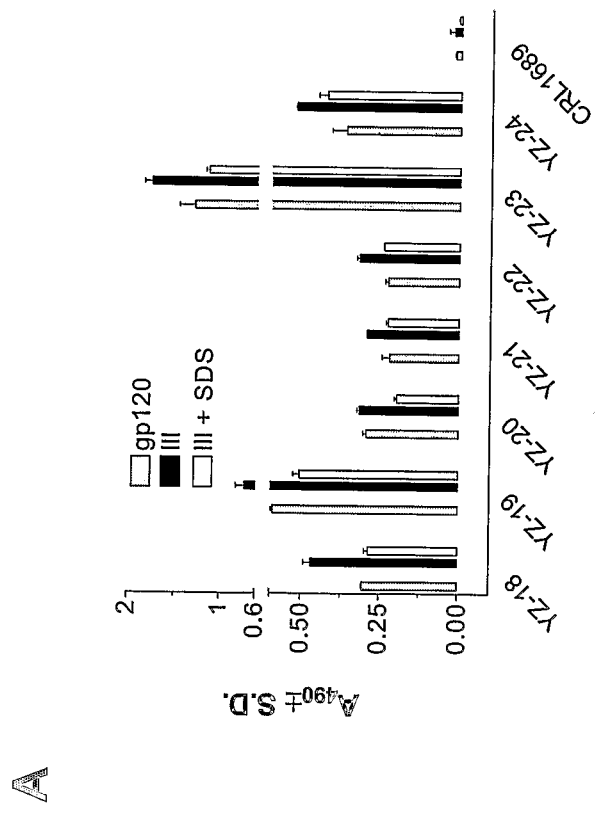
Fig 16

Fig 18
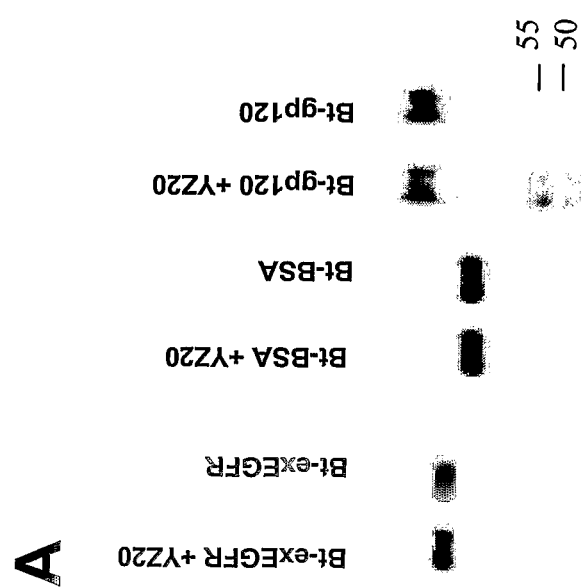
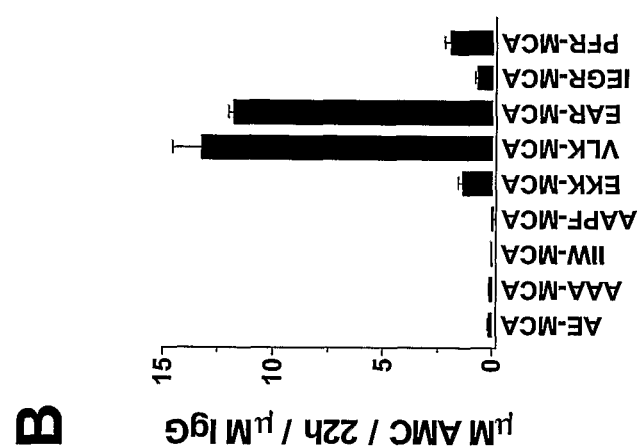
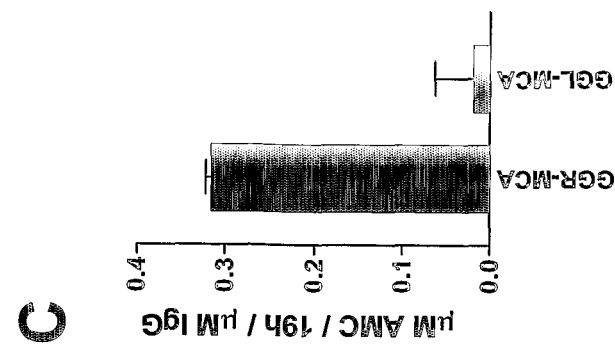

Fig 20
A
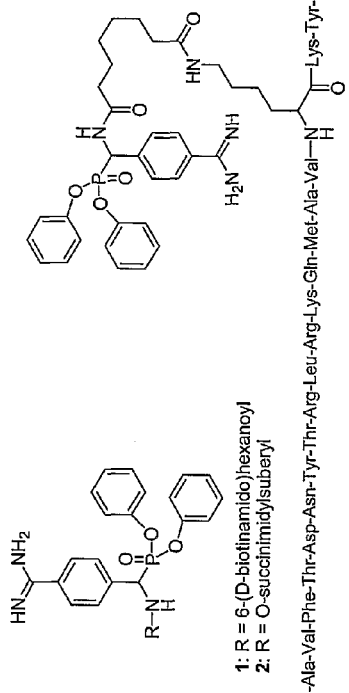
1: R = 6-(D-biotinamido)hexanoyl
2: R = O-succinimidylsuberyl
3: R = D-biotinyl
B
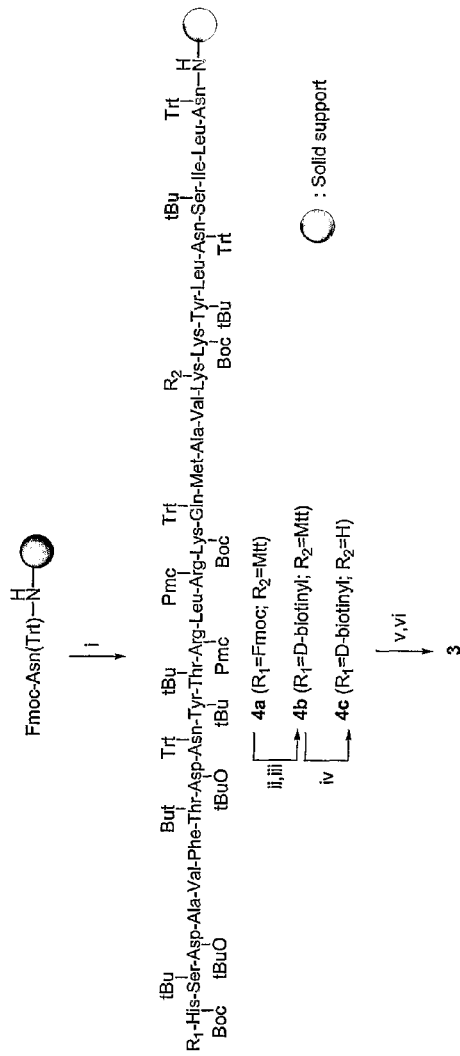

VIP-CRA 1
R--HSDAVFTDNYTRLRKQMAV-YLNSILN

VIP-CRA 2
R--HSDAVFTDNYTRLRKQMAV-YLNSILN

VIP-CRA 3
R--HSDAVFTDNYTRLRKQMAVKKYLNSILN

VIP-CRA 4
R--HSDAVFTDNYTRLRKQMAVKKYLNSILN

VIP-CRA 5
R--HSDAVFTDNYTRLRKQMAVKKYLNSILN pyruvyl VIP-CRA
R--HSDAVFTDNYTRLRKQMAVKKYLNSILN

SEQUENCE LISTING

<160> NUMBER OF SEQ ID NOS: 18

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Glu Gly Arg
  1

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 2

His His His His His His
  1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ala Pro Phe
  1

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 4

Tyr Leu Asn Ser Ile Leu Asn
  1               5

<210> SEQ ID NO 5
<211> LENGTH: 16
<212> TYPE: PRT
<213> ORGANISM: Human immunodeficiency virus type 2

<400> SEQUENCE: 5

Lys Gln Ile Ile Asn Met Trp Gln Glu Val Gly Lys Ala Met Tyr Ala
  1               5                  10                  15

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Glu Ala Arg
  1

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Glu Lys Leu Trp Val Thr Val Tyr Tyr
  1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Gln Ile Ile Asn Met Trp Gln Glu Val Gly Asn
  1               5                  10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Gln Ile Ile Asn Met Trp Gln Glu Val Gly
  1               5                  10

<210> SEQ ID NO 10
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Ser Cys Cys
  1

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Ser Asp Ala Val Phe Thr Asp Asn Tyr Thr Arg Leu Arg Lys Gln
  1               5                  10                  15

Met Ala Val

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Tyr Leu Asn Ser Ile Leu Asn
  1               5

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Ser Asp Ala Val Phe Thr Asp Asn Tyr Thr Arg Leu Arg Lys Gln
  1               5                  10                  15

Met Ala Val Lys Lys Tyr Leu Asn Ser Ile Leu Asn
                 20                  25

<210> SEQ ID NO 14
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ala Glu Phe Arg His Asp Ser Gly Tyr Glu Val His His Gln Lys
  1               5                  10                  15

Leu Val Phe Phe Ala Glu Asp Val Gly Ser Asn Lys Gly Ala Ile Ile
                 20                  25                  30

Gly Leu Met Val Gly Gly Val Val Ile Ala
         35                  40
```

```
<210> SEQ ID NO 15
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ala Glu Phe Arg His Asp Ser Gly Tyr Glu Val His His Gln Lys
 1               5                  10                  15

Leu Val Phe Phe Ala Glu Asp Val Gly Ser Asn
            20                  25

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ile Ile Gly Leu Met Val Gly Gly Val Val Ile Ala
 1               5                  10

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Val Phe Phe Ala Glu Asp Val Gly Ser Asn Lys Gly Ala Ile Ile
 1               5                  10                  15

Gly Leu Met Val Gly Gly Val Val Ile Ala
            20                  25

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      4x His tag

<400> SEQUENCE: 18

His His His His
 1
```

PROTEOLYTIC AND COVALENT ANTIBODIES

This application also claims priority to U.S. Provisional Applications 60/458,063 filed Mar. 26, 2003, and 60/534,689 filed Jan. 8, 2004, the entire disclosures of each of the foregoing applications being incorporated by reference herein.

Pursuant to 35 U.S.C. §202(c) it is acknowledged that the U.S. Government has certain rights in the invention described herein, which was made in part with funds from the National Institutes of Health, Grant Numbers: HL59746, AI31268, CA80312, AI46029 and AI058865.

FIELD OF THE INVENTION

This invention relates to the fields of immunology, molecular biology and medicine. More specifically, the invention provides novel methods and compositions for stimulating the production of novel covalent antibodies, catalytic antibodies and inhibitors thereof. Also provided are improved methods for screening phage display libraries expressing catalytic antibodies.

BACKGROUND OF THE INVENTION

Several publications and patent documents are referenced in this application in order to more fully describe the state of the art to which this invention pertains. The disclosure of each of these publications is incorporated by reference herein.

Several research groups have reported that immunization with negatively charged transition state analogs (TSAs) results in the synthesis of antibodies (Abs) with esterase activity (1,2). These attempts to prepare transacylase Abs relied on creating catalytic sites de novo over the course of somatic diversification of antibody (Ab) genes. In this strategy, induction of noncovalent shape complementary between Ab combining sites and a negatively charged oxygen atom in tetrahedral TSAs was proposed to be sufficient to achieve catalytic activity (Table 1). However, there are no examples of proteolytic Abs identified by this strategy in the peer-reviewed literature, although patents claiming peptide bond hydrolysis by Abs raised to negatively charged TSAs have been granted (e.g., U.S. Pat. No. 5,952,462). One report describes a side-by-side examination of esterase and proteolytic activities in antibodies raised to a TSA (3). The former activity was readily detected, but no peptide bond cleaving activity was observed. The failure to prepare proteolytic Abs by this approach is generally attributed to the greater energetic demands of peptide bond hydrolysis and the more complex reaction pathways for this reaction, including formation of multiple transition states in which the catalyst must form transient covalent complexes with the peptide substrates for the reaction to proceed to completion.

A breakthrough has emerged from observations that naturally occurring Abs can express proteolytic activities. Observations that vasoactive intestinal peptide (VIP) is cleaved by Abs from asthma patients provided early evidence that Abs may possess peptidase activity (4). The generality of this observation is supported by additional reports showing cleavage of thyroglobulin by auto antibodies in Hashimoto's thyroiditis (5). Further evidence for the bias towards catalytic Ab synthesis in autoimmune disease is supported by observations of DNase activity in Abs from lupus patients (6) and mouse strains with a genetic predisposition to autoimmune disease (7). More recently antibodies isolated from certain hemophilia patients were observed to hydrolyze Factor VIII, a cofactor in blood coagulation (8). Certain antibody fragments to the HIV protein gp41 are also described to hydrolyze this protein (9).

Disclosed in the present invention are data indicating that the potential for cleaving peptide bonds by a covalent catalytic mechanisms is distributed broadly in most naturally occurring Abs. Covalent catalytic mechanisms reminiscent of those utilized by non-Ab serine proteases are a distinguishing feature of the naturally occurring proteolytic Abs (10). In comparison, Abs raised to TSAs utilize noncovalent binding of the transition state, and the emergence of covalent catalytic pathways is not predicted, expect by accident.

One aspect of the present invention is to strengthen the covalent reactivity of naturally occurring Abs. This results in two outcomes: (a) the increased covalent reactivity allows emergence of Abs that can form stable bonds with polypeptides, due to the covalent character of the bonding reaction; and (b) When a water molecule is properly accommodated in the Ab active sites, the covalent Ab-polypeptide complexes can be hydrolyzed to complete the reaction cycle. To favor the latter outcome, immunization is done using polypeptide analogs that contain a bound water molecule, allowing induction of Ab active sites with sufficient room to accommodate the desired water molecule.

Proteolytic Abs can not be identified using traditional binding assays, as the catalytic cleavage of polypeptides does not allow formation of stable Ab-antigen complexes. Analogs of antigens employed previously to identify catalytic Abs have assumed that the chemical reaction center in the analogs must simulate precisely the location of the bond in polypeptide antigens that is cleaved by catalytic Abs. Disclosed in the present invention are data that the covalently reactive groups in proteolytic Abs, the serine protease-like nucleophiles, enjoys considerable conformational flexibility relative to the noncovalent binding forces responsible for the specificity of Abs for individual polypeptide epitopes.

This discovery has resulted in another major aspect of the present invention, that is, the development of polypeptide analogs in which a covalently reactive electrophile can readily be located in side chains of the amino acids instead of the polypeptide backbone. Disclosed in this invention are methods using these analogs for coordination of the Ab nucleophilic reactivity with specificity for the linear and discontinuous epitopes expressed by polypeptides, allowing the occurrence of epitope-specific nucleophilic reactions between Abs and antigens. These methods remove an important bottle-neck in development of covalent and catalytic Abs, because preparation of such antibodies to large polypeptides is presently not possible by conventional methods. Synthesis of large polypeptides with electrophiles incorporated with the backbone is outside the scope of current chemical synthesis technology, whereas the electrophiles can readily be placed on the amino acid side chains by chemical conjugation without unduly disturbing the native antigenic structure of proteins. An alternative approach to preparing electrophilic polypeptides within the backbone is the utilization of unnatural electrophilic amino acid analogs for protein synthesis by natural synthetic procedures, for example by correct recognition of the electrophilic amino acid analog by the appropriate tRNA species during the translation of mRNA in the polyribosome complex.

The proteolytic activity of naturally occurring Abs is reported to derive heritable germline lines encoding serine protease-like nucleophilic sites (11). The first Abs made by B cells over the course of their differentiation into cells that synthesize specific Abs to individual antigenic epitopes belong to the IgM class, with class switching to IgG Abs occurring at a later stage, concomitant with ongoing somatic diversification of the Ab variable domains. Disclosed in the present invention are observations indicating that IgM Abs are superior catalysts compared to IgG Abs. Also disclosed are methods to identify and induce the synthesis of antigen-specific Abs of the IgM with proteolytic activity.

REFERENCES

1. Tramontano A, Janda K D, Lemer R A. Catalytic antibodies. Science 1986 Dec. 19; 234(4783):1566-70.
2. Charbonnier J B, Carpenter E, Gigant B, Golinelli-Pimpaneau B, Eshhar Z, Green B S, Knossow M. 20 Crystal structure of the complex of a catalytic antibody Fab fragment with a transition state analog: structural similarities in esterase-like catalytic antibodies. Proc Natl Acad Sci USA 1995 Dec. 5; 92(25):11721-5.
3. Pollack S J, Hsiun P, Schultz P G. Stereospecific hydrolysis of alkyl esters by antibodies. J Am Chem Soc 1989; 111 (15):5961-2.
4. Paul S, Volle D J, Beach C M, Johnson D R, Powell M J, Massey R J. Catalytic hydrolysis of vasoactive intestinal peptide by human autoantibody. Science 1989 Jun. 9; 244 (4909):1158-62.
5. Li L, Paul S, Tyutyulkova S, Kazatchkine M D, Kaveri S. Catalytic activity of anti-thyroglobulin antibodies. J Immunol 1995 Apr. 1; 154(7):3328-32.
6. Shuster A M, Gololobov G V, Kvashuk O A, Bogomolova A E, Smirnov I V, Gabibov A G. DNA hydrolyzing auto antibodies. Science 1992 May 1; 256(5057):665-7.
7. Tawfik D S, Chap R, Green B S, Sela M, Eslhar Z. Unexpectedly high occurrence of catalytic antibodies in MRL/lpr and SJL mice imnmunized with a transition-state analog: is there a linkage to autoimmunity? Proc Natl Acad Sci USA 1995 Mar. 14; 92(6):2145-9.
8. Lacroix-Desmazes S, Moreau A, Sooryanarayana, Bonnemain C, Stieltjes N, Pashov A, Sultan Y, Hoebeke J, Kazatchkine M D, Kaveri S V. Catalytic activity of antibodies against factor VIII in patients with hemophilia A. Nat Med 1999 September; 5(9):1044-7.
9. Hifumi E, Mitsuda Y, Ohara K, Uda T. Targeted destruction of the HIV-1 coat protein gp41 by a catalytic antibody light chain. J Immunol Methods 2002 Nov. 1; 269(1-2):283-98.
10. Gao Q S, Sun M, Tyutyulkova S, Webster D, Rees A, Tramontano A, Massey R J, Paul S. Molecular cloning of a proteolytic antibody light chain. J Biol Chem 1994 Dec. 23; 269(51):32389-93.
11. Gololobov G, Sun M, Paul S. Innate antibody catalysis. Mol Immunol 1999 December; 36(18):1215-22.

SUMMARY OF THE INVENTION

The present invention provides novel compositions and methods for stimulating production of specific covalent and catalytic Abs and fragments thereof Provided herein are improved methods for identifying, isolating, refining and inhibiting these Abs for the treatment of a variety of medical diseases and disorders, including but not limited to infectious, autoimmune and neoplastic disease. These Abs will also have applications in the fields of human medicine, veterinary medicine, industrial chemical processed, basic science research and biomedical research.

According to one aspect of the invention, methods and compositions are provided herein for stimulating specific covalent and catalytic Ab production to predetermined target antigens, including but not limited to those involved in pathogenic and neoplastic processes. Polypeptide covalently reactive analogs (pCRAs) and water binding pCRAs (pCRAWs) are described which stimulate the production of covalent and catalytic Abs with therapeutic value in the treatment of a variety of medical conditions, including autoimmunity disorders, microbial diseases, lymphoproliferative disorders, cancer, septic shock, systemic inflanmmatory disease and acute respiratory distress syndrome. The Abs of the invention may also be used prophylatically to prevent the occurrence of these medical disorders.

In one aspect of the invention, pCRAs or pCRAWs are administered to a living organism under conditions whereby these compounds stimulate production of specific covalent and catalytic antibodies. These Abs are then cloned, purified and administered to a patient in need of such treatment in an amount sufficient to inactivate antigens associated with a predetermined medical disorder.

In an alternative embodiment, should the patient experience unwanted side effects, the activity of the infused catalytic antibodies may be irreversibly inactivated by administering the immunizing pCRA to said patient.

In yet another aspect of the invention, vaccination (active immunization) of humans or animals is achieved by administering the pCRAs or pCRAWs as complexes with an adjuvant to a patient to be immunized. Booster injections of the pCRA-adjuvant complex are administered as needed. This procedure induces active covalent and catalytic immunity against disease processes, that is, the production of protective covalent and catalytic Abs to antigens that are important in the initiation and maintenance of the disease process.

According to another aspect of the present invention, a method is provided for treating a pathological condition related to the presence of endogenously expressed, disease-causing catalytic Abs. Examples of such abnormal pathological conditions are certain autoimnmune and lymphoproliferative disorders. The method comprises administering to a patient having such a pathological condition a pharmaceutical preparation comprising pCRAs capable of irreversibly binding the endogenously produced catalytic Abs, in an amount sufficient to irreversibly bind and inactivate the catalytic Abs, thereby alleviating the pathological condition. In this embodiment, the pCRA contains a minimal B epitope and a T cell epitope would be omitted if possible to minimize the imnmunogenicity of the pCRA.

A further aspect of the invention comprises methods for screening Abs and their fragments displayed on the surface of B cells or a suitable vector such as a phage display vector for expression of covalent and catalytic Abs. In this embodiment, those phages or B cell which bind the pCRA are isolated. Methods for isolating and cloning the DNA encoding the covalent and catalytic Abs from phage or B cells so isolated are also within the scope of the present invention.

The methods of the present invention provide notable advantages over currently available compounds and methods for identification, isolation and inhibition of covalent and catalytic Abs specific for predetermined target antigens. Accordingly, the disclosed methods of the invention provide valuable clinical reagents for the treatment of disease.

DESCRIPTION OF THE DRAWINGS

FIG. 3: Induction of catalytic Ab synthesis. Stimulation of B cells expressing catalytic Abs on their surface results in clonal abortion, as release of the products deprives the cells of the essential antigenic stimulus necessary to induce proliferation (Top). Covalently reactive antigen analogs, in contrast bind in a stable manner to the surface Abs, stimulating clonal proliferation and maturation of the catalyst-synthesizing cells.

FIG. 4. General representation of pCRAs and pCRAWs. These compounds are composed of one or more antigenic epitopes containing an electrophilic group. The epitope is composed of continuous or discontinuous ligand components [L1 . . . Lx . . . Lm]. L' is a functional group of a ligand component Lx, to which the Y-Y'-Y" unit containing an electrophile is attached. Y is the electrophilic atom or group capable of forming a full or partial covalent bond the with nucleophilic group (Nu) of the antibody. Y' and Y" are, respectively, an optional P1 subsite and an optional adaptor functionality. Y' is an atom, bond or chemical group that connects Y and L' or Y", and can provide additional effects that regulate the reactivity of pCRAs and pCRAWs independent of the electrophilicity of Y. Y" is an atom, bond or chemical group that connect Y' and Lx' and enables control of the distance between Y and the epitope and the spatial positioning of these groups. When a water binding site is present anywhere within Y-Y'-Y", the pCRA is designated as a pCRAW. Example 1: Y is the phosphonate monophenyl ester group, which forms the covalent bond with the Ab Nu. Y' is the ethylamine group that connects Y and the β-carboxyl group (L') of Asp (Lx) via an amide bond (Y") and presents a methyl flank, which can facilitate the covalent binding to an antibody with a small hydrophobic pocket near Nu. Example 2: Y is the phosphonate diphenyl ester group, which forms the covalent bond with the Ab Nu. Y' is the (4-amidinophenyl) methylamine group that connects Y and suberic acid group (Y"). The 4-amidinophenyl flank of Y' can facilitate the covalent binding to a receptor with a negatively charged pocket near Nu. Another functionality of Y" is connected to the ε-amino group (L') of Lys (Lx). Example 3: Y is the boronic acid group, which forms the covalent bond with Nu. Y' is the 1-amino-4-guanidinobutylamine group that connects Y and γ-maleimidobutyric acid group (Y"). The guanidinopropyl flank of Y' can facilitate the covalent binding to an antibody with a negatively charged pocket near Nu. The maleimide group of Y" is connected to the sulfhydryl group (L') of Cys (Lx).

FIG. 6: Examples of suitable water-metal binding motifs for incorporation in pCRAWs.

EXAMPLE 1

Figure 7:
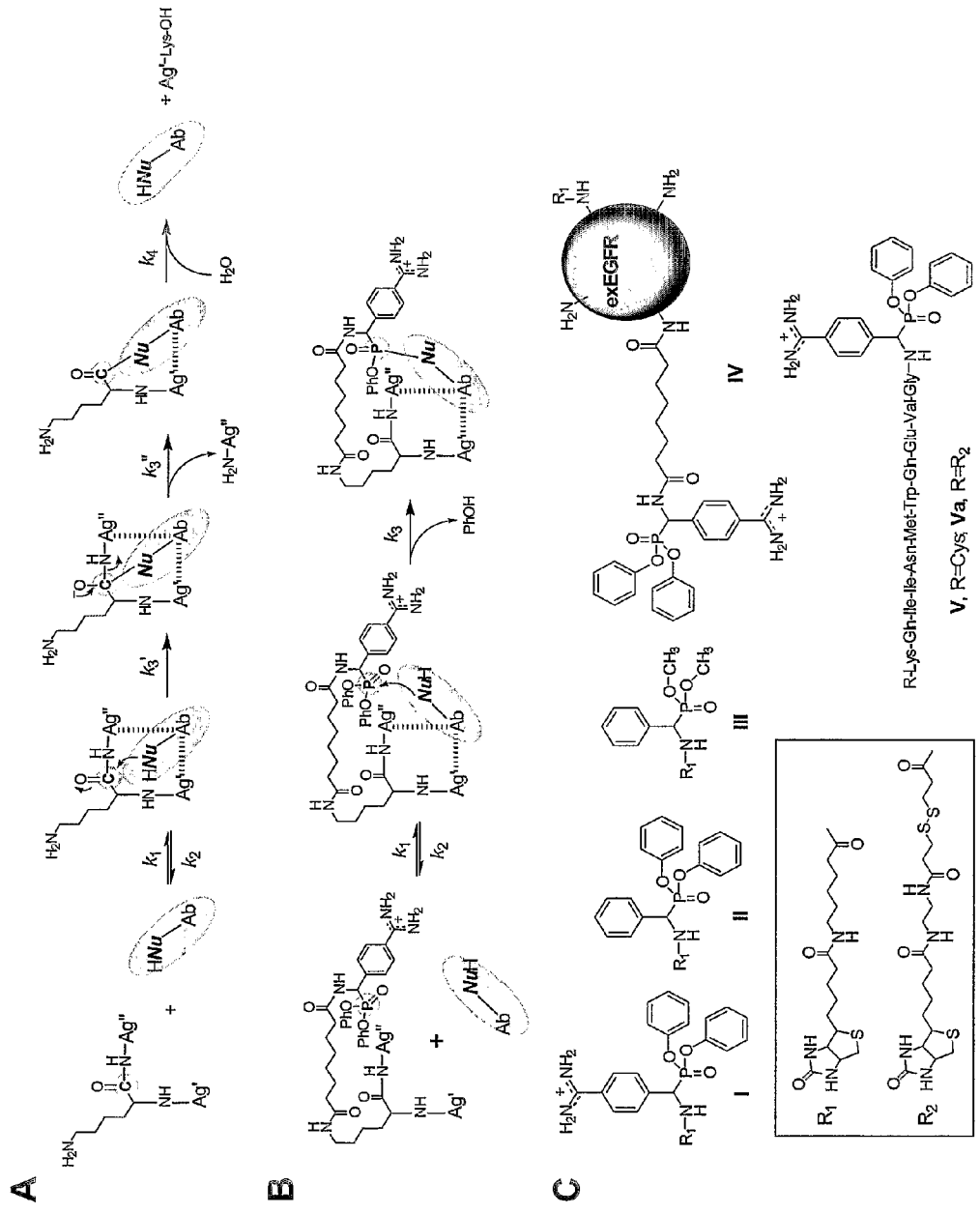

FIG. 7. Panels A and B, Reaction of serine protease-like Abs with antigens and phosphonate diester-containing antigen analogs, respectively. Panel C, CRA structures. In panel A, Nu denotes a nucleophile; Ag' and Ag" are components of the antigenic epitope at which noncovalent contact with the Ab occurs; Ag'-Lys-OH is the N-terminal antigen fragment; and NH2-Ag" is the C-terminal antigen fragment. The active site nucleopbile attacks the carbonyl carbon of the scissile bond in the antigen (substrate) to form the tetrahedral transition-state complex. The C-terminal antigen fragment is released and the acyl-Ab complex is formed. Hydrolysis of the acyl-Ab complex results in release of the N-terminal antigen fragment and regeneration of the catalytic Ab. The catalytic rate constant kcat is the sum of k3'+k3". In panel B, the Ab nucleophile attacks the electrophilic phosphonate diester (instead of the carbonyl group) and the phosphonate-containing antigen (CRA) recapitulates the remaining interactions in the ground and transition state Ab-Ag complex (noncovalent binding at peptide epitopes), but unlike the acyl-Ab intermediate, the phosphonyl-Ab adduct is a stable product. In panel C, I is an active site-directed inhibitor of trypsin-like enzymes. II and III are I-derivatives devoid of the side chain amidino function and containing a weaker leaving group, respectively. IV and V are intended, respectively, to permit detection of nucleophiles in specific Abs to exEGFR and residues 421-432 of gp120. The biotin and phosphonate diester groups were incorporated in IV at Lys side chains. Va contains biotin at the N terminus and the phosphonate diester at the C terminus.

Figure 8:
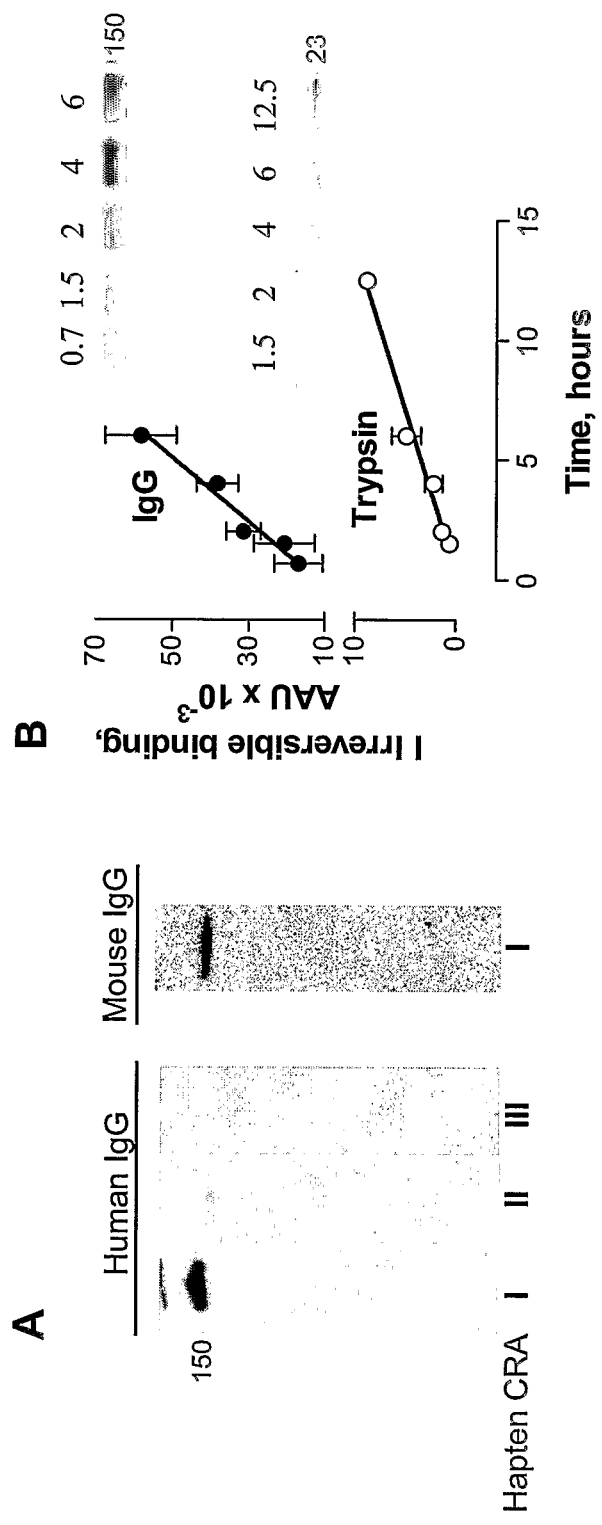

FIG. 8. Hapten CRA binding by IgG and trypsin. A, Representative streptavidin-peroxidase stained blots of SDS-polyacrylamide gels showing adducts of I with human (#1518) and murine (BALB/c) serum IgG (1 μM). A weak reaction of IgG with II was observed by exposing the gel for a prolonged period (4 h) and no reaction with III was evident. Hapten CRA, 10 μM, 60 min. B, Time course of IgG-I and trypsin-I binding determined in triplicate. Y-axis values are intensities of the 150 kD (IgG) or 23 kD (trypsin) adduct bands expressed in arbitrary area units (AAU). CRA 1, 100

μM. Inset, streptavidin-peroxidase stained blots of SDS-polyacrylamide gels showing biotin-containing adducts (top, IgG; bottom, trypsin).

Figure 9:
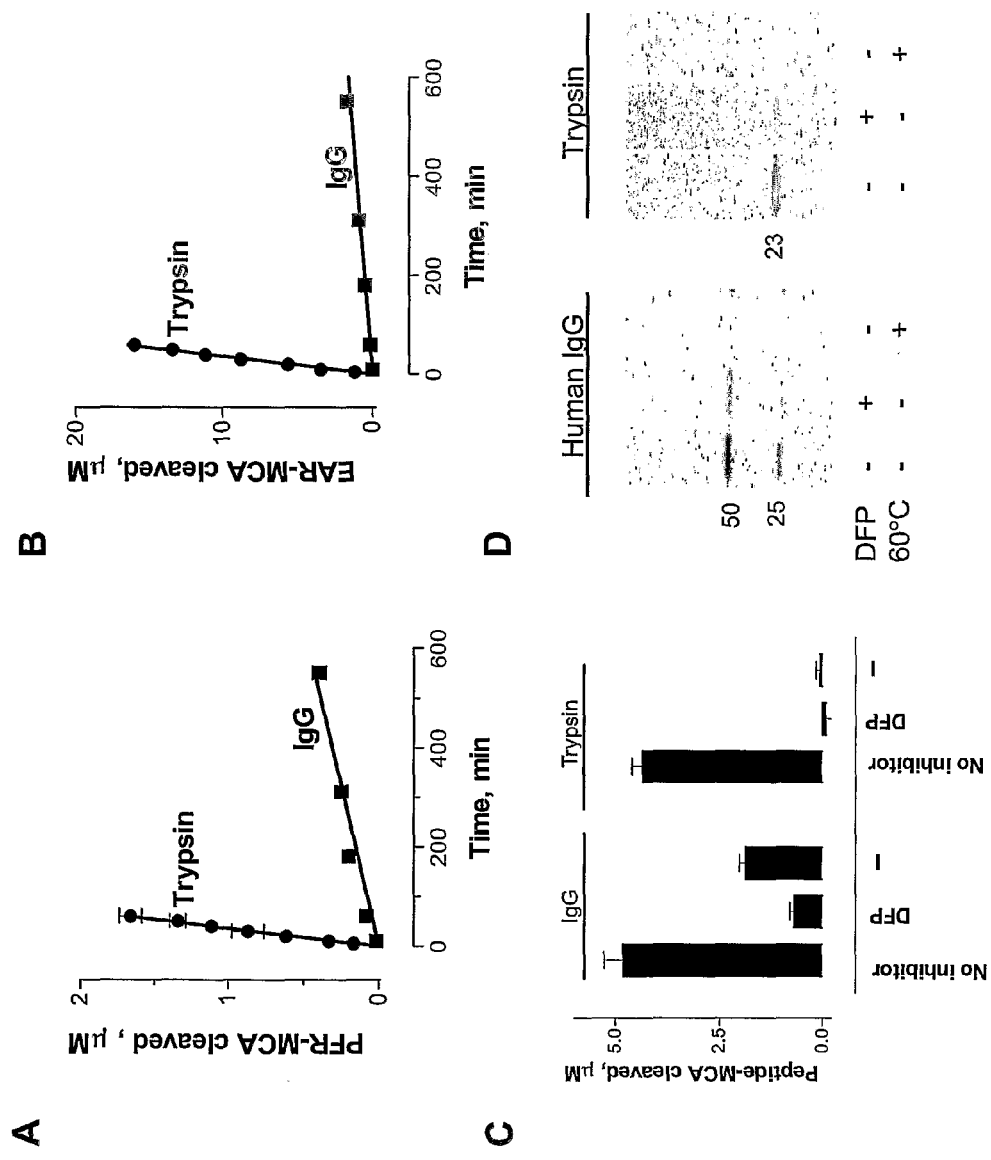

FIG. 9. Catalytic and hapten CRA I binding characteristics of human IgG (#1518) and trypsin. A, Time course of cleavage of Pro-Phe-Arg-MCA (200 μM, IgG 500 nM, trypsin 0.1 nM). B, Time course of cleavage of Glu-Ala-Arg MCA (200 μM, IgG 500 nM, trypsin 0.1 nM). C, DFP (5 mM) and CRA I (0.1 μM) inhibition of peptide-MCA (mixture of Glu-Ala-Arg-MCA, Pro-Phe-Arg-MCA and Ile-Glu-Gly-Arg-MCA; SEQ ID No. 1; 67 μM each) cleavage by IgG (375 nM) and trypsin (1 nM); respectively, 21 h and 1.5 h reaction. D, Representative streptavidin-peroxidase stained blots of reducing SDS-polyacrylamide gels showing inhibition of I (10 μM) adduct formation by DFP (5 mM) and preheating of the proteins for 10 min. IgG, 1 μM; trypsin, 1 μM. 1 h reaction. Treatment with DFP for 30 min prior to incubation with I. Values in A-C are means of 3 replicates±s.d.

Figure 10:
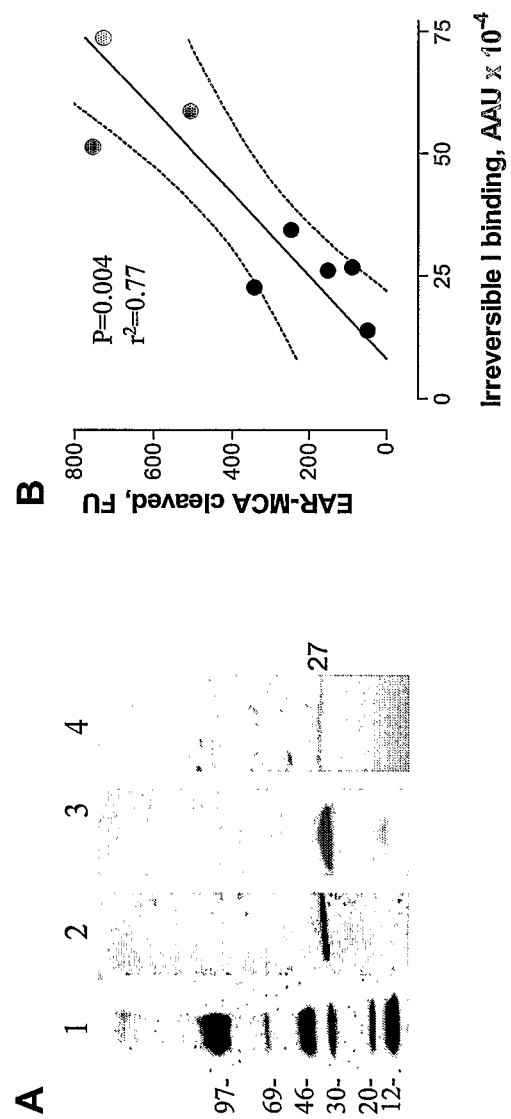

FIG. 10. Single chain Fv reactivity with hapten CRA I (A, B) and correlation with proteolysis (B). A, Reducing SDS-electrophoresis gels showing Fv (clone MMF-4) adducts with CRA I stained with streptavidin-peroxidase (lane 2), anti-c-myc antibody (lane 3) and silver (lane 4). Lane 1, standard proteins used for gel calibration. For the reaction in lane 2, Fv (0.45 μM) treated with CRA 1 (200 μM; 60 min reaction). The minor c-myc containing band in lane 2 is a degradation product that copurifies with full-length Fv on the nickel column as it contains the his6 tag. B, Shown are values for cleavage of Glu-Ala-Arg-MCA (y-axis; 200 μM; 17 h reaction time) and binding of CRA I (200 μM; 60 min) by purified Fv from eight clones (MM 18, 20, 24, F4, F5, F6, F11, F14). Correlation assessed by linear regression. Dotted lines, 95% confidence limits. FU, fluorescence units. 183 FU, 1 μM aminomethylcoumarin.

Figure 11:
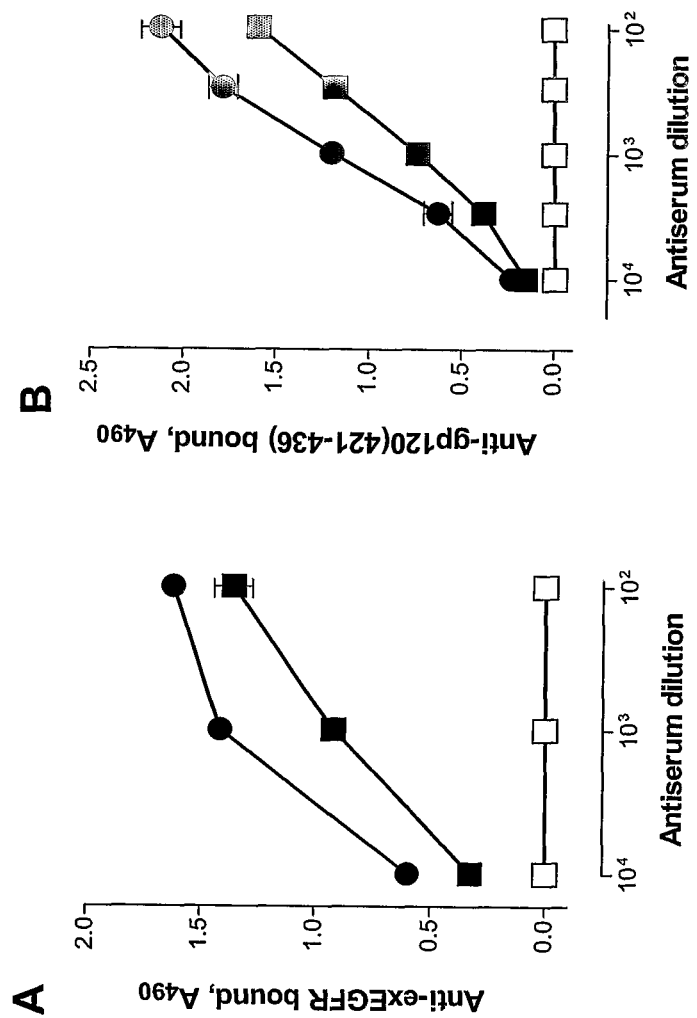

FIG. 11. Antibody binding by phosphonate diester containing protein CRA IV and peptide CRA V determined by conventional ELISA procedures. A, Comparison of binding of immobilized IV by antiserum to exEGFR (■) and control nonimmune serum (□). (●) shows binding of inunobilized exEGFR by anti-exEGFR antiserum. B, Comparison of binding of immobilized Va by antiserum to a gp120(421-436)-KLH conjugate (■) and control nonimmune serum (□). (●) shows binding of irumobilized gp120(421-436)-BSA conjugate by anti-gp120(421-436) antiserum. No binding of immobilized exEGFR or the gp120(421-436)-BSA conjugate by control nonimmune sera was evident (not shown). Shown are absorbance values (490 nm)±s.d.

Figure 12:
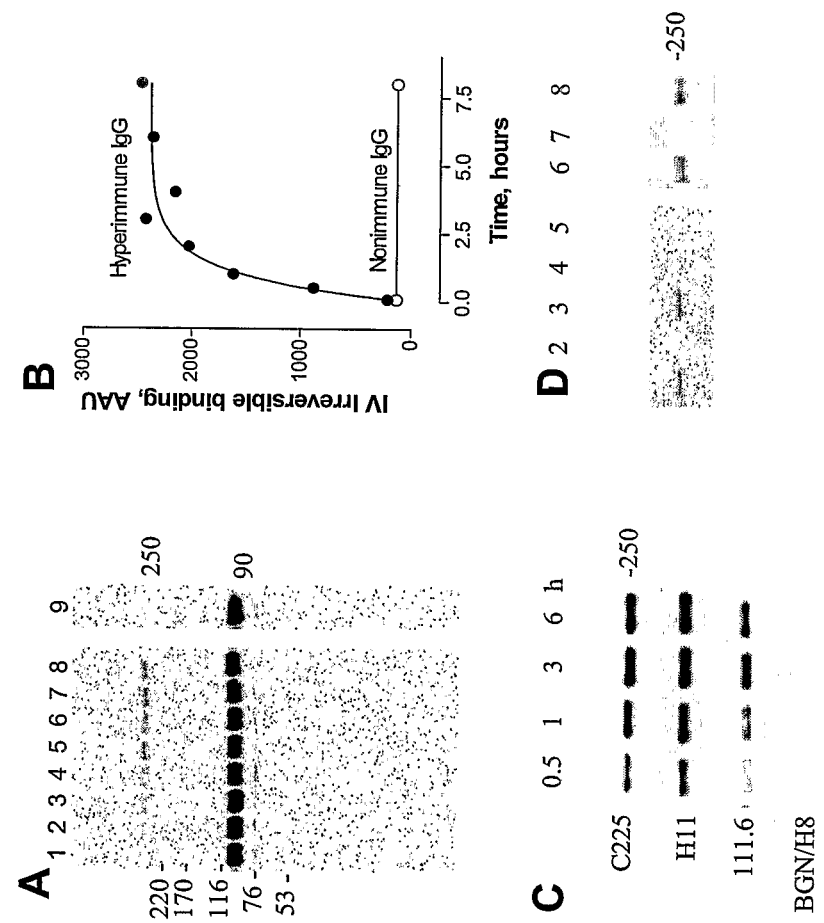

FIG. 12. Specific irreversible binding of exEGFR protein CRA IV by polyclonals and monoclonal Abs to EGFR. A, Streptavidin-peroxidase stained blot showing 250 kD adducts formed by treating IV (0.2 μM) with polyclonal anti-EGFR IgG (0.7 μM) for increasing lengths of time (0.05, 1, 2, 3, 4, 6, and 8 h; lanes 1-8, respectively). Lane 9 is the reaction mixture of IV (0.2 μM) incubated with control nonimmune IgG (0.7 μM) for 8 h. B, Intensities of the 250 kD band from panel A (in arbitrary area units). C, Accumulation of 250 kD biotin-containing adducts of IV (0.2 μM) with monoclonal Abs to EGFR (0.5 μM; clones C225, H11, 111.6) as a function of time. No adducts were formed by an equivalently treated control monoclonal Ab (BGN/H8). D, Biotin-containing 250 kD adducts formed by treatment of IV (0.2 μM) for 2 h with polyclonal IgG to exEGFR (0.5 μM) in the absence (lane 1) and presence of exEGFR (1 μM; lane 2) or calmodulin (1 μM; lane 3). In control reactions, IV (0.2 μM) was treated for 2 h with nonimmune IgG (0.5 μM; lane 4) and boiled polyclonal IgG to exEGFR (10 min at 100° C.; 0.5 μM; lane 5). IVa (0.2 μM) treated with monoclonal IgG c225 (0.5 μM) for 2 h in the absence of exEGFR is shown in lane 6, and in presence of exEGFR (1 μM) or cahnodulin (1 μM) in lanes 7 and 8, respectively. Abs treated with competitor proteins for 30 min prior to addition of IV or IVa.

Figure 13:
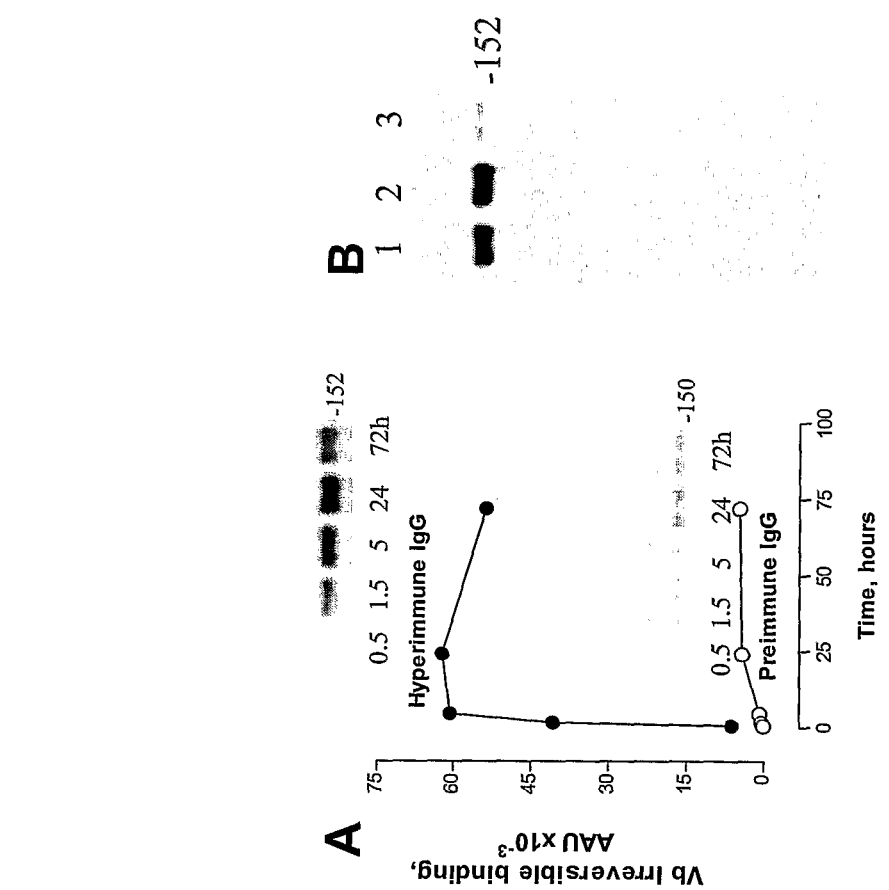

FIG. 13. Specific irreversible binding of peptidyl CRA Va by Abs to gp120(421-436). A, Time course of formation of adducts of Va (10 μM) incubated with IgG to gp120(421-436) (1 μM). Insets, streptavidin-peroxidase stained 152 kD adducts in nonreducing SDS-electrophoresis gels formed with anti-gp120(421-436) IgG (top) and equivalent concentrations of nonimmune IgG (bottom). B, streptavidin-peroxidase stained nonreducing SDS-electrophoresis gels showing Va (10 μM) adducts formed by treatmuent with anti-gp120 (421-436) IgG (1 μM; 1 h) in the absence of competitor proteins (lane 1) and presence of albumin (3 μM or gp120 (421-436)BSA (3 μM BSA equivalents; 30 μM peptide equivalents).

EXAMPLE 2

Figure 14:
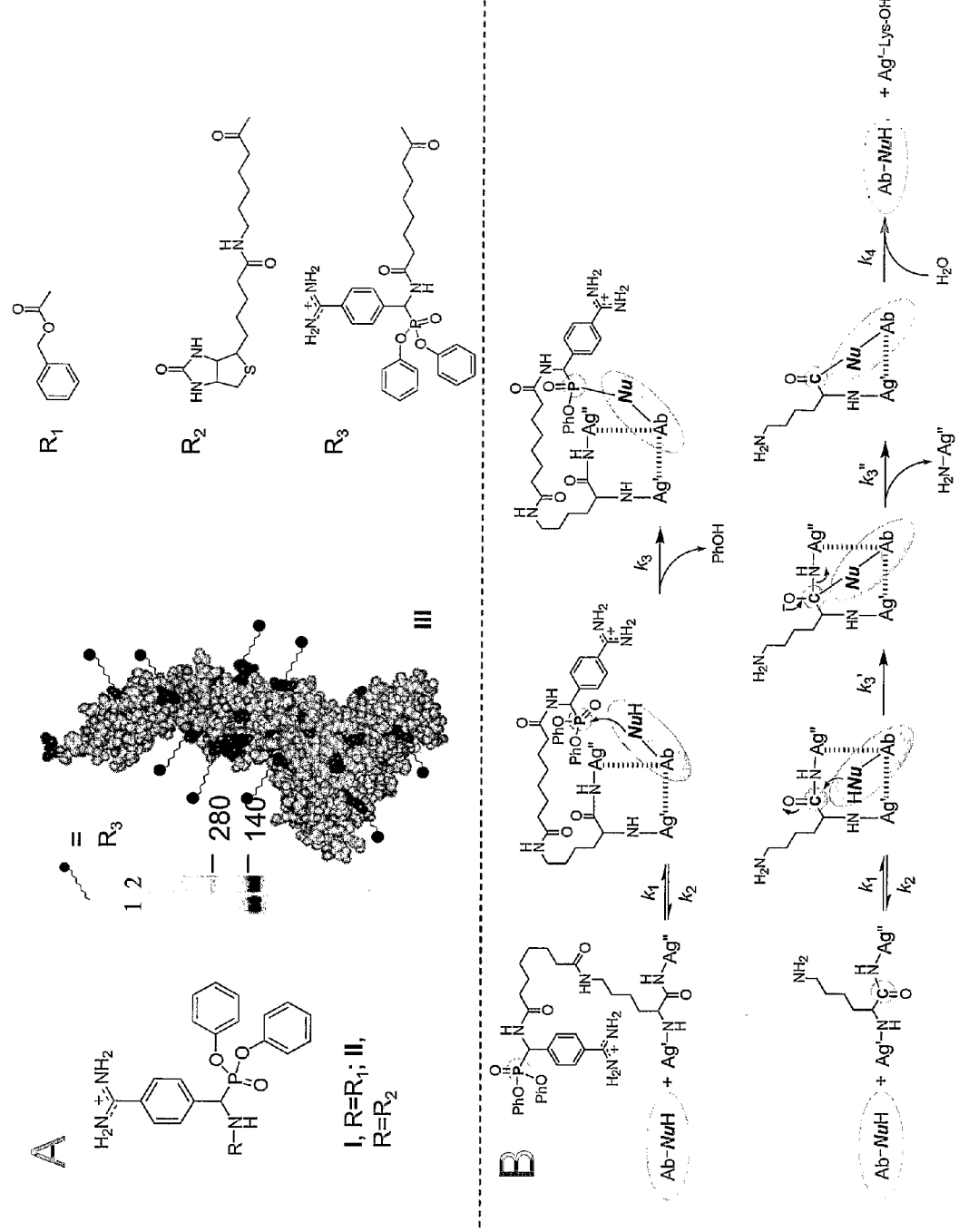

FIG. 14. CRA structures (A) and their reaction with Abs (B). III is schematic representation of gp120 with R3 substituents at Lys residues. Left of III are streptavidin-peroxidase stained blots of SDS-electrophoresis gels showing biotinylated III containing 4 mol (lane 1) and 14 mol (lane 2) phosphonate diester groups/mol gp120. In B, Nu, nucleophile; Ag'-Lys-OH, N-terminal antigen fragment; NH2-Ag", C-terminal antigen fragment; kcat=k3'+k3". A catalytic Ab forms the initial noncovalent complex by conventional epitope-paratope interactions. The active site nucleophile site attacks the carbonyl carbon of the scissile bond in Ag (substrate) to form the tetrahedral transition-state complex. The C-terninal antigen fragment is released and the acyl-Ab complex is formed. Hydrolysis of the acyl-Ab complex results in release of the N-terminal antigen fragment and regeneration of the catalytic Ab. The reaction with phosphonate-containing Ag recapitulates the interactions in the ground and transition state Ab-Ag complexes (noncovalent binding at peptide epitopes and nucleophilic attack by the Ab) but unlike the acyl-Ab intermediate, the phosphonyl-Ab adduct is a stable product. A potential weakness is that immunogen III does not contain structural feature favoring synthesis of Abs capable of rapid hydrolysis of the acyl-Ab intermediate and product release (bottom reaction scheme).

Figure 15:
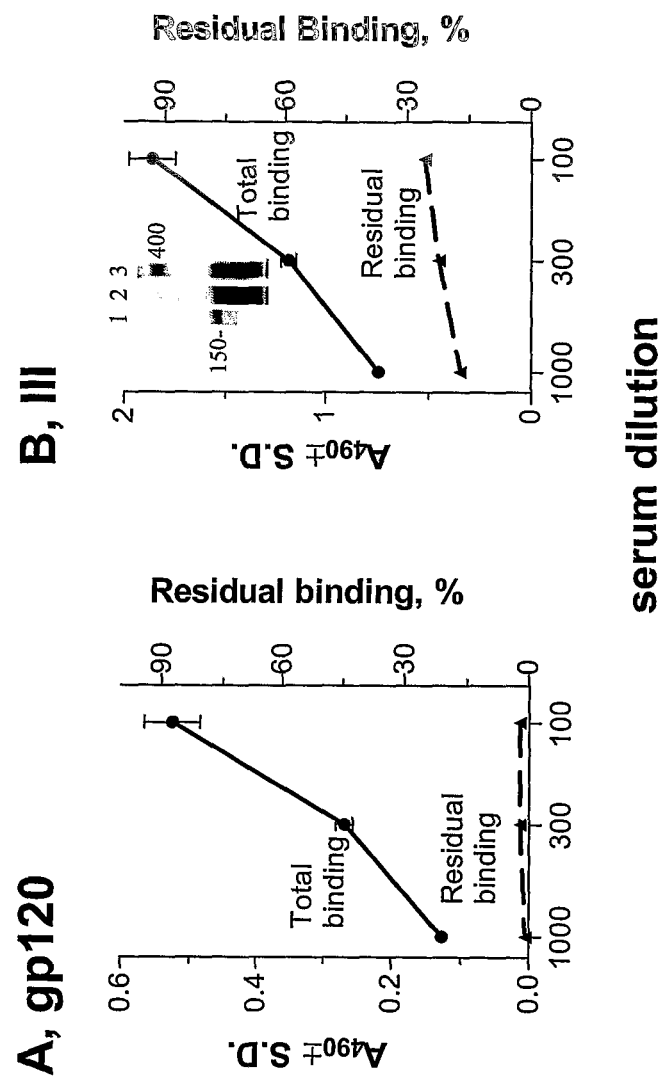

FIG. 15. Irreversible III binding by polyclonal Abs. A, Immobilized gp120. B, Immobilized III. Shown are ELISA values for binding of polyclonal Abs in serum of mice hyper immunized with III (pooled sera, N=4 mice). Binding of nonirnmune mouse serum was negligible (A490 of 1:100 nonimmune serum in A, 0.001; in B, −0.002). Residual and total binding represent A490 values in wells treated with and without SDS, respectively. Inset, Anti-IgG stained blot of SDS-electrophoresis gels showing III (0.3 μM) treated for 48 h with nonimmune IgG (lane 2, 0.1 μM) and anti-III IgG (lane 3, 0.1 μM). Large Ab-containing adducts are evident at ~400 kD in lane 3. Lane 1 is a shorter exposure of lane 2 showing a well-defined 150 kDa band at the position of the smear evident in overexposed lanes 2 and 3.

FIG. 16. Irreversible III binding by monoclonal Abs. ELISA showing SDS-resistant III binding by tissue culture supernatants containing MAbs (YZ series) (A) and monoclonal IgG purified from clone YZ18 (13) raised by immunization with gp120-CRA III. MAb CRL1689 is an irrelevant monoclonal IgG with same isotype as MAbs YZ21 and YZ23. Immobilized antigens, gp120 and III. SDS-resistant III binding indicated by bars and curve labeled III+SDS.

Figure 17:
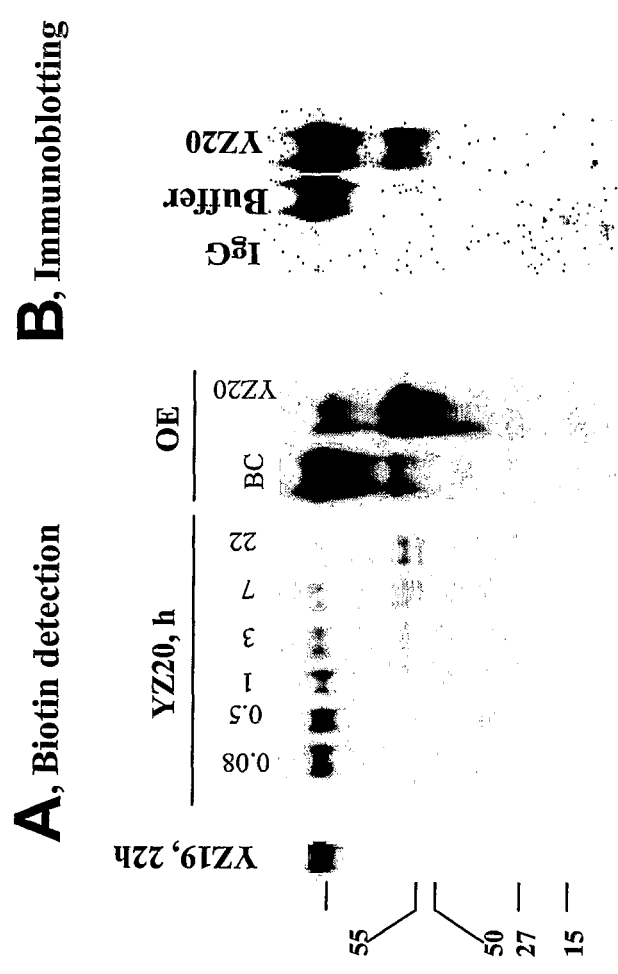

FIG. 17. Cleavage of Bt-gp120 by MAb Y20. A Streptavidin-peroxidase stained blot of SDS-electrophoresis gels showing time dependent Bt-gp120 cleavage by MAb YZ20 and lack of cleavage by MAb YZ19 (22 h incubation). IgG, 1 µM; Bt-gp120, 0.2 μM. OE, Overexposed lanes showing Bt-gp120 incubated for 22 h in diluent and with YZ20 IgG (1 μM). Product bands at 27 kDa and 15 kDa are visible in addition to the major 50-55 kDa bands. B, Anti-gp120-peroxidase stained blot of SDS-electrophoresis gel showing gp120 (1 μM) incubated with diluent or YZ20 IgG (1 μM, 24 h).

FIG. 18. Lack of cleavage of Bt-BSA and Bt-exEGFR by MAb YZ20 (A) and preferential cleavage at basic residues (B, C). A, Strepavidin-peroxidase stained blots of biotinylated proteins (0.2 μM) incubated with MAb YZ20 (1 μM, 24 h). B, Fluorimetric determination of MAb YZ20 (0.5 μM) catalyzed cleavage of peptide-MCA substrates (200 μM, 22 h). C, Cleavage of GGR-MCA and GGL-MCA by MAb YZ20 (0.5 μM). Concentration of both substrates was held at 12.5 μM because of limited solubility of Gly-Gly-Leu-MCA. Blocking groups at the N termini of the substrates were: succinyl—AE-MCA, AAA-MCA, AAPF-MCA, IIW-MCA; t-butyloxycarbonyl-EKK-MCA, VLK-MCA, IEGR-MCA, EAR-MCA; benzyloxycarbonyl—GGR-MCA, GGL-MCA. Values are means of 3 replicates±s.d.

FIG. 19. Enhanced hapten CRA I covalent binding by polyclonal IgG from mice immunized with III (A) and potent inhibition of MAb YZ20 cleavage of Bt-gp120 by hapten CRA II (B). A, Binding of hapten CRA I (10 μM) determined by incubation with IgG (0.4 μM) from BALB/c mice immunized with III (Ms9-12) or control gp120 (Ms1-4) for 60 min, SDS-electrophoresis and quantification of the biotin-containing band at 150 kDa. NI, nonimmune IgG (pooled from 20 mice). Inset, Representative SDS-electrophoresis lanes showing hapten CRA I binding by IgG from a mouse immunized with III (Ms11), amouse immunized with gp120 (Ms3) and nonimmune IgG (NI). B, Bt-gp120 (0.1 μM) cleavage by MAb YZ20 (1 μM, 4 h) and ($Tyr^{10}$-$^{125}I$)VIP (~100 pM, 45 K c.p.m.) cleavage by MAb c23.5 (20 nM, 18 h) was measured in the presence of increasing II concentrations. In the absence of II, 15% and 40% of available Bt-gp120 and VIP, respectively, were cleaved.

EXAMPLE 3

FIG. 20. (A) Structure of hapten CRA 1, VIP-CRA 3 and synthetic intermediate 2. (B) Scheme for synthesis of VIP-CRA 3. Reagents and Conditions for steps i-vi in Panel B: (i) Solid-phase peptide synthesis by 9-fluorenylmethoxycarbonyl chemistry [deprotection, 20% piperidine in DMF (3 min×2, 20 min×1); coupling, N-(9-fluorenylmethoxycarbonyl) amino acid (2.5 equiv), PyBOP (2.5 equiv), 1-hydroxybenzotriazole (2.5 equiv), N,N-diisopropylethylamine (7.5 equiv) in DMF (60 min)]; (ii) 20% piperidine in DMF (3 min×2, 20 min×1); (iii) D-biotin (2.5 equiv), PyBOP (2.5 equiv), 1-hydroxybenzotriazole (2.5 equiv), N,N-diisopropylethylamine (7.5 equiv) in DMF (60 min); (iv) 1% TFA in $CH_2Cl_2$ (5 min×10); (v) 2 (3 equiv), 0.1 mM N,N-diisopropylethylamine in DMF (overnight); (vi) TFA-ethanedithiol-thioanisole-phenol (90:1:1:8, 2 h). All steps at room temperature. Protecting groups: Boc, tert-butoxycarbonyl; tBu, tert-butyl; Pmc, 2,2,5,7,8-pentamethylchroman-6-sulfonyl; Trt, trityl; Mtt, 4-methyltrityl.

FIG. 21. Specific covalent VIP-C binding by monoclonal anti-VIP IgG (clone c23.5). Panel A: Accumulation of VIP-CRA 3 or hapten CPA 1 adducts shown in arbitrary area units (AAU) of the adduct bands determined by electrophoresis and densitometry. Reaction conditions: 1 μM IgG, 10 μM CRA, 37° C. Data are means of closely agreeing duplicates. Correlation coefficients for curves fitted to progress curves by linear regression were 0.9 or greater. All reactions analyzed at 6 time points as shown for anti-VIP L chain. For clarity, only the final data points at 120 min are shown for anti-VIP H chain and control Ab H and L chains (UPC10 IgG). Inset, Streptavidin-peroxidase stained blots of SDS-gels showing 3-adducts of the c23.5 light (29 kD) and heavy (58 kD) chains. Lanes 1-6 correspond to the reaction time shown in the graph (10, 20, 40, 60, 90, and 120 min). Panel B: Representative plot showing inhibition by VIP (10 μM) of formation of anti-VIP light chain adducts with VIP-CRA 3. % Inhibition determined as: 100-100($V_{app,\ +VIP}$)/($V_{app,\ -VIP}$), where +VIP and −VIP refer to the presence and absence of VIP, respectively. Inset, Streptavidin-peroxidase stained electrophoresis cutouts showing light chain adducts formed in the absence and presence of VIP. Headers 1 through 6 correspond to the progressively increasing reaction time shown in the graph. Panel C: Streptavidin-peroxidase stained blots of SDS-electrophoresis gels showing CRA binding to anti-VIP Ab in the presence of human plasma (1% volume/volume; 1 h; CRAs, 10 μM each; exogenously added Abs, 10 μM). Exogenous Abs and CRAs used are: Anti-VIP c23.5 IgG+VIP-CRA 3 (lane 1); Control UPC 10 IgG+VIP-CRA 3 (lane 2); VIP-CRA 3 alone (lane 3); Anti-VIP c23.5+hapten 1 (lane 4), UPC10 IgG+hapten 1 (lane 5); and, hapten 1 alone (lane 6). Biotin-containing bands in lanes 1-6 detected as in panel A. Lanes 7 and 8 are silver stained blots of human plasma (1% volume/volume) and molecular-weight standards, respectively. Panel D: Streptavidin-peroxidase stained blots of reducing SDS-electrophoresis gels showing inhibition of VIP-CRA binding to anti-VIP c23.5 light chain by DFP. Anti-VIP IgG c23.5 (1 μM) was incubated with or without DFP (5 mM) for 5 min, and then allowed to react with VIP-CRA 3 (2 μM) for 60 min.

FIG. 22. Inhibition of anti-VIP light chain c23.5 catalyzed Pro-Phe-Arg-AMC hydrolysis by VIP-CRA 3. Panel A: Progress curves of Pro-Phe-Arg-AMC (0.2 mM) cleavage by the light chain (0.8 μM) in the absence (○) and presence (●) of VIP-CRA 3 (3 μM). Curves are least-square-fits to the equation [AMC]=V·t ($r^2$ 0.99) (○) or $[AMC]/[AMC]_{max}=1-e^{-k_{obs}\cdot t}$ ($r^2$ 0.89) (●), where V is the velocity of AMC release; [AMC]max, the extrapolated maximum value of AMC release, and $k_{obs}$, the observed first-order rate constant. Data are means of 3 replicates±SD. Fluorescence values expressed as released AMC by comparison with a standard curve constructed using authentic AMC. Background fluorescence in the absence of catalyst corresponded to 0.05±0.03 μM AMC. Panel B: Comparison of VIP-CRA 3 (●) and hapten CRA 1 (○) inhibition of light chain catalyzed Pro-Phe-Arg-AMC hydrolysis. Curves are fitted to the equation: % inhibition=$100/(1+10^{\log EC50-\log [CRA]})$ where EC50 is the concentration yielding 50% inhibition ($r^2$ 0.98). Reaction conditions as in Panel A except that varying CRA concentrations were employed (1, 3, 10, 30 μM). % inhibition computed as: 100 $(V-V_{13})/V$, where $V_{13}$ represents the residual activity after incubation for 13 h (tangents of the least-square-fit progress curves obtained as in Panel A). Values are means of 3 replicates±SD. In the absence of CRAs, the reaction rate was 22 nM AMC $h^{-1}$. Panel C: Stoichiometry of antibody light chain (c23.5) reaction with VIP-CRA 3. Shown is the plot of residual catalytic activity (Pro-Phe-Arg-AMC hydrolysis) of the light chain in the presence of varying VIP-CRA 3 concentrations (reaction conditions as in Panel B except that the VIP-CRA concentrations were 0.03, 0.1, 0.3, 1.0 and 3.0 μM, and reaction time was 36 h). Residual activity was determined as $100Vi/V$, where V is the velocity in the absence of inhibitor and Vi is a computed value of the velocity under conditions of complete inhibitor consumption. Vi values were obtained from least-square-fits to the equation $[AMC]=Vi \cdot t + A(1-e^{-k_{obs} \cdot t})$, where A and $k_{obs}$ represent, respectively, the computed AMC release in the stage when inhibitor consumption is ongoing and the observed first-order rate constant, respectively ($r^2$ for individual progress curves, >0.97). The equation is valid for reactions with an initial first order phase and a subsequent zero order phase. The X-intercept shown in the plot was determined from the least-square-fit for data points at [VIP-CRA 3]/[light chain] ratio<1. Inset, Example progress curve from which Vi values were computed. VIP-CRA 3, 0.03 µM.

Figure 23:
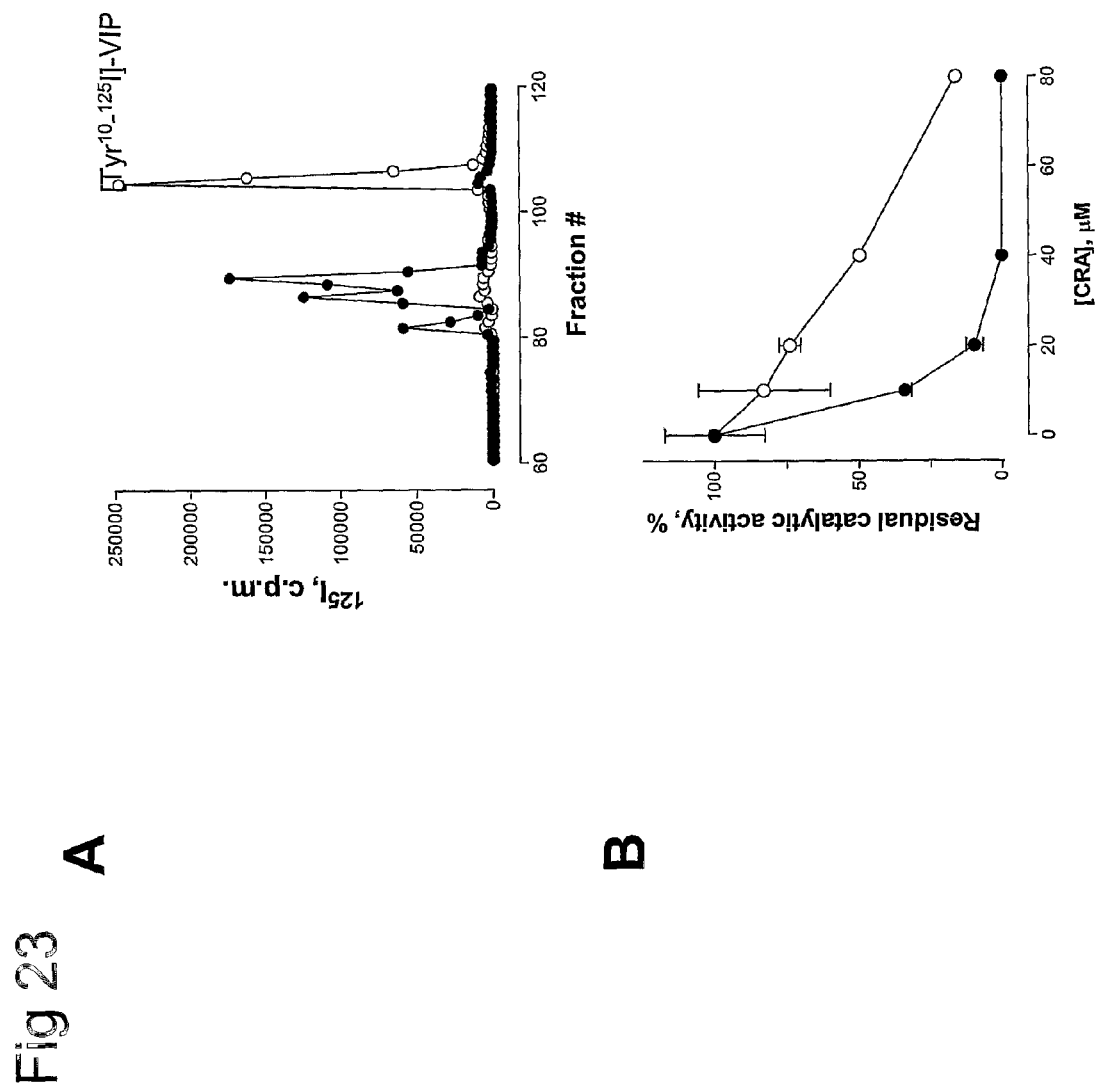

FIG. 23. Inhibition of polyclonal antibody catalyzed VIP cleavage by VIP-CRA 3 and hapten CRA 1. Panel A: Reversed-phase HPLC profiles showing cleavage of $[Tyr^{10}-{}^{125}I]$-VIP at multiple sites by human IgG HS-2. $[Tyr^{10}-{}^{125}I]$-VIP incubated in the presence (●) or absence (○) of HS-2 IgG (2 µM) for 16 h and subjected to HPLC [Nova-pak C, 3.9×150 mm; 0.1% TFA in water: 0.1% TFA in 80% acetonitrile 95:5 for 10 min, 95:5 to 30:70 in 55 min, 30:70 to 0:100 in 5 min, 0:100 for 5 min (0.5 ml/min)]. Shown are values of $^{125}I$ radioactivity recovered in the HPLC fractions (0.5 ml). Panel B: Irreversible inhibition of HS-2 IgG-catalyzed $[Tyr^{10}-{}^{125}I]$-VIP cleavage by VIP-CRA 3 and hapten CRA 1. IgG (2 µM) was preincubated for 16 h in the absence or presence of increasing concentrations of VIP-CRA 3 (●) or hapten CRA 1 (○). Following removal of unreacted CRA by chromatography on immobilized Protein G, the residual catalytic activity of the IgG was measured using $[Tyr^{10}-{}^{125}I]$-VIP as substrate. Data are means±SD. Control HS-2 IgG incubated in the absence of CRAs cleaved 2791 c.p.m. $[Tyr^{10}-{}^{125}I]$-VIP.

EXAMPLE 4

Figure 24:
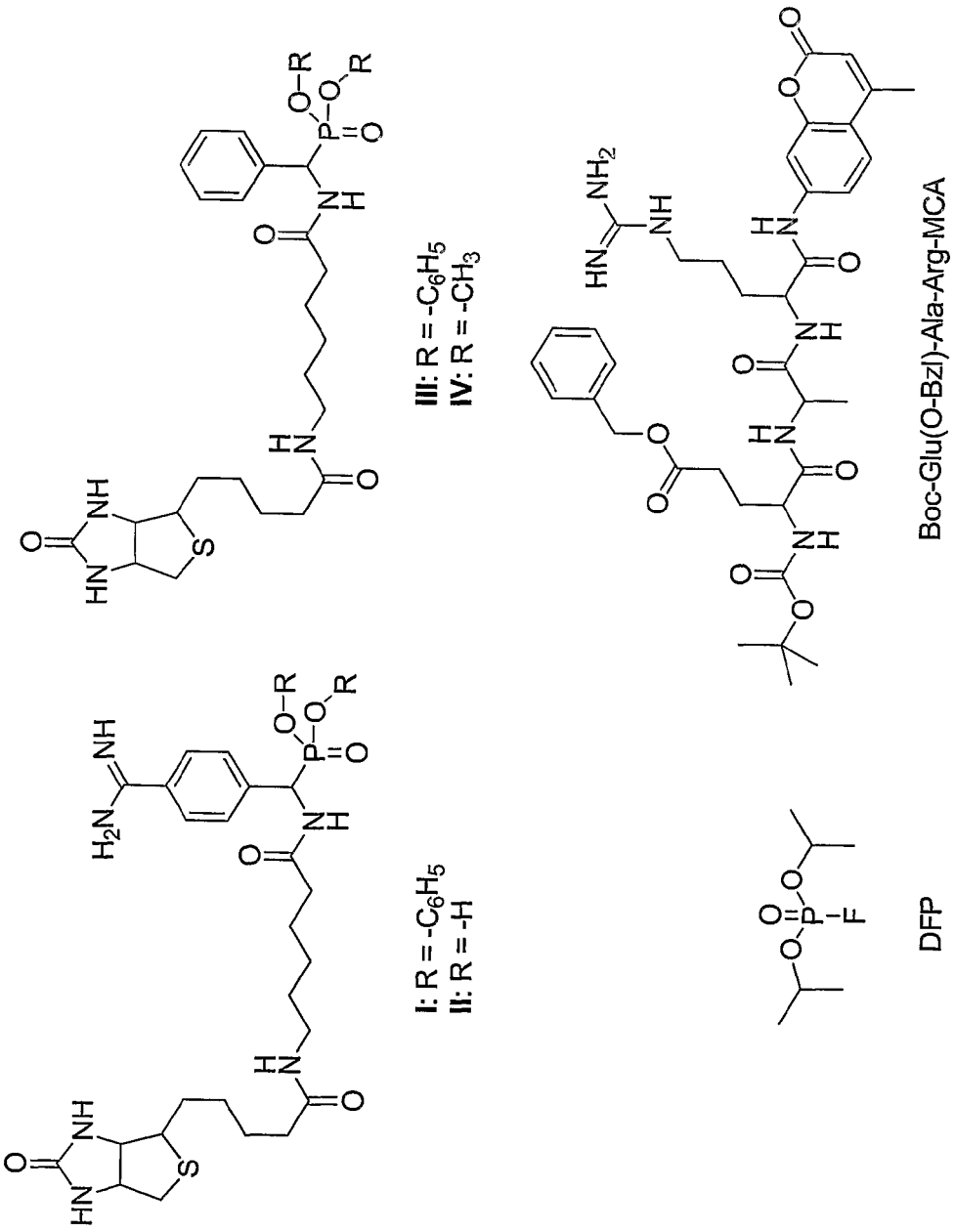

FIG. 24. Compounds I-IV, diisopropyl fluorophosphates (DFP) and Glu-Ala-Arg-AMC. Hapten CRA I is an active site-directed inhibitor of trypsin-like enzymes. Compound II is the unesterified phosphonic acid analog of I devoid of covalent reactivity. III and IV are I-derivatives devoid of the side chain amidino function and contain a weaker leaving group, respectively. These structures are analogs of the irreversible serine protease inhibitor DFP. Boc-Glu(OBzl)-Ala-Arg-AMC is an example of a commercially available synthetic substrate in which cleavage of the amide bond between Arg and the methylcouniarinamide group releases fluorescent 7-amino-4-methylcoumarin.

Figure 25:
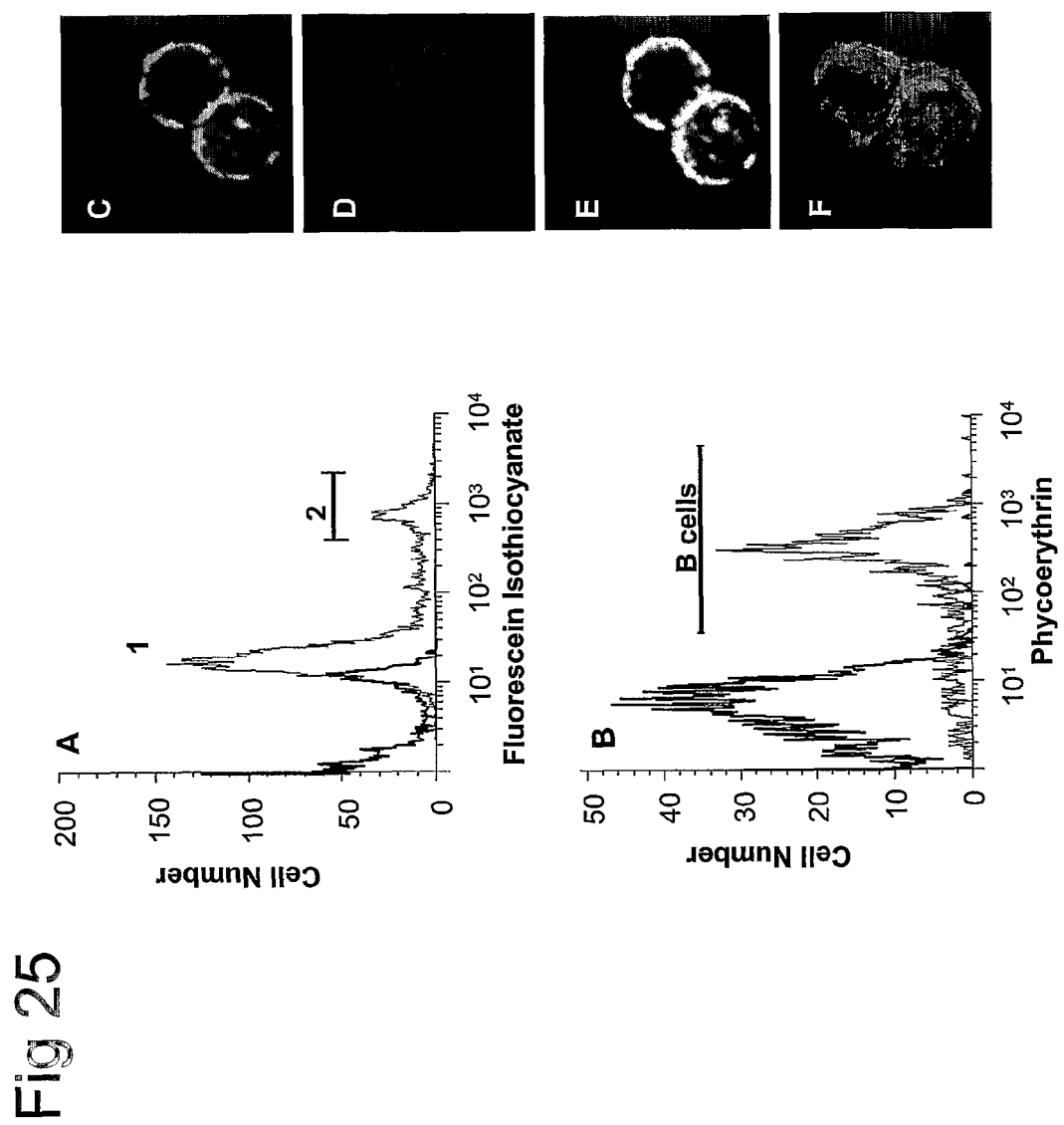

FIG. 25. Hapten CRA I reactivity with spleen cells. A, Flow cytometry of murine splenocytes (naïve BALB/c mouse) stained with biotinylated hapten CRA I (grey line) and compound II (black line; both compounds 100 µM, 4 hours; streptavidin-FITC (50 µg/ml). Twenty five thousand cells counted. B, Anti-CD19 Ab staining (grey line; phycoerytlirin conjugate) of hapten CRA I labeled cells; streptavidin-FITC 1 µg/ml). (black line) shows staining with the phycoerythrin conjugate of the isotype matched control antibody. C-F, Deconvoluted (5 iterations) fluorescence acquisitions showing two B cells labeled with CRA I (streptavidin-FITC, 1 µg/ml, panel C) and phycoerythrin conjugated anti-CD19 Ab (panel D). E shows a merged rendition of the FITC and phycoerythrin probes. F is a 3D wire frame model of the FITC emission patterns compiled from 30 individual sections and then subjected to split screen extraction. Blue counter stain, 4',6-diamidino-2-phenylindole.

Figure 26:
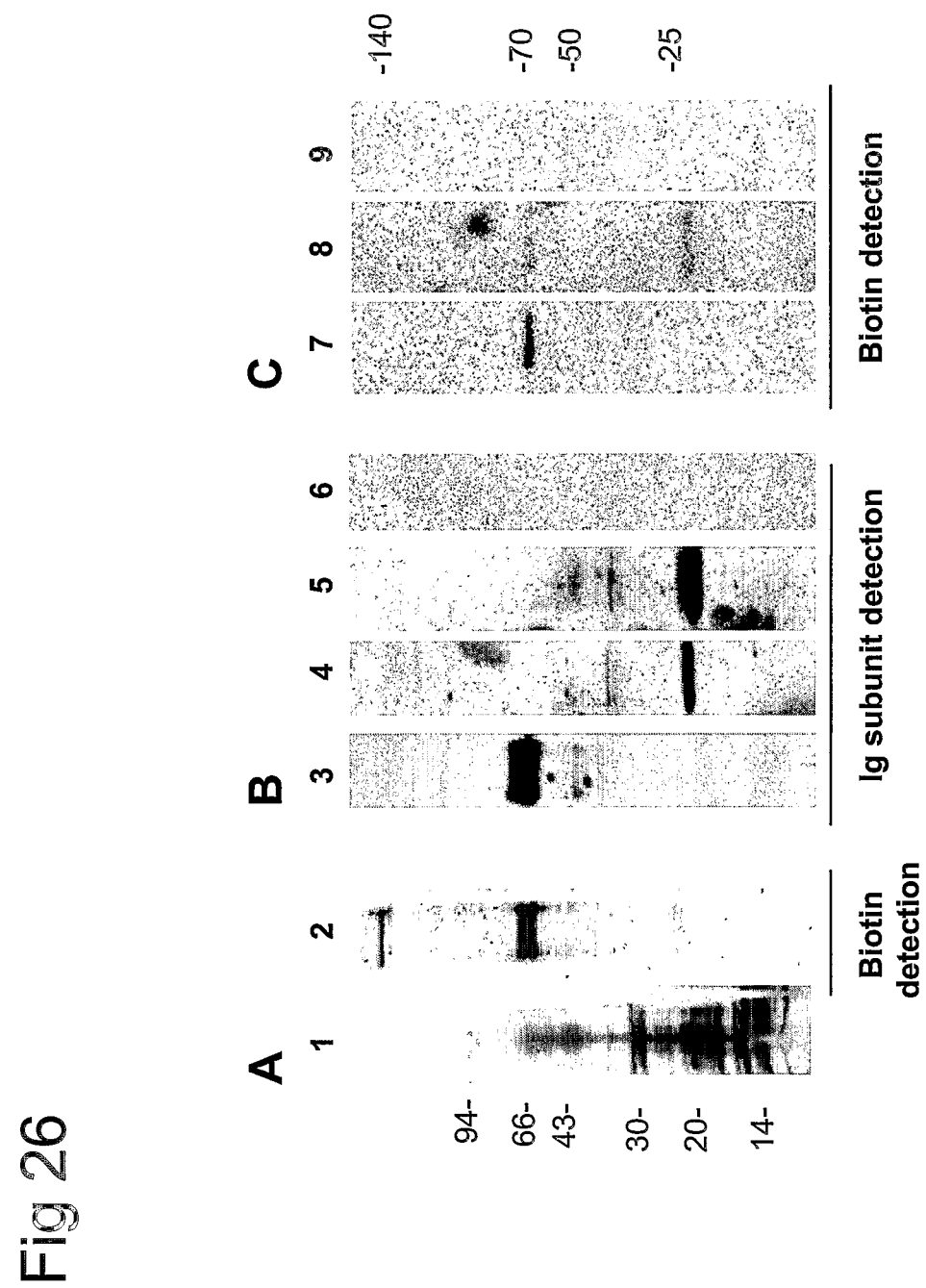

FIG. 26. Immunochemical identification of hapten CRA I labeled Ig subunits in B cell extracts. A, SDS-gel electrophoresis lanes showing extract of B cells labelled with hapten CRA I (100 µM, 4 hours) following staining with silver (lane 1) and peroxidase conjugated streptavidin (lane 2). Migration of marker proteins shown on left. B, SDS-gel immunoblots of hapten CRA I labeled B cell extract stained with Abs to µ (lane 3), λ (lane 4), κ (lane 5) and γ (lane 6) chains. C, Streptavidin-peroxidase stained SDS-gels showing hapten CRA I labeled proteins recovered by affinity chromatograpy of splenocyte extract on immobilized anti-µ (lane 7), anti-κ/λ (lane 8) and anti-γ Abs (lane 9).

Figure 27:
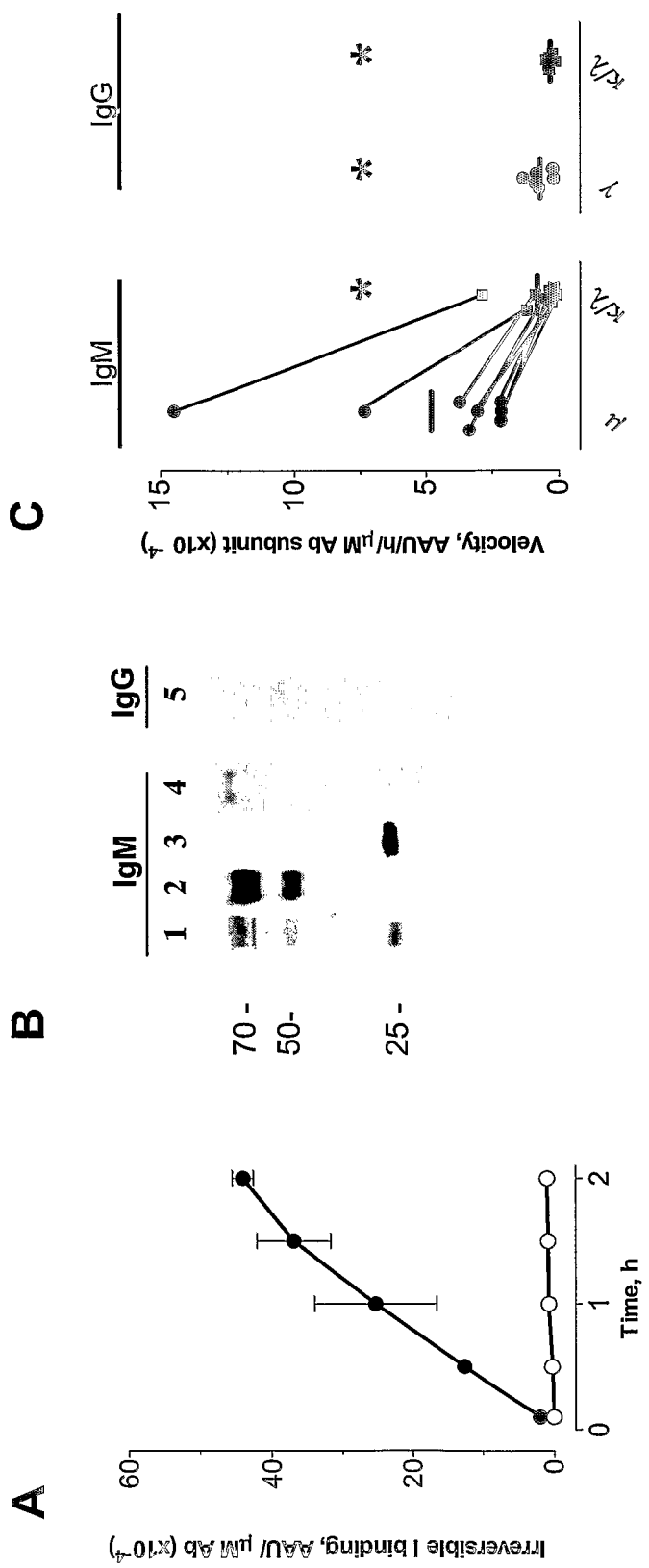

FIG. 27. Irreversible hapten CRA I binding to IgM and IgG Abs. A, Progress curves for polyclonal murine Ab-CRA adduct formation. AAU, Arbitrary area units. Reaction conditions: IgM 0.2 µM or IgG 1 µM (equivalent combining concentration); hapten CRA I 0.1 mM. Values are sums of intensities of the H chain-CRA and L chain-CRA bands for IgM (●) and IgG (○; means of closely agreeing duplicates). B, Examples of reducing SDS-gel lanes showing CRA-Ab subunit adducts at 2 hours. Lanes 4 and 5: Streptavidin-peroxidase-stained blots showing adducts of IgM subunits and IgG subunits, respectively. IgM subunits stained with compasses blue, anti-µ chain Ab and anti-κ/λ chain are shown in lanes 1, 2 and 3, respectively. C, Comparative initial velocities of hapten CRA I adduct formation at the subunits of IgM and IgG. Each point represents a different Ab. For comparison, data points corresponding to the µ and κ/λ chains of individual IgM Abs are connected. Abs studied: polyclonal human IgM, polyclonal mouse IgM, 5 monoclonal murine IgM Abs (clones 8702, 8704, 9008, 9010, 9020), monoclonal human IgM Yvo, polyclonal human IgG, polyclonal mouse IgG and 4 monoclonal IgG Abs (clones c23.4, c39.1, HP6045, HP6054). *P<0.05 versus µ chain group in each case (Student's t-test, 2 tailed).

Figure 28:
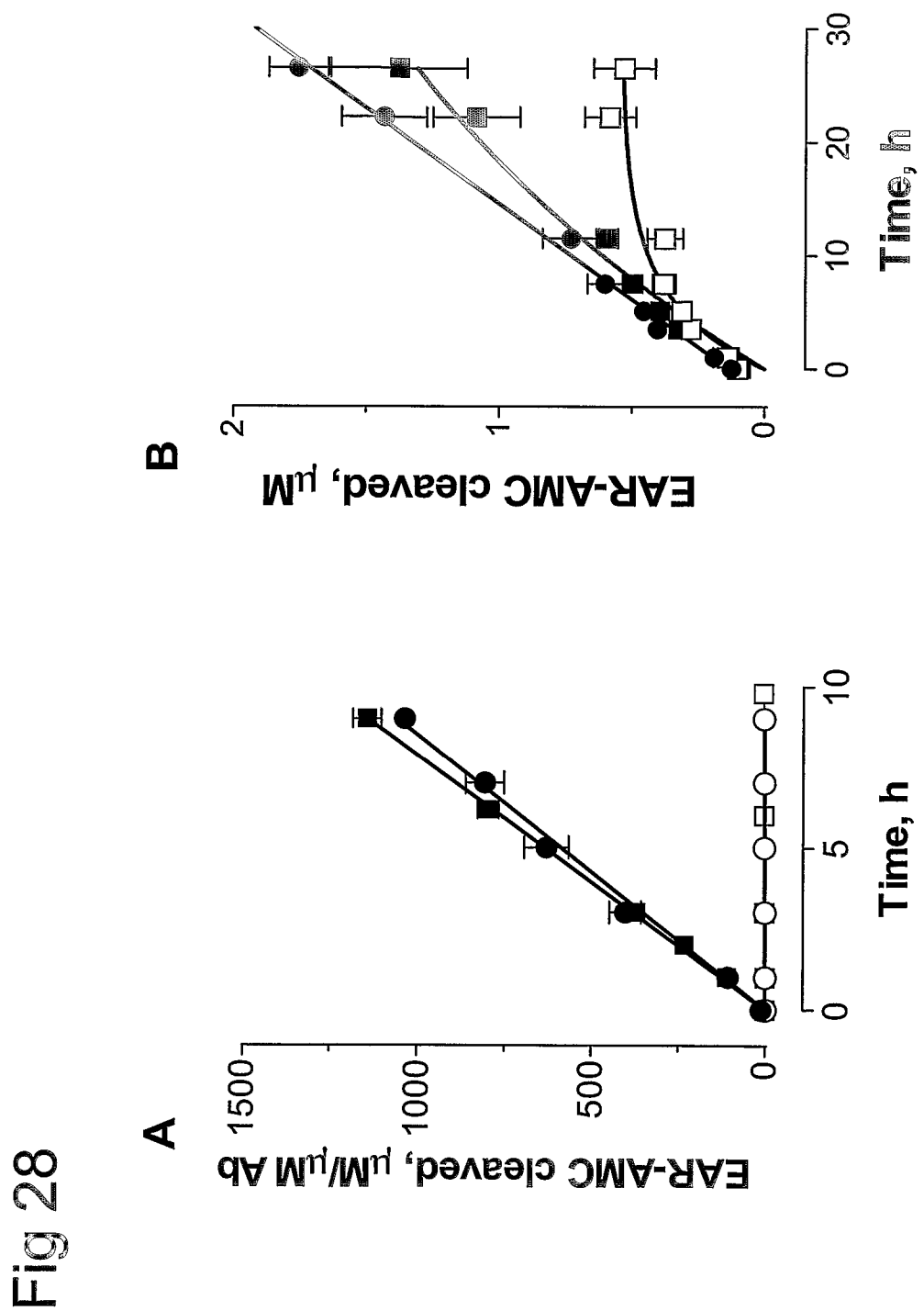

FIG. 28. Proteolytic activities of IgM and IgG Abs. A, Cleavage of Glu-Ala-Arg-AMC (400 µM) by polyclonal murine IgM (●), human IgM (■), polyclonal murine IgG (○) and polyclonal human IgG (□). IgM, 5 nM; IgG, 160 nM B, Inhibition of polyclonal murine IgM (5 nM) catalyzed Glu-Ala-Arg-AVC (400 µM) cleavage by hapten CRA I (■, 30 µM; □, 100 µM). ■, progress curve without inhibitor. Values are means of triplicates±s.d.

Figure 29:
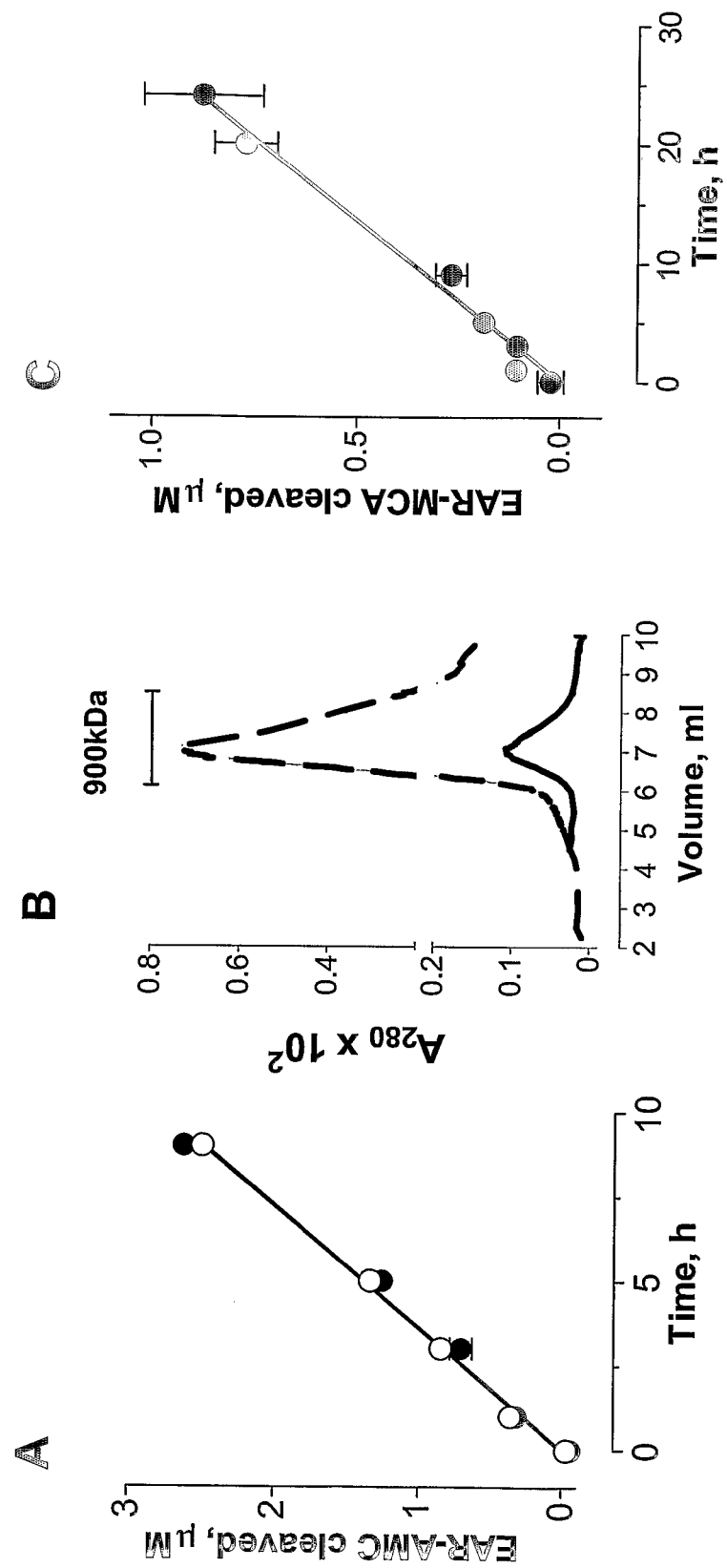

FIG. 29. IgM purity. A, Purification of polyclonal murine IgM to constant specific activity. ○, IgM purified by anti-g affinity chromatography; ■, affinity purified IgM subjected to further fractionation by FPLC gel filtration. IgM, 5 nM; Glu-Ala-Arg-AMC, 200 µM. B, Denaturing gel filtration profiles (Superose 12 column) of polyclonal murine IgM conducted in 6 M guanidine hydrochloride. The IgM fractions under the bar from the first cycle of denaturing chromatography (----) were pooled and subjected to 2 additional cycles of denaturing gel filtration. IgM recovered from the third chromatography cycle (—) was analyzed for catalytic activity in Panel C. C, Progress curve for cleavage of Glu-Ala-Arg-AMC (200 µM) by IgM (2.5 nM) purified by 3 cycles of denaturing gel filtration in Panel B.

Figure 30:
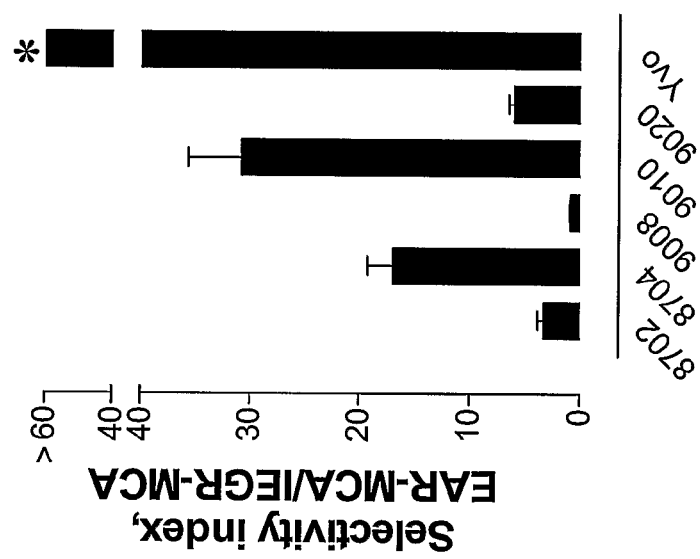

FIG. 30. Divergent substrate selectivities of monoclonal IgM Abs. Data are expressed $V_{i,\ Glu-Ala-Arg-AMC}/V_{i,\ Ile-Glu-Gly-Arg-AMC}$, where $V_i$ represents initial velocity computed from progress curves. Substrates, 200 µM. Designations 8702, 8704, 9008, 9010, 9020 and Yvo indicate the individual IgM Abs (5 nM). *, IgM Yvo did not cleave Ile-Glu-Gly-Arg-AMC detectably (<0.0125 µM AMC).

Figure 31:
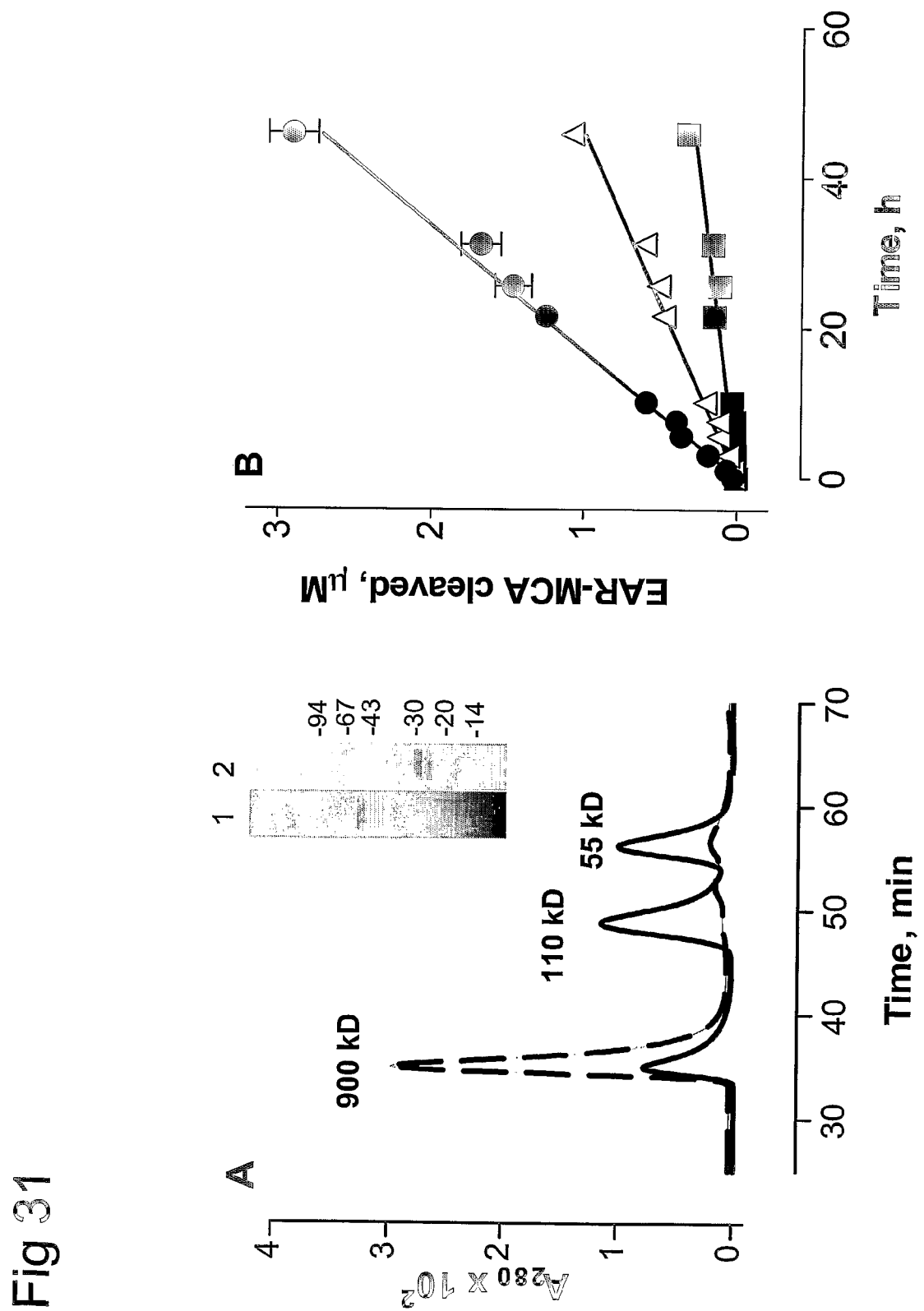

FIG. 31. Cleavage of Glu-Ala-Arg-AMC by IgM Fab fragments. A, Gel filtration profile (Superose 12) of IgM Yvo without (---) and with (—) digestion with immobilized pepsin. Inset, Silver stained nonreducing (lane 1) and reducing (lane 2) SDS gels of the 55 kD Fab fragments. The higher and lower Mr fragments in the reducing lane correspond to the Fab heavy chain fragment and light chain component. B, Progress curves of Glu-Ala-Arg-AMC (400 µM) cleavage at 1.2 µM (○), 0.4 µM (Δ) and 0.12 µM (□) Fab.

EXAMPLE 5

Figure 32:
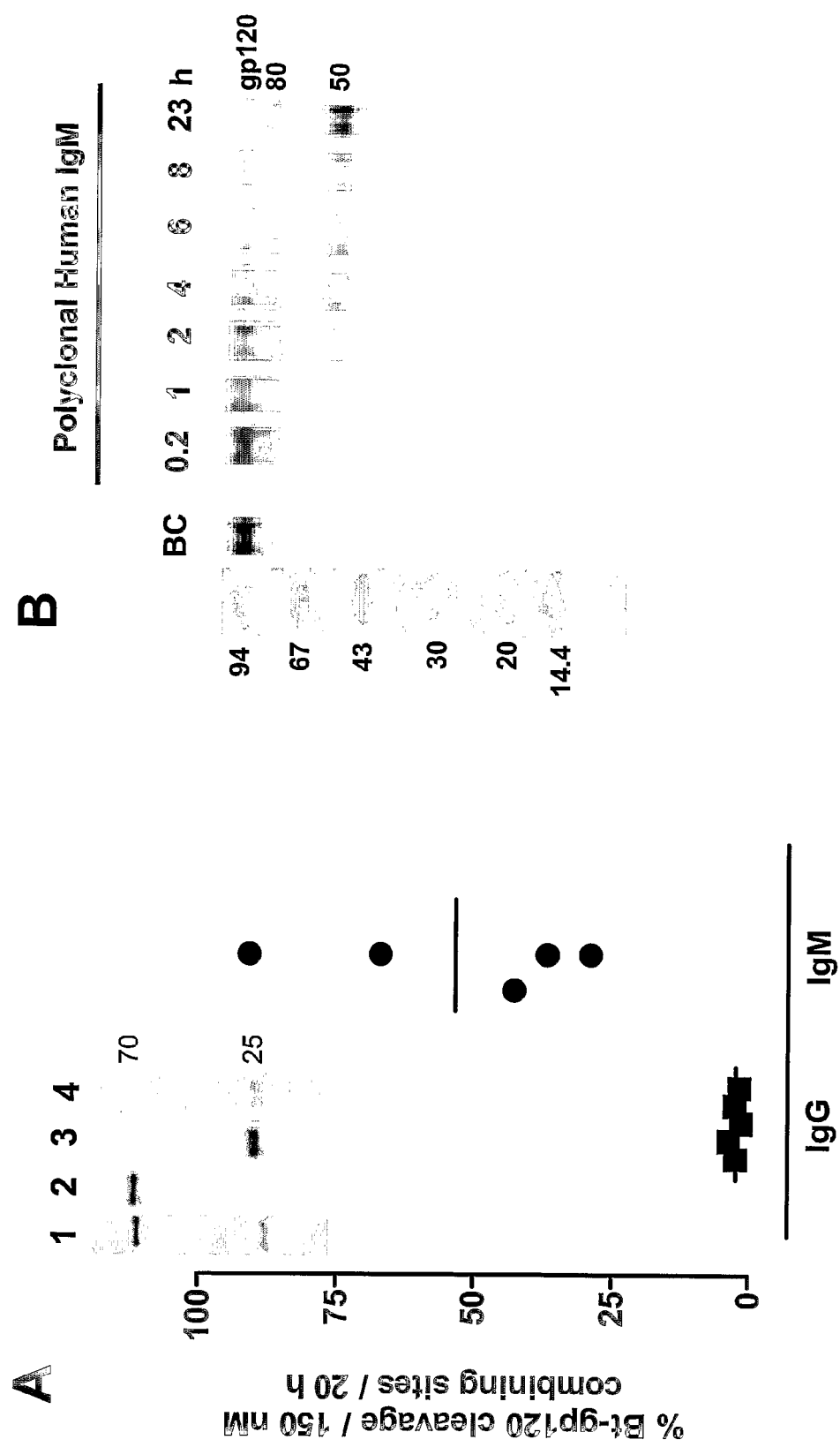

FIG. 32. Cleavage of biotinylated gp120 (Bt-gp120) by polyclonal human IgM and IgG preparations. A, Scatter plot of gp120 cleaving activity of IgM and IgG Ab fractions from 5 healthy humans. Ab combining site concentration 150 nM (decavalent IgM, 15 nM; bivalent IgG, 75 nM). Reaction conditions: 20 hours, 37° C., 100 nM Bt-gp120. Solid lines are means [IgM, 53.3±25.4%; cleavage is below detection limit (<5%)]. Inset, Typical reducing SDS-electrophoresis (4-20% gels) results showing human serum IgM purified by affinity chromatography on immobilized anti-IgM Ab and stained with compasses blue (lane 1) and peroxidase conjugated Abs to human µ chains (lane 2), κ chains (lane 3) and λ chains (lane 4). B, Streptavidin-peroxidase stained reducing SDS-gel lanes showing time-dependent cleavage of Bt-gp120 by pooled polyclonal human IgM. BC, Bt-gp120 incubated for 23 h in the absence of Abs. IgM, 50 nM; Bt-gp120, 100 nM.

Figure 33:
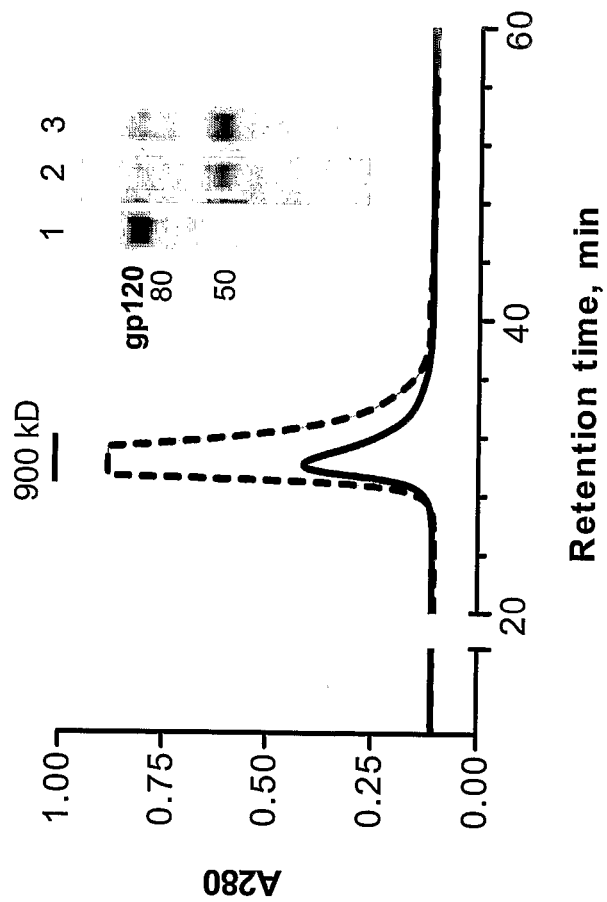

FIG. 33. gp120 cleavage by IgM subjected to denaturing gel filtration. Pooled human serum IgM purified by affinity chromatography on immobilized anti-µ Abs was subjected to cycles of denaturing gel filtration (cycle 1--- cycle 2—, Superose 12 column) in 6 M guanidine hydrochloride. Inset, Streptavidin peroxidase stained SDS-gel lanes showing cleavage of Bt-gp120 (0.1 µM) by IgM (50 nM) obtained by denaturing gel filtration (lane 3) and control IgM analyzed without denaturation (lane 3). Reaction time, 16 h. Lane 1, Bt-gp120 incubated for 16 h with diluent instead of IgM.

Figure 34:
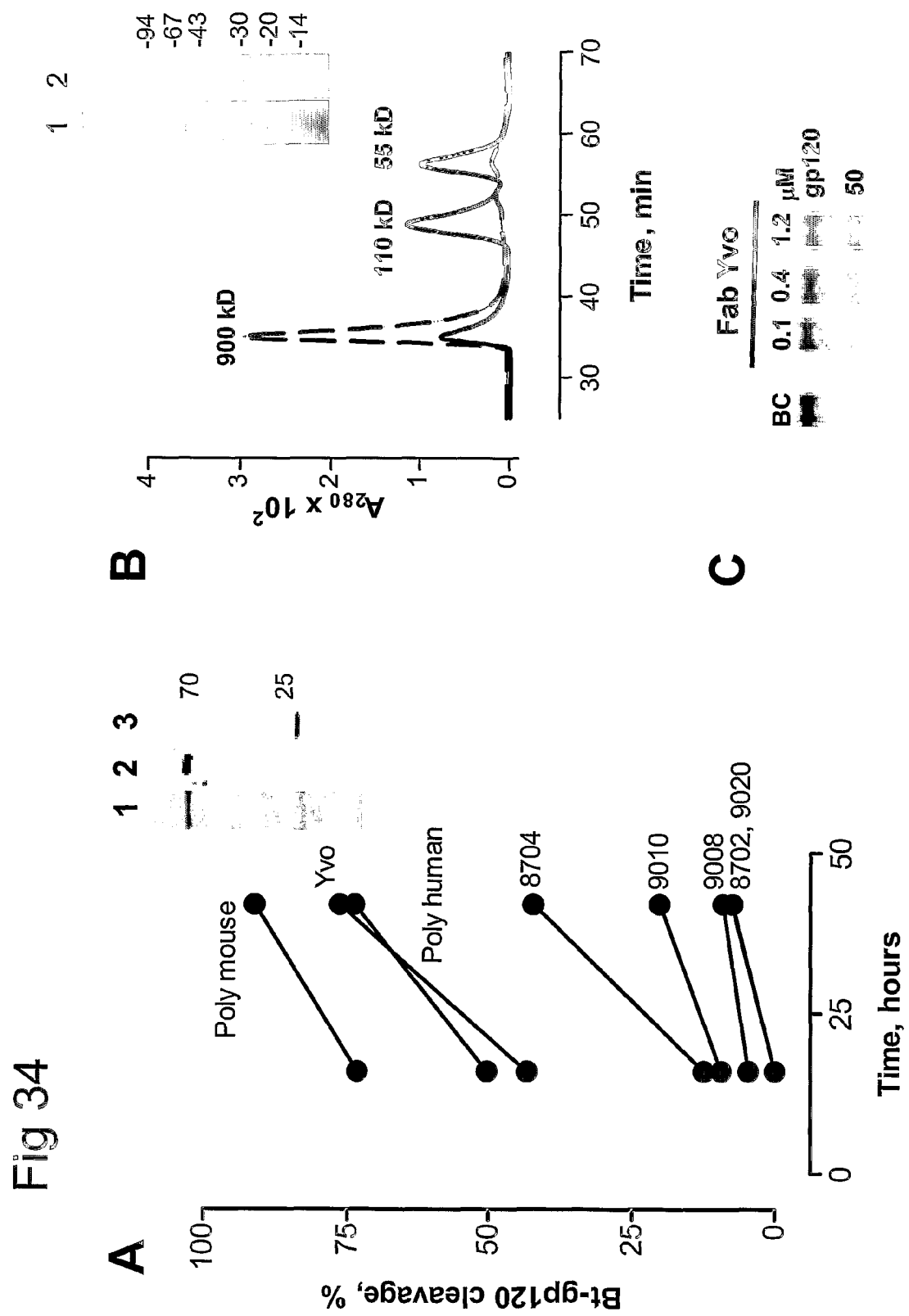

FIG. 34. gp120 cleavage by monoclonal IgA antibodies. A, Divergent catalytic activities of human monoclonal IgM; murine IgM clones 8702, 8704, 9008, 9010 and 9020 and polyclonal IgM purified from pooled human and mouse sera. Biotinylated gp120 0.1 µM; IgM 17 nM. Data obtained by densitometry of streptavidin-peroxidase stained reducing SDS-gels. Inset, SDS-gel showing IgM Yvo stained with compasses blue (lane 1), anti-human µ chain Ab (lane 2) and anti-κ chain Ab (lane 3). B, Gel filtration profile (Superose 12) of IgM Yvo without (---) and with (—) digestion with immobilized pepsin. Inset, Silver stained nonreducing (lane 1) and reducing (lane 2) SDS gels of the 55 kD Fab fragments. The higher and lower Mr fragments in the reducing gel correspond to the Fab heavy chain fragment and light chain component. C, streptavidin-peroxidase stained SDS-gels showing cleavage of biotinylated gp120 (0.1 µM) incubated with increasing concentrations of Fab Yvo for 48 h.

Figure 35:
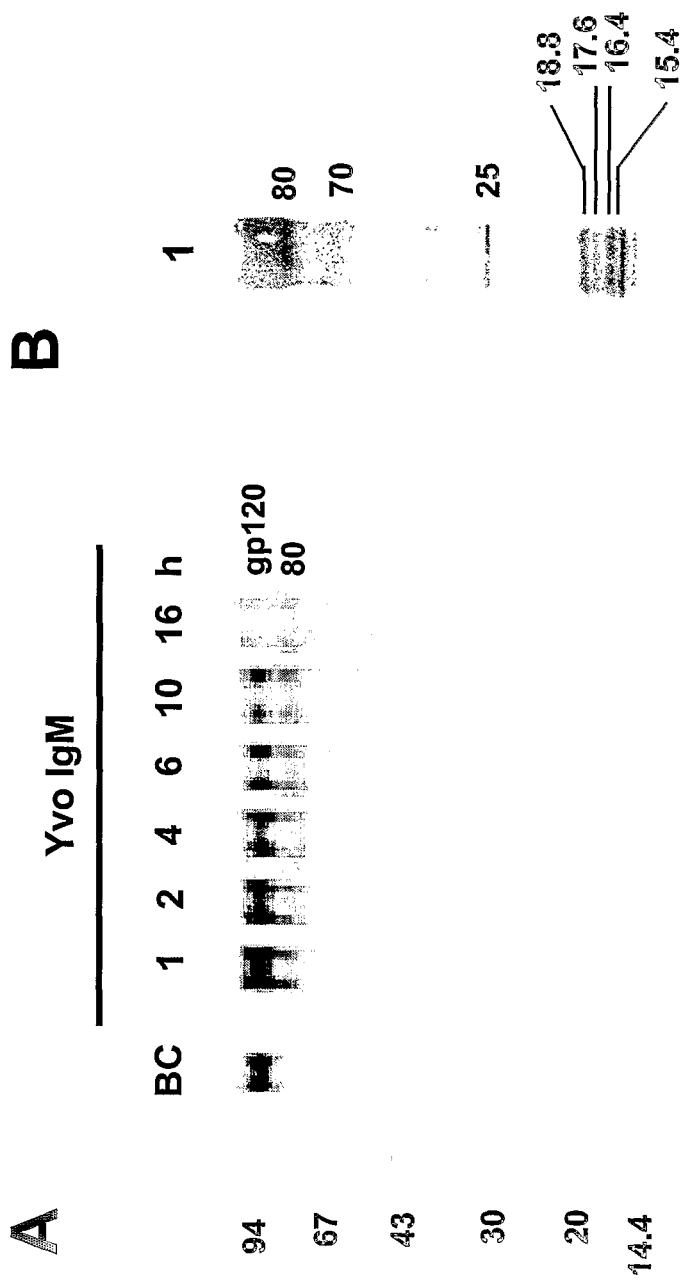

FIG. 35. gp120 cleavage by monoclonal IgM Yvo. A, Time course of biotinylated gp120 (0.1 µM) cleavage by IgM Yvo (50 nM). Shown are streptavidin peroxidase stained reducing SDS-gel electrophoresis lanes. BC, Control lane showing Bt-gp120 incubated for 16 h without the IgM. The major biotinylated product is the 80 kD band. B, Compasses blue stained SDS-gel lane showing the reaction mixture of gp120 (8.5 µM) with IgM yvo (50 nM) (lane 1), IgM Yvo alone (lane 2) and gp120 alone (lane 3) incubated for 46 h. The 70 and 25 kD bands correspond to IgM heavy and light chains, respectively. Blots regions corresponding to 15.4-16.4 kD, 17.6 kD, 18 kD and 80 kD were subjected to N terminal sequencing in Table 8.

Figure 36:
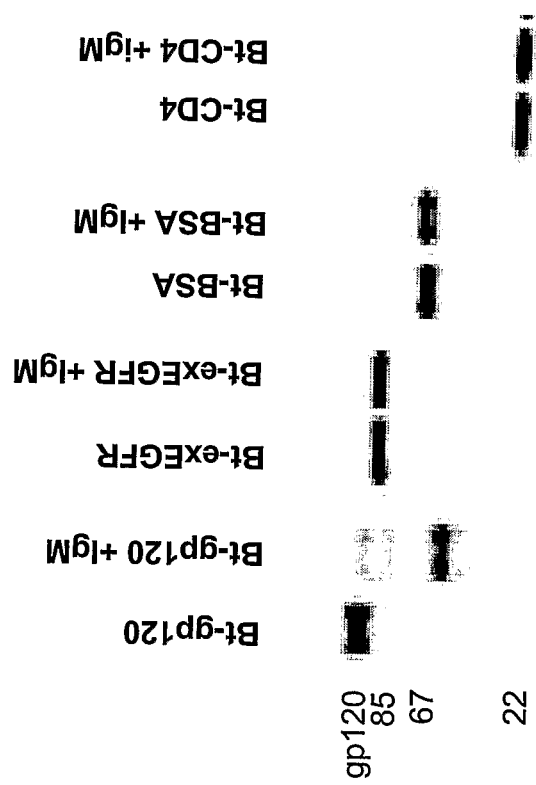

FIG. 36. Selectivity of gp120 cleavage. Streptavidin peroxidase stained reducing SDS-polyacrylamide gels showing Bt-gp120, Bt-sEGFR, Bt-BSA and Bt-sCD4 incubated for 22 h in diluent or polyclonal human IgM (50 nM). Bt-protein, 0.1 µM.

Figure 37:
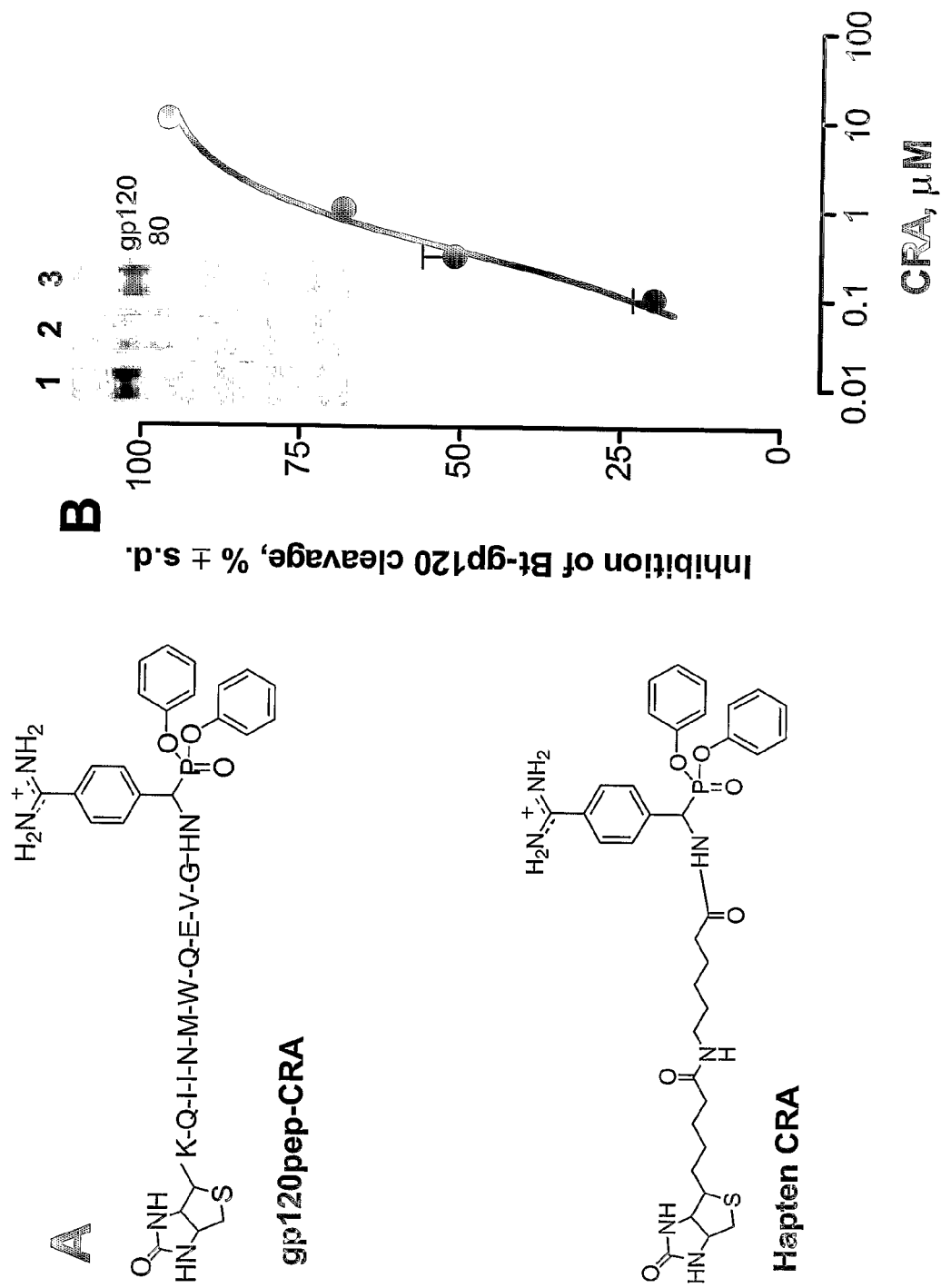

FIG. 37. gp120(421-431)-CRA inhibition of Yvo IgM gp120ase activity. A, Phosphonate diester analog of gp120 residues 421-433 (gp120pep-CRA) and the haptenic phosphonate diester devoid of the gp120 peptide sequence (hapten CRA). B, Inhibition of IgM Yvo (50 nM) catalyzed Bt-gp120 (0.1 µM) by gp120pep-CRA. Incubation for 15 hours. Inset, Streptavidin peroxidase stained SDS-gels showing Bt-gp120 incubated with IgM Yvo in the absence (lane 2) and presence of gp20pep-CRA (10 µM, lane 2). Lane 1, Control Bt-gp120 incubated in diluent.

Figure 38:
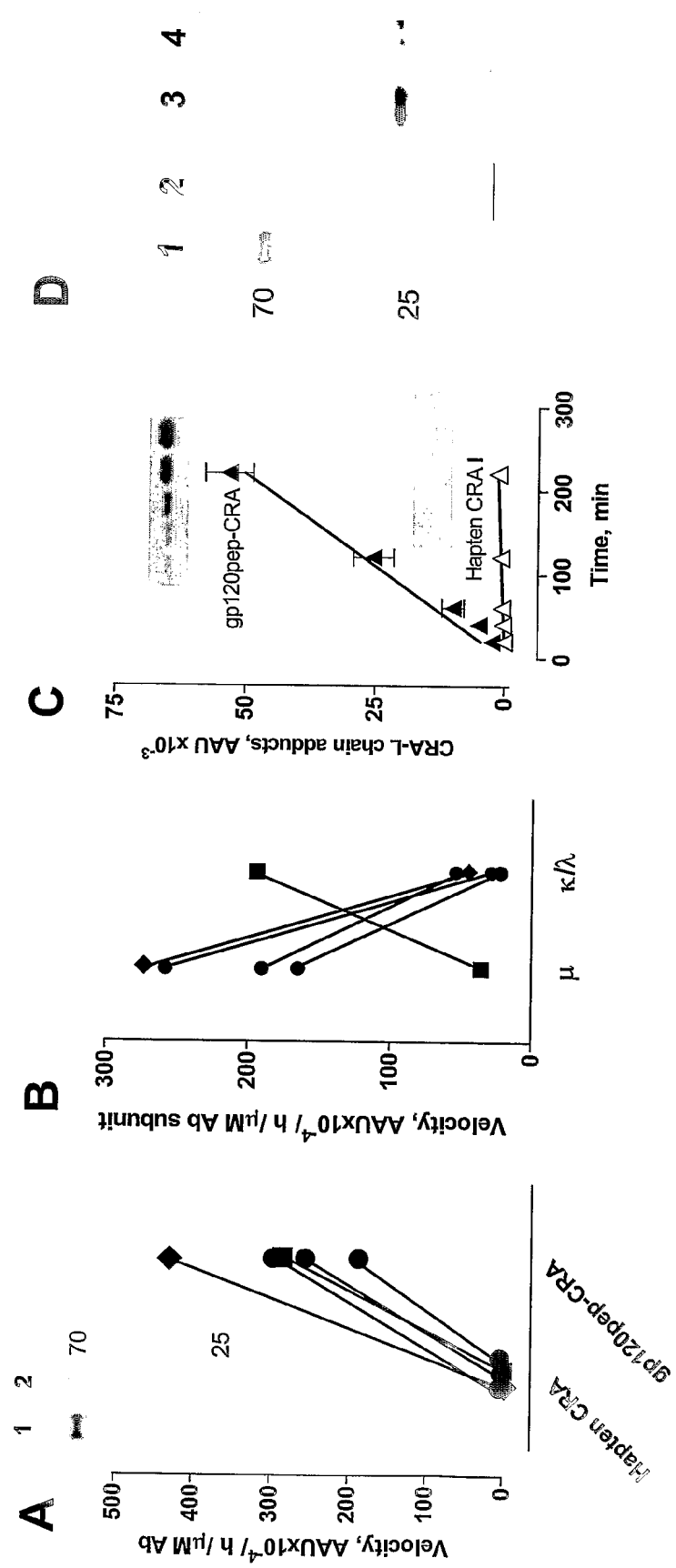

FIG. 38. Irreversible gp120(421-31)-CRA binding by IgM. A, Comparative initial velocities for formation of hapten CRA adducts and gp120pep-CRA adducts by monoclonal IgM Yvo, 8704 and 9020 (•), IgM from pooled human serum (♦) and IgM from pooled mouse serum (■). Initial velocities were computed from progress curves for irreversible CR binding by the Abs measured in duplicate, and represent the sum is of intensities of the H chain-CRA and L chain-CRA bands. AAU, Arbitrary area units. Reaction conditions: IgM 150 nM; hapten CRA or gp120pep-CRA 10 µM. Inset, Streptavidin peroxidase stained reducing SDS-gels showing adducts of gp120pep-CRA (lane 1) and hapten CRA (lane 2) formed by polyclonal mouse IgM. B, Comparative initial velocities for formation gp120pep-CRA adducts by µ chains and κ/λ chains of monoclonal IgM Yvo, 8704 and 9020 (•), IgM from pooled human serum (♦) and IgM from pooled mouse serum (■). Reactions from panel A. C, Example of progress curve data. Shown are accumulation of gp120pep-CRA adducts and hapten CRA adducts with the L chain of IgM Yvo. Reactions as in panel A. Inset, Cut-outs of the L chain adduct bands at the indicated time points from streptavidin-peroxidase stained SDS-gels. D, Streptavidin peroxidase stained reducing SDS-gels showing adducts of gp120pep-CRA formed by polyclonal human IgM in the absence (lane 1) and presence of synthetic gp20(421-436) (500 µM, lane 2) and by IgM Yvo in the absence (lane 3) and presence of synthetic gp20(421-436) (500 µM, lane 4). Reaction conditions as in Panel A. Incubation for 4.5 hours.

EXAMPLE 6

Figure 39:
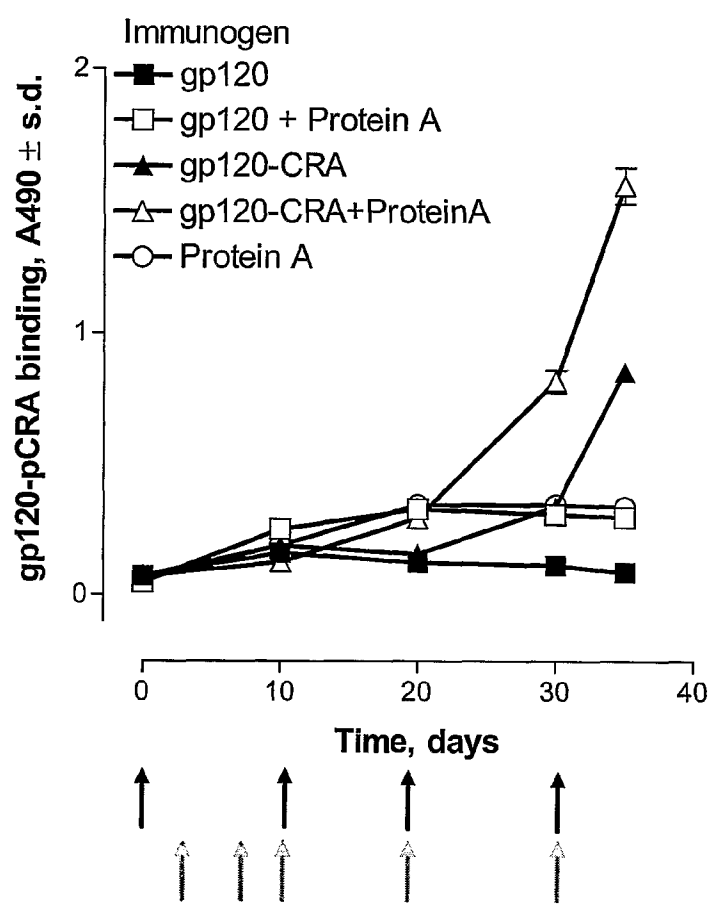

FIG. 39: ELISA showing binding of gp120-CRA by IgM Abs in sera from BALB/c mice immunized with the indicated antigens. Black arrows indicate administration of the antigen (10 µg protein). Grey arrows indicate administration of protein A (1000 µg). Sera diluted 1:100. The binding was visualized using anti-peroxidase conjugated anti-mouse IgM Ab.

Figure 40:
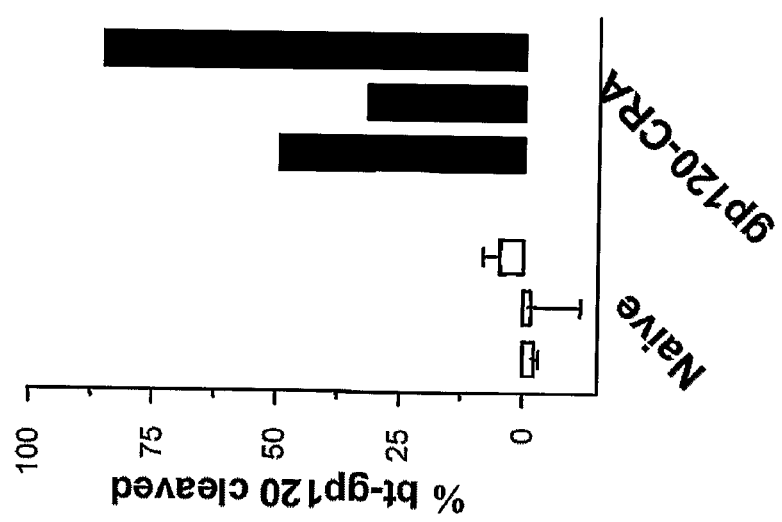

FIG. 40: Increased IgM catalyzed gp120 cleavage by covalent immunization. Shown are the values of biotinylated gp120 cleavage by three monoclonal IgM antibodies obtained from a mouse immunized with gp120-CRA (closed bars; number of IgM secreting hybridomas screened, 96). Under these conditions, cleavage by IgM from an unimmunized mice was undetectable (open bars show 3 of 137 IgM clones screened). IgM purified from culture supernatants by chromatography on immobilized anti µ-chain Ab. IgM, ~5 nM; Bt-gp120, 100 nM; 15 h. Cleavage determined by SDS-gel electrophoresis.

Figure 41:
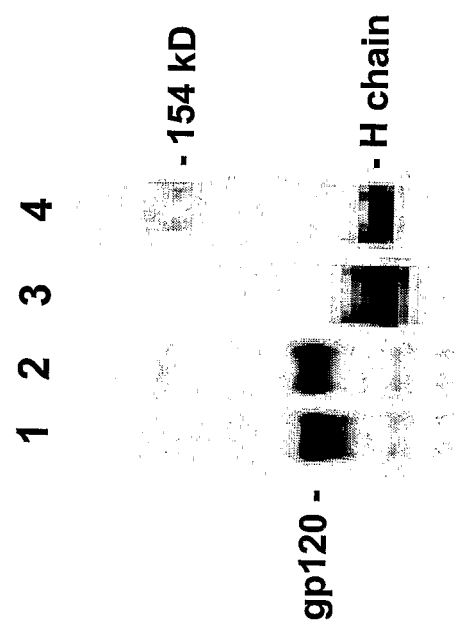

FIG. 41. Irreversible gp120 binding by anti-gp120-CRA IgG antibodies. Shown are streptavidin-peroxidase stained blots of SDS electrophoresis gels of biotinylated gp120 incubated with IgG clone F223-3 (lane 2) and a control IgG clone (lane 1, clone F223-1). Lanes 2 and 4 show the anti-IgG stained gels of the reaction mixtures with clone F223-3 and F-223-1, respectively. The 154 kD band represents the irreversible gp120-IgG subunit complex. IgG, 0.1 µM; biotinylated gp120 0.1 µM, reaction time 15 h.

Figure 42:
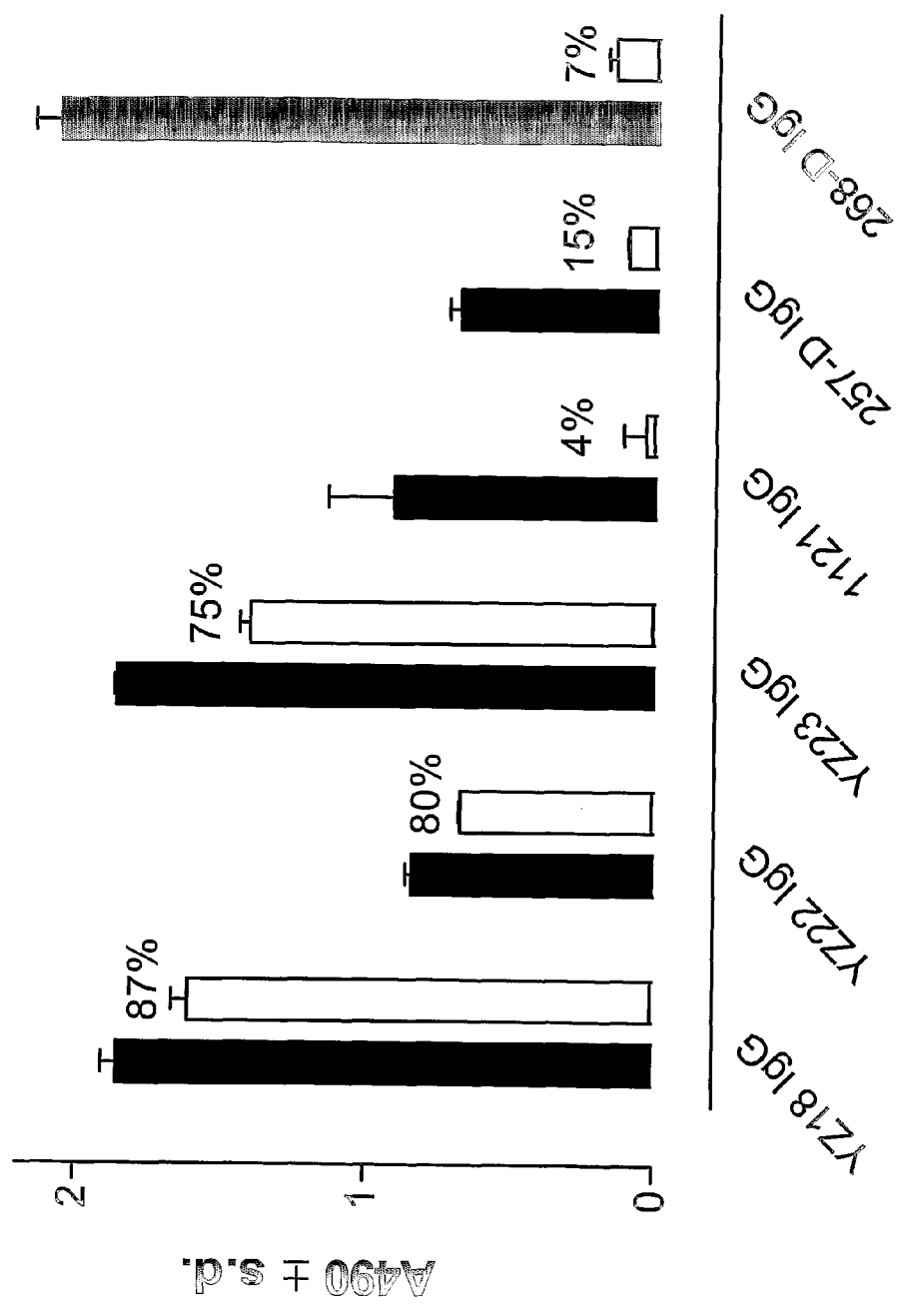

FIG. 42. Irreversible gp120 binding by MAbs. ELISA showing SDS-resistant gp120 binding by purified MAbs raised by immunization with gp120-CRA (Clones YZ18, YZ22_ and YZ23). Control anti-gp120 MAbs studied were murine IgG #1121 (Immunodiagnostics Inc.) and human MAbs 257-D and 268-D from NIH AIDS Reagent Repository (all directed against the V3 loop of gp120). Black bars: ELISA plates washed with PBS, pH7.4, following anti-gp120 binding to immobilized gp120. White bars: Plates washed with 2% SDS in PBS following anti-gp120 binding to inunobilized gp120. % residual gp120 binding after treatment with SDS is indicated above SDS-resistant bars. 40 ng gp120/well; IgG, 0.5 µM.

Figure 43:
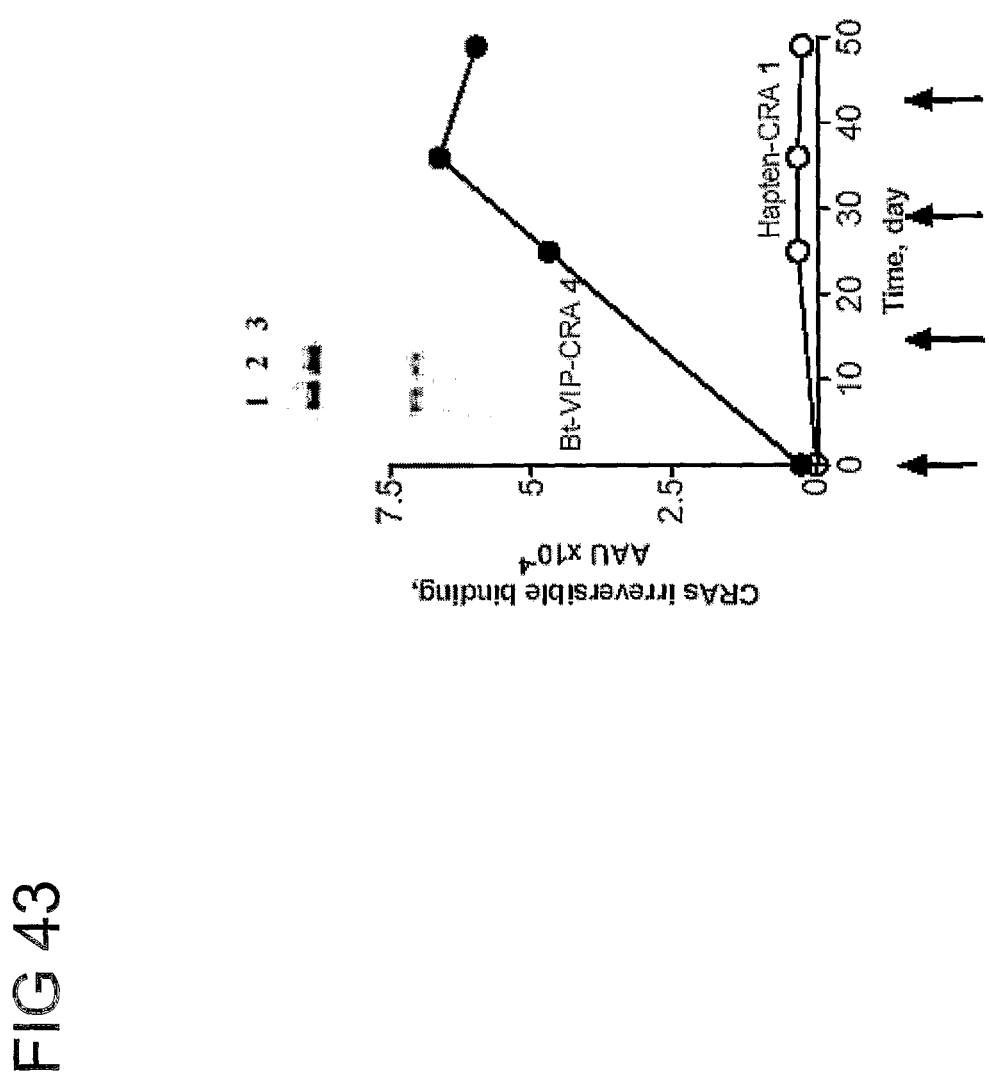

FIG. 43: Specific murine nucleophilic antibody response to VIP-CRA. Data represent the intensities of covalent IgG adducts of VIP-CRA 4 identified by SDS-electrophoresis (sum of heavy and light chain adducts in arbitrary area units (AAU) from a representative mouse). Arrows indicate intraperitoneal immunization of the mice (BALB/c) N=5) with the VIP-CRA (84 µg) in RIBI adjuvant. IgG purified by protein G-Sepharose chromatography (100 nM) was incubated with Bt-VIP-CRA 4 (●) or hapten-CRA 1 (○) (10 µM, 4 h).

EXAMPLE 7

Figure 44:
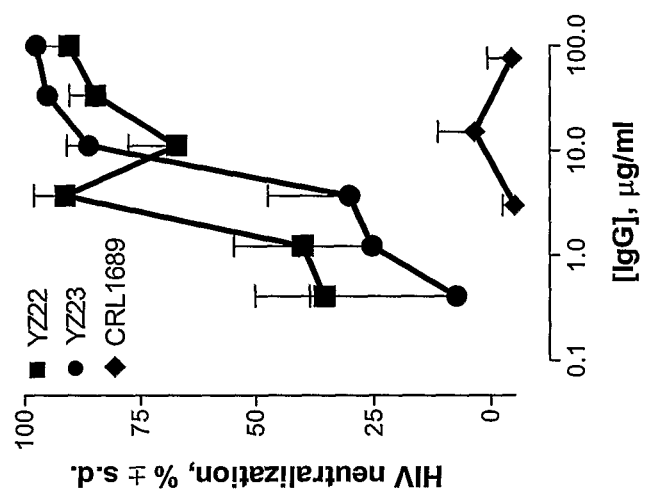

FIG. 44. Concentration-dependent HIV-1 neutralization by two monoclonal IgG antibodies raised by immunization with gp120-CRA. PBMC infected with primary HIV-1 isolate ZA009 (clade C, R5-dependent). Equivalently purified irrelevant control Ab CRL1689 was studied in parallel. Neutralization determined by measuring p24 levels (see text).

EXAMPLE 8

Figure 45:
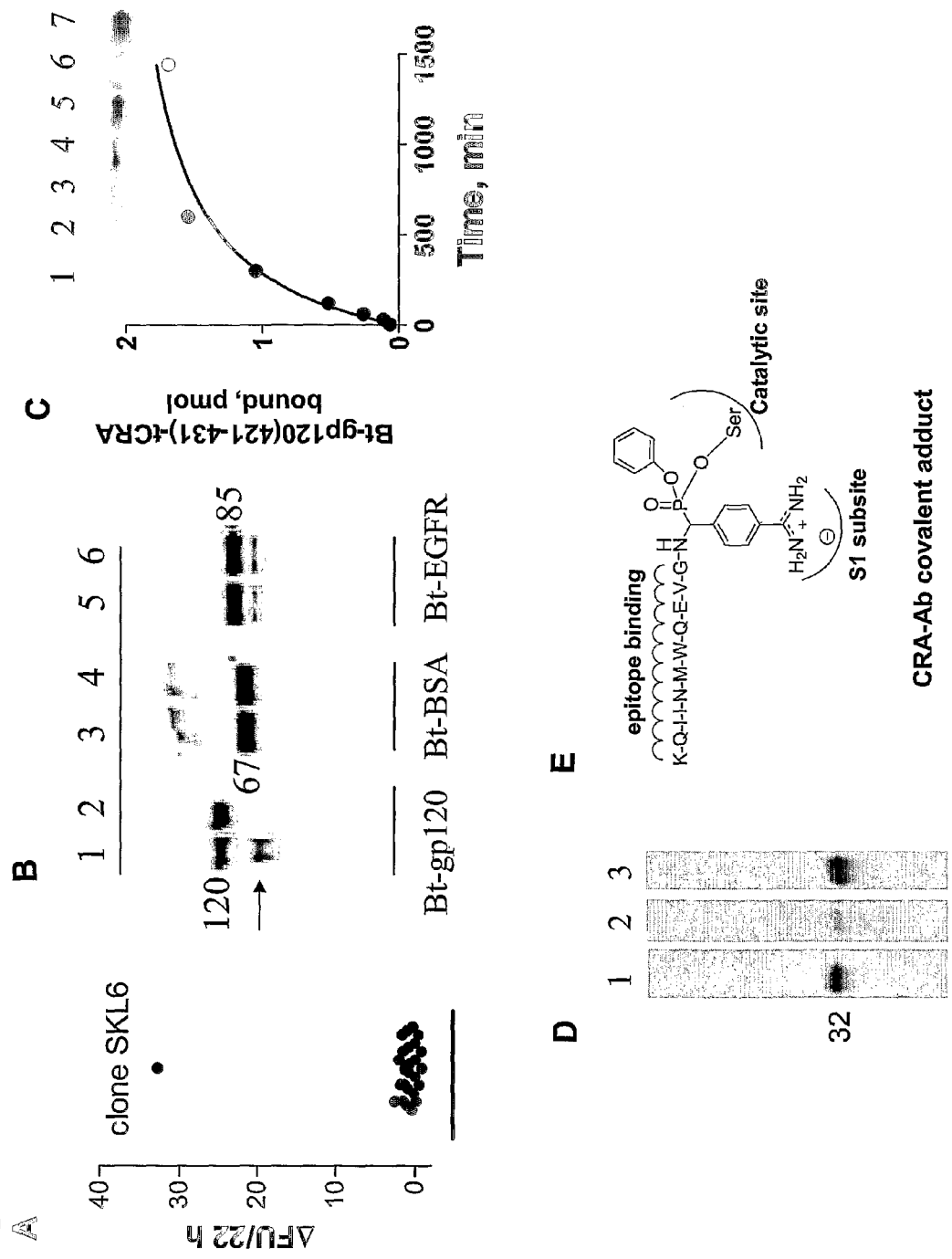

FIG. 45. Characteristics of lupus L chain clone SKL6 isolated by phage binding to gp120(421-431)-CRA. A, Cleavage of synthetic gp120(421-432)-methylcoumarinamide (MCA) by L chains selected using gp120(421-431)-CRA. Cleavage reaction monitored by fluorimetry (release of the C terminal MCA group). L chains clones purified by metal affinity chromatography analyzed, N=28. Substrate, 5 µM. B, Streptavidin-peroxidase SDS-gels showing cleavage (arrow) of biotinylated gp120 (Bt-gp120) by L chain SKL6 and lack of cleavage of unrelated proteins (biotinylated BSA and extracellular domain of EGFR). Lanes 1, 3 and 5 show SKL6-gp120 reaction mixtures; lanes 2, 4 and 6 show control non-catalytic L chain-gp120 reaction mixtures. Substrate proteins, 0.3 µM (each protein biotinylated at Lys residues). 0.3 mol biotin/mol gp120. L chains, 0.03 µM, 24 hours incubation. C: Covalent L chain SK16 binding of Bt-gp120(421-431)-CRA as a function of time. L chain 1 µM, CRA 10 µM. Inset, streptavidin-peroxidase stained blots of SDS-gels corresponding to the time points in the graph. D, Active site protection by gp120(421-436). Shown are streptavidin-peroxidase stained SDS gels of covalent Bt-gp120(421-436) (10 µM) adducts formed with the L chain (1 µM) in the absence (lane 1) and presence of gp120(421-436) (10 µM; lane 2) and an irrelevant peptide [EGFR(351-364), 10 µM; lane 3]. E, Model of peptidyl CRA interactions with the L chain active site.

Figure 46:
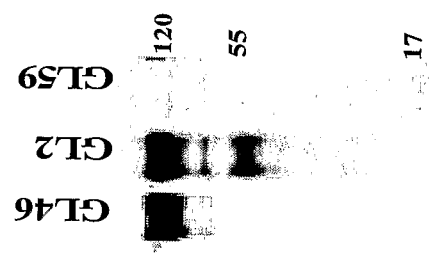

FIG. 46. Cleavage of Bt-gp120(0.1 µM) by purified lupus single chain Fv clones GL2 and GL59. Fv, 55 nM, 24 h incubation. Fv GL46 analyzed in parallel is devoid of cleavage activity (indistinguishable from Bt-gp120 treated with diluent).

EXAMPLE 10

Figure 47:
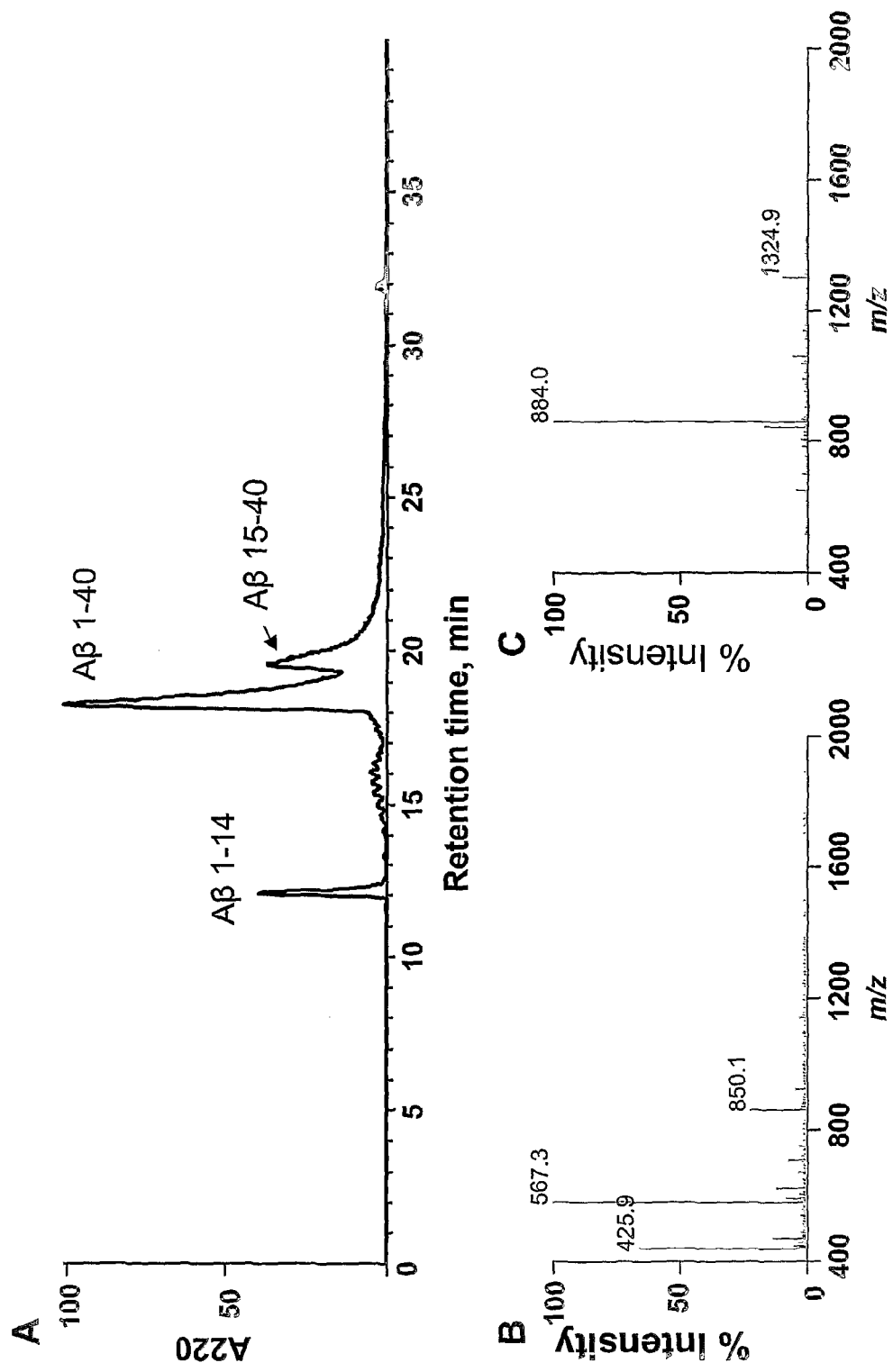

FIG. 47. Aβ1-40 cleavage by IgL hk14 under conditions of reduced aggregation (100 µM). Aβ1-40 was incubated with 2.5 µM IgL for 24 h. An aliquot was analyzed by HPLC with on line ESI mass spectroscopy. Conditions: C18 column, solvent: A=0.2% formic acid in water, B=0.2% formic acid in acetonitrile. Gradient: A:B 97:3, 5 min; 97:3 to 40:60, 20 min; 40:60 to 0:100, 1 min. ESI mass spectroscopy, positive mode, 0-2000 amu range. A is the A220 trace from the HPLC column. Peak identification in A was by mass spectra shown in B (Aβ1-14) and C (Aβ15-40). Observed ion series in B (m/z 425.9, 567.3, 850.1) correspond to exact mass values of multiply charged Aβ1-14 species [(M+4H)4+, (M+3H)3+, (M+2H)2+]. Observed ion series in C (m/z 884.0, 1324.9) correspond to the exact mass values of Aβ15-40 (M+3H)3+ and 1324.9 (M+2H)2+ ions.

Figure 48:
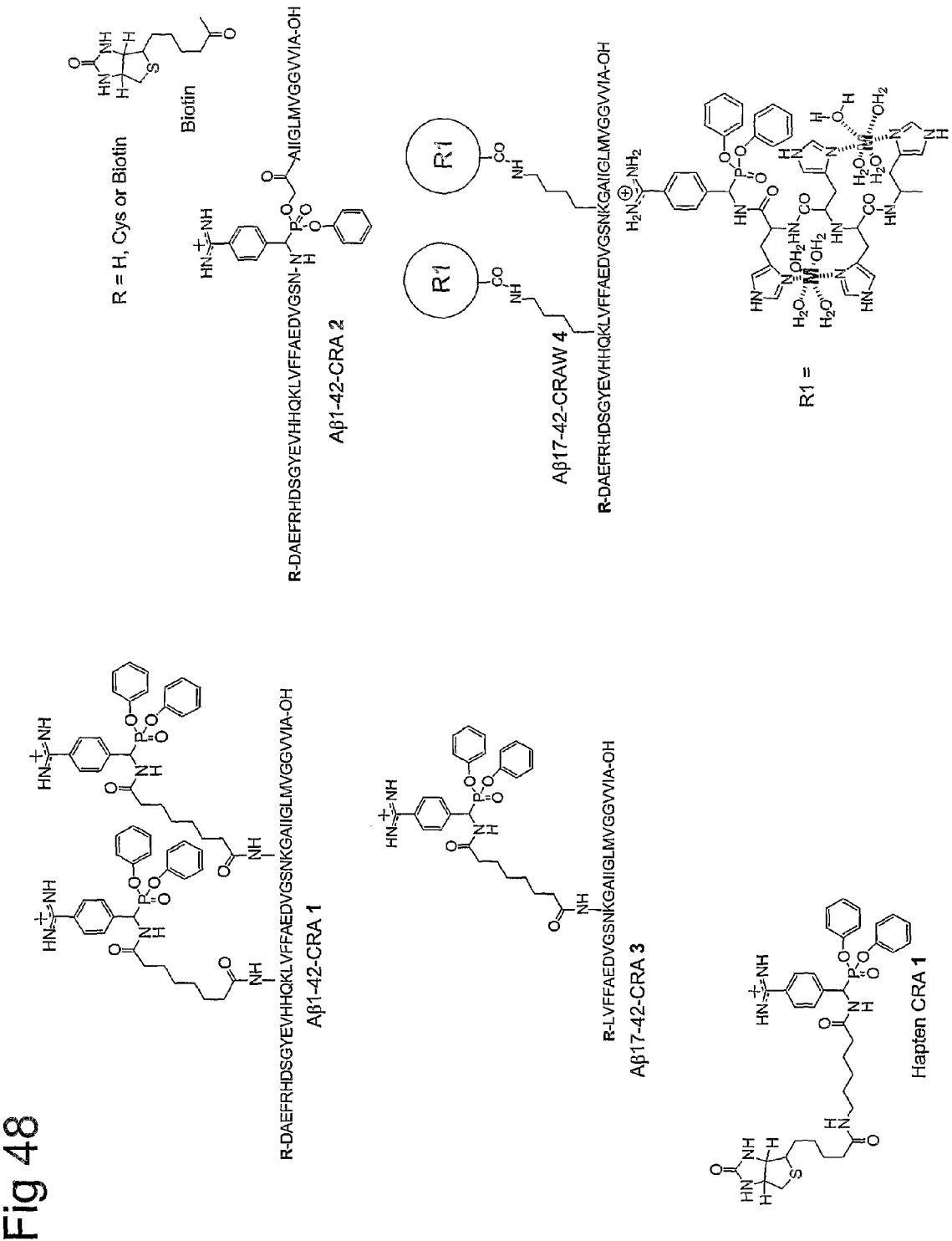

FIG. 48. Aβ-CRA and Aβ-CRAW structures. For conjugation to carrier proteins, a Cys is placed at the N terminus. Covalent adduct formation can be monitored using CRAs with biotin at the N terminus. In CRAW 4, the His$_4$ sequence in R1 permits binding of metals (M) such as $Zn^{+2}$ and $Cu^{+2}$, which can coordinate water molecules forming a hexakis complex. The hapten CRA allows detection of covalent reactivity independent of Aβ noncovalent recognition.

EXAMPLE 11

FIG. 49. VIP-CRAs and pyridyl VIP-CRA. R, H or biotin.

DETAILED DESCRIPTION OF THE INVENTION

1. Serine Protease-Like Abs.

Figure 1:
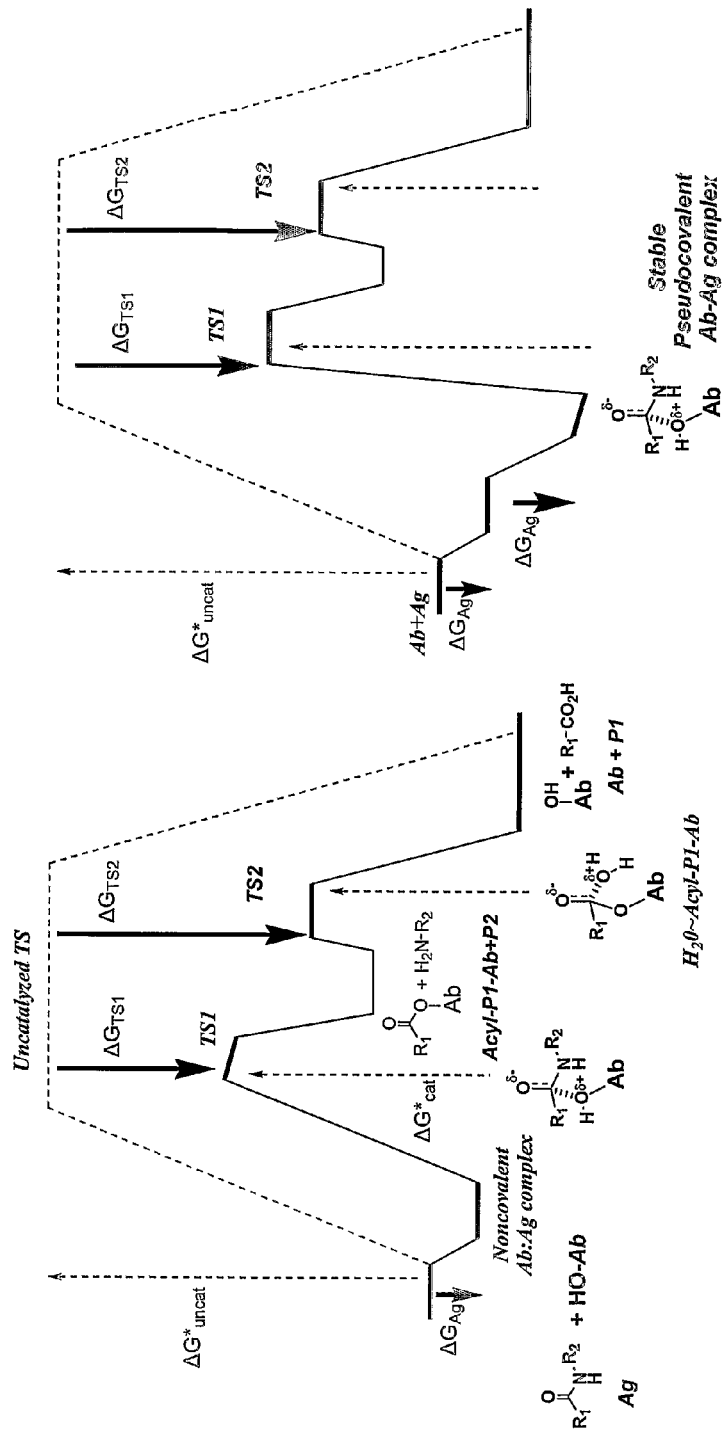
FIG. 1: Reaction mechanism for serine protease Abs. Left, Abs stabilize the antigen ground state noncovalently ($\Delta G_{Ag}$). Nucleophiles such as an activated Ser residue attacks the peptide bond, forming an unstable resonant transition state (TS1). Completion of this reaction forms the covalent acyl-Ab intermediate, with release of the C terminal peptide fragment. In the second reaction, a water molecule hydrolyzes the covalent intermediate via a second tetrahedral transition state (TS2). Right, The reaction proceeds as above, except that the resonant antigen-Ab complex containing partial covalent bonds (TS1 above) is more stable than the ground state of the antigen-Ab complex. $\Delta G^\dagger_{uncat}$ and $\Delta G^\dagger_{cat}$ correspond to activation energies for the uncatalyzed and catalyzed reactions, respectively. $K_m$ is a function of the extent of ground state stabilization ($\Delta G_s$). $k_{cat}/K_m$ is a function of extent of transition state stabilization relative to the catalyst-substrate ground state complex.

Nucleophilic reactivity is the basis for Ab proteolysis (FIG. 1). The nucleophilicity derives from activation of certain amino acid side chains. In serine proteases, precise spatial positioning of the Ser-His-Asp triad allows formation of a hydrogen bonded network that imparts nucleophilic reactivity to the Ser oxygen. Abs were predicted in 1973 to express proteolytic activity based on sequence homology between CDR1 of Bence Jones proteins and the peptide region surrounding the active site Ser residue of serine proteases (1). A catalytic triad akin composed of Ser27a-His93-Asp1 has been identified in the light chain (L chain) of an Ab to VIP by site-directed mutagenesis (2). As in non-Ab serine proteases, hydrogen bonding with His93 appears to confer nucleophilic reactivity to the Ser residues and Asp1 is correctly positioned to serve as the third component of the triad.

Recent studies indicate that a large proportion if not all Abs express serine protease-ike nucleophilic reactivity at levels greater than conventional enzymes (3). These Abs were identified using covalently reactive hapten phosphonate esters (4,5), the electrophilic phosphorus atom in which forms a stable covalent bond with activated nucleophiles. Previous mutagenesis studies along with screening for catalysis has indicated that the nucleophilic and proteolytic activities are heritable traits, encoded by germline V domains (6). [About 50 $V_H$ and 50 $V_L$ genes along with a smaller number of diversity and joining genes constitute the inherited Ab repertoire.]. Because the catalytic activity is germline-encoded, in principle, the immune system should be capable of mounting catalytic Ab responses to any polypeptide antigen. The ability to produce catalytic Abs depends, then, upon success in recruiting the germline V genes and inducing their adaptive specialization for recognition and cleavage of the polypeptide.

It is important to note that the covalent reactivity is a necessary but not sufficient condition for catalysis. This is because completion of the catalytic cycle requires facilitation of events occurring after formation of the covalent acyl-enzyme intermediate, i.e., hydrolysis of the intermediate and release of product peptides. Nucleophilic proteins devoid of this capability will not express catalytic activity. Therefore, only a subset of nucleophilic Abs, are anticipated to express catalytic activity.

2. Innate Nucleophilic and Catalytic Activities.

The Ser27a-His93-Asp1 site of the VIPase L chain cited in the preceding paragraph is also present in it germline VL counterpart (7). Four replacement mutations were identified, however, in the adaptively matured L chain (compared to the germline protein). These were reverted to the germline configuration by mutagenesis without loss of catalytic activity (6), confirming the germline origin of the activity. This is in line with findings that Abs and L chains in unimmunized humans and animals express promiscuous peptide bond cleaving activity (8-10).

IgM Abs from immunologically naive mice and healthy humans are disclosed in the present invention to display nucleophilic and proteolytic activities exceeding IgG Abs. Moreover, μ chain-containing B cell receptors (BCRs) expressed on splenic B cells account for most of the nucleophilic staining of the cells by hapten CRAs. Several previous studies have suggested important roles for serine protease activities in B cell development but the molecular identity of the activities was not determined. The serine protease inhibitors disiopropyl fluorophosphates (DFP) and α-1 antitrypsin inhibit B cell division in response to nitrogens (11,12). The DFP-sensitive enzyme is cell-associated and prefers Arg-containing substrates (13). The stimulatory effect anti-μ Ab on BCR activated signal transduction is inhibited by serine protease inhibitors (14), and anti-μ Ab mediated B cell activation induces appearance of a serine protease activity on the cell surface (15). CRAs are serine protease inhibitors. As the major CRA-reactive constituents on the B cell surface are the BCRs themselves, endogenous covalently reactive ligands are hypothesized to bind the nucleophilic sites and influence B cell development.

3. Antigen-specific nucleophilic and catalytic activities. Functional coordination between the traditional non-covalent binding forces responsible for antigen-specific recognition of mature Abs and their nucleophilic sites was examined using polypeptide CRAs. These CRAs contain the electrophilic group within the peptide backbone or the side chain groups ofproteins (FIG. 2). Abs specific for the peptide epitopes incorporated in polypeptide CRAs (pCRAs) displayed irreversible binding at levels exceeding irrelevant Abs (3). This was true for every Ab examined. The results using the pCRAs provide support for the split-site model of the active site (16), in which distinct amino acids are responsible for the nucleophilic reactivity and noncovalent binding interactions.

Despite excellent antigen-specific nucleophilic reactivity, most IgG Abs do not express antigen-specific catalytic activity. The main hurdle in inducing antigen-specific proteolytic Ab responses has been the existence of physiological regulatory processes that limit adaptive improvement of the catalytic function over the course of the immune response (FIG. 3). This may be explained by hypothesizing the existence of barriers to catalyst synthesis under physiological conditions. Occupancy of the BCR (surface Ab associated with Igα/Igβ) by the antigen drives B cell proliferation. Efficient BCR catalysis will abort clonal proliferation if the rate of product release is more rapid than BCR transmembrane signaling necessary to induce cell division. Catalyst synthesis maybe permissible, therefore, only to the extent that the rate of product release is slower than the rate of transmembrane signaling. In comparison, there is no bar to improved Ab nucleophilicity if this prolongs BCR occupancy. In the extreme case, increased nucleophilicity could result in formation of a full covalent bond with the antigen. A lesser manifestation is the formation of partial covalent bonds by resonant electron sharing mechanisms (see FIG. 1; a familiar example of a weak bond with partial covalent character is the hydrogen bond). A nucleophilic Ab may also form stable, dead-end covalent complexes with the antigen—two such examples are published (17,18), and in an unpublished study in our lab, we observed stable binding of albumin by certain Abs that were resistant to SDS treatment.

The hurdle cited in the preceding paragraph has been surmounted as disclosed here by immunization with a pCRA derived from the HIV-1 coat protein gp120. The gp120-CRA induced the production of gp120-specific catalytic Abs (19). This strategy is designed to induce adaptive maturation of Ab V domains for noncovalent recognition of peptide epitopes and simultaneously strengthen the chemical reactivity of the germline Ab nucleophiles. The noncovalent binding ensures Ab specificity for individual antigens. FIG. 1 depicts the reaction scheme of catalytic Abs with the antigen and their CRA analogs. Synthesis of Abs with increased nucleophilicity is promoted by incorporating within the peptide epitopes tetrahedral phosphonate diesters capable of selective covalent binding of nucleophilic residues (4, 5, 20). A positively charged amidino group is incorporated in proximity to the phosphonate group—this group is a mimic of Lys/Arg residues, introduced into the pCRAs because many (but not all) proteolytic Abs cleave peptide bonds on the C terminal side of positively charged residues (4, 8, 10). Proteolytic Abs can also cleave other types of bonds, including bonds that contain neutral, negatively charged, aromatic and bulky groups at the P1 and P1' positions (corresponding to the immediate amino acids at the N and C terminal flanks of the scissile bond; ref 24). Recently, we identified certain Abs that cleave a His-Gln bond in the β-amyloid 1-40 peptide (Paul and coworkers, unpublished).

Leaving group strength in the pCRAs is another determinant of their covalent reactivity—use of strong leaving groups such the p-nitrophenol and phenol groups allowing covalent binding to weak nucleophiles. The design of peptidyl- and protein-CRAs is based on the split-site model of the active site, in which distinct amino acids are responsible for the nucleophilic reactivity and noncovalent binding interactions. In this model, the nucleophile makes little or no contact with the Ag until the after noncovalent binding is complete. Once initial binding has occurred, flexibility in the active site allows the nucleophile to contact the Ag and initiate the chemical reaction.

Exploiting the structural features of natural proteolytic Abs is an essential element of design principles underlying immunogens capable of bypassing the physiological restriction on catalyst synthesis. Additional refinements in the structure of the immunogens and immunization regimen are readily conceived, including use of carbon-based pCRAs with longer half-lives than the phosphonate compounds and inclusion of a motif that promotes accommodation of a water molecule close to the reaction center in the Ab active site. The phosphorus atom is important only inasmuch that it can express covalent reactivity when the phosphonate group is appropriately esterified. Carbon can express chemical reactivities similar to the phosphorus and elements such as boron and vanadium also offer appropriate electrophilic reactivity to serve as replacements for the phosphorus atom. In addition to enhancing Ab nucleophilicity, noncovalent stabilization of the transition state reaction center is desirable to enhance the quality of the elicited catalytic response. Recent studies by our group indicate that negatively charged phosphonate monoesters express sufficient electrophilicity to form covalent bonds with nucleophiles found in serine proteases. This allows design of pCRAs that combine both features of peptide bond transition state implicated in rapid catalysis, i.e., electrostatic interactions at the negatively charged oxygen atom and covalent reactivity of the carbon atom (4, 5).

As noted previously, immunization with negatively charged (oxy anionic) haptenic TSAs allows induction of esterase but not proteolytic Abs (21,22). In comparison, success in inducing proteolytic Abs by the compounds disclosed in the present application can be understood from recruitment of the innate forces utilized by Abs in their interactions with the antigen, that is, nucleophilic reactivity coordinated with noncovalent binding at epitope constituents distant from the reaction center.

3. Adaptive Regulatory Processes in Autoimmune Disease.

As noted above, the main hurdle in routine generation of antigen-specific proteolytic Ab responses is the existence of physiological regulatory processes that limit adaptive improvement of the catalytic function over the course of the immune response. Autoimmune disease is associated with comparatively high turnover catalytic Abs (23-27). For instance, healthy humans express low affinity VIP-binding auto antibodies that bind VIP (28), but VIP-specific catalytic Abs are found only in autoimmune disease (29). Catalytic autoantibody V domains are adaptively matured, judged from their CDR/framework mutational patterns (30) and high affinity for the autoantigen (23). This suggests the existence of pathophysiological mechanisms allowing evasion of physiological restrictions on catalysis. Intrinsically accelerated BCR signaling rates in autoimmune disease appears to explain adaptive improvements of BCR catalytic activity to levels precluded under physiological conditions (FIG. 3). Several reports have linked autoimmunity with dysfunctional B cell transmembrane signaling. CD 19, a membrane protein associated with the BCR (31), diminishes the threshold for antigenic stimulation of B cells (32, 33), and another membrane protein, CD22, increases the threshold (34). Lyn, a Src protein tyrosine kinase, also transduces antigen-stimulated BCR signaling (35). Dysfunction of these proteins is associated with autoantibody production.

An alternative explanation for enhanced production of proteolytic Abs in autoimmune disease is the hypothesis of endogenous compounds that bind covalently to the BCR nucleophilic site. Immunization with a poylpeptide CRA was shown to surmount the physiological barriers to adaptive improvement of Ab proteolytic activity (19). Naturally occurring serine protease inhibitors and reactive carbonyl compounds previously shown to bind covalently to nucleophilic sites can be conceived as potential endogenous CRAs. For example, an amidino derivative of pyruvate has been shown to react covalently with the Ser nucleophile of trypsin and thrombin (36, 37; the amidino group occupies the P1 subsite without participating in the covalent reaction). Additional candidate CRAs are electrophiles produced as a result of lipid peroxidation and protein glycation (Maillard's reaction), processes that occur at enhanced levels in autoimmune disease (38-40). Well known examples are 4-hydroxy-2-nonmental and malondialdehyde (products of lipid peroxidation; refs 41, 42) and glyoxal, methylglyoxal and pentosidine (reactive carbonyl compounds generated during sugar metabolism; ref 43). These compounds are capable of reacting covalently with enzymatic active site nucleophiles (44), and at slower rates, with Arg and Lys residues (41).

CRA structural design principles are critical to isolation of catalytic Abs from the autoimmune repertoire. For example, catalytic Abs in the Ab repertoire expressed by patients with the autoinumune disease systemic lupus erythmetosus express specificity for recognition of gp120. Identification of these Abs is enabled by pCRAs that contain the appropriate peptide epitopes of gp120 apposed to a tetrahedral phosphonate diester capable of covalent binding to Abs nucleophilic residues (see FIGS. 45 and 46). This is important because the Abs from lupus patients are directed to a comparatively conserved epitope and they neutralize viral infection in tissue culture (45). Several reports in the clinical literature have discussed the rarity of AIDS in lupus patients (46-48). Disclosed in the present invention are catalytic Ab fragments from a lupus phage display library by binding to gp120-CRAs.

Figure 2:
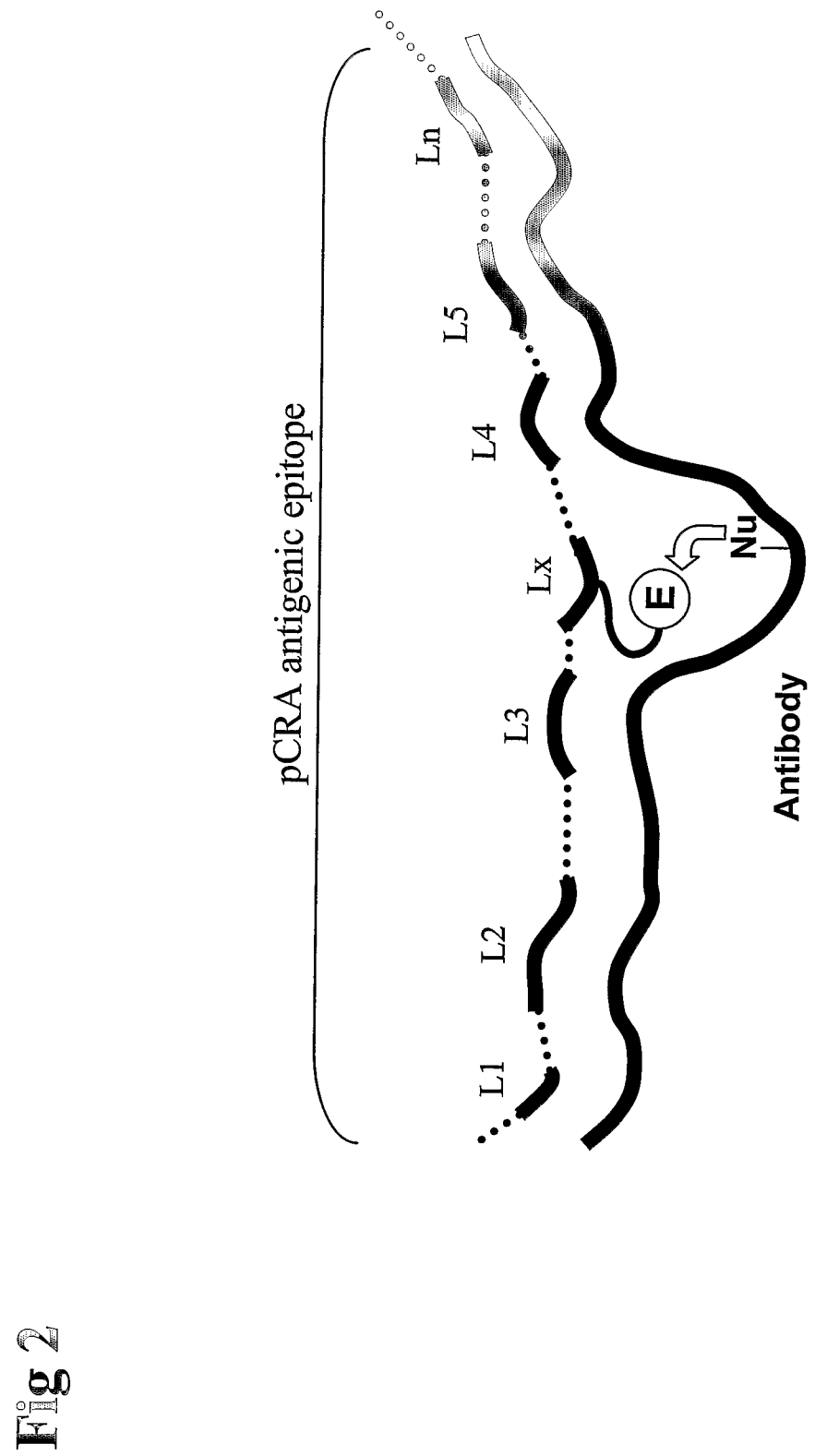
FIG. 2: Polypeptide covalently reactive analogs (pCRAs). pCRAs are derivatives of proteins and polypeptides in which one or more amino acid side chains are linked to the electrophilic group (E, e.g. phosphonate ester). L correspond to a linear or discontinuous antigenic epitopes [L1-Lm] that are spatially in proximity with the attached electrophile E and recognized by the antibody. Dotted lines connecting [L1-Lm] represent short or extended lengths of the ligand region that do not serve as antigenic epitope. Linkage of E to the amino acid side chain can be accomplished directly or through the use of an adaptor functionality, which is then considered to be a component of E in the general pCRA formula shown here. Lx corresponds to amino acid to which E is coupled Typical examples of Lx are Lys, Asp, Glu, Cys, Ser, Thr and Tyr. Examples of the site of linkage of E to these amino acids include the —NH2, —COOH, —SH and —OH groups. As proteins can express one or more antigenic epitope, the pCRA may contain one or more set of reactive units composed of [L1-Lm] and E.

4. pCRAs.

pCRA structure is based on the split site model of covalent/catalytic antibodies in which the antibody paratope and nucleophilic regions are treated as two distinct subsites pCRAs are derivatives of proteins and polypeptides in which one or more amino acid side chains are linked to the electrophilic group (E) (FIG. 2). Linkage of E to the amino acid side chain can be accomplished directly or through the use of an adaptor functionality, which is then considered to be a component of E in the general pCRA formula shown in FIG. 4. Lx corresponds to any amino acid at which E is coupled. Typical examples of Lx are Lys, Asp, Glu, Cys, Ser, Thr and Tyr. Examples of the site of linkage of E to these amino acids include the —NH2, —COOH, —SH and —OH groups. L correspond to a linear or discontinuous antigenic epitopes [L1 . . . Lm] that are spatially in proximity with the attached electrophile E and recognized by the antibody. Dotted lines connecting L1-Lm represent short or extended lengths of the ligand region that do not serve as components of the antigenic epitope. As proteins can express one or more antigenic epitope, the pCRA may contain one or more sets of each reactive unit composed of [L1 . . . Lm], Lx and E. X-ray crystallography studies have shown that [L1 . . . Lm] can be composed of few as 4 amino acids and as many as 30 amino acids in the case of polypeptide antigens.

Figure 5B:
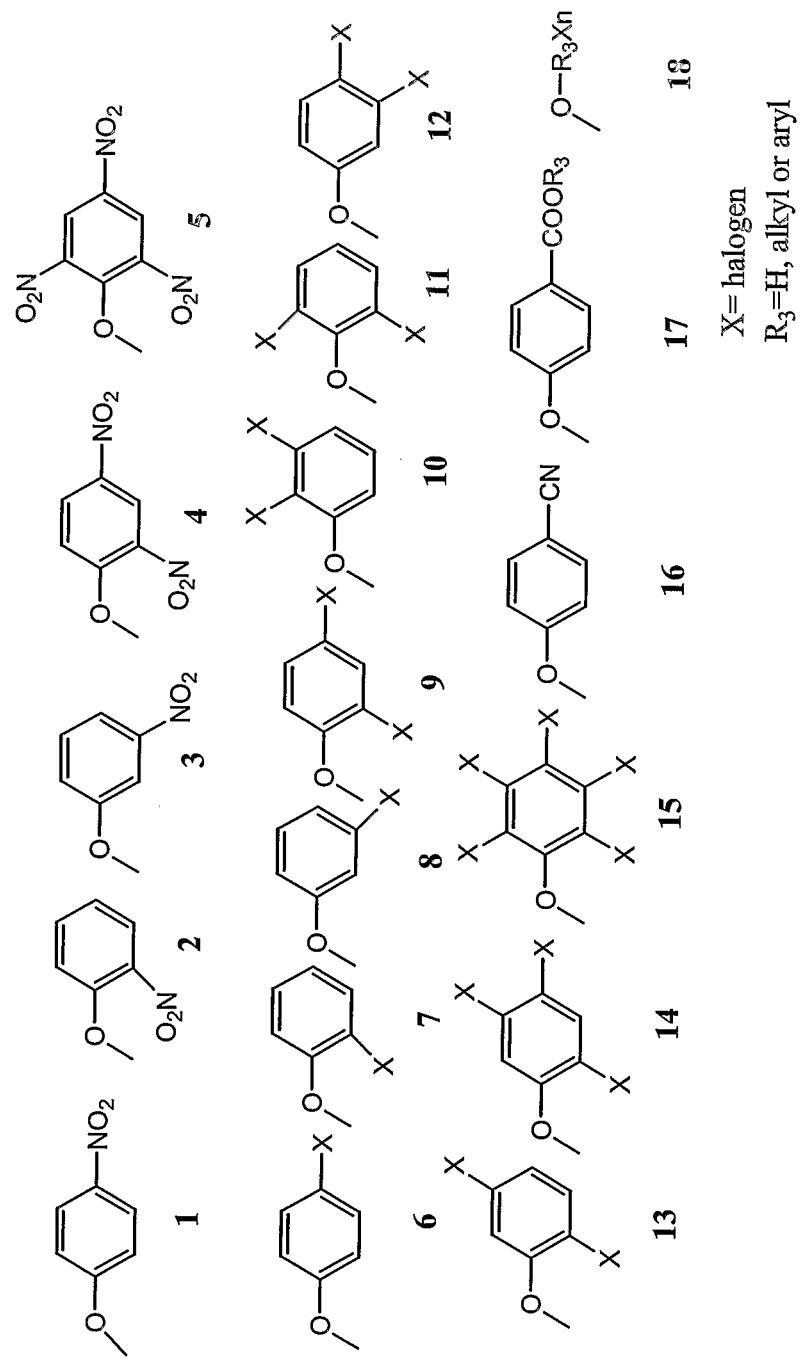
FIG. 5. (A) Y variants. The electrophilic group Y is composed of an electron deficient atom (Z), which forms a covalent bond with Nu, and one (Example 2) or more (Example 1) substituents (—R1 and —R2) attached to Z. R1 and R2 can be any atoms or groups that permit covalent bonding between Z and Nu. Typical examples of R1 and R2 include alkyl groups, alkoxy groups, aryl groups, aryloxy groups, hydrogen, and hydroxyl group. R1 and R2 can be pairs of the same or different substituents. (B) Examples of R1 and R2 that increase the covalent reactivity of Y. The electronic characteristics of R1 and R2 control the electrophilic reactivity of Y. (C) Examples of R1 and R2 that decrease the covalent reactivity of Y. (D) Examples of R1 and R2 with peptide extensions.
Figure 5C:
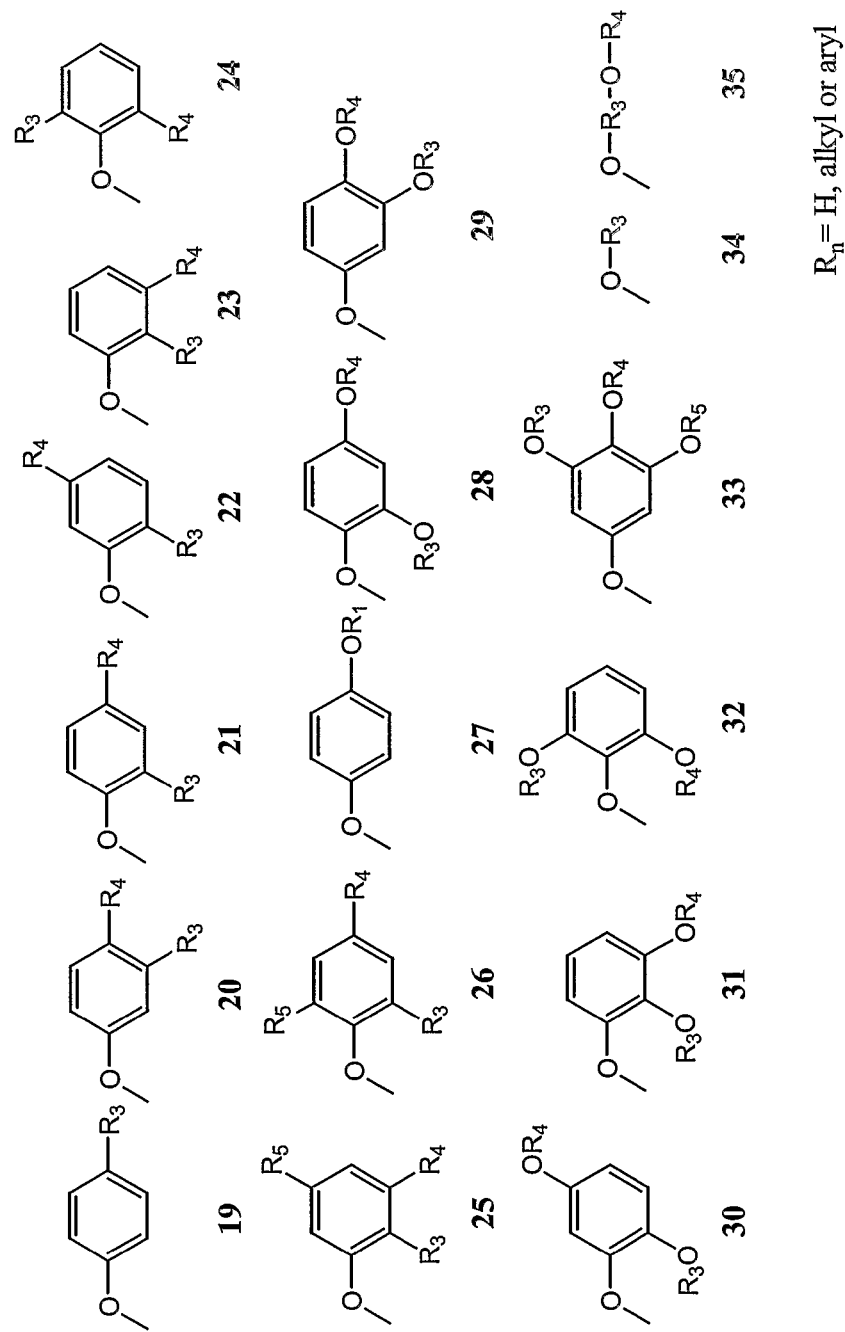

E can be any electrophile capable of forming a covalent bond with nucleophiles expressed by secreted Abs and Abs expressed on the cell surface. Examples of suitable electrophiles are the phosphorus atom in phosphonate esters; the carbon atom in carbonyl esters, carbonyl amides, carbonates, aldheydes, ketones and and aliphatic and aromaric carbonyl compounds; the boron atom in boronates and the vanadium atom in vanadates. Optionally, Y can include a partially or fully negatively charged atom attached to the electrophilic atom, for example, the negatively charged oxygen atom close to the electrophilic phosphorus atom in phosphonate monoesters. Electron, withdrawing and donating groups are linked directly to the electrophilic atom or via spacer groups to enhance and decrease the covalent reactivity with nucleophiles in Abs owing to inductive effects. Examples of such groups are provided in FIG. 5 Substituents 1-18 represent groups with varying electron withdrawing capacity. The ideal substituent is one that permits selective binding to the active site of the desired catalyst without binding other catalysts that utilize nucleophilic covalent mechanisms. For example, increasing the covalency of the phosphorus atom to very high levels is undesirable because this permits it to bind enzymes essential to life, such as acetylcholinesterase. Decreases in the covalency of the phosphorus atom are achieved using 19-35 substituent.

Optionally, a positive charge or a negative charge is placed in the vicinity of the electrophilic atom to mimic the basic residue and acidic residue specificity of covalent and catalytic Abs, respectively. Similarly, the bulk, hydrophobic character and hydrogen bonding propensity of groups in the vicinity of the electrophilic atom can be varied to optimize neighboring group specificity of the Abs. The flexibility of the adaptor group through which E is linked to the amino acid side chains is varied to ensure that noncovalent epitope binding occurs in coordination with the nucleophilic reaction.

Hydrolysis of covalent Ab-antigen complexes can be a limiting factor in the catalytic reaction. To facilitate synthesis of efficient proteolytic antibodies in which the hydrolysis reaction occurs readily, a water binding site can be placed in the vicinity of E in the pCRA immunogen. Examples of the water binding sites are shown in FIG. 6. Such water binding pCRAs are designated pCRAWs. Examples of pCRAWs are shown in FIG. 6. A fully assembled pCRAW analog of a β-amylod peptide is shown in FIG. 48. In these examples, the water binding group is a metal ion chelated within the pCRA structure. In the case of pCRAWs containing phosphonate monoesters as the electrophilic group, the phosphorus atom itself provides a metal ion chelating ability, which could bring bound water even closer to the electrophilic reaction center. Immunization with pCRAWs allows synthesis of antibodies that have sufficient room in their active sites to allow water to diffuse to the reaction center. There is no requirement that the Ab must bind a metal or contain an activated water molecule bound to the metal, although such an occurrence is within the scope of the present invention. Essentially, Abs to pCRAWs express three coordinated activities required for specific, high turnover proteolysis; i.e., specific noncovalent recognition of an antigenic epitope, covalent binding to an electrophile and sufficient space to acconimodate a water molecule capable of facilitating the hydrolysis reaction.

The electrophile and the noncovalent groups of pCRAs and pCRAWs must be in register spatially, as the purpose is to combine covalent binding of these compounds to Ab nucleophiles with noncovalent binding to Ab paratope. Placement of the electrophile on the side chains of various amino acids in the pCRA and pCRAW preparations permits its simultaneous covalent binding to the antibody nucleophile, and of the antigenic epitope, to the antibody paratope. Although the electrophile is not located in the polypeptide backbone, flexibility in the antibody and pCRA or pCRAW allows the reaction to proceed. This allows affinity maturation of the variable domains of antibodies following immunization with the pCRA or pCRAW, resulting in increased nucleophilicity and increased paratope binding affinity. The antigenic determinants of the pCRA or pCRAW are structurally similar to the antigenic determinants found in targeted protein antigen. The electrophile in the pCRA or pCRAW corresponds to electrophilic group susceptible to covalent nucleophilic attack in the targeted protein, e.g., the carbonyl group of the peptide bond or the amide bond in Gln and Asn side chains. Thus, antibodies displaying high noncovalent binding affinity and rapid covalent reaction with pCRAs also display high affinity and covalent reactivity with the targeted natural protein. Antibodies that bind covalently to the natural protein inactivate the latter molecule permanently. In comparison, ordinary noncovalent antibodies dissociate from antigen-antibody complexes, regenerating biologically effective antigen.

Examples I-XI disclosed in this invention illustrate various methods useful for the following purposes: (a) Induction of synthesis of Abs that can bind covalently and specifically with the target polypeptide antigen; (b) Induction of synthesis of Abs that can specifically catalyze the hydrolysis of various target polypeptide antigens; (c) Isolation of specific covalent and catalytic Abs from the natural Ab repertoire expressed in patients with autoimmune disease; (d) Permanent inactivation of pathogenic catalytic Abs expressed by patients with autoimmune disease; (e) Use of transonic mice with dysfunctional B cell transmembrane as hosts to raise catalytic Abs; and (f) Use of transonic mice expressing the human Ab genes to raise human covalent and catalytic Abs.

Covalently reactive antigen analogs (CRAA) have been described in U.S. Pat. No. 6,235,714. These can be used to raise covalent and catalytic Abs by the methods described in the present invention. Similarly, covalently reactive transition state analogs (CRTSAs) are disclosed in U.S. patent application Ser. No. 10/114,716 (filing date Apr. 1, 2002), and these can be used to raise covalent and catalytic Abs by the methods described in the present invention.

In one aspect of the invention, pCRAs and pCRAWs are administered to a living organism along with an immunological adjuvant under conditions whereby they stimulate production of antigen-specific proteolytic Abs. The dose of the immunogen, schedule of immunization and adjuvant are adjusted to allow elicitation of long-lasting immunity, including memory T and B cells that can rapidly mount a proteolytic immune response upon exposure to disease-causing agents like microbes and cancer cells. In this aspect of the invention, pCRAs and pCRAWs serve as prophylactic vaccines. The constitution of the vaccine is not limited to purified proteins and peptides. pCRA and pCRAW versions of whole microbes can be prepared to induce broad covalent and catalytic immunity against a variety of surface expressed antigens.

In another aspect of the invention, the pCRAs and pCRAWs are applied for isolation of therapeutic Abs, for example by: (a) preparing monoclonal Abs from ordinary mice and transonic mice expressing the human Ab repertoire; (b) chemical selection of the desired antibodies from autoimmune phage display libraries; and (c) directed evolution of the Abs in vitro. In each case, efficient methods for screening and selection are applied to permit isolation of rare Abs with the desired activities. The covalent and catalytic Abs so generated would then be administered to patients to inactivate targeted antigen moieties. In this scenario, should the patient experience adverse side effects, the immunizing pCRA or pCRAW maybe administered to irreversibly inactivate the catalytic antibody.

Finally, the pCRAs of the invention may be administered to patients who are currently expressing catalytic antibodies in association with a medical disorder such as autoimmune disease or multiple myeloma. pCRAs are designed to specifically react with the antibodies present. Inhibition of catalytic function should result in an amelioration of the disease state. These pCRAs are designed to contain a minimally immunogenic B cell epitope and are administered without adjuvant, so that they do not induce the synthesis of Abs.

The detailed description set forth below describes preferred methods for practicing the present invention. Methods are disclosed for stimulating synthesis of catalytic Ab and covalent antibodies of predetermined specificity by the immune system. In one embodiment of the invention compositions and methods are provided for the generation of catalytic antibodies to a polypeptide antigen of choice. In another embodiment, compositions and methods are provided which are useful in passive immunotherapy modalities for the treatment of HIV-1 infection, cancer and other medical conditions.

In another embodiment of the invention, vaccination protocols are described which elicit catalytic Ab and covalent Ab production to predetermined viral or pathogenic antigens.

5. Identification and preparation of suitable pCRAs and pCRAWs.

The structure of the pCRAs and pCRAWs is based on the structure of the targeted polypeptides. Examples of suitable polypeptides are shown in Table 2. pCRAs and pCRAWs can be prepared using synthetic peptides such as VIP and beta-amyloid peptides; full-length proteins such as gp120, EGFR, IgE and Factor VIII; mixtures of pure peptides and proteins; whole viruses like HIV-1; and whole protozoans and bacteria.

Examples of suitable targets include those peptides and proteins that are already validated as targets of therapeutic monoclonal Abs, e.g., EGFR, VEGF and TNF-α; and, peptides and proteins derived from microbial organisms and the microorganisms themselves. Endogenous human polypeptides to be targeted include soluble ligands and the membrane bound receptors for these ligands. Inflammatory mediators are also suitable targets for catalysis. Exemplary molecules in this group include TNF, IL-1beta, IL-4 as well as their cognate receptors. Microbial proteins can also be targeted for catalysis by the antibodies of the present invention. These include but are not limited to gp120, gp160, Lex1 repressor, gag, pol, hepatitis B surface antigen, bacterial exotoxins (diptheria toxin, *C. tetanzi* toxin, *C. botulinzuin* toxin, *pertussis* toxin). Cancer-associated antigens to be targeted include but are not limited to EGF, TGFA, p53 products, prostate specific antigen, carcinoembryonic antigen, prolactin, human chorionic gonadotropin, c-myc, c-fos, c-jun, p-glycoproteins, multidrug resistance associated proteins, metalloproteinases, angiogenesis factors, EGFR, EGFR mutants, HER-2, prolactin receptors, and steroid receptors.

To identify of the biologically important determinants in proteins serves as a guide to identify synthetic peptides suitable as starting material for pCRAs and pCRAWs. For example, the binding of HIV gp120 to host cell receptors is mediated by a discontinuous determinant that contains residues located in the C4 region of the protein. Peptides corresponding to this region (e.g., residues 421-436) can serve as suitable starting material for the pCRAs and pCRAWs. Many of the important determinants in viral and cancer associated proteins have been mapped using conventional monoclonal Ab-based methods. This knowledge facilitates the design of efficacious pCRAs and pCRAWs useful as catalytic antibody inhibitors as well as inducers of catalytic antibodies with specificity against predetermined epitopes.

Preexisting catalytic antibodies are found in autoimmune disease and lymphoproliferative disorders. The harmful actions of these catalytic antibodies will be inhibited by administering pCRAs to patients. pCRAs are designed to be non-immunogenic or weakly immunogenic. Examples of catalytic Abs to be inactivated by pCRAs are those directed to VIP, Factor VIII, fibrils-1, DNA, Arg-vasopressin, thyroglobulin, thyroid peroxidase, IL-1, IL-2, interferons, proteinase-3, glutamate decarboxylase.

Example I describes an exemplary peptide derived from the CD4 binding site of gp120 that is suitable for preparation of pCRAs and pCRAWs for raising covalent catalytic and catalytic Abs to HIV-1 gp120. This peptide is a mimetic of residues 421-433 of gp120.

Efficient Ab synthesis by B cells is dependent in part on recruitment of T helper cells, which, once sensitized, secrete the necessary stimulatory cytokines and activate B cells by direct contact mediated through accessory molecules, such as CD4 on T helper cells and B7 on B cells. Recruitment of Ag-specific T cells occurs through recognition by the T cell receptor (TCR) of the complex of a processed Ag epitope bound to MHC class II molecules.

T cell help for Ab synthesis is potentially subject to restriction in different individuals due to MHC polymorphism. The pCRAs and pCRAWs are conjugated to a suitable carrier protein such as tetatus toxoid or key hole limpet hemocyanin, which serve as a source of universal T epitopes. Alternatively, a peptide known to serve as a universal T cell epitope can be incorporated into the immunogens (49).

Empirical experimental criteria considered significant in designing the structure of the pCRAs and pCRAWs include:

Potency of inhibition of catalytic activity and potency of covalent binding to Abs (Ki). The best pCRAs and pCRAWs are identified by screening panels of these compounds for the ability to inhibit non-Ab serine proteases and Ab serine proteases.

Ability of pCRAs and pCRAWs to select high turnover, specific catalysts from displayed antibody libraries (see ref 4 for phage display methods; other display methods such as bacterial and yeast display are also suitable).

Immunization of experimental animals with pCRAs and pCRAWs followed by analysis of polyclonal serum antibodies and monoclonal antibodies from the immunized animals for the desired covalent and catalytic activity.

6. Administration of pCRAs and pCRAWs pCRAs and pCRAWs as described herein are intended to be administered to a patient as a pharmaceutical preparation. The term "patient" as used herein refers to human or animal subjects. The pharmaceutical preparation comprising the pCRAs and pCRAWs of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of pCRAs and pCRAWs in the chosen medium will depend on the hydrophobic or hydrophilic nature of the medium. Solubility limits maybe easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the pCRAs and pCRAWs to be administered, its use in the pharmaceutical preparation is contemplated.

Conventional immunization methods are applied to induce catalytic Ab synthesis. Several injections of the immunogens (about 100 µg peptide each) are administered to induce Ab synthesis. RIBI will be used in the animal studies. For human use, alum will be employed as the adjuvant. Alum is approved for human use. RIBI is a low toxicity replacement for Freund's Complete Adjuvant, and reproducibly facilitates good Ab responses to a variety of Ags. The immunogens may be administered parenterally by intravenous injection into the blood stream, or by subcutaneous, intramuscular or intraperitoneal injection. Pharmaceutical preparations for parenteral injection are commonly known in the art.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The pharmaceutical preparation intended to inhibit catalytic Abs maybe administered at appropriate intervals, for example, once a day until the pathological symptoms are reduced or alleviated, after which the dosage may be reduced to a maintenance level. The appropriate interval in a particular case would normally depend on the condition and the pathogenic state sought to be treated in the patient.

7. Administration of Covalent Antibodies and Catalytic Antibodies

The covalent antibodies and catalytic Abs described herein are generally administered to a patient as a pharmaceutical preparation.

The pharmaceutical preparation of the invention are conveniently formulated for administration with a acceptable medium such as water, buffered saline, ethanol, polyol (for example, glycerol, propylene glycol, liquid polyethylene glycol and the like), dimethyl sufoxide (DMSO), oils, detergents, suspending agents or suitable mixtures thereof. The concentration of the Abs in the chosen medium will depend on the hydrophobic or hydrophilic nature of the medium, as well as the other properties of the catalytic antibodies. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the catalytic antibody to be administered, its use in the pharmaceutical preparation is contemplated.

Conventional passive immunization methods will be employed when administering the Abs. In a preferred embodiment, Abs will be infused intravenously into the patient. For treatment of certain medical disorders, steps must be taken to ensure that sufficient amounts of the molecules reach their target cells to exert abiological effect.

The lipophilicity of the molecules, or the pharmaceutical preparation in which they are delivered may have to be increased so that the molecules can arrive at their target locations. Furthermore, the Abs of the invention may have to be delivered in a cell-targeted carrier so that sufficient numbers of molecules will reach the target cells. Methods for increasing the lipophilicity and targeting of therapeutic molecules, which include capsulation of the Abs of the invention into antibody studded liposomes, are known in the art.

The covalent and catalytic Abs that are the subject of the present invention can be used as Ab fragments or whole Abs or they can be incorporated into a recombinant molecule or conjugated to a carrier such as polyethylene glycol. In addition any such fragments or whole Abs can be bound to carriers capable of causing the transfer of said Abs or fragments across cell membranes as mentioned above. Carriers of this type include but are not limited to those described (50).

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. For example, the half-life of syngeneic IgG in the human is about 20 days. Over this period, 60,480 Ag molecules will be cleaved by one molecule of an antibody with a turnover of 2.1/min (51). It can be seen, therefore, that the peptidase antibodies can express considerably more potent antigen neutralizing activity than stoichiometric, reversibly-binding molecules.

The pharmaceutical preparation comprising the catalytic Abs may be administered at appropriate intervals, for example, twice a week until the pathological symptoms are reduced or alleviated, after which the dosage may be reduced to a maintenance level. The appropriate interval in a particular case would normally depend on the condition and the pathogenic state sought to be treated in the patient.

pCRAs and pCRAWs will be selected that will generate Abs suitable for passive or active immunotherapy that will fulfill the standard criteria for acceptable prophylatic or therapeutic agents: (1) Covalent binding or cleavage of the target peptide antigen by the Abs will lead to a beneficial change in a pathological process by either functionally activating or functionally inactivating the target peptide antigen; and (2) Administration of said Abs or the induction of their production in the body by means of immunization with pCRAs or pCRAWs will result in a favorable therapeutic index such that the clinical benefit gained outweighs the morbidity associated with any side-effects. Discussions of how such criteria are established for the acceptability of prophylatic or therapeutic agents are common in the art can can be found in such texts as *Guide to Clinical Trials* by Bert Spilker, Raven Press, New York, 1991. Acceptable criteria for demonstration of efficacy include, for example, in the case of tumor therapy, a reduction in tumor volume, time to progression and improved survival. In the case of HIV immunotherapy, efficacy is determined by measuring viral burden in the blood, CD4+ T cell counts and the incidence of opportunistic infections.

Conventional monoclonal Abs that act to inhibit the function of particular target molecules are among the most common type of therapeutic agent under development for clinical use by biotechnology and pharmaceutical companies. Some of these have shown substantial clinical promise. For example, in the field of organ transplantation, a MoAb (OKT3) which binds to the T cell receptor has been employed to deplete T cells in vivo.

Additionally, MoAbs are being used to treat graft v. host disease with some success. A clinical trial has been established which is assessing the ability of anti-CD4 moAB to deplete a subset of T cells in the treatment of multiple schlerosis. Accordingly, methods of administration of monoclonal antibodies are well known to clinicians of ordinary skill in the art.

Any exposed peptide target antigen known to be suitable for conventional monoclonal Abs is a particularly suitable candidate target for the covalent and catalytic Abs that are the subject of the present invention. The Abs contemplated in the present invention will constitute a major improvement over such conventional monoclonals because of their superior potency, resulting in dramatic decrease in the cost of treatment. A listing of some of the antigens targeted by conventional monoclonal Abs showing clinical promise and the corresponding medical indications are shown in Table 2.

Suitable categories of prophylatic or therapeutic target peptide antigens for the practice of the present invention include but are not limited to cytokines, growth factors, cytokine and growth factor receptors, proteins involved in the transduction of stimuli intiated by growth factor receptors, clotting factors, integrins, antigen receptors, enzymes, transcriptional regulators particularly those involved in cellular program (differentiation, proliferation and programmed cell death) control, other inducers of these cellular programs, cellular pumps capable of expelling anticancer agents, microbial and viral peptide antigens.

Active immunization will be done using previously developed methods with vaccines designed to elicit protective antibody responses against the desired antigens. For example, the pCRAs and pCRAWs mixed with a suitable adjuvant formulation such as alum can be administered intramuscularly at a dose optimized for maximum antibody synthesis, and two or three booster injections can be administer at 4 week intervals, until the catalytic antibody concentration in the serum reaches plateau levels. The protective immunity so generated is anticipated to last for several years, because vaccination will result in formation of specific, long lived memory cells that can be stimulated to produce Abs upon exposure to the offending organism or cancer cell. Descriptions and methods to determine the catalytic Abs are set forth in the Examples. Because Ab synthetic response to most antigens are T cell dependent, an appropriate T cell epitope can be incorporated into the immunogen by peptide synthesis. Alternatively, a carrier such as keyhole limpet hemocyanin can be conjugated to the pCRA and pCRAW via coupling through lys side chain amino groups or Cys side chain sulfahydryl groups to maximize the antibody response if necessary.

While certain of the preferred embodiments of the present invention have been described and specifically exemplified above, it is not intended that the invention be limited to such embodiments. Various modifications may be made thereto without departing from the scope and spirit of the present invention. The following examples are provided to facilitate an understanding of the present invention.

REFERENCES

1. Erhan S, Greller L D. Do immunoglobulins have proteolytic activity? Nature 1974 Sep. 27; 251(5473):353-5.
2. Gao Q S, Sun M, Rees A R, Paul S. Site-directed mutagenesis of proteolytic antibody light chain. J Mol Biol 1995 Nov. 10; 253(5):658-64.
3. Planque S, Taguchi H, Burr G, Bhatia G, Karle S, Zhou Y X, Nishiyama Y, Paul S. Broadly Distributed Chemical Reactivity of Natural Antibodies Expressed in Coordination with Specific Antigen Binding Activity. J Biol Chem 2003 May 30; 278(22):20436-20443.
4. Paul S, Tramontano A, Gololobov G, Zhou Y X, Taguchi H, Karle S, Nishiyama Y, Planque S, George S. Phosphonate ester probes for proteolytic antibodies. J Biol Chem 2001 Jul. 27; 276(30):28314-20.
5. Nishiyama Y, Taguchi H, Luo J Q, Zhou Y X, Burr G, Karle S, Paul S. Covalent reactivity of phosphonate monophenyl esters with serine proteinases: an overlooked feature of presumed transition state analogs. Arch Biochem Biophys 2002 Jun. 15; 402(2):281-8.
6. Gololobov G, Sun M, Paul S. Innate antibody catalysis. Mol Immunol 1999 December; 36(18):1215-22.
7. Gao Q S, Sun M, Tyntyalkova S, Webster D, Rees A, Tramontano A, Massey R J, Paul S. Molecular cloning of a proteolytic antibody light chain. J Biol Chem 1994 Dec. 23; 269(51):32389-93.
8. Kalaga R, Li L, O'Dell J R, Paul S. Unexpected presence of polyreactive catalytic antibodies in IgG from unimmunized donors and decreased levels in rheumatoid arthritis. J Immunol 1995 Sep. 1; 155(5):2695-702.
9. Matsuura K, Yamamoto K, Sinohara H. Amidase activity of human Bence Jones proteins. Biochem Biophys Res Commun 1994 Oct. 14; 204(1):57-62.
10. Paul S, Li L, Kalaga R, Wilkins-Stevens P, Stevens F J, Solomon A. Natural catalytic antibodies: peptide-hydrolyzing activities of Bence Jones proteins and VL fragment. J Biol Chem 1995 Jun. 23; 270(25): 15257-61.
11. Ku G S, Quigley J P, Sultzer B M. Time-dependent inhibition of tuberculin-induced lymphocyte DNA synthesis by a serine protease inhibitor. J Immunol. 1981 June; 126 (6):2209-14.
12. Jeannin P, Lecoanet-Henchoz S, Delneste Y, Gauchat J F, Bonnefoy J Y. Alpha-1 antitrypsin up-regulates human B cell differentiation selectively into IgE- and IgG4-secreting cells. Eur J Immunol 1998 June; 28(6):1815-22.
13. Ku G S, Quigley J P, Sultzer B M. The inhibition of the niitogenic stimulation of B lymphocytes by a serine protease inhibitor: commitment to proliferation correlates with an enhanced expression of a cell-associated arginine-specific serine enzyme. J Immunol. 1983 November; 131 (5):2494-9.
14. Mizuguchi J, Utsunomiya N, Nakanishi M, Arata Y, Fnukazawa H. Differential sensitivity of anti-IgM-induced and NaF-induced inositol phospholipid metabolism to serine protease inhibitors in BAL17 B lymphoma cells. Biochem J. 1989 Nov. 1; 263(3):641-6.
15. Biro A, Sarmay G, Rozsnyay Z, Klein E, Gergely J. A tyypsin-like serine protease activity on activated human B cells and various B cell lines. Eur J Immunol. 1992 October; 22(10):2547-53.
16. Sun M, Gao Q S, Kimarskiy L, Rees A, Paul S. Cleavage specificity of a proteolytic antibody light chain and effects of the heavy chain variable domain. J Mol Biol 1997 Aug. 22; 271(3):374-85.
17. Rao G, Philipp M. Irreversible inhibition of a monoclonal antibody by a nitrophenyl ester. J Protein Chem 1991 February; 10(1): 117-22.
18. Lefevre S, Debat H, Thomas D, Friboulet A, Avalle B. A suicide-substrate mechanism for hydrolysis of beta-lactams by an anti-idiotypic catalytic antibody. FEBS Lett 2001 Jan. 26; 489(1):25-8.
19. Paul S, Planque S, Zhou Y X, Taguchi H, Bhatia G, Karle S, Hanson C, Nishiyama Y. Specific HIV gp120-cleaving Antibodies Induced by Covalently Reactive Analog of gp120. J Biol Chem 2003 May 30; 278(22):20429-20435.
20. Kolesnikov A V, Kozyr A V, Alexandrova E S, Koralewski F, Demin A V, Titov M I, Avalle B, Tramontano A, Paul S, Thomas D, Gabibov A G, Friboulet A. Enzyme mimicry by the antiidiotypic antibody approach. Proc Natl. Acad Sci USA 2000 Dec. 5; 97(25):13526-31.
21. Schultz P G, Lemer R A. From molecular diversity to catalysis: lessons from the immune system. Science 1995 Sep. 29; 269(5232):1835-42.
22. Pollack S J, Hsiun P, Schultz P G. Stereospecific hydrolysis of alkyl esters by antibodies. J Am Chem Soc 1989; 111(15):5961-2.
23. Paul S, Volle D J, Beach C M, Johnson D R, Powell M J, Massey R J. Catalytic hydrolysis of vasoactive intestinal peptide by human autoantibody. Science 1989 Jun. 9; 244 (4909): 1158-62.
24. Paul S, Mei S, Mody B, Eklund S H, Beach C M, Massey R J, Hamel F. Cleavage of vasoactive intestinal peptide at multiple sites by auto antibodies. J Biol Chem 1991 Aug. 25; 266(24):16128-34.
25. Shuster A M, Gololobov G V, Kvashuk O A, Bogomolova A E, Smirnov I V, Gabibov A G. DNA hydrolyzing autoantibodies. Science 1992 May 1; 256(5057):665-7.
26. Lacroix-Desmazes S, Moreau A, Sooryanarayana, Bonnemain C, Stieltes N, Pashov A, Sultan Y, Hoebeke J, Kazatchkine M D, Kaveri S V. Catalytic activity of antibodies against factor VIII in patients with hemophilia A. Nat Med 1999 September; 5(9):1044-7.

27. Gololobov G V, Chemova E A, Schourov D V, Smirnov I V, Kudelina I A, Gabibov A G. Cleavage of supercoiled plasmid DNA by autoantibody Fab fragment: application of the flow linear dichroism technique. Proc Natl Acad Sci USA 1995 Jan. 3; 92(1):254-7.
28. Bangale Y, Cavill D, Gordon T, Planque S, Taguchi H, Bhatia G, Nishiyama Y, Arnett F, Paul S. Vasoactive intestinal peptide binding auto antibodies in autoimmune humans and mice. Peptides 2002 December; 23(12):2251-7.
29. Bangale Y, Karle S, Planque S, Zhou Y X, Taguchi H, Nishiyama Y, Li L, Kalaga R, Paul S. VIPase autoantibodies in Fas-defective mice and patients with autoimmune disease. FASEB J 2003 April; 17(6):628-35.
30. Tyutyulkova S, Gao Q S, Thompson A, Rennard S, Paul S. Efficient vasoactive intestinal polypeptide hydrolyzing autoantibody light chains selected by phage display. Biochim Biophys Acta 1996 Aug. 23; 1316(3):217-23.
31. Carter R H, Doody G M, Bolen J B, Fearon D T. Membrane IgM-induced tyrosine phosphorylation of CD19 requires a CD19 domain that mediates association with components of the B cell antigen receptor complex. J Immunol. 1997 Apr. 1; 158(7):3062-9.
32. Sato S, Ono N, Steeber D A, Pisetsky D S, Tedder T F. CD19 regulates B lymphocyte signaling thresholds critical for the development of B-1 lineage cells and autoimmunity. J Immunol. 1996 Nov. 15; 157(10):4371-8.
33. Hasegawa M, Fujimoto M, Poe J C, Steeber D A, Tedder T F. CD19 can regulate B lymphocyte signal transduction independent of complement activation. J Immunol. 2001 Sep. 15; 167(6):3190-200.
34. O'Keefe T L, Williams G T, Batista F D, Neuberger M S. Deficiency in CD22, a B cell-specific inhibitory receptor, is sufficient to predispose to development of high affinity auto antibodies. J Exp Med 1999 Apr. 19; 189(8):1307-13.
35. Hasegawa M, Fujimoto M, Poe J C, Steeber D A, Lowell C A, Tedder T F. A CD19-dependent signaling pathway regulates autoimmunity in Lyn-deficient mice. J Immunol. 2001 Sep. 1; 167(5):2469-78.
36. Walter J, Bode W. The X-ray crystal structure analysis of the refined complex formed by bovine trypsin and p-amidinophenylpyravate at 1.4 A resolution. Hoppe Seylers Z Physiol Chem. 1983 August; 364(8):949-59. Related Articles, Links
37. Chen Z, Li Y, Mulichak A M, Lewis S D, Shafer J A. Crystal structure of human alpha-thrombin complexed with hirugen and p-amidinophenylpyruvate at 1.6 A resolution. Arch Biochem Biophys 1995 Sep. 10; 322(1):198-203.
38. Ames P R, Alves J, Murat I, Isenberg D A, Nourooz-Zadeh J. Oxidative stress in systemic lupus erythematosus and allied conditions with vascular involvement. Rheumatology (Oxford). 1999 June; 38(6):529-34.
39. Lucey M D, Newkirk M M, Neville C, Lepage K, Fortin P R. Association between IgM response to IgG damaged by glyoxidation and disease activity in rheumatoid arthritis. J Rheumatol. 2000 Febuary; 27(2):319-23.
40. Basta G, Lazzerini G, Massaro M, Simoncini T, Tanganelli P, Fu C, Kislinger T, Stern D M, Schmidt A M, De Caterina R. Advanced glycation end products activate endothelium through signal-transduction receptor RAGE: a mechanism for amplification of inflammatory responses. Circulation. 2002 Feb. 19; 105(7):816-22.
41. Bernoud-Hubac N, Roberts L J 2nd. Identification of oxidized derivatives of neuroketals. Biochemistry. 2002 Sep. 24; 41(38):11466-71.
42. Tuma D J, Kearley M L, Thiele G M, Worrall S, Haver A, Klassen L W, Sorrell M F. Elucidation of reaction scheme describing malondialdehyde-acetaldehyde-protein adduct formation. Chem Res Toxicol. 2001 July; 14(7):822-32.
43. Lo T W, Westwood M E, McLellan A C, Selwood T, Thomalley P J. Binding and modification of proteins by methylglyoxal under physiological conditions. A kinetic and mechanistic study with N alpha-acetylarginine, N alpha-acetylcysteine, and N alpha-acetyllysine, and bovine serum albumin. J Biol Chem. 1994 Dec. 23; 269(51):32299-305.
44. Crabb J W, O'Neil J, Miyagi M, West K, Hoff H F. Hydroxynonenal inactivates cathepsin B by forming Michael adducts with active site residues. Protein Sci. 2002 April; 11(4):831-40.
45. Bermas B L, Petri M, Berzofsky J A, Waisman A, Shearer G M, Mozes E. Binding of glycoprotein 120 and peptides from the HIV-1 envelope by auto antibodies in mice with experimentally induced systemic lupus erythematosus and in patients with the disease. AIDS Res Hum Retroviruses 1994 September; 10(9):1071-7.
46. Daikh, B. E. and Holyst, M. M. Lupus-specific auto antibodies in concomitant human immunodeficiency virus and systemic lupus erythematosus: case report and literature review. Semin. Arthritis Rheum. 30:418-425, 2001.
47. Diri, E., Lipsky, P. E. and Berggren, R. E. Emergence of systemic lupus erythematosus after initiation of highly active antiretroviral therapy for human immunodeficiency virus infection. J. Rheumatol. 27:2711-2714, 2000.
48. Bermas, B. L., Petri, M., Berzofsky, J. A., Waisman, A., Shearer, G. M. and Mozes, E. Binding of glycoprotein120 and peptides from the HIV-1 envelope by auto antibodies in mice with experimentally induced systemic lupus erythematosus and in patients with the disease. AIDS Res. Hum. Retroviruses 10:1071-1077, 1994.
49. Karle S, Nishiyama Y, Taguchi H, Zhou Y X, Luo J, Planque S, Hanson C, Paul S. Carrier-dependent specificity of antibodies to a conserved peptide determinant of gp120. Vaccine 2003 Mar. 7; 21(11-12):1213-8.
50. Cruikshank W W, Doctrow S R, Falvo M S, Huffinan K, Maciaszek J, Viglianti G, Raina J, Kormfeld H, Malfroy B. A lipidated anti-Tat antibody enters living cells and blocks HIV-1 viral replication. J Acquir Immune Defic Syndr Hum Retrovirol. 1997 Mar. 1; 14(3):193-203.
51. Planque S, Bangale Y, Song X T, Karle S, Taguchi H, Poindexter B, Bick R, Edmundson A, Nishiyama Y, Paul S. Ontogeny of proteolytic inmmunity: IgM serine proteases. J Biol Chem in press (published on line ahead of print on Jan. 15, 2004 as 10.1074/jbc.M312152200).

EXAMPLE I

Broadly Distributed Chemical Reactivity of Natural Antibodies Expressed in Coordination with Specific Antigen Binding Activity Many enzymes exploit covalent interactions with substrates to catalyze chemical transformations. Most studies on Ab catalysis, on the other hand, have focused on non-covalent binding forces as the mechanism by which the energy barrier between reactant and products is lowered, e.g., the electrostatic forces that stabilize the negatively charged oxy anionic transition state of ester hydrolysis (reviewed in 1, 2). The underlying assumption has been that Abs interact with their ligands exclusively by non-covalent means. Initial indications that natural Abs express chemical reactivity indistinguishable from enzymes came from reports of proteolytic and nuclease activity of autoantibodies (3, 4). Similar activities were later found in Ab light chains from multiple myeloma patients (5), autoantibodies from patients with transfusion-induced hemophilia (6), Abs raised by routine immunization with polypeptides (7, 8) and anti-idiotypic Abs to anti-enzyme Abs (9). From mutagenesis and inhibitor studies, it appears that the proteolytic activity of natural Abs originates from nucleophilic mechanisms similar to those utilized by conventional serine proteases (10,11). The catalytic activity of natural Abs could be construed to violate the principles of B cell clonal selection theory. Antigen-specific Abs develop over the course of the immune response by sequence diversification of germline genes encoding the V domains, followed by selective antigen binding by B cell receptors with the greatest affinity, which stimulates clonal proliferation Abs. Catalysis entails chemical transformation of the antigen and release of products (surface immunoglobulins associated with Igα and Igγ subunits), which is predicted to result in cessation of B cell selection. Adaptive selection of Ab catalytic activity, therefore, may be a disfavored event. For this reason, catalysis by naturally occurring Abs is often assumed to be a molecular accident arising from sequence variability of the V domains, as opposed to a general phenomenon with functional implications.

The foregoing restrictions do not apply to the initial step in the catalytic cycle of serine proteases catalyst. In analogy with conventional enzymes, a nucleophile belonging to a proteolytic Ab (Nu in FIG. 7A) is conceived to initiate nucleophilic attack on the antigen following formation of the noncovalent ground state complex. Adaptive development of Ab nucleophilicity is fully compatible with B cell clonal selection if the outcome is formation of a covalent acyl-Ab complex, as occupancy of the B cell receptor will be maintained. Whether the catalytic cycle is completed depends on the efficiency of hydrolysis of the acyl-Ab complex and release of the product. Recently, hapten phosphonate esters have been developed as probes for covalent binding to the active site nucleophiles in Abs displaying serine protease and serine esterase activity (11,12) (designated CRAs, covalently reactive antigen, analogs). These compounds can be applied for direct study of Ab chemical activity independant of additional activities needed for accomplishment of catalysis. In addition, the phosphonates can be placed within peptides and proteins (FIGS. 7B and 7C) for studying the interplay between Ab nucleophilic reactivity and noncovalent forces permitting specific recognition of individual polypeptides.

We describe here observations suggesting the broad distribution of nucleophilic reactivity in IgG and recombinant Fv preparations at levels exceeding that of the conventional serine protease trypsin. Originally prepared as probes for catalytic Abs, CRA analogs of EGFR and an HIV gp120 synthetic peptide were observed to form covalent adducts with ordinary Abs raised by immunization with antigens devoid of the phosphonate groups, suggesting that adaptive maturation processes favor expression of nucleophilic reactivity. These observations argue for Ab nucleophilicity as a force responsible for shaping the expressed Ab repertoire and suggest novel routes towards permanent inactivation of Abs.
Methods Abs. Human polyclonal IgG was prepared by affinity chromatography on Protein G-Sepharose (Amersham Pharmacia) from sera of 6 healthy human subjects (lab codes 1086, 1087, 1088, 1091, 1092, 1518). IgG from pooled serum from 8 BALB/c mice (4-5 wk) was obtained similarly. Preparation of polyclonal Abs by hyperimmunization with synthetic Cys-gp120(421-436) (KQIINMWQEVGKAMYA; SEQ ID No 5; residues 421-436 of gp120 HIV SF2 strain) conjugated to KLH is described in (13). Polyclonal Abs to exEGFR were raised by immunizing female BALB/c mice (5-6 wk) intraperitoneally with exEGFR (10 .mu.tg/injection) on days 0, 27 and 41 in RIBI adjuvant and with A431 tumor cells (10.sup.7 cells in saline) on day 14. Monoclonal Abs to exEGFR (clones C225, H11, and C111.6) were purchased from Labvision (Fremont, Calif.). A control monoclonal anti-BSA IgG (clone BGN/H8) was from Biogenesis (Kingston, N.H.) Single chain Fv constructs (N=15) were picked randomly from a human Fv library derived from lupus patients described in (11) (MM series clones; 12, 14, 18, 20, 24, F1, F2, F4, F5, F6, F7, F11, F12, F14, F17, F18). The scFv proteins were purified to electrophoretic homogeneity (27 kDa band) by metal affinity chromatography on Ni-NTA columns (11). Expression levels were 0.3-5.7 mg/liter bacterial culture. The library contains diverse scFv clones determined by nucleotide sequencing (11), assuring a broad sampling of Ab V domains. One of the scFv clones examined in the present study, MM-F4, was sequenced (GenBank #AF522073) and its VL and VH domains were determined to belong to families 1 and 1, respectively, and the germline gene counterparts were V1-13 and VH1-2, respectively. Confirmation of scFv band identities in SIDS-electophoresis gels was by immunoblotting using a monoclonal Ab to c-myc (10).

Probes for Nucleophiles.

Synthesis of hapten CRA I (FIG. 7) and its covalent reactivity with naturally occurring proteolytic Abs has been described previously (11,14). The electrophilic phosphonate diestermimnics the peptide bond, the positively charged amnidino group mimics the Lys/Arg P1 preference of naturally occurring proteolytic Abs (11), and the biotin group permits sensitive detection of Abphosphonate adducts. II was prepared by condensation of diphenyl amino(phenyl)methanephosphonate (compound a) and 6-biotinamidohexanoic acid N-hydroxysuccinimnide ester (Sigma) as described for I. For preparation of III, compound a (160 mg, 0.34 mmol) was treated with 30% HBr/CH3COOH (5 ml). The resulting diphenyl amino(phenyl)methanephosphonate hydrobromide (100 mg, 0.24 mmol) was dissolved in 0.5 M sodium methoxide in methanol (9.5 ml), and the solution was stirred under $N_2$ (room temperature, 2 h). After removing solvent under reduced pressure, the residue was extracted with $CH_2Cl_2$ (50 ml), the extract washed with water (5 ml×3), dried over $Na_2SO_4$, and evaporated to dryness. The yellowish oily residue was dissolved in diethyl ether (30 ml). HCl (1 M) in diethyl ether (0.25 ml) was added, yielding a precipitate that was collected by filtration and washed with diethyl ether; yield 35 mg, 68%; $t_R$ 11.8 min (>97% purity; C18 column, 5-80% acetonitrile in 0.1% trifluoroacetic acid, 50 min, 1.0 ml/min; m/z by electrospray ionization mass spectroscopy 216 (MH+). Biotinylation of this compound was done as usual (14). To prepare IV, diphenyl N—[O-(3-sulfosuccinimidyl)suberoyl]amino(4amidinophenyl)methanephosphonate (compound b) was first synthesized by mixing diphenyl amino(4-amidinophenyl)methanephosphonate (0.13 mmol) in DMF (2 ml) containing N,N-diisopropylethylamnine (0.11 ml, 0.63 mmol) and bis(sulfosuccinimidyl)suberate disodium salt (150 mg, 0.26 mmol; Pierce) for 2 h. b was purified by reversed-phase HPLC and lyophilized to give a colorless powder; yield 54%, 50 mg; m/z 715 (MH+). Electrophoretically pure exEGFR (0.5 mg; from Dr. O'Connor-McCourt, ref 15) was reacted with 6-biotinamidohexanoic acid N-hydroxysuccinimide ester (59 nmol; Sigma) in 0.53 ml 10 mM HEPES, 150 mM NaCl, 0.1 mM CHAPS, pH 7.5 buffer (50 min, 25° C.). Unreacted biotinylation reagent was removed by gel filtration (Micro Bio-Spin 6 colunmn, BioRad). Biotinylated exEGFR (0.33 mg) was then reacted with compound b (136 nmol) in 3.3 ml buffer for 2 h. Following removal of excess b by gel filtration in 50 mM Tris-HCI, 100 mM glycine, 0.1 mM CHAPS, pH 7.8, the concentration of free amines in the initial and CRA-derivitized proteins was measured using fluorescamine (16). Biotin content determined using 2-(4'-hydroxyazobenzene)benzoic acid (17) was 1.1 mol/mol exEGFR. The density of phosphonate diester labeling was 19 mol/mol exEGFR. Total protein was measured using BCA (Pierce). Some experiments were done using exEGFR CRA IVa. This compound is identical to IV but for the presence of a disulfide bond in linker. To prepare IVa, the precursor diphenyl N-((3-sulfosuccinimidyl)-3,3'-dithiobispropionyl)amino(4-amidinophenyl) methanephosphonate (compound c) was obtained as described for compound b using 3,3'-dithiobis(sulfosuccinunidylpropionate) (Pierce); yield 6.0 mg, 21.4%; tR24.49 min, >98 purity; 20-50% acetonitrile in 0.1% TFA, 60 min); m/z 751 (MH+). Labeling with biotin and c was as described for IV (biotin and phosphonate diester content of IVa, respectively, 2.3 mol and 18.3 mol/mol exEGFR). Synthesis of peptidyl-CRAs V and Va and their chemical characterization are described in (18). V was conjugated with BSA using γ-maleimidobutyric acid N-hydroxysuccinimide ester as in (13). BSA was pretreated with diphenyl N-(benzyloxycarbonyl)amino(4-amidinophenyl) methanephosphonate (BSA, 21.3 µM; phosphonate, 0.5 mM; solvent, 10 mM PBS containing 5% DMSO; 15.5 h) to block potential V binding sites. V/BSA molar ratio was 3.9 determined from consumption of —SH groups using Ellman's reagent. Storage of I-III was at −70° C. as 10 mM solutions in N,N-dimethylformamide. IV and IVa were stored at −70° C. in 50 mM Tris-HCl, pH 8.0, 0.1M glycine, 0.1 mM CHAPS. V and Va were stored at −70° C. as 10 mM solutions in N,N-dimethylformamide.

ELISA.

Maxisorp 96-well microtitre plates (Nunc) were coated with gp120(421-436) conjugated to BSA (20 ng peptide equivalent/well; see ref 13 for peptide conjugation method), V conjugated to BSA (20 ng peptide-CRA equivalent/well), exEGFR (200 ng/well) or exEGFR-CRA V (200 ng protein equivalent/well) in 100 mM sodium bicarbonate buffer (pH 8.6, 2 h). ELISA procedures were essentially as described in (13). Bound murine IgG was detected with goat anti-mouse IgG-HRP conjugate (Fc specific; Sigma, Saint-Louis, Mo.; 1:1000).

Irreversible CRA Binding.

Following incubation of biotinylated CRAs with Abs or trypsin (porcine, type IX, Sigma) in 50 mM Tris, HCl, 100 mM glycine, 0.1 mM CHAPS, pH 7.7 at 37° C., the reaction mixtures were boiled (5 min) in 2% SDS and subjected to SDS-PAGE (4-20%, Biorad or 8-25% Phast gels, Amersham). Electroblotting and biotin detection procedures using streptavidin-HRP and a chemiluminescent substrate (Supersignal, Pierce) are described in (11). Imaging and quantification was on X ray film (Kodak) using Unscan-it software (Silk scientific, Orem, Utah) or Fluoro-STM Multlmager (Biorad). Band intensities are expressed in arbitrary area units (AAU). Valid comparisons of band intensities from different experiments is not possible as exposure and development times were not held constant. Diisopropyl fluorophosphate (Sigma) was kept at 4° C. until used. In some experiments, biotinylated BSA (Pierce, 8 mol biotin/mol protein) was electrophoresed at several concentrations in parallel with the samples and the biotin content of the CRA adducts was determined. Pseudo-first order rate constants ($kob_{obs}$) were computed from reaction progress curves by fitting to the equation $B_t=B_{max}(1-\exp(-k_{obs}t))$ where $B_t$ represents adduct concentration at various times and $B_{max}$, the initial Ab concentration. Inmnunoblotting with goat anti-mouse IgG Abs was as in (7).

Proteolysis assay. Catalytic activity was measured by fluorimetric determination ($\lambda_{ex}$ 360 nm, $\lambda_{em}$ 470 nm; Varian Cary Eclipse) of the cleavage of amide bond linking aminomethylcoumrain to the C terminal amino acid in short peptide-MCA substrates (10). Catalysts were incubated with peptide-MCA substrates (Pro-Phe-Arg-MCA, Boc-Glu-Ala-Arg-MCA, Boc-Ile-Glu-Ala-Arg-MCA; 200 µM; Peptide International) in 50 mM Tris HCl, 0.1M glycine, 0.025% Tween-20, pH 8.0 at 37° C. in 96-well plates. In some assays, comparison of IgG and trypsin proteolytic activity was done in 10 mM sodium phosphate, pH 7.4, 0.137M NaCl, 2.7 mM KCl, 0.1 mM CHAPS. Authentic aminomethylcoumarin (Peptide International) was used to construct a standard curve from which product release was computed in molar values.

Results

Ab Nucleophilicity Identified with Hapten CRAs.

Phosphonate hapten CRAs I-III (FIG. 7) are analogs of known active site-directed inhibitors of serine proteases (19). Like the serine protease trypsin, IgG from ahealthyhuman subject formed adducts with CRA I that were resistant to boiling and the denaturant SDS (FIG. 8; IgG, 150 kD adducts; trypsin, 21 kD adducts). Pooled IgG from immunologically unmanipulated BALB/c mice formed similar I adducts. The positively charged amidino group in CRA I was originally incorporated in this compound to allow selective recognition of trypsin, which displays preference for basic residues at the P1 site (the residue immediately adjacent to the cleavage site in peptide substrates; ref 20). CRA II lacks the positively charged amidino group adjacent to the covalently reactive phosphorus atom. IgG was 240-fold less reactive with II than I, suggesting the trypsin-like P1 specificity of Abs. III, which contains a weaker leaving group than I did not form detectable adducts with IgG (the presence of methoxy leaving groups reduces the electrophilicity of the phosphorus atom; methoxy-containing phosphonate diesters are reported to bind weakly with certain serine proteases, ref 21). Increasing formation of covalent I adducts with IgG and trypsin was evident as a function of reaction time (FIG. 8B). The velocity of the reaction for IgG was 14.5 fold greater than for trypsin measured under identical conditions (172.7±14.2 and 11.9±0.6 AAU/min, respectively; from linear regression of FIG. 8B data Assuming hydrolysis of the phosphonylated-protein complex is equivalent (see reaction scheme in FIG. 7), it may be concluded that the nucleophilic efficiency of IgG is superior to that of trypsin.

IgG preparations from healthy humans and inmmunologically unmanipulated mice have been documented to cleave small model peptide substrates on the C terminal side of basic residues; the cleavage activity was observed in each of several IgG preparations examined; the activity comigrated with intact 150 kD IgG in denaturing gel filtration studies, and it was expressed by Fab preparations prepared by papain digestion (22). In the present study, we compared the proteolytic activity of trypsin and IgG from a healthy human subject (the same preparation as in FIG. 8 nucleophilicity studies). With Glu-Ala-Arg-MCA and Pro-Phe-Arg-MCA substrates, initial rates of proteolysis by IgG were, respectively, $1.8 \times 10^5$-fold and $6.8 \times 10^5$-fold smaller than by trypsin (FIGS. 9A and B, determined from the slopes of the progress curves). Glu-Ala-Arg-MCA is the preferred substrate for trypsin. Glu-Ala-Arg-MCA and Pro-Phe-Arg-MCA are the preferred substrates for human IgG determined from previous screening of a panel of peptide-MCA substrates (22). The magnitude of proteolysis by this IgG preparation falls within the range reported previously for other human IgG preparations.

Despite its superior nucleophilic reactivity, the IgG is evidently a poor catalyst compared to trypsin.

CRA I and DFP (another active-site directed inhibitor of serine proteases) inhibited the catalytic activity of IgG-catalyzed peptide-MCA cleavage (FIG. 9 C), and DFP inhibited the irreversible binding of CRA I by the IgG (by 95%). These results provide assurance that CRA I binds the catalytic sites of IgG. As DFP binds the active site of serine proteases, its inhibitory effect confirms the serine protease character of the I binding sites of IgG. Electrophoresis of I-IgG adducts under reducing conditions revealed labeling of both subunits by the hapten CRA, evident as biotin-containing bands at 50 kD heavy chain bands and 25 kD light chain bands (FIG. 9 D). Irreversible I binding activity of IgG was lost by preheating the protein at 60° C. for 10 min, indicating the dependence of the nucleophilic reactivity on the native protein confirmation.

Each of 5 polyclonal IgG preparation from healthy humans displayed irreversible binding to I (Table 3). Each of 16 randomly picked scFv clones from a human library formed I-adducts (see example in FIG. 10A), indicating the V domain location of the binding site and suggesting that the nucleophilic reactivity is a shared property of diverse Abs. Ninety one % of the total protein available in Fv MM-F4 shown in FIG. 10A (GenBank #AF522073) displayed nucleophilic reactivity [computed as mol biotin/mol Fv protein in the 27 kD I adduct band; Fv valency 1; reaction conditions as in FIG. 10]. Analyzed by electrophoresis under nonreducing conditions, some scFv reaction mixtures contained CRA I adducts at 55-90 kD in addition to the monomer scFv adducts at 27 kDa. All of the CRA-adduct bands were also stainable with Ab to c-myc, confirming the presence of scFv in the adducts (the recombinant proteins contain a 10 residue c-myc peptide, ref 10). The tendency of scFv to form aggregates has been reported previously (23). Diminished levels of I-adducts were detected when an scFv clone was treated with DFP prior to I-treatment (by 72%). The rate of covalent adduct formation by different Fv clones was variable over a 34-fold range (Table 3), indicating distinct levels of nucleophilic reactivity of different Abs. The reactivity of the 5 polyclonal IgG samples, which represent mixtures of different Abs, was less variable (by 5.4). Comparison of the peptide-MCA cleaving activity (Glu-Ala-Arg-MCA substrate) and irreversible I binding by the scFv clones indicated a strong correlation ($P<0.005$, $r^2=0.77$; FIG. 10B), confirming the functional importance of superior nucleophilic reactivity.

Specific Covalent Binding of Peptidyl and Protein CRA.

Protein CRA IV and peptide CRA Va were analyzed to assess whether antigen-specific Abs can express nucleophilic reactivity coordinated with noncovalent recognition of the antigen. CRA IV is the extracellular domain of a tumor-associated protein, exEGFR, presenting diverse antigenic epitopes derivitized at Lys side chains with the phosphonate diester (19 mol/mol) along with a small amount of biotin to allow detection of adducts. SDS-electrophoresis of CRA IV revealed a major silver-stained and biotin-containing band with nominal mass 90 kDa (mass of exEGFR 85 kDa; mass of hapten phosphonate group, 714 Da). CRA V corresponds to residues 421-431 of the HIV coat protein gp120, along with the amidino surrogate of Lys432 and the covalently reactive phosphonate diester group located at the C terminus. The purity and chemical characterization of this peptidyl CRA has been reported previously (18). Abs raised by routine immunization with exEGFR and the synthetic peptide corresponding to residues 421-436 of gp120 were initially employed to assure the antigenic integrity of these CRAs. ELISA studies indicated that binding of IV and Va (conjugated to BSA) by polyclonal Abs to exEGFR and synthetic gp120(421-436), respectively, was only marginally lower than of the control antigens devoid of phosphonate diester groups, i.e., exEGFR and gp120(421-436), respectively (FIG. 11). Evidently, the epitope structure of the the two antigens is preserved despite the introduction of the phosphonate diester in Lys side chains (IV) and at the C terminus (Va). No binding of anti-exEGFR or anti-gp120(421-436) Abs to immobilized calmodulin and albumin was detected ($A490<0.05$ at antisera dilution 1:1000), confirming the absence of nonspecific protein binding effects. Immobilized CRA IV and CRA Va (conjugated to BSA) did not display unusual binding to nonimmune Abs used as controls for ELISA, indicating that the phosphonate diester group does not result in indiscriminate covalent binding effects.

Covalent binding by the Abs was studied using denaturing electrophoresis as described for the hapten CRAs. Saturable formation of biotin-containing IV adducts with Abs to exEGFR was evident (nominal mass 250 kD). IV adducts of nonimmune IgG were not detectable (FIG. 12). As the IV concentration is small (0.2 µM in FIG. 12) formation of adducts similar to those observed using hapten CRA I is not predicted (FIG. 8; 100 µM I). Little or no adducts were formed in the presence of exEGFR (1 µM) but adduct formation was not impeded by an equivalent concentration of calmodulin, indicating that the covalent binding reaction is at or near the antigen binding site of the Abs. The 250 kD IV adducts were stainable with anti-IgG (data not shown). Each of 3 commercially available monoclonal Abs to exEGFR formed covalent adducts with IVa (according to the suppliers, Ab C225 binds residues 351-364 in the extracellular domain of EGFR; the linear peptide determinant recognized by Abs H11 and C111.6 is not known, but both Abs bind the extracellular domain of the protein), an irrelevant monoclonal Ab did not, and formation of the adducts by the monoclonal Abs was inhibited by exEGFR devoid of phosphonate diester groups but not by the unrelated protein calmodulin. Essentially similar results were obtained using CRA Va (FIG. 13). Formation of biotin-containing 152 kD adducts was saturable as a function of time (mass of Va, 2.2 kD), adduct formation was inhibited by the gp120(421-436)-BSA conjugate (3 µM) but not an equivalent concentration of BSA, and the reaction with nonimmune Abs proceeded slowly compared to the specific Abs.

The pseudo-first order rate constant $k_{obs}$, for accumulation of IV adducts of polyclonal IgG to exEGFR was $1.0\pm0.1$ h$^{-1}$. As no reaction was detected with nonimmune IgG, a precise estimate of $k_{obs}$ is not possible. Using the detection sensitivity of the imaging system as the upper limit for accumulation of adducts over the period of observation in FIG. 12 (133 AAU), the upper limit for $k_{obs}$ is $7.2\times10^{-3}$h$^{-1}$. Similarly, $k_{obs}$ for accumulation of anti-peptide IgG adducts of Va was 496-fold greater than of nonimmune IgG adducts ($17.8\pm3.3$ h$^{-1}$ and $0.4\times10^{-1}\pm0.1\times10^{-1}$ h$^{-1}$, respectively; FIG. 13 data), Discussion Activated nucleophilic residues in conventional serine proteases react covalently with phosphonate diesterprobes, e.g., the Ser residue activated by hydrogen bonding in the catalytic Ser-His-Asp triad of serine proteases. The presence of such nucleophiles in proteolytic and esterolytic Abs has been deduced from mutagenesis and covalent phosphonate binding studies (10-12). Nucleophilic attack on the substrate is the rate limiting step in catalysis by certain enzymes (24). As the reported catalytic rate constants (kcat) of Abs are generally orders of magnitude lower than of enzymes, it has generally been assumed that the deficiency resides in the nucleophilic reactivity of Abs. Studies reported here indicate otherwise. Despite their low proteolytic activity, IgG preparations displayed stronger nucleophilic reactivity than rypsin determined from rates of formation of covalent adducts with hapten phosphonate diesters. Study of polyclonal IgG and individual scFv clones indicated an apparently universal nucleophilic reactivity. In control experiments, the reactivity was lost upon thermal denaturation, consistent with expectations that activation of the nucleophile is dependent on the native structure of the protein. Covalent Ab binding to the phosphonate diester was inhibited by the established serine protease-reactive reagent DFP. Moreover, Ab proteolytic activity was inhibited by the phosphonate as well as DFP, confirming the serine protease-like character of nucleophiles reactive with the phosphonate. These studies suggest nucleophilic reactivity as an intrinsic property of Abs expressed independent of noncovalent antigen binding forces developed over the course of the immune response. This conclusion is consistent with our previous report that the catalytic triad of a proteolytic Ab light chain is encoded by a germline V gene (25).

Both Ab subunits of IgG displayed covalent binding of hapten phosphonate diester I, consistent with studies in which catalytic Ser nucleophiles have been identified in the light (8,10) and heavy chains (12, 26). Study of recombinant scFv clones confirmed the presence of nucleophilic sites in the V domains. The nucleophiles are located within or in the immediate vicinity of the antigen binding site, as suggested by observations of improved covalent binding of antigen-specific Abs to protein CRA IV and peptidyl CRA Va. We did not examine the presence of nucleophilic sites in the constant domains, as the present study was conducted in the context of catalytic activity attributed to the V domains. As the genes encoding the V and constant domains express certain sequence identities (27), the existence of constant domain nucleophiles can not be excluded. Notwithstanding their impressive nucleophilic reactivity, the rate of catalysis by Abs is limited. Presumably, this is because of energetic barriers associated with the deacylation and product release steps (FIG. 7). This statement does not conflict with observations of correlated proteolysis and nucleophilicity of the scFv clones, as increased accumulation of the acylated reaction intermediate will accelerate proteolysis according to the laws of mass action regardless of limitations at subsequent steps in the reaction cycle. In addition to proteases, diverse enzymes involved in chemical transformation of lipids, carbohydrates and nucleic acids owe their catalytic power to covalent mechanisms (28-30). Some of these enzjmes are reported to react with phosphonate probes (e.g., 31). An aldolase Ab has been raised by immunization with a phosphonate diester hapten (32), but its relationship with innate Ab nucleophilicity is unclear. In addition to protease and esterase activities, Abs express nuclease (4), peroxidase (33) and kinase (34) activities. Conceivably, nucleophilic Ab reactivity described here may play a role in these reactions.

Specific polyclonal and monoclonal Abs to EGFR and synthetic gp120(421-436) peptide displayed covalent binding to the CRA-analogs of these antigens (IV and Va, respectively) at levels substantially greater than nonimmune IgG, indicating that the nucleophiles express their reactivity in coordination with noncovalent antigen binding interactions. Noncovalent Ab-antigen binding may be interpreted, therefore, as a mechanism that permits more efficient delivery of the electrophiles (phosphonate groups) to the Ab nucleophiles. The cognate antigens devoid of phosphonate diester groups inhibited the covalent reaction, suggesting spatial proximity between the nucleophile and residues at which non-covalent binding takes place. The following conditions must be met to explain the experimentally observed antigen-specific formation of the CRA adducts: (a) the gernline-encoded nucleophiles must be retained in the Ab combining sites or novel nucleophiles must generated over the course of adaptive Ab specialization; (b) a mechanism must be available to allow improved approach of the Ab nucleophile within covalent binding distance of the phosphonate probe. Precise spatial alignment of Ab nucleophiles in register with the phosphonate groups in IV and Va is unlikely because the Abs were raised by immunization with polypeptides that do not contain these groups. Conversely, the phosphonate electrophiles were placed at the side chain Lys residues of protein IV and the C terminus of peptide Va without foreknowledge of the spatial relationship between the noncovalent and nucleophilic binding sites in the Abs. These considerations suggest that the nucleophiles enjoy sufficient conformational freedom to make contact with imprecisely located phosphonate electrophiles in the antigenic epitope. The mobility of individual amino acids in Ab combining sites following binding to antigen has been reported by other groups (35,36). Previous epitope mapping and mutagenesis studies indicated that the catalytic residues of proteolytic Abs participate minimally in stabilizing the Ab-antigen ground state complex (11, 37), suggesting that the mobility of the nucleophile is not restricted by noncovalent binding interactions. Further support for this model is available from observations that MAbs to VIP (38) and gp41 (8) can cleave multiple peptide bonds in these antigens, presumably by formation of alternate transition states in which the nucleophile is free to initiate attack on spatially neighboring peptide bonds.

Adaptive improvement in the rate of catalysis by Abs is limited by the mechanisms responsible for clonal selection of B cells. If product release exceeds the rate of transmembrane signaling by the BCR necessary to stimulate cell division, cellular proliferation will cease. On the other hand, there is no bar to adaptive improvement of Ab nucleophilicity, as suggested by the results of the present study. The improved nucleophilic reactivities of antigen-specific Abs described here results from routine immunization with polypeptides. It is difficult to ascribe the reactivity to a fortuitous immunological phenomenon, as it was observed in polygonal Abs directed to two different antigens and three distinct monoclonal Abs. Nucleophilic attack on the natural counterparts of the phosphonate groups in IV and Va, e.g., the electrophilic carbonyl groups in the peptide backbone and side chain amides, is predicted to result in formation of covalent acyl-Ab complexes (FIG. 7), allowing prolonged occupancy of the BCR and favoring emergence of Abs with improved reactivity. Admittedly, the phosphonate diester group in CRAs is more electrophilic than the carbonyl group in proteins antigens, but Ab nucleophilicity is comparable or superior to that of trypsin, suggesting the feasibility of nucleophilic Ab attack on protein antigens. Two examples of Abs with the ability to form irreversible covalent complexes with hapten antigens have been reported (39, 40) and certain Abs display SDS-resistant binding to albumin (Paul and coworkers, to be published elsewhere). Ab nucleophilic reactivity could conceivably contribute to Ab-antigen binding without formation of stable covalent bonds. For instance, the nucleophilic reaction may lead to a structure with partial covalent character that does not progress to the acyl-Ab complex because no mechanism is available to donate a proton to the nitrogen atom of the leaving group (C terminal peptide fragment in FIG. 7; ammonia if attack occurs on side chain amide groups).

Important biological effects have been ascribed to the proteolytic activity of Abs found in autoimmune, autoimmune and lymphoproliferative disease (41), e.g., interference with the immunoregulatory (42) and smooth muscle relaxant effects (43) of the neuropeptide VIP. In view of enhanced covalent Ab binding of phosphonate diester groups facilitated by noncovalent binding interactions, peptidyl and proteinic CRAs may be hypothesized to permit permanent and selective blockade of the catalytic activity. Moreover, to the extent that expression of nucleophilicity coordinated with noncovalent antigen binding is a general Ab characteristic, CRA inhibition may be generally useful means to inhibit Ab biological effects regardless of catalytic activity. CRAs IV and Va, for instance, may be used to study the functional roles of Abs from patients with systemic sclerosis and lupus, which are reported to bind EGFR (44) and synthetic gp120(421-436) (45), respectively.

References for Example I

1. Schultz, P. G., and Lerner, R. A. (1995) *Science* 269, 1835-1842
2. Stewart, J. D., and Benkovic, S. J. (1995) *Nature* 375, 388-391
3. Paul, S., Volle, D. J., Beach, C. M., Johnson, D. R., Powell, M. J., and Massey, R. J. (1989) *Science* 244, 1158-1162
4. Shuster, A. M., Gololobov, G. V., Kvashuk, O. A., Bogomolova, A. E., Smirnov, I. V., and Gabibov, A. G. (1992) *Science* 256, 665-667
5. Matsuura, K., and Sinohara, H. (1996) *Biol Chem.* 377, 587-589
6. Lacroix-Desmazes, S., Moreau, A., Sooryanarayana-Bonnemain, C., Stieltjes, N., Pashov, A., Sultan, Y., Hoebeke, J., Kazatchkine, M. D., and Kaveri, S. V. (1999) *Nat. Med.* 5, 1044-1047
7. Paul, S., Sun, M., Mody, R., Tewary, H. K., Stenuner, P., Massey, R. J., Gianferrara, T., Mehrotra, S., Dreyer, T., Meldal, M., and Tramontano, A. (1992) *J. Biol. Chenm.* 267, 13142-13145
8. Hifumi, E., Okamoto, Y., and Uda, T. (1999) *J. Biosci. Bioengin.* 88, 323-327
9. Izadyar, L., Friboulet, A., Remy, M. H., Roseto, A., and Thomas, D. (1993) *Proc. Natl. Acad. Sci. USA* 90, 8876-8880
10. Gao, Q.-S., Sun, M., Rees, A., and Paul, S. (1995) *J. Mol. Biol.* 253, 658-664
11. Paul, S., Tramontano, A., Gololobov, G., Zhou, Y.-X., Taguchi, H., Karle, S., Nishiyama, Y., Planque, S., and George, S. (2001) *J Biol. Chem.* 276, 28314-28320
12. Kolesnikov, A. V., Kozyr, A. V., Alexandrova, E. S., Koralewski, F., Demin, A. V., Titov, M. I., Avalle, B., Tramontano, A., Paul, S., Thomas, D., Gabibov, A. G., and Friboulet, A. (2000) *Proc. Natl. Acad. Sci. USA* 97, 13526-13531
13. Karle, S., Nishiyama, Y., Zhou, Y.-X., Luo, J., Planque, S., Hanson, C., and Paul, S. (2003) *Vaccine* 21, 1213-1218
14. Nishiyama, Y., Taguchi, H., Luo, J. Q., Zhou, Y.-X., Burr, G., Karle, S., and Paul, S. (2002) *Arch. Biochem. Biophys.* 402, 281-288
15. Brown, P. M., Debanne, M. T., Grothe, S., Bergsma, D., Caron, M., Kay, C., and O'Connor-McCourt, M. D. (1994) *Eur. J. Biochem.* 225, 223-233
16. Udenfriend, S., Stein, S., Bohlen, P., Dairman, W., Leirngruber, W., and Wegele, M. (1972) *Science* 178, 871-872
17. Green, N. M. (1965) *Biochem. J.* 94, 23c-24c
18. Taguchi, H., Burr, G., Karle, S., Planque, S., Zhou, Y.-X., Paul, S., and Nishiyama, Y. (2002) *Bioorg. Med. Chem. Lett.* 12, 3167-3170
19. Oleksyszyn, J., and Powers, J. C. (1994) in Methods in Enzymology vol. 244 (Barrett, A. J., ed.) pp. 423-441, Academic Press, New York
20. Oleksyszyn, J., Boduszek, B., Kam, C. M., and Powers, J. C. (1994) *J. Med. Chem.* 37, 226-231
21. Zhao, Q., Kovach, I. M., Bencsura, A., and Papathanassiu, A. (1994) *Biochemistry* 33, 8128-8138
22. Kalaga, R., Li, L., O'Dell, J. R., and Paul, S. (1995) *J. Immunol.* 155, 2695-2702
23. Whitlow, M., Bell, B. A., Feng, S. L., Filpula, D., Hardman, K. D., Hubert, S. L., Rollence, M. L., Wood, J. F., Schott, M. E., Milenic, D. E. and et al. (1993) *Protein Eng.* 6, 989-995
24. Fersht, A. (1985) Enzyme Structure and Mechanism, W. H. Freeman and Company, New York
25. Gololobov, G., Sun, M., and Paul, S. (1999) *Mol. Immunol.* 36, 1215-1222
26. Zhou, G. W., Guo, J., Huang, W., Fletterick, R. J., and Scanlan, T. S. (1994) *Science* 265, 1059-1064
27. Wuilmart, C., and Urbain, J. (1976) J. Immunogenet. 3:1-14
28. Jia, Y., Kappock, T. J., Frick, T., Sinskey, A. J., and Stubbe, J. (2000) *Biochern.* 39, 3927-3936
29. Vocadlo, D. J., Davies, G. J., Laine, R., and Withers, S. G. (2001) *Nature* 412, 835-838
30. Interthal, H., Pouliot, J. J., and Charnpoux, J. J. (2001) *Proc. Natl. Acad. Sci. USA* 93, 12009-12014
31. Crennell, S. J., Garman, E. F., Philippon, C., Vasella, A., Laver, W. G., Vimr, E. R., and Taylor, G. L. (1996) *J. Mol. Biol.* 259, 264-280
32. Wirsching, P., Ashley, J. A., Lo, C. L., Janda, K., and Lerner, R. (1995) *Science* 270, 1775-1782
33. Takagi, M., Kohda, K., Hamuro, T., Harada, A., Yamaguchi, H., Kamachi, M., and Imanaka, T. (1995) *FEBS Lett.* 375, 273-276
34. Nevinsky, G. A., Kit, Y. Ya., Semenov, D. V., Khlimankov, D. Yu., and Buneva, V. N. (1998) *Appl. Biochem. Biotechnol.* 75, 77-91
35. Jimenez, R., Salazar, G., Baldridge, K. K., and Romesberg, F. E. (2003) *Proc. Natl. Acad. Sci. USA* 100, 92-97
36. Braden, B. C., and Poljak, R. J. (1995) FASEB J. 1, 9-16
37. Paul, S., Volle, D. J., Powell, M. J., and Massey, R. J. (1990) *J. Biol. Cheim.* 265, 11910-11913
38. Sun, M., Gao, Q. S., Kirnarskiy, L., Rees, A., and Paul, S. (1997) *J. Mol. Biol.* 271, 374-385
39. Rao, G., and Philipp, M. (1991) *J. Protein Chem.* 10, 117-122
40. Lefevre, S., Debat, H., Thomas, D., Friboulet, A., and Avalle, B. (2001) *FEBS Lett.* 489, 25-28
41. Paul, S. (2000) in Chemical Immunology: Catalytic Antibodies, Vol. 77 (Paul, S., ed) pp. 1-158, S. Karger and A.G. Basel, Switzerland
42. Berisha, H. I., Bratut, M., Bangale, Y., Colasurdo, G., Paul, S., and Said, S. I. (2002) *Pulm. Pharmacol. Ther.* 15, 121-127
43. Voice, J. K., Grinninger, C., Kong, Y., Bangale, Y., Paul, S., and Goetzl, E. J. (2003) *J. Immunol.* 170, 308-314
44. Planque S., Zhou Y.-X., Nishiyama Y., Sinha, M., O'Connor-McCourt M., Arnett F. C. and Paul S. (2003) *FASEB J.* 17, 136-143
45. Bermas, B. L., Petri, M., Berzofsky, J. A., Waisman, A., Shearer, G. M., and Mozes, E. (1994) *AIDS Res. Hum. Retroviruses* 10, 1071-1077

[1] Abbreviations: Ab, antibody; AMC, 7-amino-4-methylcoumarin; BSA, bovine serum albumin; CRA, covalently reactive antigen analog; DFP, diisopropyl fluorophosphate; exEGFR, extracellular domain of human epidermal growth factor receptor; KLH, keyhole limpet hemocyanin; MCA, methylcoumarinamide; V domain, variable domain; VIP, vasoactive intestinal peptide

EXAMPLE II

Specific HIV gp120 Cleaving Antibodies Induced by Covalently Reactive Analog of gp120

Promiscuous cleavage of small peptide substrates is a heritable function of Abs[1] encoded by germline gene V domains (reviewed in 1). Peptide bond cleaving Abs with specificity for individual polypeptides have been identified in patients with autoimmune (1) and autoimmune disease (2). Specific monoclonal Abs and Ab L chain subunits displaying proteolytic activities can be raised by routine immunization with polypeptides (3, 4). Under ordinary circumstances however, adaptive maturation of the catalytic activity may not be a favored event. B cell clonal selection occurs by sequence diversification of genes encoding the Ab V domains, followed by selective binding of the antigen to cell surface Abs with the greatest affinity, which drives proliferation of the B cells (5). Catalysis entails chemical transformation of the antigen and release of products from the Ab, which may cause cessation of B cell proliferation when the catalytic rate exceeds the rate of transmembrane signaling necessary to stimulate cell proliferation.

Originally developed as irreversible inhibitors of conventional serine proteases, haptenic phosphonate esters are reported to bind the nucleophilic sites of natural proteolytic Abs covalently (6, 7). The haptenic phosphonates could potentially serve as covalently reactive analogs (CRAs) for inducing the synthesis of Abs with improved nucleophilicity. To the extent that Ab nucleophilicity is rate limiting in proteolysis, its enhancement may permit more rapid peptide bond cleavage, i.e., if the subsequent steps in the catalytic reaction cycle (hydrolysis of the acyl-Ab complex and product release do not pose significant energetic hurdles; FIG. 14). The innate character of Ab nucleophilic reactivity is the central element of this approach, and there is no requirement for de novo formation of chemically reactive sites over the course of V domain sequence diversification. Most previous attempts to program the structure of catalytic sites in Abs, in comparison, have relied on noncovalent stabilization of the oxy anionic transition state (i.e., by immunization with transition state analogs; 8, 9). An Ab with esterase activity (10) and another with aldolase activity (11) utilize covalent catalytic mechanisms, but the relationship of these activities to innate Ab nucleophilicity is unclear.

An ideal antigen-specific proteolytic Ab may be conceived to combine traditional noncovalent binding interactions in the ground state of the Ab-antigen complex with nucleophilic attack on the peptide backbone. The ground state interactions are desirable to obtain specificity for individual polypeptide antigens. No impediments for catalysis are presented by the stable ground state complexes, provided the noncovalent interactions are carried over into the transition state complex and are properly coordinated with nucleophilic attack at the reaction center. In theory, synthesis of antigen-specific proteolytic Abs could be induced by an analog that presents a mimetic of the chemical reaction center in the context of classical antigenic epitopes available for noncovalent binding interactions. If the reaction proceeds by a lock-and-key stereo chemical mechanism, the mimetic must be located precisely at the position of the intended scission bond in the backbone of the polypeptide antigen. In the instance of large proteins, locating the mimetic within the protein backbone is outside the range of present-day synthetic technologies. A potential solution is to place the mimetic group at amino acid side chains using chemical linker techniques. An Ab nucleophile that recognizes the side chain mimetic could facilitate proteolysis if it enjoys sufficient conformational freedom to approach the polypeptide backbone of the substrate and form the acyl-Ab complex (FIG. 14).

We describe here the characteristics of Abs induced by a covalently reactive analog (CRA) of the HIV-1 coat protein gp120 (gp120-CRA), consisting of phosphonate diester groups located in Lys side chains of the protein. Enhanced serine protease-like nucleophilic reactivity of the Abs was observed. One monoclonal Ab cleaved gp120 slowly and specifically, it displayed preference for cleavage on the C terminal side of Lys/Arg residues, and the catalytic reaction was susceptible to CRA inhibition. These findings are the first indications that Abs with proteolytic activity specific for individual proteins can be raised on demand.

Materials and Methods

Hapten, gp120-CRAs and Biotinylated Proteins. Synthesis of hapten CRAs I and II (FIG. 14) and their characterization by ESI-mass spectroscopy and elemental analyses have been described previously (12). For preparation of gp120-CRA III, the precursor diphenyl N—[O-(3-sulfosuccinimidyl)suberoyl]amino(4amidinophenyl)methanephosphonate (IV) was synthesized by mixing a solution of diphenyl amino(4-arnidinophenyl)methanephosphonate (79 mg, 0.13 mmol) in DMF (2 ml) containing N,N-diisopropylethylamine (0.11 ml, 0.63 mmol) and bis(sulfosuccinimidyl)suberate disodium salt (150 mg, 0.26 mmol; Pierce) for 2 h. IV was obtained by reversed-phase HPLC (12) and lyophilized to give a colorless powder (yield 54%, 50 mg; m/z 715 (MH+) by electrospray ionization mass spectroscopy). IV (1.1 mg) was reacted with electrophoretically pure gp120 (0.5 mg; Immunodiagnostic Inc, MN strain, purified from baculovirus expression system) in 5 ml 10 mM HEPES, 25 mM NaCl, 0.1 mM CHAPS, pH 7.5 buffer (2 h, 25° C.). Excess IV was removed by gel filtration (Micro Bio-Spin 6 disposable column, BioRad), and the concentration of free amines in the initial protein and CRA-derivitized protein was measured using fluorescamine (13). The density of labeling was varied as needed from 4.0 to 32.6 mol CRA/mol gp120 by varying the concentration of IV. Preparation of gp120 labeled at Lys residues with biotin (Bt-gp120) was by similar means using 6-biotinamidohexanoic acid N-hydroxysuccinimide ester (Sigma). The reaction time and reactant concentrations were controlled to yield biotin/gp120 molar ratios 0.8-1.9. Unreacted biotinylation reagent was removed using a disposable gel filtration column in 50 mM Tris-HCl, 100 mM glycine, 0.1 mM CHAPS, pH 7.8. The biotin content was determined using 2-(4'-hydroxyazobenzene)benzoic acid (14). Total protein measurements were done using the BCA method (Pierce kit). Biotinylated III was prepared from Bt-gp120 as described for III. With increasing incorporation of the hapten groups, biotinylated III tended to form dimmers and trimers evident in SDS-electrophoresis gels as bands at ~240 kD and 380 kD (nominal mass of monomer gp120, 120 kD). Biotinylated III at hapten density similar to the non-biotinylated III employed as immunogen (23 mol/mol gp120) contained the monomer, dimer and trimer species at proportions of 50%, 21% and 29%, respectively. Protein-CRAs were lyophilized and stored at −20° C. until used. Bt-gp120 was stored at −70° C. in 50 mM Tris-HCl, pH 8.0, 0.1M glycine, 0.1 mM CHAPS. Storage of I and II was at −70° C. as 10 mM solutions in N N-dimethylformamide. The extracellular domain of EGFR (exEGFR) obtained from Dr. Maureen O'Connor (15) was biotinylated as described for gp120 (0.9 mol biotin/mol exEGFR).

Antibodies.

MAbs were prepared from female MRL/MpJ-Fas$^{lpr}$ mice (Jackson Laboratory, Bar Harbor, Me.; 4-5 wk) inmmunized with gp120-CRA III (23 mol phosphonate diester/mol gp120). The mice were injected intraperitoneally on days 0, 14 and 28 days with gp120-CRA III (11 μg) in Ribi adjuvant (MPL+TDM emulsion; Sigma) followed by a fourth intravenous booster without adjuvant on day 55. Blood was obtained from the retroorbital plexus over the course of the immunization schedule. Three days following the final injection, hybridomas were prepared by fusion of splenocytes with myeloma cell line (NS-1; 3). Following identification of wells secreting the desired Abs by ELISA, monoclonal cell lines were prepared by two rounds of cloning by limiting dilution. Monoclonal IgG was prepared from tissue culture supernatants containing MAbs (200 ml) by affinity chromatography on immobilized Protein G (3). Control MAbs (anti-VIP clone c23.5 and anti-yellow fever virus antigen clone CRL 1689; ATCC) and serum IgG were purified similarly. The IgG preparations were electrophoretically homogeneous, determined by silver staining of overloaded IgG and immunoblotting with specific Abs to mouse IgG (3). Additional immunizations of female BALB/c mice (Jackson; 4-5 wk) with gp120 or gp120-CRA were carried out similarly. MAb heavy and light chain isotypes were determined by ELISA as described (3).

ELISA.

Maxisorp 96-well microtitre plates (Nunc) were coated with gp120 or gp120-CRA (40-100 ng/well) in 100 mM bicarbonate buffer, pH 8.6. Routine ELISAs were carried out as described (16). For assay of irreversible binding, the Abs were allowed to bind the plates and the wells were treated for 30 min with 2% SDS in 10 mM sodium phosphate, 137 mM NaCl, 2.7 mM KCl, 0.05% Tween-20, pH 7.4 (PBS-Tween) or PBS-Tween without SDS (control wells for measurement of total binding). The wells were then washed 3 times with PBS-Tween and bound IgG was determined as usual using a peroxidase conjugate of goat anti-mouse IgG (Fc specific; Sigma, Saint-Louis, Mo.). Observed values of binding were corrected for nonspecific binding in wells containing nonimmune IgG or nonimmune mouse serum (A490<0.03). Percent residual binding in SDS-treated wells was computed as: $(A_{490, \text{ SDS treated wells}}) \times 100/(A_{490, \text{ PBS-Tween treated wells}})$.

Electrophoresis of Ab-CRA Complexes.

Irreversible binding of biotinylated CRAs by purified IgG was determined by denaturing electrophoresis (6). Briefly, the reaction mixtures were incubated at 37° C. in in 50 mM Tris-HCl, 0.1 M glycine pH 8.0. SDS was added to 2%, the mixtures boiled (5 min) and then subjected to SDS-PAGE (4-20%, Biorad, Hercules, Calif.; or 8-25% Phast gels, Amersham). Following electroblotting onto nitrocellulose membranes (0.22 μm, Biorad), the membranes were blocked with 5% skim milk in PBS-Tween and processed for detection of IgG or biotin using peroxidase conjugated goat anti-mouse IgG (Sigma) or peroxidase conjugated streptavidin, respectively. Imaging and quantification were using X ray film (Kodak) with Unscan-it software (Silk scientific, Orem, Utah) or a Fluoro-STM MultiImager (Biorad). Biotinylated BSA (11 mol biotin/mol BSA; Sigma) was employed to construct a standard curve (0.06-1.5 pmol biotin/lane).

Hydrolysis Assays.

Biotinylated proteins were incubated with IgG in 50 mM Tris-HCl, 0.1 M glycine, 0.1 mM CHAPS, pH 8 at 37° C., the reaction was terminated by addition of SDS to 2%, the samples were boiled (5 min) and then analyzed by reducing SDS-gel electrophoresis (4-20%, BioRad). Biotin containing protein bands in blots of the gel were identified and quantified as in the preceding section. In some blots, reaction products were identified by immunoblotting using peroxidase conjugated goat anti-gp120 Abs (Fitzgerald, Concord, Mass.; cat #60-H14) (16). N terminal sequencing of protein bands from electrophoresis gels was done as described previously (17). Hydrolysis of peptide-MCA substrates (Peptide Intn, Louisville, Ky. or Bachem Biosci., King of Prussia, Pa.) was determined in 96-well plates by fluorimetric detection of aminomethylcoumarin (Varian Cary Eclipse; $\lambda_{ex}$360 nm, $\lambda_{em}$470 nm) with authentic aminomethylcoumarin as standard (6). Cleavage of (Tyr$^{10}$-$^{125}$I)VIP by MAb c23.5 was measured as the radioactivity rendered soluble in trichloroacetic acid (17). Kinetic parameters for cleavage of increasing concentrations of peptide-MCA substrates were determined from the Michaelis-Menten equation: $v=(V_{max}[S])/(K_m+[S])$. Because of the expense of studying gp120 cleavage at large concentrations of the protein, $K_d$ (~$K_m$) and $k_{cat}$ for this reaction were obtained from the general quadratic equation (17): $[CS]^2-[CS]([C_t]+[S_t]+K_d)+[C_t][S_t]=0$, where $[C_t]$ and $[S_t]$ are the total concentrations of catalyst and substrate, and [CS] is the catalyst-substrate concentration. The method consists of calculation of [CS] at a series of assumed $K_d$ values. The assumed $K_d$ value yielding the best fit (by linear regression) between the observed reaction velocity and [CS] represents the experimentally determined $K_d$. $k_{cat}$ is computed as the slope of the observed velocity versus [CS] plot.

Results gp120-CRA design and validation. Synthesis of hapten CRAs I and II (FIG. 14) and their covalent reactivity with naturally occurring proteolytic Abs has been described previously (6,7). The electrophilic phosphonate mimics the peptide bond carbonyl group susceptible to nucleophilic attack, the positively charged amidino group adjacent to the phosphonate diester serves as a nimic of Lys/Arg P1 residues at which cleavage by germline encoded proteolytic Abs is observed (6), and the biotin group in I permits sensitive detection of Ab-phosphonate adducts. gp120-CRA III contains phosphonate diester groups in spatial proximity with antigenic epitopes presented by the protein. Multiple phosphonate diester groups were available per molecule of gp120, allowing presentation of the electrophilic hapten in conjunction with diverse antigenic epitopes.

Robust polyclonal Ab responses in MRL/lpr and BALB/c mice immunized with III were observed by routine ELISA. Abs raised to III were bound at somewhat greater levels by immobilized III than control gp120 devoid of phosphonate diester groups (FIG. 15). Conversely, Abs raised to control gp120 recognized immobilized III, but the binding was 3-4 fold lower than by immobilized gp120 (e.g., at serum dilution of 1:1000, A490 0.44±0.03 for immobilized III and 1.40±0.03 for immobilized gp120). III-binding by nonimmune Abs was negligible, indicating that indiscriminate covalent binding at the hapten groups was not a problem. The observed differences in the antigenic reactivity of gp120 and III were held to be sufficiently small to proceed with further Ab studies. To facilitate high-throughput screening, the feasibility of measuring irreversible III-binding by Abs was studied by ELISA. Following binding of polyclonal Abs anti-III Abs to the immobilized antigens, ELISA plates were treated with the denaturant SDS to remove reversibly bound Abs. SDS treatment allowed essentially complete removal of anti-III Abs bound by control gp120 devoid of hapten phosphonate groups. In comparison, 13-40% of the overall anti-III Ab binding activity consistently remained bound to immobilized III following SDS treatment in 3 repeat experiments. SDS-electrophoresis and immunoblotting with Abs to mouse IgG confirmed formation of irreversible Ab-III complexes in boiled reaction mixtures (FIG. 15 inset, lane 3, estimated mass from extrapolated standard curve of molecular mass standards, ~400 kD; large complexes can be formed by binding of multiple Abs to hapten groups in III).

Catalytic Activity.

MAbs were prepared from MRL/lpr mice immunized with gp120-CRA III. This mouse strain develops lupus-like autoimmune disease attributable to the dysfunctional Fas-receptor gene. Spontaneous development of proteolytic Abs (18) and increased synthesis of esterase Abs in response to immunization with phosphonate monoester haptens (19,20) have been reported in this mouse strain. Supernatants from 712 hybridoma wells (two splenocyte-myeloma cell fusions) were screened for SDS-resistant binding to III. IgG from seven wells was positive for this activity. Following cloning of the cells by limiting dilution, monoclonal IgG from the supernatants of the seven cell lines was purified and the binding assays were repeated (FIG. 16; clones YZ 18, IgG2a,κ; YZ19, IgG2b,κ; YZ20, IgG2a,κ; YZ21, lgG2a,κ; YZ22, IgG2a,κ; YZ23, IgG2a,κ and YZ24, IgG1,κ). Of total binding observed without SDS treatment of the ELISA plates, residual binding following the detergent treatment was 43-83% in 4 repeat assays. All seven MAbs were also bound by gp120 devoid of hapten CRA groups determined by routine ELISA without SDS treatment, indicating that they are not directed to neoepitopes generated by chemical modification procedures used for III preparation. An irrelevant MAb (clone CRL 1689) displayed no detectable binding of III or gp120.

Of seven MAbs with irreversible III-binding activity, slow cleavage of Bt-gp120 by three MAbs was detected (YZ18, YZ20, YZ24), determined by appearance of biotin-containing fragments of the protein in SDS-electrophoresis gels. The electrophoretic pattern of Bt-gp120 cleaved by MAbs YZ18 and YZ24 were similar to that shown for MAb YZ20 in FIG. 17. MAb YZ20 was studied further as it cleaved Bt-gp120~5 fold more rapidly than the other two MAbs. The consumption of gp120 was time dependent (FIG. 17A). Major biotin-containing cleavage products with apparent mass 55 kD and 50 kD were observed, along with less intensely stained bands at 27 kD and 15 kD. A band at 35 kD was visible in overexposed gels, but this does not represent a product of MAb cleavage, as it was present at similar density in control incubations of Bt-gp120 in diluent. A control irrelevant MAb (clone CRL 1689) did not cleave Bt-gp120. Immunoblotting using polyclonal anti-gp120 Abs confirmed that non-biotinylated gp120 is also susceptible to cleavage by the MAb (55 kD cleavage product, FIG. 17B). Both detection methods allow quantification of gp120 cleavage by measuring depletion of intact gp120. Neither method provides guidance about the complete product profile or product concentration, as Bt-gp120 contains minimal amounts of biotin (~1 mol/mol gp120), and the polyclonal Abs used for immunoblotting do not react equivalently with the cleavage products.

MAb YZ20 did not cleave biotinylated BSA or the extracellular domain of the epidermal growth factor (exEGFR), Indicating selectivity for gp120 (FIG. 18A). Attempts to identify the bonds cleaved by MAb YZ20 were unsuccessful. N-terminal sequencing of the 55 kD and 50 kb bands yielded identical sequences (TEKLVVVTVYY; SEQ ID No. 7), corresponding to the N terminal residues of gp120. Sequencing of the 15 kD band from the YZ20 reaction mixture did not yield detectable phenylthiohydantoin derivatives of amino acids, possibly due to a blocked N termrinus. Identification of the 27 kD gp120 fragment is complicated because of its configuration with the Ab light chain in reducing gels. As identification of the precise bonds in gp120 cleaved by the MAb was not central to the present study, we turned to the use of model peptide substrates for determination of scission bond preferences. A fluorimetric assay was employed to determine MAb-catalyzed cleavage of the amide bond linking aminomethylcoumarin to the C terminal amino acid in a panel of peptide-MCA substrates (FIG. 18B). The peptide-MCA substrates are used at excess concentration (200 .mu.M), permitting detection of even weakly cross-reactive catalytic Abs. Selective cleavage at Arg-MCA and Lys-MCA was observed, with no evident cleavage on the C terminal side of neutral or acidic residues. To confirm that the rate differences are due to recognition of the basic residue at the cleavage site (as opposed to remote residues), we studied two tripeptide substrates identical in sequence except for the N terminal residue at the scission bond, Gly-Gly-Arg-MCA attd Gly-Gly-Leu-MCA. The former substrate was cleaved at detectable levels by Ab YZ20 [0.31.+−.0.01 (s.d.).mu.M AMC/19 h/.mu.M IgG], whereas the fluorescence intensity in reaction mixtures of the latter substrate and the Ab was statistically indistinguishable from background values observed in assay diluent [0.02.+−.0.04.mu.M AMC/19 h/.mu.M IgG; P>0.05; student's t-test; unpaired; FIG. 18C]. The basic residue preference is consistent with the presence of positively charged amidino groups neighboring the phosphonate groups in the immunogen (III) and selective cleavage on the C terminal side of Arg/Lys residues by germline encoded proteolytic Abs observed previously (21,22).

Attainment of the desired catalytic properties, i.e., the ability to combine high affinity for individual antigens with rapid turnover, can be judged from the Km and kcat parameters (moles antigen cleaved/mol Ab/unit time). The Km of MAb YZ20 for Bt-gp120 was about 200-fold smaller than its preferred peptide-MCA substrate (E-A-R-MCA; Table 4; single letter code for amino acids), consistent with development of specificity for gp120 by immunization with III. Twelve mol E-A-R-MCA were cleaved per mole MAb YZ20 over the course of the reaction (22 h), indicating that the MAb is capable of turnover, a defining feature of a catalyst. Turnover of Bt-gp120 was ~10-fold lower than of E-A-R-MCA. Previously, conventional non-Ab serine proteases were reported to cleave short peptide more rapidly than large proteins (23), presumably because the former substrates are more readily accessible to the catalytic site.

Nucleophilic Reactivity.

gp120 hydrolysis by MAb YZ20 was inhibited by hapten CRA II (FIG. 19), confirming the serine protease-like character of the MAb. II inhibition of MAb YZ20 cleavage of gp120 was 90-fold more potent than inhibition of MAb c23.5 cleavage of VIP (IC50, 0.4 µM and 36.0 µM, respectively). The latter MAb was obtained by immunization with VIP devoid of phosphonate diester groups (3). Superior reactivity of the hapten CRA with MAb YZ20 is consistent with the conclusion of strengthened Ab nucleophilicity in response to immunization with phosphonate groups present in the gp120-CRA immunogen.

Figure 19:
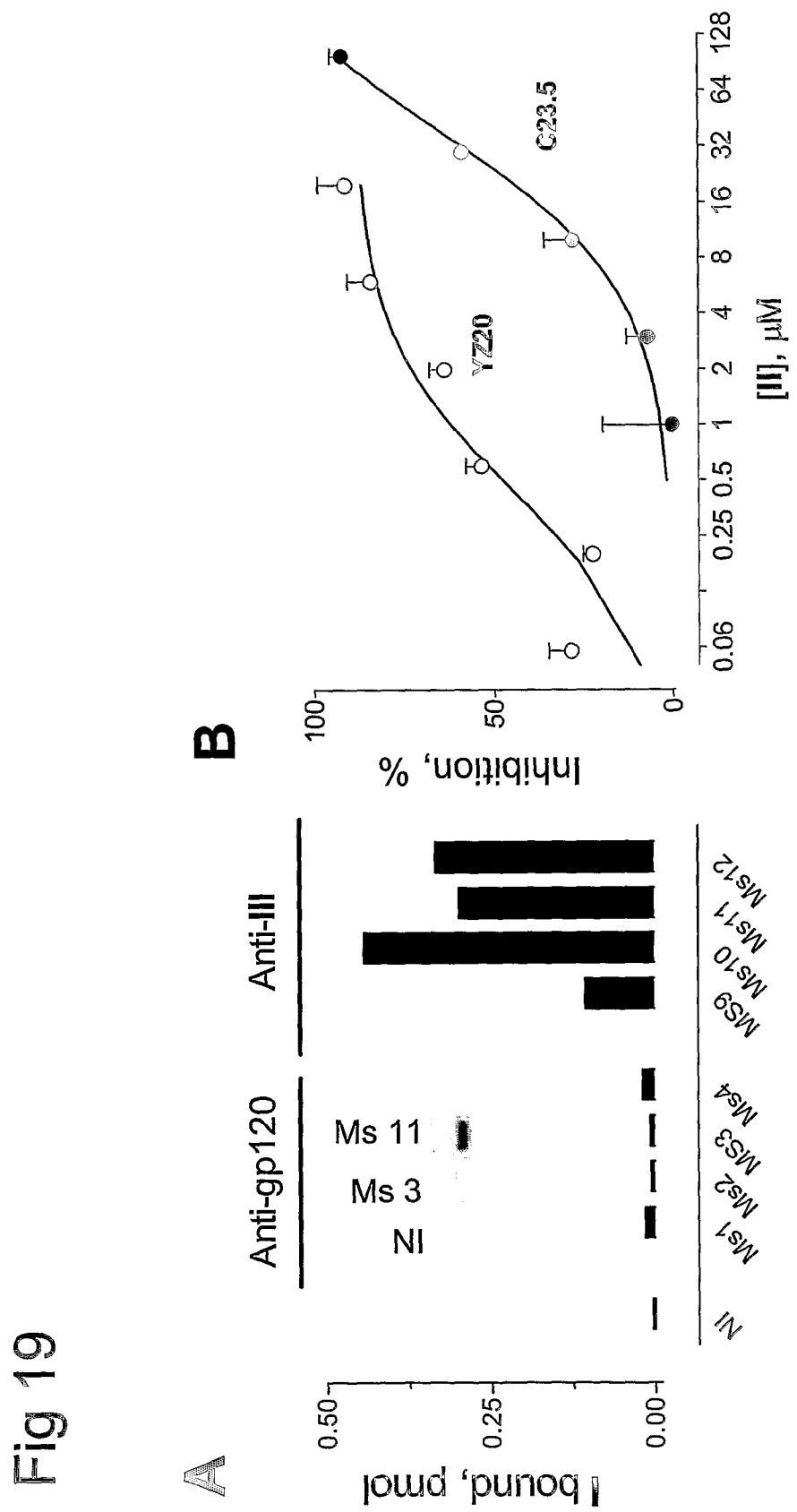

To confirm induction of nucleophilicity, irreversible hapten CRA I binding by polyclonal IgG was measured. The hapten CRA does not contain antigenic epitopes belonging to gp120 and noncovalent binding interactions are not anticipated to contribute to its irreversible binding by Abs. IgG samples from all four mice immunized with III displayed superior I binding compared to IgG from mice immunized with control gp120 (mean values, 0.31 and 0.01 pmol I; P<0.02, Student's t test, unpaired observations) as well as pooled nonimmune IgG (FIG. 19). BALB/c mice were studied in this immunization. It may be concluded that synthesis of nucleophilic Abs in response to immunization with III is not restricted to autoimmune hosts (MAbs to gp120-CRA III were prepared from MRL/lpr mice).

Discussion

The goal of this study was to strengthen the intrinsic serine protease-like reactivity of Abs and direct the reactivity to cleavage of gp120. Improved irreversible binding of hapten CRAby Abs following immunization with gp120-CRA III was evident, and the hapten CRA was a potent inhibitor of gp120 cleavage by a MAb. These observations suggest adaptive improvement of Ab nucleophilicity induced by the phosphonate diester groups. Specificity of the Abs for gp120 was obtained by traditional noncovalent mechanisms, i.e., recognition of gp120 epitopes located in the proximity of the phosphonate diester groups. No cleavage of unrelated proteins by the gp120 cleaving MAb was observed and the Km value of cleavage of a model peptide was 200-fold greater than of gp120 cleavage, indicating absence of indiscriminate proteolysis.

Proteolysis entails Ab attack on the backbone of gp120 whereas the phosphonate electrophiles are located in Lys side chains of the immunogen. As MAbs raised to gp120-CRA displayed proteolytic activity, the nucleophile developed to recognize the side chain electrophiles must enjoy sufficient conformational freedom to attack the polypeptide backbone. Movements of individual amino acids in Ab combining sites following binding to antigen have been reported (24,25). Epitope mapping and mutagenesis studies of certain proteolytic Abs have indicated that the catalytic residues do not participate in stabilization of the Ab-antigen ground state complex (26,27), suggesting that the mobility of the nucleophile may not be restricted by initial noncovalent Ab-antigen interactions. Naturally occurring MAbs to VIP (17) and gp41 (4) cleave multiple peptide bonds in these antigens, which may be explained by hypothesizing formation of alternate transition states in which the nucleophile is free to initiate nucleophilic attack on spatially neighboring peptide bonds (reviewed in 28). Understanding the extent of conformational freedom of Ab nucleophiles is important, as there is no viable alternative to locating the peptide bond mimetic in the side chains when large proteins must be used to induce the synthesis of catalytic Abs. In addition to direct structural analysis of nucleophile movements in available catalytic Abs, the length and flexibility of the linker utilized to attach the phosphonate groups at Lys side chains can be varied in future studies to assess the flexibility of the catalytic site. In the case of synthetic peptide immunogen, the phosphonate groups can be incorporated within the peptide backbone to better mimic the intended scission bond (7). However, synthetic peptides often fail to assume conformations similar to their cognate determinants in full-length proteins, in which case anti-peptide Abs do not recognize the parent proteins.

The fully competent catalytic machinery found in modern non-Ab serine proteases has presumably evolved in response to selection pressures that optimized each of the rate limiting steps in the catalytic cycle. In comparison, a CRA immunogen can at best select for Abs with the greatest covalent attack capability. No selection for hydrolysis of the acyl-Ab complex or the subsequent product release steps is anticipated, which may account for observations of limited Ab turnover. Two previous attempts to raise esterase Abs indicated the formation of irreversible substrate binding by Abs (29,30), suggesting the need to optimize events occurring after nucleophilic attack by the Abs. Further, structural refinements of the immunogen could be implemented to help guide the Ab-antigen complex towards the catalytic pathway, e.g., inclusion of a component that bind a water molecule and facilitate hydrolysis of the acyl-protein complexes. Notwithstanding this weakness, the results reported here represent a significant advance towards developing antigen-specific proteolytic Abs. Previously, several Abs with haptenic ester hydrolyzing activity have been raised based on the premise that catalytic sites capable of noncovalent stabilization of the oxyanionic transition states can be formed de novo over the course of adaptive sequence diversification of Ab V domains (8,9). This approach has not been successful for development of proteolytic Abs. Pollack and Schultz described the failure of a phosphonate monoester analog of Phe-Leu-Ala to induce proteolytic Ab synthesis (31). No attempt was made in this study to recruit the intrinsic properties of natural Abs for the purpose of protease synthesis, i.e., their nucleophilicity and selective recognition of basic residues adjacent to the cleavage site. Recently, phosphonate monoester were discovered to form covalent bonds with nucleophiles in serine proteases, but their reactivity is weaker than the diester used in the present study, and no detectable reaction occurs unless an adjacent positive charge is present (6,12).

Evidence for increased potency due to the catalytic function has recently been published in regard to Ab antagonism of the biological effects of VIP, a 28-amino acid neuropeptide (32,33). Concerning gp 120, a major hurdle has been to induce the synthesis of Abs that recognize the determinants involved in viral entry, i.e., the binding sites for host CD4 and chemokine receptors. Most Abs raised to monomer gpl20 are directed to its variable region epitopes, and the Abs do not neutralize diverse HIV-1 strains found in different geographical locations (34). Reversibly binding Abs must bind at or near the receptor binding sites of gp120 to sterically hinder HIV entry into host cells. Proteolytic Abs offer the potential advantage of gp120 inactivation even if cleavage occurs at a site that does not itself participate in binding to host cells. Discussion of the immunity herapeutic potential of MAbs to gp120-CRA III is beyond the scope of the present study, but initial HIV-1 neutralization studies suggest that certain MAbs raised to gp120-CRA III neutralizes HIV-1 primary isolate ZA009 (peripheral blood mononuclear cell cultures, infection measured by determining p24 antigen concentrations; Paul and coworkers, to be published elsewhere). A potential pitfall is that proteolytic Abs to monomer gp 120-CRA may not recognize trimeric gp120 on the surface of HIV-1, as observed for reversibly binding Abs to the protein (35). The CRA immunogen techniques described in the present study are readily applicable to recently developed recombinant mimetics of trimeric gp120 (36), as well as whole HIV-1 particles.

References for Example II

1. Tramontano, A., Golobov, G., and Paul, S. (2000) in *Catalytic Antibodies, Chern Inzrnunol* Vol. 77, (Paul, S., ed), pp. 1-17, Karger, New York.
2. Lacroix-Desmazes, S., Moreau, A., Sooryanarayana-Bonnemain, C., Stieltjes, N., Pashov, A., Sultan, Y., Hoebeke, J., Kazatchkine, M. D., and Kaveri, S. V. (1999) *Nat. Med.* 5, 1044-1047
3. Paul, S., Sun, M., Mody, R., Tewary, H. K., Stemmer, P., Massey, R. J., Gianferrara, T., Mehrotra, S., Dreyer, T., Meldal, M., and Tramontano, A. (1992) *J. Biol. Chem.* 267, 13142-13145
4. Hifurni, E., Okamoto, Y., and Uda, T. (1999) *J. Biosci. Bioengin.* 88, 323-327
5. Nossal, G. J. (2002) *Immunol. Rev.* 185, 15-23
6. Paul, S., Tramontano, A., Gololobov, G., Zhou, Y. X., Taguchi, H., Karle, S., Nishiyama, Y., Planque, S., and George, S. (2001) *J. Biol. Chem.* 276, 28314-28320

7. Taguchi, H., Burr, G., Karle, S., Planque, S., Zhou, Y. X., Paul, S., and Nishiyama, Y. (2002) *Bioorg. Med. Chem. Lett.* 12, 3167-3170
8. Tramontano, A., Janda, K. D., and Lerner, R. A. (1986) *Proc. Natl. Acad. Sci. USA* 83, 6736-6740
9. Schultz, P. G., and Lerner, R. A. (1995) *Science* 269, 1835-1842
10. Wagner, J., Lerner, R. A., and Barbas, C. F., 3rd. (1995) *Science* 270, 1797-1800
11. Zhou, G. W., Guo, J., Huang, W., Fletterick, R. J., and Scanlan, T. S. (1994) *Science* 265, 1059-1064
12. Nishiyama, Y., Taguchi, H., Luo, J. Q., Zhou, Y. X., Burr, G., Karle, S., and Paul, S. (2002) *Arch. Biochein. Biophys.* 402, 281-288
13. Udenfriend, S., Stein, S., Bohlen, P., Dairman, W., Leimgruber, W., and Weigele, M. (1972) *Science* 178, 871-872
14. Green, N. M. (1965) *Biochlen. J.* 94, 23c-24c
15. Brown, P. M., Debanne, M. T., Grothe, S., Bergsma, D., Caron, M., Kay, C., and O'Connor-McCourt, M. D. (1994) *Eur. J. Biochem.* 225, 223-233
16. Karle, S., Nishiyama, Y., Zhou, Y. X., Luo, J., Planque, S., Hanson, C., and Paul, S. (2003) *Vaccine* 21, 1213-1218
17. Sun, M., Gao, Q. S., Kirnarskiy, L., Rees, A., and Paul, S. (1997) *J. Mol Biol.* 271, 374-385
18. Bangale, Y., Karle, S., Zhou, Y. X., Lan, L., Kalaga, R., and Paul, S. (2003) *FASEB J.* In press
19. Tawfik, D. S., Chap, R., Green, B. S., Sela, M., and Eslihar, Z. (1995) *Proc. Natl. Acad. Sci USA* 92, 2145-2149
20. Sun, J., Takahashi, N., Kakinuma, H., and Nishi, Y. (2001) *J. Immunol.* 167, 5775-5785
21. Kalaga, R., Li, L., O'Dell, J. R., and Paul, S. (1995) *J. Immunol.* 155, 2695-2702
22. Gololobov, G., Sun, M., and Paul, S. (1999) *Mol. Immunol.* 36, 1215-1222
23. Noda, Y., Jujiwara, K., Yamamoto, K., Fukuno, T., and Segawa, S. I. (1994) *Biopolymers* 34, 217-226
24. Jimenez, R., Salazar, G., Baldridge, K. K., and Romesberg, F. E. (2003) *Proc. Natl. Acad. Sci. USA* 100, 92-97
25. Braden, B. C., and Poljak, R. J. (1995) *FASEB J.* 1, 9-16
26. Gao, Q. S., Sun, M., Rees, A., and Paul, S. (1995) *J. Mol. Biol.* 253, 658-664
27. Paul, S., Volle, D. J., Powell, M. J., and Massey, R. J. (1990) *J. Biol Chem.* 265, 11910-11913
28. Paul, S. (1996) *Mol. Biotechnol.* 5, 197-207
29. Rao, G., and Philipp, M. (1991) *J. Proteinz Chem.* 10, 117-122
30. Lefevre, S., Debat, H., Thomas, D., Friboulet, A., and Avalle, B. (2001) *FEBS Lett.* 439, 25-28
31. Pollack, S. J., Hsiun, P., and Schultz, P. G. (1989) *J. Am. Chem. Soc.* 111, 5961-5962
32. Berisha, H. I., Bratut, M., Bangale, Y., Colasurdo, G., Paul, S. and Said, S. I. (2002) *Pulm. Pharmacol. Ther.* 15, 121-127
33. Voice, J. K., Grinninger, C., Kong, Y., Bangale, Y., Paul, S., and Goetzl, E. J. (2003) *J. Immunol.* 170, 308-314
34. Moore, J., and Trkola, A. (1997) *AIDS Res. Hum. Retroviruses* 13, 733-736
35. Kwong, P. D., Doyle, M. L., Casper, D. J., Cicala, C., Leavitt, S. A., Majeed, S., Steenbeke, T. D., Venturi, M., Chaiken, I., Fung, M., Katinger, H., Parren, P. W., Robinson, J., Van Ryk, D., Wang, L., Burton, D. R., Freire, E., Wyatt, R., Sodroski, J., Hendrickson, W. A. and Arthos, J. (2002) *Nature* 420, 678-682
36. Kwong, P. D., Wyatt, R., Sattentau, Q. J., Sodroski, J., Hendrickson, W. A. (2000) *J. Virol.* 74, 1961-1972

[1] Abbreviations. Ab, antibody; BSA, bovine serum albumin; Bt, biotin; CRA, covalently reactive antigen analog; L chain, light chain; MAb, monoclonal antibody; MCA, methylcoumarinamide; TSAs, transition state analogs; V domain, variable domain; VIP, vasoactive intestinal peptide

EXAMPLE III

Towards Selective Covalent Inactivation of Pathogenic Antibodies: A Phosphonate Diester Analog of Vasoactive Intestinal Peptide that Inactivates Catalytic Autoantibodies Specific antigen recognition by the variable domains underlies the pathogenic effects of certain Abs[1] produced as a result of autoimmune, allergic and anti-transplant reactions. For instance, Abs found in myasthenia gravis (reviewed in ref. 1) and hemophilia (reviewed in ref. 2) bind important epitopes of the acetylcholine receptor and Factor VIII, respectively, which interfere with the biological activity of these proteins by a steric hindrance mechanism. Other Abs utilize their Fc region to mediate pathogenic effects but antigen recognition by Ab variable domains is the stimulus initiating these effects, e.g., Ab recognition of erythrocyte antigens stimulates complement activation by the Fc region in autoimmune hemolytic anemia and incompatible blood transfusions. Similarly, allergen recognition by IgE bound to Fc receptors on the surface of mast cells stimulates their degranulation. In other diseases, the mechanism of Ab pathogenicity is less clear. For example, Abs to nucleic acids in lupus (reviewed in ref. 3) and to thyroglobulin in Hashimoto's thyroiditis (reviewed in ref. 4) are unambiguously disease-associated, but additional immune abnormalities are also evident in these diseases, and the precise functional effects of the Abs remain debatable. Recently, a novel variable domain mechanism underlying Ab pathogenicity has emerged, viL., the catalytic cleavage of antigens. Hydrolytic catalysts such as Abs to polypeptides (5-8) and nucleic acids (9) hold the potential of permanent antigen inactivation. Moreover, catalysts are endowed with turnover capability, i.e., a single Ab molecule can hydrolyze multiple antigen molecules, suggesting that such Abs may exert functional effects that are more potent than Abs dependant on stoichiometric antigen recognition.

Abs that catalyze the cleavage of VIP have been identified in patients with autoimmune disease (10). VIP is a 28 amino acid peptide with important biological actions, including immunoregulation via actions on T lymphocytes (reviewed in ref. 11) and control of blood and air flow via actions on the smooth muscle (reviewed in ref. 12). A model proteolytic Ab interferes with cytokine synthesis by cultured T cells accompanied by depletion of cellular VIP (13) and administration of the Ab to mice interferes with relaxation of airway smooth muscle (14). Proteolytic Abs to VIP appear to utilize a covalent catalytic mechanism reminiscent of serine proteases. This is suggested by studies in which replacement of the active site Ser residue resulted in loss of catalytic activity (15), and by inhibition of catalysis by haptenic phosphonate diesters (10). These compounds form adducts with the activated nucleophiles of enzymes by virtue of the covalent reactivity of the electrophilic phosphorus atom (reviewed in ref. 16), and have been developed recently as probes for the active site nucleophiles in Abs displaying serine protease and serine esterase activity (17,18) [designated covalently reactive antigen analogs (CRAs)].

As in the case of ordinary Abs, traditional noncovalent antigen recognition is hypothesized to underlie the specificity of the proteolytic Abs for VIP. CRAs of the VIP sequence represent, therefore, a potentially specific means to target the Abs by virtue of offering a reaction surface that combines covalent binding to the Ab active site with noncovalent binding at neighboring peptide epitope(s). Here we describe the antigen-specific covalent reaction of monoclonal and polyclonal Abs with a synthetic VIP-CRA compound. Despite positioning of the phosphonate group at a single site, Lys20, the covalent reaction resulted in irreversible inhibition of polyclonal Abs that cleave VIP at several peptide bonds located between residues 7 and 22. The results suggest the feasibility of targeted inactivation of individual Ab populations based on their antigenic specificity.

Materials and Methods

CRAs.

Diphenyl N-(6-biotinamidohexanoyl)amino(4-amidinophenyl)methanephosphonate (1) was prepared from diphenyl amino(4-amidinophenyl)methanephosphonate (19,20) and 6-biotinamidohexanoic acid (Anaspec; San Jose, Calif.) by the aid of PyBOP (Novabiochem; San Diego, Calif.). The HPLC-purified material [retension time 20.76 min, purity 95% (220 nm); YMC ODS-AM column (4.6×250 mm), 0.05% TFA in water (A):0.05% TFA in acetonitrile (B) 90:10 to 20:80 in 45 min (1.0 m/min)] was characterized by ESI-MS [Observed m/z 721.3 ($MH^+$; calculated $MH^+$ for $C_{36}H_{45}N_6O_6PS$, 721.3)] and stored as 10 mM solution in DMF at −70° C. The active ester 2 was prepared by acylating the same precursor amine with disuccinmidyl suberate (Pierce; Rockford, Ill.) and characterized in the same way [Observed m/z, 635.3 ($MH^+$; calculated $MH^+$ for $C_{32}H_{35}N_4O_8P$, 635.2)]. VIP-CRA (3) was synthesized as follows. The VIP sequence with N-terminal biotin was constructed on Rink arnide MBHA resin (0.72 mmol/g; Novabiochem) by the standard 9-fluorenylmethoxycarbonyl protocol (21) except that 4-methyltrityl (22) was used for side-chain protection of Lys20. The peptide-resin was treated with 1% TFA in dichloromethane (5 min×10) to remove the 4-methyltrityl group and the deprotected amino group of Lys20 was acylated with 2 in 1-methyl-2-pyrrolidinone containing 0.1 mM N,N-diisopropylethylamine. The peptide resin was treated with TFA-ethanedithiol-thioanisole-phenol (90:1:1:8) at room temperature for 2 h. After removing the resin by filtration, diethyl ether was added to the solution to afford a precipitate, which was collected by centrifugation and washed with diethyl ether. The HPLC-purified material [retention time 50.25 min, purity 96% (220 nm); Vydac 214TP C4 column (4.6×250 mm); A:B 90:10 to 60:40 in 60 min (1.0 ml/min)] was characterized by ESI-MS [Observed nlz, 4071.4 ($MH^+$; calculated $MH^+$ for $C_{185}H_{282}N_{49}O_{49}PS_2$, 4072.0) and stored as 10 mM solution in DMSO at −70° C.

Abs.

Monoclonal anti-VIP IgG clone c23.5 and control isotype-matched IgG clone UPC10 (IgG2a, κ; Sigma; St. Louis, Mo.) were purified from ascites by affinity chromatography on immobilized Protein G-Sepharose (23). Polyclonal IgG from the serum of a human subject with chronic obstructive pulmonary disease (designated HS2 in ref. 24) was also purified by Protein G-Sepharose chromatography. The recombinant light chain of anti-VIP Ab clone c23.5 (GenBank # L34775) was expressed in bacterial periplasmic extracts and purified by binding of the his6 tag to a Ni-affinity column (15). All Abs were electrophoretically homogeneous. Protein concentrations were determined with Micro BCA Protein Assay kit (Pierce).

CRA Adducts.

Covalent binding assays were carried out as described previously (17,20). Briefly, IgG (1 μM) was incubated with compound 1 or 3 (10 μM) in 10 mM sodium phosphate, 0.137 M NaCl, 2.7 mM KCl (PBS, pH 7.4) containing 1 mM CHAPS and 0.1% DMSO (in 3-binding experiments) or 0.1% DMF (in 1-binding experiments) at 37° C. In some experiments, the reaction was conducted in the presence of human plasma collected in EDTA (pooled from 8 healthy blood donors; 1% v/v). Aliquots of the reaction mixtures at 10, 20, 40, 60, 90 and 120 min were boiled in 2% SDS containing 3.3% 2-mercaptoethanol in a water bath (5 min) and then subjected to electrophoresis (4-20% polyacrylamide gels; Bio-Rad; Hercules, Calif.). Following electroblotting onto nitrocellulose membranes (TransBlot; Bio-Rad), biotin-containing adducts were stained with a streptavidin-peroxidase conjugate and a chemiluminiscent substrate kit (Supersignal; Pierce). Band density was expressed in arbitrary area units (AAU) determined using a Fluoro-STM MultiImager (Bio-Rad), taking care that the densities were within the linear response range.

Catalysis Assays.

Pro-Phe-Arg-AMC (0.2 mM; Peptides International, Louisville, Ky.) was incubated with Ab (0.8 μM) in 96 well plates in 50 mM Tris.HCl-0.1M glycine (pH 8.0) containing 0.6% DMSO and 0.025% Tween 20 at 37° C. and release of AMC determined by fluorometry (λem 470 nm, λex 360 nm; Cary Eclipse spectrometer; Varian; Palo Alto, Calif.). Preparation and assay of cleavage of [$Tyr^{10}$-$^{125}I$]-VIP were described previously (24). To determine if the CRAs inhibit Abs irreversibly, IgG (2 μM) was incubated (37° C.) with 1 or 3 for 16 h in 50 mM Tris.HCl-0.1M Gly (pH 8.0) containing 2.5% DMSO and 0.025% Tween 20. Unreacted 1 or 3 was then removed by chromatography of the reaction mixtures (0.2 ml) on protein G columns as in ref35 (50 μl settled gel; washed with 0.8 ml 50 mM Tris.HCl, pH 7.4; eluted with 0.2 ml 0.1 M Gly.HCl, pH 2.7; neutralized with 1M Tris.HCl, pH 9). Fifty μl aliquots of the recovered IgG (and IgG-CRA complexes) were incubated with [$Tyr^{10}$-$^{125}I$]-VIP (86,000 c.p.m.) for 18 h and peptide cleavage was determined by measuring the radioactivity soluble in trichloroacetic acid. Control IgG samples were incubated without CRA, chromatographed and analyzed for VIP cleaving activity in the same way.

Results

VIP-CRA.

Important features in design of the VIP-CRA (compound 3, FIG. 20A) are: (a) Inclusion of the electrophilic phosphonate diester group capable of selective reaction with activated nucleophiles such as are found in serine proteases (16); (b) Location of the positively charged amidino group in proximity to the phosphonate to allow recognition by the model proteolytic IgG clone c23.5, which cleaves peptide bonds preferentially on the C terminal side of basic amino acids (Arg/Lys) (23,25); and (c) Incorporation of these groups on the side chain of Lys20 in the sequence of VIP. Hapten CRA 1 contains the phosphonate diester and amidino groups but is devoid of the VIP sequence. Location of the covalently reactive moiety at Lys20 is based on observations that the Lys20-Lys21 peptide bond is one of the bonds cleaved by monoclonal Ab clone c23.5 (23) and polyclonal human IgG preparations containing Abs to VIP (24). Peptide inhibitors of proteases customarily contain the covalently reactive group located within the peptide backbone or at the peptide termini (e.g., 26,27). In the present study, our purpose was to maximize the opportunity for approach of the phosphonate group within covalent binding distance of the nucleophile contained in diverse Ab active sites. For this reason, the phosphonate group was placed at the side chain of Lys20 using a flexible linker, which allows rotation at several C—C bonds (as opposed to inclusion of the phosphonate within the peptide backbone, which may impose a greater level of conformational constraints on accessibility of this group).

VIP-CRA 3 was synthesized by the regioselective on-resin acylation as outlined in FIG. 20B. The VIP sequence was constructed by solid-phase peptide synthesis with standard 9-fluorenylmethoxycarbonyl chemistry except that the 4-methyltrityl group was used for side-chain protection of Lys at position 20 (4a). After selective removal of 4-methyltrityl, peptide resin 4b was acylated with 2, which was prepared from diphenyl amino(4-amidinophenyl)methanephosphonate and disuccinimidyl suberate. The resulting peptide resin 4c was treated with anhydrous TFA to give 3, which was purified with HPLC, yielding a single species with the anticipated mass (m/z, 4071.4; calculated value, 4072.0).

Covalent Ab Labeling.

Figure 21:
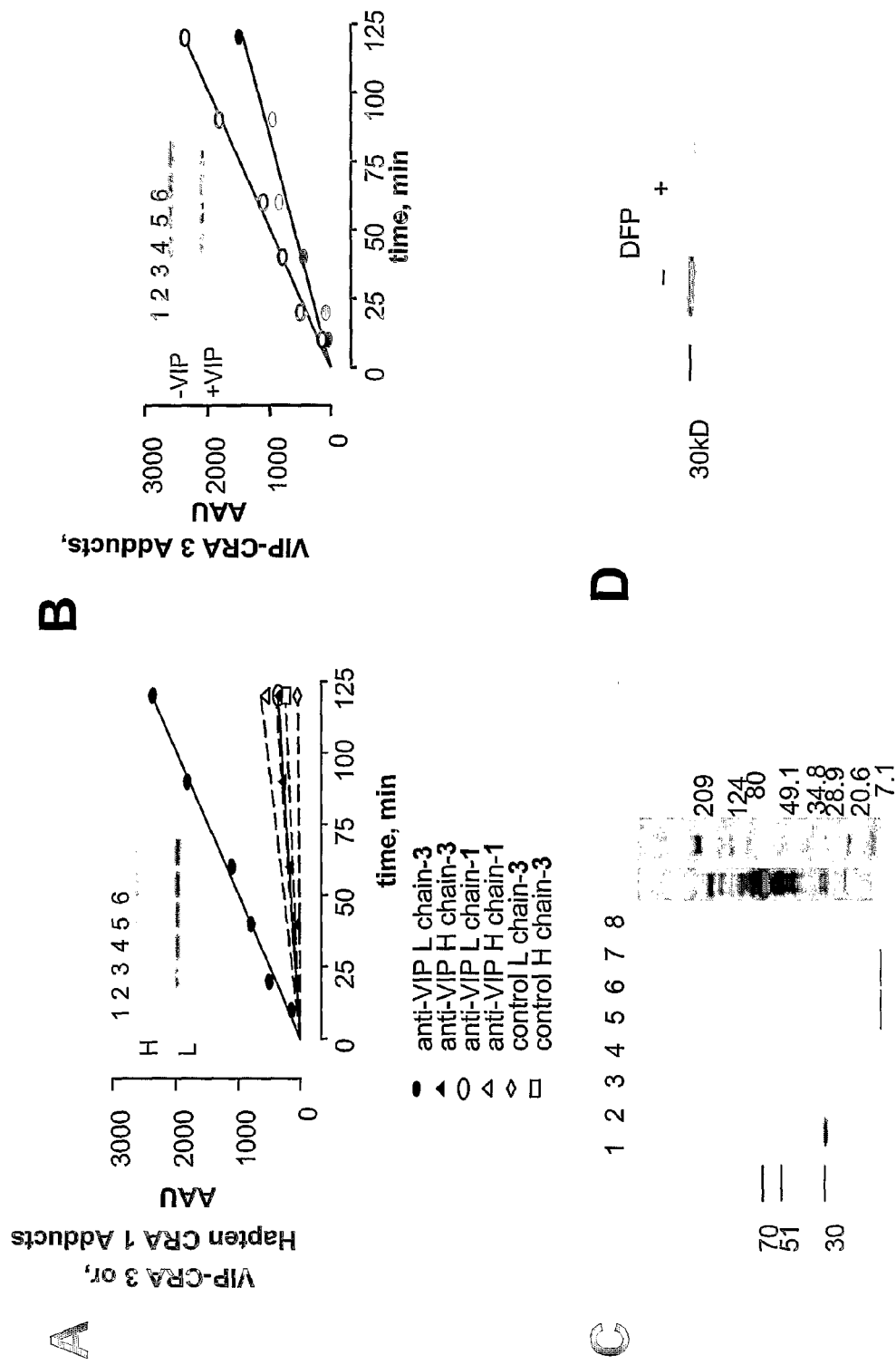

Monoclonal Ab c23.5, raised by hyperimmunization with VIP. It is characterized by strong recognition of the ground state of VIP (Kd 1.9 nM; Km 0.34 nM), made possible by traditional noncovalent Ab paratope-epitope interactions (23). The catalytic site of the Ab is located in the light chain subunit and is composed of a serine protease-like catalytic triad (15). Here, we compared the covalent binding of this Ab by VIP-CRA 3 and hapten CRA 1. The isotype-matched Ab UPC 10 (IgG2a, κ) served as the control to determine background Ab nucleophilic reactivity independent of noncovalent recognition of VIP. The covalent reaction was visualized by boiling the reaction mixtures followed by denaturing SDS-electrophoresis and detection of biotin-containing adducts (FIG. 21A, inset). Accumulation of covalent VIP-CRA 3 adducts with the anti-VIP Ab increased linearly as a function of time,[2] with the light chain subunit accounting for the majority of the adducts (nominal mass 29 kD determined by comparison with molecular mass standards). Adducts of VIP-CRA 3 with the control Ab were formed at lower levels. Similarly, hapten CRA 1 reacted with anti-VIP and control Abs slowly compared to the VIP-CRA, and there was no preference for covalent binding of the hapten CRA at the light chain subunit. Apparent reaction velocities ($V_{app}$) were obtained from the slopes of linear regression curves fitted to the progress data by least square analysis ([Ab–CRA]=$V_{app}$·t, where [Ab–CRA] represents the intensity of Ab–CRA adduct band in AAU, and t, the reaction time]. $V_{app}$ values are compiled in Table 5. For the anti-VIP Ab, $V_{app}$ of the VIP-CRA 3 reaction with the light chain was 6.6-fold greater than the heavy chain. Hapten CRA 1 $V_{app}$ values for the two subunits of this Ab were nearly equivalent. $V_{app}$ for the reaction of VIP-CRA with the anti-VIP light chain was 66-fold greater than the corresponding reaction with the control Ab light chain. These observations indicate the selective nucleophilic reactivity of the ant-VIP light chain. Inclusion of VIP devoid of the phosphonate group in the reaction mixture inhibited the formation of VIP-CRA 3 adducts with the anti-VIP light chain (FIG. 21B; inhibition in 3 repeat experiments, 41.0±7%). It may be concluded that selective covalent binding of VIP-CRA 3 by the anti-VIP Ab is made possible by noncovalent interactions due to the presence of the VIP sequence.

Pooled plasma from healthy humans was included in the reaction along with VIPase c23.5 to investigate further the selectivity of the VIP-CRA. As expected, the predominant VIP-CRA 3 adduct appeared at the position of the light chain subunit of the VIPase Ab (FIG. 21C). Little or no reaction of the VIP-CRA with plasma proteins and the control IgG subunits was observed. Similarly, the reaction mixtures of hapten CRA 1 yielded little or no adduct formation with plasma proteins or the exogenously added monoclonal Abs. Faint biotin bands were observed upon prolonged exposure in each of the lanes shown in FIG. 21C at mass 67-70 kD. These bands presumably reflect low level adduct formation of the hapten-CRA and VIP-CRA with albumin, the major protein present in plasma (see silver-stained electrophoresis lane in FIG. 21C). Covalent reactions of albumin with organophosphorus compounds have been reported previously (28,29).

Diisopropyl fluorophosphate (DFP), a well-established serine hydrolase inhibitor, was previously reported to inhibit catalysis by anti-VIP light chain c23.5 (15). In the present study, DFP inhibited the covalent VIP-CRA binding to the light chain (FIG. 21D), consistent the presence of a serine protease-like binding site(s).

Inhibition of Catalytic Activity.

Figure 22:
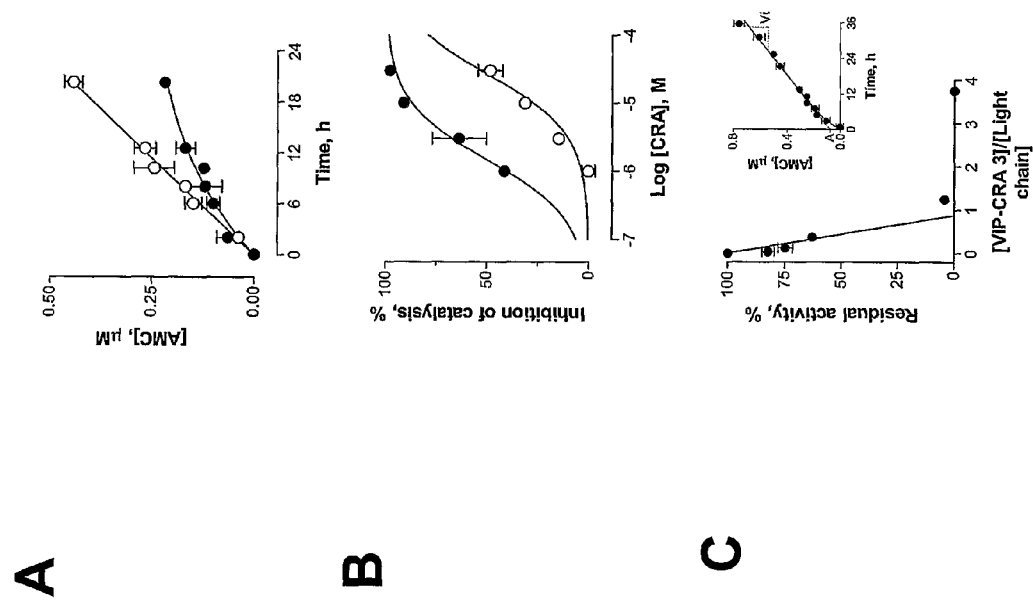

The cleavage of the model peptide substrate Pro-Phe-Arg-AMC by the recombinant light chain of anti-VIP Ab c23.5 has been reported previously (15). Site-directed mutagenesis studies have suggested that the light chain contains a catalytic triad similar to the active site of serine proteases (15). Here, the progress of Pro-Phe-Arg-AMC cleavage by the light chain was measured fluorimetrically by determining AMC generated due to cleavage at the Arg-AMC amide bond. As expected, a linear increase of AMC fluorescence was evident (FIG. 22A). Inclusion of VIP-CRA 3 in the reaction mixture inhibited the reaction in a time dependent manner. The deviation of the progress curve from linearity in the presence of VIP-CRA suggests an irreversible inhibition mode (30). Inhibitory potency comparisons using VIP-CRA 3 and hapten CRA 1 indicated the superior potency of the former compound (IC$_{50}$ 1.5 µM and 27 µM, respectively; FIG. 22B). The superior potency of VIP-CRA 3 is consistent with the covalent adduct data reported in the preceding section and may be attributed to improved noncovalent recognition of the peptidyl component of VIP-CRA 3. The stoichiometry of the inhibition was determined by titration with limiting amounts of VIP-CRA 3 ([3]/[light chain] ratio: 0.0375-3.75; FIG. 22C). The x-intercept of the residual activity (%) vs [VIP-CRA 3]/[light chain] plot was 0.89, suggesting a 1:1 stoichiometry. This is consistent with the observed molecular mass of the light chain:VIP-CRA adduct, ie., 29 kD (light chain, 25 kD; VIP-CRA, 4 kD).

Next, we turned to a human polyclonal IgG preparation isolated from a subject with airway disease (designated HS-2 in ref. 24). Cleavage of VIP by this preparation has been attributed to IgG autoantibodies based on retention of the activity in Fab fragments, adsorption of the activity by IgG binding reagents and absence of VIP cleavage by control, identically-purified human IgG preparations. N-terminal sequencing of VIP fragments generated by this IgG has identified the following scission bonds: Thr7-Asp8, Arg14-Lys15, Gln16-Met17, Met17-Ala18, Ala 18-Val19, Lys20-Lys21 and Lys21-Tyr22 (24). Here, we initially confirmed the ability of the polyclonal IgG preparation to cleave multiple peptide bonds in VIP. Three new radioactive peaks were generated from [Tyr$^{10}$-$^{125}$I]-VIP by treatment with the IgG (FIG. 23A). The observed radioactive product peaks in FIG. 23A likely represent mixtures of peptide fragments, as the VIP fragments generated by cleavage at the aforestated peptide bonds have previously been noted to elute from the HPLC with similar retention times (24).

To determine whether VIP-CRA 3 is an irreversible inhibitor, aliquots of the IgG treated with varying concentrations of this compound (10, 20, 40, 80 µM) were subjected to affinity chromatography on protein G to remove the unreacted inhibitor, followed by assay of the cleavage of [Tyr$^{10}$-$^{125}$I]-VIP (FIG. 24B). Control IgG was subjected to an identical incubation without VIP-CRA followed by the chromatographic procedure. Dose-dependent inhibition of catalytic activity was evident, and near-complete inhibition of catalysis was observed at VIP-CRA concentrations >20 µM. The observed irreversible inhibition suggests that VIP-CRA forms covalent adducts with the polyclonal Abs, similar to its behavior with the monoclonal Ab examined in the preceding section. Selectivity of the VIP-CRA inhibitory effect was confirmed by comparison with happen CRA 1. As expected, the VIP-CRA inhibited the cleavage of VIP more potently than the hapten CRA ($IC_{50}$: 7 µM and 36 µM, respectively).

Discussion

The following conclusions may be drawn from these data: (a) Functionally coordinated noncovalent and covalent interactions allowed nucleophilic anti-VIP Abs to form specific and covalent adducts with the VIP-CRAs; and (b) The VIP-CRA inhibits each of the reactions involving cleavage of VIP at several peptide bonds, indicating its potential as a universal inhibitor of diverse anti-VIP catalytic Abs. The importance of noncovalent Ab paratope-antigen epitope binding in directing the VIP-CRA to the Ab nucleophile is evident from the following observations: lower reactivity of the anti-VIP monoclonal Ab with the hapten CRA devoid of the VIP sequence; limited reactivity of the irrelevant isotype-matched Ab and plasma proteins with the VIP-CRA; and, inhibition of the anti-VIP Ab covalent reaction with the VIP-CRA by VIP devoid of the CRA moiety. Recently, CRA derivatives of other polypeptide antigens (HIV gp120 and epidermal growth factor receptor) have also been reported to form covalent adducts with specific Abs directed to these antigens, with only minor levels of reactions evident with Abs directed to irrelevant Abs (31,32). Taken together, these considerations open the route towards permanent inhibition of individual Ab subpopulations based on their antigenic specificity.

The light chain subunit accounted for most of the covalent reactivity of the anti-VIP monoclonal Ab with the VIP-CRA. Reactivity with the hapten CRA serves as an index of Ab nucleophilicity independent of traditional noncovalent forces responsible for Ab-antigen complexation. Hapten CRA reactivities of the anti-VIP heavy and light chain subunits were comparable, suggesting that differences in intrinsic nucleophilic reactivity do not account for rapid formation of adducts of the light chain with the VIP-CRA. It may be concluded that the light chain nucleophile is in the immediate vicinity of the Ab noncovalent binding site, and the noncovalent binding interactions facilitate covalent binding. This statement is consistent with observations that the purified light chain of this Ab is capable of specifically catalyzing the cleavage of VIP (25). Previously, the purified light and heavy chain subunits of the Ab were reported to bind VIP independently, determined by a conventional assay for noncovalent Ab-antigen complexes (Kd for light chain, heavy chain and intact IgG, respectively: 10.1, 6.8 and 1.9 nM; ref. 33). In addition to the light chain, the heavy chain subunit appears to contribute noncovalent binding energy for Ab complexation with VIP, but the heavy chain nucleophile does not seem to be sufficiently in register with the phosphonate group of the VIP-CRA to participate in the covalent reaction.

Additional evidence for irreversible and specific Ab recognition by the VIP-CRA is available from the catalysis assays. VIP-CRA adducts of the Abs obtained following removal of unreacted VIP did not display catalytic activity. Catalytic cleavage of Pro-Phe-Arg-AMC by the recombinant light chain of the monoclonal Ab has been documented previously (15). This reaction is characterized by 57.5-fold higher Km than the cleavage of VIP by the light chain, and is attributed to cross-reactivity of the catalytic site with peptide substrates devoid of an antigenic epitope capable of participating in high affinity noncovalent binding. Pro-Phe-Arg-AMC cleavage by the light chain was inhibited more potently by the VIP-CRA than the hapten CRA. Similarly, the cleavage of VIP by polyclonal human autoantibodies to VIP was inhibited more potently by the VIP-CRA than the haptenCRA.

Ab diversity poses an interesting challenge in achieving antigen-specific covalent inactivation of pathogenic Abs. Structural differences in the variable domains underlies Ab specificity for individual antigenic epitopes, and even Abs to small molecules presenting a limited surface area can contain structurally distinct binding sites (e.g., 34, 35). Catalytic IgG preparations from patients with autoimmune disease cleave several backbone bonds in polypeptide (7, 24) and oligonucleotide (9) antigens. This may be due to the presence of multiple Ab species in polyclonal IgG preparations, each with a distinct scissile bond specificity. We have suggested previously that the nucleophiles enjoy some measure of mobility within Ab active sites that is not subject to restriction when noncovalent binding of Abs and antigens takes place (31,32). To the extent this hypothesis is valid, Abs with differing peptide bond specificity could react covalently with the VIP-CRA even if the phosphonate group is located somewhat imprecisely in the antigenic epitope. In the present study, placement of the phosphonate on the Lys20 side chain (as opposed to the peptide backbone) and inclusion of a flexible linker represent attempts to expand farther the conformational space available for the covalent reaction. Complete inhibition of catalytic hydrolysis of VIP by polyclonal Abs that cleave several bonds between VIP residues 7 and 22 by the VIP-CRA was evident. Promising means to obtain antigen-specific covalent inhibition of diverse Abs include, therefore, the exploitation of intrinsic conformational properties of Ab catalytic sites and the provision of enhanced access to the phosphonate group by manipulating the linker structure. In comparison, if Ab-antigen binding is conceived as a rigid body interaction involving inflexible surface contacts, covalent inhibitor design must entail close topographical simulation of the transition state of each scission bond, and individual inhibitors must be developed to effectively inhibit different catalytic Abs. The importance of evaluating conformational factors in inhibitor design is supported by previous reports suggesting a split-site model of catalysis (31,32) in which antigen binding at the noncovalent subsite imposes little or no conformational constraints on the catalytic subsite, allowing the catalytic residue to become positioned in register with alternate peptide bonds as the transition state is formed.

As noted previously, catalytic Abs are proposed to contribute in the pathogenesis of autoimmune disease. Specific covalent inhibitors represent a novel means to help define the precise finctional effects of the Abs. Such inhibitors may serve as prototypes for development of therapeutic agents capable of ameliorating harmful Ab effects. In addition to inactivation of secreted Abs, reagents such as the VIP-CRA may be useful in targeting antigen-specific B cells. The feasibility of this goal is indicated by evidence that CRAs bind covalently to Abs expressed on the surface of B cells as components of the B cell receptor.[3] Ab nucleophilicity may be viewed as an indication of their competence in completing the first step in covalent catalysis, i.e., formation of an acyl-Ab reaction intermediate. This is supported by observations that the magnitude of Ab nucleophilic reactivity is correlated with their proteolytic activity (31). A recent study suggests that noncatalytic Abs also contain nucleophiles but are unable to facilitate steps in the catalytic cycle following covalent attack on the antigen, viz., water attack on the acyl-Ab intermediate and product release (31). Regardless of the physiological functions of nucleophiles expressed by noncatalytic Abs, their presence may allow CRA-targeting of Ab popula-

References for Example III

1. Vincent, A. (2002) *Nat. Rev. Immunol.* 2, 797-804
2. Gilles, J. G., Vanzieleghem, B., and Saint-Remy, J. M. (2000) *Semin. Thromb. Hemost.* 26, 151-155
3. Rekvig, O. P., and Nossent, J. C. (2003) *Arthritis Rheum.* 48, 300-312
4. Tomer, Y. (1997) *Clin. Immunol. Immunopathol.* 82, 3-11
5. Paul, S., Volle, D. J., Beach, C. M., Johnson, D. R., Powell, M. J., and Massey, R. J. (1989) *Science* 244, 1158-1162
6. Matsuura, K., and Sinohara, H. (1996) *Biol. Chem.* 377, 587-589
7. Lacroix-Desmazes, S., Moreau, A., Sooryanarayana, Bonnemain, C., Stieltjes, N., Pashov, A., Sultan, Y., Hoebeke, J., Kazatchkine, M. D., and Kaveri, S. V. (1999) *Nat. Med.* 5, 1044-1047
8. Hatiuchi, K., Hifumi, E., Mitsuda, Y., and Uda, T. (2003) *Immunol. Lett.* 86, 249-257
9. Shuster, A. M., Gololobov, G. V., Kvashuk, O. A., Bogomolova, A. E., Smirnov, I. V., and Gabibov, A. G. (1992) *Science* 256, 665-667
10. Bangale, Y., Karle, S., Planque, S., Zhou, Y. X., Taguchi, H., Nishiyama, Y., Li, L., Kalaga, R., and Paul, S. (2003) *FASEB J.* 17, 628-635
11. Voice, J. K., Dorsam, G., Chan, R. C., Grinninger, C., Kong, Y., and Goetzl, E. J. (2002) *Regul. Pept.* 109, 199-208
12. Maggi, C. A., Giachetti, A., Dey, R. D., and Said, S. I. (1995) *Physio. Rev.* 75, 277-322
13. Voice, J. K., Grinninger, C., Kong, Y., Bangale, Y., Paul, S., and Goetzl, E. J. (2003) *J. Immunol.* 170, 308-314
14. Berisha, H. I., Bratut, M., Bangale, Y., Colasurdo, G., Paul, S., and Said, S. I. (2002) *Pulm. Pharmacol. Ther.* 15, 121-127
15. Gao, Q. S., Sun, M., Rees, A. R, and Paul, S. (1995) *J. Mol. Biol* 253, 658-664
16. Oleksyszyn, J., and Powers, J. C. (1994) in *Methods in Enzymology*, (Barrett, A. J., ed) Vol. 244, pp. 423-441, Academic Press, San Diego, Calif.
17. Paul, S., Tramontano, A., Gololobov, G., Zhou, Y. X., Taguchi, H., Karle, S., Nishiyarna, Y., Planque, S., and George, S. (2001) *J. Biol. Chem.* 276, 28314-28320
18. Kolesnikov, A. V., Kozyr, A. V., Alexandrova, E. S., Koralewski, F., Demin, A. V., Titov, M. I., Avalle, B., Tramontano, A., Paul, S., Thomas, D., Gabibov, A. G., and Friboulet, A. (2000) *Proc. Natl. Acad. Sci. U.S.A.* 97, 13526-13531
19. Oleksyszyn, J., Boduszek, B., Kam, C. M., and Powers, J. C. (1994) *J. Med. Chem.* 37, 226-231
20. Nishiyama, Y., Taguchi, H., Luo, J. Q., Zhou, Y. X., Burr, G., Karle, S., and Paul, S. (2002) *Arch. Biochem. Biophys.* 402, 281-288
21. Wellings, D. A., and Atherton, E. (1997) in *Methods in Enzymology* (Fields, G. B., ed) Vol. 289, pp. 44-67, Academic Press, New York, N.Y.
22. Aletras, A., Barlos, K., Gatos, D., Koutsogianni, S., and Mamos, P. (1995) *Int. J. Pept. Protein Res.* 45, 488-496
23. Paul, S., Sun, M., Mody, R., Tewary, H. K., Stemmer, P., Massey, R. J., Gianferrara, T., Mehrotra, S., Dreyer, T., Meldal, M., and Tramontano, A. (1992) *J. Biol. Chem.* 267, 13142-13145
24. Paul, S., Mei, S., Mody, B., Eklund, S. H., Beach, C. M., Massey, R. J., and Hamel, F. (1991) *J. Biol. Chem.* 266, 16128-16134
25. Sun, M., Gao, Q. S., Kirnarskiy, L., Rees, A., and Paul, S. (1997) *J. Mol. Biol.* 271, 374-385
26. Oleksyszyn, J., and Powers, J. C. (1991) *Biochemistry* 30, 485-493
27. Sampson, N. S., and Bartlett, P. A. (1991) *Biochemistry* 30, 2255-2263
28. Means, G. E. and Wu, H. L. (1979) *Arch. Biochem. Biophys.* 194, 526-530
29. Schwartz, M. (1982) *Clin. Chim. Acta* 124, 213-223
30. Marangoni, A. G. (2003) *Enzyme Kinetics: A Modern Approach*, John Wiley and Sons, Hoboken, N.J.
31. Planque, S., Taguchi, H., Burr, G., Bhatia, G., Karle, S., Zhou, Y. X., Nishiyama, Y., and Paul, S. (2003) *J. Biol. Chem.* 278, 20436-20443
32. Paul, S., Planque, S., Zhou, Y. X., Taguchi, H., Bhatia, G., Karle, S., Hanson, C., and Nishiyama, Y. (2003) *J. Biol. Chem.* 278, 20429-20435
33. Sun, M., Li, L., Gao, Q. S., and Paul, S. (1994) *J. Biol. Chem.* 269, 734-738
34. Kaartinen, M., Pelkonen, J., and Makela, O. (1986) *Eur. J. Immunol.* 16, 98-105
35. Mitchell, T. J., and Reilly, T. M. (1990) *Pept. Res.* 3, 277-281

Footnotes

[1] Abbreviations used are: AAU, arbitrary area unit; Ab, antibody; AMC, 7-amino-4-methylcoumarin; CHAPS, 3-[(3-cholamidopropyl)dimethylamnmonio]-1-propanesulfonic acid; CRA, covalently reactive analog; DMF, N,N-dimethylformamide; DMSO, dimethyl sulfoxide; ESI-MS, electrospray ionization-mass spectrometry; Fc, fragment constant; PyBOP, (benzotriazole-1-yl)oxytris(pyrolidino)phosphonium hexafluorophosphate; SDS, sodium dodecylsulfate; TFA, trifluoroacetic acid; $V_{app}$, apparent reaction velocity; VIP, vasoactive intestinal peptide.

[2] The CRA-Ab reactions are predicted to follow the second-order rate law, but linear adduct accumulation will occur in the initial stage of the reaction.

[3] S. Paul and coworkers, unpublished data.

EXAMPLE IV

Ontogeny of Proteolytic Immunity: IgM Serine Proteases

Antigen-specific IgG Abs in autoimmune and autoimmune disease are described to catalyze chemical reactions (1-3). Examples of catalytic Abs raised by routine experimental immunization with ordinary antigens have also been published (4-7). However, no consensus has developed whether naturally occurring catalytic Abs represent rare accidents arising from adaptive sequence diversification processes or genuine enzymes with important finctional roles. The major reason is that the turnover ($k_{cat}$) of antigen-specific IgG Abs is low. Some catalytic Abs express catalytic efficiencies ($k_{cat}/K_m$) comparable to conventional enzymes, but this is due to high affinity recognition of antigen ground state (reviewed in 8).

Certain enzymes cleave peptide bonds by a mechanism involving the formation of a transient covalent intermediate of the substrate and a nucleophilic residue present in the active site. The nucleophiles are generated by intramolecular activation mechanisms, e.g., the activation of Ser/Thr side chain hydroxyl groups by hydrogen bonding to His residues, and can be detected by covalent binding to electrophilic phosphonate diesters (9,10). Using these compounds as covalently reactive analogs of antigens (CRAs), we observed that IgG Abs express nucleophilic reactivities comparable to trypsin (11). Despite their nucleophilic competence, IgG Abs display low efficiency proteolysis, presumably due to deficiencies in steps occurring after formation of the acyl-Ab intermediate, viz., water attack on the intermediate and product release. Occupancy of the B cell receptor (BCR, surface Ig complexed to $\alpha$ and $\beta$ subunits along with other signal transducing protein) by the antigen drives B cell clonal selection. Proteolysis by the BCR is compatible with clonal selection, therefore, only to the extent that the release of antigen fragments is slower than the rate of antigen-induced transmembrane signaling necessary for induction of cell division. Immunization with haptens mimicking the charge characteristics of the transition state (12) has been suggested as a way to surmount the barrier to adaptive improvement of catalytic rate constants. Catalysis by 'designer' IgG Abs obtained by these means, however, also proceeds only slowly.

In mice and humans, the initial Ab repertoire consists of ~100 heritable VL and VH genes. Adaptive maturational processes expand the repertoire by several orders of magnitude. The initial BCR complex on the pre-B cell surface contains V-(D)-J rearranged Ig $\mu$ chains as a complex with surrogate L chains (reviewed in 13). Precise assignment of the B cell differentiation stage at which cell division becomes antigen-dependent is somewhat ambiguous, but it is generally believed that non-covalent antigen binding to the pre-BCR is not required for initial cell growth. $\kappa/\lambda$ chains replace the surrogate L chain at the later stages of antigen-driven B cell differentiation, which is accompanied by diversification via somatic hypermutation processes and continued gene rearrangements (14,15). V-(D)-J gene rearrangements allow development of specificity for individual antigens by IgM (16) but antigen binding affinities tend to be low compared to IgG Abs. Somatic mutations accumulating in the V domains following isotype switching to IgG promote high affinity antigen recognition. In some anatomic locations, IgM Abs can be extensively mutated and can display high affinity antigen binding (17). Loss of a membrane anchoring peptide at the C terminus of the H chain results in production of secreted IgM and IgG Abs.

Very little information is available about the developmental aspects of Ab catalysis. Here, we report the nucleophilic reactivity of secreted IgM and the Ig subunits expressed on the surface of B cells. Cell surface $\mu$ and $\kappa/\lambda$ chains were the major sites of covalent reaction of a hapten CRA with B cells, and the magnitude of nucleophilic and proteolytic activities of secreted IgM Abs was consistently superior to IgG Abs.

Experimental Procedures

Splenocyte-CRA Binding.

Synthesis of compounds I-IV and confirmation of their chemical identity have been published (11,18). Compounds I, III and IV are diphenyl phosphonate esters reactive with nucleophilic sites (9,10,18). Biotin incorporated in these compounds allowed the visualization of Ab-CRA adducts. Diisopropyl fluorophosphate (DFP) was from Sigma. BALB/c mice (5-6 weeks, female, Jackson Laboratories, Maine) were euthanized by cervical dislocation and splenocytes were prepared in RPMI-1640 (Gibco) by teasing apart the spleen and removing undissociated tissue (unit gravity sedimentation). Erythrocytes were lysed in hypotonic ammonium chloride (5 min; ACK Lysis Buffer, Cambrex, Walkersville, Md.) and the cells washed twice with 10 mM sodium phosphate, pH 7.5, 137 mM NaCl, 2.7 mM KCl (PBS). B cells were isolated from splenocytes using a B cell negative selection isolation kit (Miltenyi, Auburn, Calif.) according to manufacturer's instructions and verified to be >95% CD19+ by flow cytometry as described below. Viability was determined using 0.05% Trypan Blue (90-95%). The cells (2-5×$10^6$ cells) were incubated with hapten CRA I or compound II (37° C.; final DMSO concentration 1%) in 0.5 ml PBS, washed thrice and treated with 100 µl anti-CD16/32 Ab (10 µg/ml µl; BD Pharmingen, San Diego, Calif.; 5 min, 4° C.) to block Ab binding to Fc receptors. Staining was with FITC-conjugated streptavidin (1 µg/ml or as stated; Molecular Probes, Eugene, Oreg.) and PE-conjugated rat monoclonal Ab to CD19 (10 µg/ml; Caltag, Burlingame, Calif.) in 100 µl for 20 min at 4° C. Following further washing with PBS (2×), the cells were fixed with 2% paraformaldehyde (1 hour, 4° C.), washed once and resuspended in PBS. In control incubations, an equivalent concentration of PE conjugated isotype-matched rat Ab to an irrelevant antigen (Pharmingen) replaced the anti-CD19 Ab. Deconvolution microscopy was performed employing an Olympus IX-70 inverted microscope and Applied Precision Delta work station (SoftWoRx™ software; ref 19). Stained cells were subjected to multiple acquisitions at a thickness of 0.25 µm, and the images were stacked. The images were subjected to deconvolution (5 iterations) for each probe (FITC; $\lambda$ex 488 nm, $\lambda$em 525 nm; DAPI; $\lambda$ex 350 nm, $\lambda$em 470 nm; phycoerythrin; $\lambda$ex 565 nm, $\lambda$em 578 nm). Flow cytometry was performed in the Baylor Medical College Core Facility (EPICS XL-MCLs Beckman-Coulter flow cytometer, EXPO32 software). Instrument calibration to minimize cross-detection of PE and FITC was done using cells stained individually with these fluorochromes. Forward and side scatter measurements allowed exclusion of dead cells from the gated cell population. CRA-stainable cells were identified as the population showing staining above the level observed for compound II staining. CRA stainable CD19+ cells were estimated by subtraction of background observed using the isotype-matched Ab. Cell extraction was by treatment with the detergent CHAPS (12 mM, 2 hours at 4° C.). The extract was centrifuged (10,000 g, 30 min), the supernate diluted with PBS to 1 mM CHAPS and then subjected to affinity chromatography using goat polyclonal Abs (IgG) to mouse µ, $\gamma$, $\delta$, $\lambda$, and $\kappa$ chains (Caltag) immobilized on Protein G-Sepharose columns (100 µl settled gel; 0.6×5 cm columns; Pharmacia, Piscataway, N.J.). For this purpose, the Abs (50 µg) were mixed with the Protein G gel in a column (15 min, 4° C.) in PBS containing 1 mM CHAPS (PBS-CHAPS), the gel allowed to settle, the unbound fraction collected and the columns washed with PBS-CHAPS. The cell extract (1.4 ml; diluted to 1 mM CHAPS; from 3×$10^6$ cells) was passed through the column, the column washed with PBS-CHAPS (9 volumes) and bound proteins were eluted with 100 mM glycine-HCl, pH 2.7 (8 column volumes) and subjected to reducing SDS-polyacrylamide gel electrophoresis (4-20%, Bio-Rad). Protein-CRA adducts were visualized by staining nitrocellulose electroblots of the gels with streptavidin-peroxidase as in (11). For immunoblotting, the blots were stained with goat polyclonal Abs (IgG) to mouse µ, $\gamma$, $\delta$, $\lambda$, and $\kappa$ chains followed by peroxidase conjugated rabbit anti-goat IgG (Fc specific, 1:1000; Pierce) as in (11). Nominal mass values were computed by comparison with standard proteins (14 kD-220 kD; Pharmacia).

Secreted Ab-CRA Binding.

Human serum Abs were from subjects without evidence of infection or immunological disease (2 females, 3 males; age 23-45 y). Mmme serum Abs were from BALB/c mice (purchased from Harlan, Indianapolis, Id.; pooled from 150 mice;

8-12 weeks). Murine monoclonal IgM Abs used here are directed against major histocompatibility antigens (clones corresponding to catalog #8702, 8704, 9008, 9010, 9020; cell-free ascites; Cedarlane, Ontario, Canada). Monoclonal ISYvo is from a patient with Waldenstrom's macroglobulinemia (20). All monoclonal IgM Abs contain κ chains. The 4 murine monoclonal IgG Abs used here were: clone c23.4 (anti-VIP; ref 6), clone c39.1 (anti-glucagon; S. Paul and coworkers, unpublished); ATCC clones HP6045 (anti-Fab$_2$, γ) and ATCC clone HP6054 (anti-Ig λ chain). All monoclonal IgG Abs contain γ2a heavy chains and a light chains. Serum or ascites fluid (1 ml) was mixed for 1 h with 1 ml Sepharose 4B conjugated rat anti-mouse IgM Abs (settled gel; Zymed, San Francisco, Calif.) or agarose conjugated goat anti-human IgM Abs (Sigma, St. Louis, Mo.) with IgM binding capacities 0.8 and 3 mg, respectively, in 50 mM Tris-HCl, pH 7.5, 0.1 mM CHAPS (buffer A). The unbound fraction was recovered and the gel washed with 20 buffer A volumes taking care that protein in the effluent had returned to undetectable levels prior to elution ($A_{280}$<0.001). Elution was with 100 mM glycine pH 2.7 (0.5 ml/fraction into 25 μl 1M Tris-HCl, pH 9.0). Further purification was on a Superose-6 FPLC gel filtration column (1×30 cm; 0.25 ml/min; Pharmacia) in two different solvents: 50 mM Tris-HCl, pH 7.7, 0.1 M glycine, 0.15 M NaCl, 0.025% Tween-20 (buffer B) or 6 M guanidine hydrochloride in buffer B adjusted to pH 6.5 with HCl (buffer C). Prior to column fractionation, the affinity purified IgM was dialyzed against buffer C. Column calibration was with thyroglobulin (660 kD), IgG (150 kD) and albumin (67 kD). IgM with Mr 900 kD eluted close to the void volume of the column. IgM was renatured following buffer C chromatography by dialysis against buffer B (21). IgMYvo, a cryoglobulin, was purified from serum by repetitive warming (37° C.) and cooling (4° C.; 3 cycles; ref 20) followed by affinity chromatography on the anti-human IgM column. IgG was purified on Protein G-Sepharose columns (21) using as starting material the unbound fraction from the anti-IgM columns or cell-free ascites. FPLC gel filtration of IgG was as described for IgM except that a Superose 12 column was employed. Fab fragments were prepared by digesting IgM (300 μl, 1 mg/ml) with agarose conjugated pepsin (0.6 ml gel, 30 min, 37° C.) in 100 mM sodium acetate, pH 4.5, 150 mM NaCl, 0.05% NaN$_3$, 0.1 mM CHAPS) as recommended by the manufacturer (Pierce). The unbound fraction was dialyzed against buffer B, purified by FPLC gel filtration on a Superose 12 column and dialyzed against 50 mM Tris-HCl, pH 7.7, 0.1 M glycine, 0.1 mM CHAPS. Total protein was determined by the bicinchoninic acid method (Pierce). Immunoblotting of SDS-gels containing murine Abs was as in the preceding section. Human Ab gels were immunoblotted using peroxidase conjugated goat anti-human, μ, anti-human κ and anti-human λ Abs (Sigma, St Louis, Mo.).

Purified Abs were treated with the biotinylated CRAs in 50 mM Tris, HCl, 100 mM glycine, 0.1 mM CHAPS, pH 7.7 at 37° C. Formation of Ab-CRA adducts was determined by SDS-electrophoresis as in the preceding section. Band intensities are expressed in arbitrary area units (AAU) determined by densitometry (11). Initial velocities were computed as the slopes of progress curves plotted as a function of time (initial 60 min).

Proteolysis Assays.

Cleavage of the amide bond linking aminomethylcoumarin to the C terminal amino acid in peptide-AMC substrates (Peptide International, Louisville, Ky. or Bachem, King of Prussia, Pa.) was measured in 50 mM Tris HCl, pH 7.7, 0.1 M glycine, 0.025% Tween-20 at 37° C. in 96-well plates by fluorimetry ($\lambda_{ex}$ 360 nm, $\lambda_{em}$ 470 nm; Varian Cary Eclipse) (21). Authentic aminomethylcoumarin was used to construct a standard curve. Kinetic parameters were obtained by fitting rate data obtained at increasing concentrations of peptide-AMC substrates to the Michaelis-Menten-Henri equation: $v=(V_{max}[S])/(K_m+[S])$. Progress curves in the presence of inhibitors were fitted to the equation: $[AMC]/[AMC]_{max}=1-e^{-kobs \cdot t}$. where $[AMC]_{max}$ is the AMC concentration in the absence of inhibitor. IC50 (concentration yielding 50% inhibition) was obtained from the equation: % inhibition=100/ $(1+10^{log\ IC50-log\ [Inhibitor]})$ with the curve forced through 0.

Results

Irreversible CRA-B Cell Binding.

Hapten CRAs such as compound I (FIG. 24) react irreversibly with nucleophilic sites in conventional serine proteases and Abs (9-11,18). To evaluate the nucleophilic reactivity expressed on the surface of B cells in the preimmune repertoire (viz., the repertoire developed spontaneously without purposeful immunological challenge), viable splenocytes from BALB/c mice were treated with hapten CRA I. The control compound II is identical in structure to hapten CRA I, except that the phosphonate group is not esterified, which results in loss of covalent reactivity with nucleophilic residues (11,18). Treatment with hapten CRA I resulted in staining of most of cells at levels greater than compound II, with a minority of the cells displaying intense staining (11±2, N 3 experiments; determined by counting 400 lymphocytes using a UV microscope). All of the CRA I-stained cells displayed lymphocytic morphology, with no evident staining of monocytes or the occasional basophil. No loss of viability of the cells was evident following incubation with CRA I or compound II, as determined by trypan blue exclusion. Flow cytometry confirmed the microscopy results. Seventy nine percent of the CRA I-treated cells displayed fluorescence intensities exceeding the compound II-treated cells, including a minority subpopulation with very high fluorescence intensity (14%; subpopulation 2 in FIG. 25A). In 3 repeat experiments, the proportion of CRA I-stained cells that were positive for the B cell marker CD19 was 82±4% (FIG. 25B). Deconvolution microscopy indicated that the fluorescence pattern due to hapten CRA I binding was nearly coincident with the anti-CD19 Ab fluorescence pattern (FIG. 25C-E). Most of the CRA fluorescence was restricted to the surfaces of the B cells (FIG. 25F).

To identify the nucleophilic molecules on the cell surface, purified B cells were labeled with CRA I, detergent extracts of the cells were boiled and then analyzed by SDS-electrophoresis. Only limited CRA-containing proteins were evident (FIG. 26A). As expected, silver staining revealed the presence of heterogeneous species, reflecting the complex protein constitution of the cells. The mass of the predominant CRA adduct band was 70 kD, and this band was stainable by anti-μ chain Ab (FIG. 26B). Smaller amounts of CRA-containing bands were evident at 25 kD, 40 kD, 50 kD, 55-60 kD, 90-135 kD and 140 kD. The bands at 55-60 kD and 140 kD were stainable by the anti-μ Ab, and the bands at 25 kD and 50 kD were stainable with anti-κ/λ Ab. The anomalous μ and κ/λ bands at mass range different from the full-length monomer proteins presumably represent unreduced oligomers, breakdown products and truncated B cell Ig products, as also observed in previous studies of secreted Abs and B cell extracts (22-24). The minor bands at 40 kD and 90-135 kD that were not stainable with Abs to μ, γ, κ/γ (FIG. 26B) and δ chains (not shown) presumably represent non-Ig proteins. No CRA-containing adduct corresponding to Ig γ chains were detected. Immunoblotting of the cell extracts identified a band at 50 kD stainable with anti-γ Ab, but the band was visible only in highly overexposed gels, suggesting that only small amounts of γ chains were present in the extract.

Confirmation that the CRA I adducts contain Ig subunits was by affinity chromatography on columns of immobilized Abs to μ, δ, γ and κ/λ chains followed by SDS-electrophoresis (FIG. 26C). CRA-containing μ and κ/λ bands were evident in eluates from the anti-μ and anti-κ/λ columns. Recovery of CRA-containing μ chains in the eluate from the anti-κ/λ column can be explained by the presence of disulfide bonded light and heavy chain complexes on the cell surface. No CRA-containing bands were evident in eluates from the anti-γ and anti-δ columns (not shown), but this can not be interpreted to reflect deficient γ/δ chain nucleophilic reactivity, as these proteins are expressed only at low levels in B cells from immunologically naïve mice. To determine the proportion of overall cellular CRA staining attributable to complexation with Ig subunits, the B cell extract was fractionated on a single affinity column composed of immobilized Abs to μ and κ/λ chains. Eighty percent of the total CRA content of the cells was adsorbed by the column (not shown), determined by densitometry of the biotin-containing bands in the unbound fraction and the extract loaded on the column. Taken together, these observations indicate that most of the CRA staining of intact B cells is attributable to irreversible binding to surface Ig, with the μ chain accounting for most of the covalent reactivity.

Nucleophilic Reactivity of Secreted IgM.

The initial velocity for formation of hapten CRA I adducts by IgM purified from the pooled serum of immunologically naïve BALB/c mice was 40-fold greater than by IgG (FIG. 27A; values are sums of velocities for the reactions occurring at the two Ab subunits expressed per unit concentration of intact Abs). The velocity difference is 8-fold when expressed per unit combining site concentration[2] (10 and 2 combining sites, respectively, in IgM and IgG). Three CRA-containing bands were observed in reducing SDS-gels of the IgM reaction mixtures at 70, 50 and 25 kDa (FIG. 27B). The 70 kDa and 25 kDa bands were stainable with anti-μ and anti-κ/λ Abs, respectively. The 50 kDa band was stainable with anti-μ Ab and presumably represents a μ breakdown product. Two CRA-containing bands corresponding to γ and κ/λ chains were observed in reducing gels of the IgG reaction mixtures. Similar results were obtained with a panel of 6 randomly selected monoclonal IgM Abs (5 murine and 1 human) and 4 monoclonal IgG Abs (all murine). The monoclonal IgM Abs uniformly displayed superior rates of irreversible CRA I binding compared to the IgG Abs (FIG. 27C; mean±SEM: 62.6±24.4×10$^4$ and 1.9±0.4×10$^4$ AAU/μM Ab/hour, respectively; P<0.01, Mann-Whitney U test, 2 tailed). Consistent with the polyclonal Ab experiments, the μ chain accounted for most of the covalent binding in the polyclonal and monoclonal IgMs, but smaller levels of binding at the κ/λ chain subunit were also observed for every Ab preparation (for clarity, μ chain and the corresponding κ/λ chain data points from individual IgM preparations are connected in FIG. 27C; data are expressed per μM subunit concentration to allow ready comparison). The 4 monoclonal IgG Abs contain γ2a heavy chains, and all monoclonal IgM/IgG Abs contain κ light chains. No attempt was made to determine the nucleophilic reactivity of various γ chain isotypes. However, the polyclonal Ab data indicate that the average nucleophilic reactivity of the IgG isotype mixture in blood is lower than the IgM reactivity. A similar argument can be presented in regard to antigenic specificity. The 5 murine IgM Abs and 4 IgG Abs were raised by experimental immunization and bind different antigens (MHC antigens, VIP, glucagon, Ig subunits; refs 6,25 and specifications provided by the manufacturers). The sixth monoclonal IgM was from a patient with Waldenström's macroglobulinemia with unknown antigenic specificity (20). The monoclonal IgM Abs uniformly displayed superior reactivity to IgG Abs, suggesting that divergent antigenic specificities do not account for the reactivity difference.

One of the monoclonal IgM Abs, Yvo, was employed to help define the structural requirements favoring hapten CRA covalent binding. Compound II, which contains the unesterified phosphonate, did not form adducts with the IgM at incubation times up to 3 hours (reaction conditions as in FIG. 26B). Similarly, the neutral hapten CRA III devoid of the amidino group and the hapten CRA IV with weak leaving groups (methyl instead of phenyl groups) failed to form detectable adducts with this IgM Ab. These reactivity characteristics are similar to those of IgG Abs reported previously (11).

Secreted IgM Catalytic Activity.

The catalytic activity of polyclonal IgM and IgG prepared from pooled mouse serum was initially measured using Glu-Ala-Arg-AMC as substrate (FIG. 28A). Cleavage of the amide bond linking the AMC to the C terminal Arg residue of this peptide has been validated as a surrogate for peptide bond hydrolysis by IgG Abs (21). Cleavage of Glu-Ala-Arg-AMC by polyclonal murine and human IgM fractions proceeded at rates 344-fold and 237-fold greater, respectively than the IgG fractions from the same sera (computed from initial velocity data; expressed per unit intact Ab concentration). If all 10 IgM valencies[2] and both IgG valencies are filled, the velocities for individual combining sites of murine and human IgM are 69-fold and 47-fold greater than the corresponding IgG velocities. Consistent with the irreversible binding data in the preceding section, Glu-Ala-Arg-AMC cleavage by murine polyclonal IgM was inhibited by hapten CRA I (FIG. 28B) and the serine protease inhibitor diisopropylfluorophosphate (not shown; 63% and 93% inhibition at 30 μM and 100 μM DFP, respectively after 12 hours). The deviation of the progress curve from linearity in the presence of CRA I suggests an irreversible inhibition mode (26). Progressively increasing inhibition of the murine IgM activity (9-100%) at increasing hapten CRA I concentrations (10-300 μM) was evident (IC50 42 μM; not shown). inhibition, 111 μM).

Contamination of IgM with conventional proteases was studied by methods employed previously to validate IgG and Ab light chain enzymatic activities (21,27). The IgM obtained by affinity chromatography on the anti-μ column displayed essentially identical levels of catalytic activity as the 900 kD IgM fraction obtained by ftuther purification by FPLC gel filtration (FIG. 29A). This fiulfils the criterion of purification to constant specific activity required for assignment of enzymatic activity to IgM. Next, we examined IgM treated with 6M guanidine hydrochloride to dissociate any noncovalently associated contaminants. For this purpose, the affinity purified IgM was subjected to three cycles of gel filtration in 6M guanidine hydrochloride (FIG. 29B) and the 900 kD fraction from the final gel filtration cycle was renatured by dialysis. Time-dependent Glu-Ala-Arg-AMC cleavage by IgM subjected to these procedures was observed (FIG. 29C).

Substrate selectivity of the polyclonal IgM preparations and 6 monoclonal IgM Abs was studied using a panel of 10 peptides-AMC conjugates. The rates shown in Table 6 were computed as slopes of the progress curves. Only substrates containing a basic residue at the cleavage site were hydrolyzed by the IgM Abs. No hydrolysis was detected with substrates containing acidic and neutral residues at the cleavage site. All 6 monoclonal IgM Abs displayed catalytic activity, but the activity levels for different Abs were not identical (varying, for example, over a 24-fold range with Glu-Ala- Arg-AMC as substrate). The Abs displayed different substrate selectivity profiles. For example, the ratio of Glu-Ala-Arg-AMC and Ile-Glu-Gly-Arg-AMC cleavage rates varied from 0.9 to 30.0 for the 5 murine monoclonal IgMs, and the human monoclonal IgM cleaved the former substrate at a robust rate without cleaving the latter substrate detectably (FIG. 30). Hydrolysis of Gly-Gly-Arg-AMC and Gly-Gly-Leu-AMC by IgM 9020 was compared to confirm the requirement for a basic residue at the cleavage site. These substrates are identical except for the Arg-AMC/Leu-AMC linkage, eliminating the possibility of confounding remote residue effects. Cleavage of Gly-Gly-Arg-AMC was detectable, but cleavage of Gly-Gly-Leu-AMC was not (12.6±0.6 and <0.13 µM AMC/µM Ab/hour, respectively).

The constant domain scaffold in the 5 murine monoclonal IgM Abs is identical. Observations of divergent catalytic activity levels and substrate selectivities suggested that the catalytic site is located in the V domains. To confirm this, IgM Yvo was digested with immobilized pepsin and Fab fragments were purified by gel filtration as the 55 kD proteinpeak (FIG. 31A). Concentration dependent cleavage of Glu-Ala-Arg-AMC by the Fab fragment was observed (FIG. 31B). Next, we considered the possibility that pepsin released from the column could be responsible for the observed Fab activity. The pH optimum of pepsin is 1.5-2.7 depending on the substrate (28). The catalysis assays were repeated in 0.1 M glycine, pH 2.7, 1 mM CHAPS. At Fab concentrations affording readily detectable catalytic activity at neutral pH (FIG. 31B), no detectable cleavage of Glu-Ala-Arg-AMC by the Fab was evident at pH 2.7. The cleavage site preference of pepsin (hydrolysis on the C terminal side of aromatic and hydrophobic residues) is dissimilar to the basic residue preference of IgM Abs. Purified pepsin did not cleave Glu-Ala-Arg-AMC under conditions yielding readily detectable catalysis by the Fab (675 nM pepsin; other reaction conditions as in FIG. 31B). These data indicate that pepsin contamination is not a factor in the observed Fab Activity.

Determination of reaction rates for 4 IgM preparations at increasing Glu-Ala-Arg-AMC concentrations indicated typical enzymatic kinetics (polyclonal murine and human IgM, monoclonal IgM 9020 and IgM 9008). The rates were saturable at excess substrate concentration and consistent with the Michaelis-Menten-Henri kinetics (Table 7). Observed $K_m$ values were in the high micromolar range, reminiscent of the recognition characteristics of conventional proteases. Catalytic antibodies that are adaptively specialized to recognize individual antigens, on the other hand, display $K_m$ values in nanomolar to low micromolar range, e.g., IgG c23.5 shown in Table 7 cleaves the autoantigen VIP with $K_m$ 0.4 nM (from ref 6). Apparent $k_{cat}$ values for the IgMs exceed those reported previously for IgG (21).

Discussion

IgM Abs, the first class of Abs produced by B cells, displayed superior nucleophilic and catalytic reactivities compared to IgG Abs. This contrasts with the noncovalent antigen binding function of Abs, which improves adaptively over the course of the immune response. The nucleophilic and catalytic IgM activities were identified in unimmunized mice and healthy humans. Preferential IgM recognition of the positive charged group adjacent to the phosphonate group of the hapten CRAs and the scission bond in peptide substrates presumably reflect an intrinsic property of the preimmune Ab repertoire. This noncovalent recognition motif enables low affinity interactions with the peptide substrates, whereas traditional noncovalent epitope-paratope binding is characterized by high affinity antigen recognition (nanomolar range $K_d$).

Hapten CRA I was validated previously as a probe for nucleophilic reactivities expressed by serine proteases, including IgG Abs (11,28). The extent of irreversible CRA binding activity correlates approximately with the catalytic activity (11,29). In the present study, hapten CRA I adducts were located in close proximity to CD19 on the surface of B cells. The latter protein fulfills a signal transducing role as a component of the BCR throughout B cell development (30). Immunochemical and affinity chromatography studies suggested that the majority of the B cell surface staining is attributable to covalent binding by Ig subunits, with the µ chain providing the dominant contribution, and κ/λ chains, a smaller contribution. This is consistent with the superior nucleophilic reactivity of the µ chain subunit of secreted IgMs. The control phosphonic acid hapten, which stained the cells poorly, does not react with nucleophiles due to the poor electrophilicity of the phosphorus atom (11,18). Monoclonal BCRs were not included here, but all six monoclonal IgM Abs examined expressed nucleophilic reactivity, suggesting that the reactivity may also be expressed by a significant proportion of BCRs. A minority of the B cells was stained intensely by the CRA. These cells are of interest as a potential source of catalysts in future studies. Observations that both Ig subunits express nucleophiles are consistent with the ability of light and heavy chains to independently catalyze the cleavage of peptide bonds in the absence of their partner subunit (31). Site-directed mutagenesis studies have indicated a serine protease-like catalytic triad in the light chain of an IgG Ab (32) and the heavy chain of other IgG Abs is reported to contain nucleophilic Ser residues (e.g., 33).

Functional roles for serine protease activities have been deduced in B cell developmental processes, but the molecules responsible for the activities have not been identified to our knowledge. The serine protease inhibitors DFP and α-1 antitrypsin inhibit mitogen induced B cell division (34,35) and up-regulate the synthesis of certain Ab isotypes by cultured B cells (35). The DFP-sensitive enzyme is B cell-associated and prefers Arg-containing substrates (36). Serine protease inhibitors are reported to inhibit anti-IgM induced BCR signal transduction (37), and anti-IgM mediated B cell activation is correlated with the appearance of a serine protease activity on the cell surface (38). Undoubtedly, conventional serine proteases may contribute to B cell regulation, but it remains that the major CRA binding components on the B cell surface evident in the present study are the BCRs themselves. It is logical to hypothesize, therefore, that stimulation of BCR nucleophilic sites may influence B cell development. Such compounds include naturally occurring serine protease inhibitors and reactive carbonyl compounds capable of irreversible binding to nucleophilic amino acids (39).

Observations of divergent levels of catalytic activity of monoclonal IgM Abs, their differing substrate preference and retention of the activity in the Fab fragments suggest that the catalytic site is located in the V domains. The catalysis assays were conducted in solution phase and at excess concentrations of the small peptide substrate. These conditions will not support binding of a single peptide molecule by more than one Ab valency. Dissociation of antigen bound reversibly at the individual combining sites may increase antigen availability for neighboring sites. However, such an effect will influence the rate of catalysis only when initial antigen concentration is limiting, and there will be no change in the observed Vmax. Therefore, multivalent binding by non-interacting sites (avidity effects) is an unlikely explanation for the superior activity of decavalent IgM compared to the divalent IgG. The following explanations can be presented for the superior IgM activity. First, loss of catalytic activity may be attendant to V domain somatic diversification after isotype switching from IgM to IgG. Second, distinctive IgM constant domain characteristics maybe important in maintaining the integrity of the catalytic site, in which case isotype switching itself may result in reduced catalytic activity. These explanations are not mutually exclusive. Both explanations are consistent with the argument that catalysis is a disfavored phenomenon in the advanced stages of B cell development (as efficient BCR catalysis will result in reduced BCR occupancy). We did not attempt to address these points experimentally in the present study. However, the monovalent Fab studies suggested that disruption of the constant domain architecture of IgM is deleterious for catalysis. The Fab preparations displayed ~10-fold lower activity than computed for the individual combining sites of pentameric IgM. Pepsin employed to prepare Fab cleaves μ chains on the C terminal side of the CH2 domain (40), which is distinguished by its conformational flexibility (41). Alterations of antigen binding activity when the same V domains are expressed as full-length IgG Abs belonging to different isotypes are described (e.g., 42), but we are not aware of IgM-IgG V domain swapping experiments in the literature. Allosteric combining site activation due to filling of individual Ab valencies has previously been considered in the case of divalent IgG preparations (43). The temporal sequence of events as the individual IgM combining sites bind antigen has not been elucidated. At excess antigen, only 5 of the 10 IgM combining sites are thought to be filled (e.g., 44), suggesting that favorable allosteric effects on antigen binding, if present, must be restricted to conditions of limiting antigen concentrations.

Our screening experiments were restricted to a few IgMs and a few commercially available substrates. Additional studies are necessary to define the physiological substrates for IgM Abs and the upper limit for catalytic rates. However, certain conclusions can be reached from the available data. Apparent turnover numbers ($k_{cat}$) for the IgM preparations were as high as 2.8/min. Serum IgM concentrations (1.5-2.0 mg/ml; ~2 μM) are ~3-4 orders of magnitude greater than conventional enzymes (for example, thrombin found at ng-μg/ml in serum as a complex with antithrombin III; ref 45), and IgM $k_{cat}$ values are ~2 orders of magnitude smaller than conventional serine proteases. If catalysis proceeds at the rate observed in vitro, 2 μM human IgM with turnover 2.8/min will cleave ~24,000 μM antigen present at excess concentration ($>>K_m$) over 3 days (corresponding to the approximate half-life of IgM in blood). Maximal velocity conditions can be approached in the case of antigens present at high concentrations, e.g., albumin and IgG in blood; polypeptides accumulating at locations close to their synthetic site, such as thyroglobulin in the lumen of thyroid follicles; and bacterial and viral antigens in heavily infected locations. Inhibitors regulate the activity of conventional proteases in vivo such as the enzymes responsible for blood coagulation. Unregulated catalysis may lead to disruption of homeostasis. Inhibitory mechanisms regulating conventional enzymes are conceivable in regard to IgM proteolysis.

Identification of promiscuous IgM proteolytic activities in the preimmune repertoire raises important question concerning the existence antigen-specific catalytic IgM Abs. Under conditions of limiting antigen concentration, catalyst competence is measured as the $k_{cat}/K_m$ parameter ($K_m \approx K_d$[3]). As illustrated for the anti-VIP IgG in Table 7, large gains in catalytic competence occur due to enhanced antigen binding affinity (reduced $K_m$). Certain polypeptides are recognized by IgM Abs present in the preimmune repertoire with high affinity, for example, the superantigens Staphylococcal Protein A and HIV gp120[4] are recognized by IgM Abs containing VH3 family domains with $K_d$ in the nanomolar range (46,47). Moreover, specific IgM Abs with improved affinity for individual antigens emerge by adaptive V domain maturation processes (16,48). Similarly, future study of catalytic IgMs specialized to recognize individual autoantigens is of interest. IgM Abs from patients with autoimmune disease express glycosidase activity (49). Autoimmune humans and mice tend to synthesize catalytic Abs at increased levels (50-53), and a proteolytic IgG preparation to VIP is shown to interfere with the physiological smooth muscle relaxant effect of VIP (54).

References for Example IV

1. Paul, S., Volle, D. J., Beach, C. M., Johnson, D. R., Powell, M. J., and Massey, R. J. (1989) *Science* 244, 1158-1162
2. Shuster, A. M., Gololobov, G. V., Kvashuk, O. A., Bogomolova, A. E., Smirnov, I. V., and Gabibov, A. G. (1992) *Science* 256, 665-667
3. Lacroix-Desmazes, S., Moreau, A., Sooryanarayana, B. C., Stieltjes, N., Pashov, A., Sultan, Y., Hoebeke, J., Kazatchkine, M. D., and Kaveri, S. V. (1999) *Nat. Med.* 5, 1044-1047
4. Raso, V., and Stollar, B. D. (1975) *Biochemistry* 14, 591-599
5. Kohen, F., Kim, J. B., Linder, H. R., Eshhar, Z., and Green B. (1980) *FEBS Lett.* 111, 427-431
6. Paul, S., Sun, M., Mody, R., Tewary, H. K., Mehrotra, S., Gianferrara, T., Meldal, M., and Tramontano, A. (1992) *J. Biol. Chem.* 267, 13142-13145
7. Hifumi, E., Okamoto, Y., and Uda, T. (1999) *J. Biosci. Bioengin.* 88, 323-327
8. Paul, S., Ed. (2000) *Chemical Immunology: Catalytic Antibodies*, Vol. 77, pp. 1-161, S. Karger GmbH, Basel, Switzerland
9. Oleksyszyn, J., and Powers, J. C. (1994) in *Methods in Enzymology*, (Barrett, A. J., ed) Vol. 244, pp. 423-441, Academic Press, San Diego, Calif.
10. Sampson, N. S., and Barton, P. A. (1991) *Biochemistry* 30, 22255-22263
11. Planque, S., Taguchi, H., Burr, G., Bhatia, G., Karle, S., Zhou, Y.-X., Nishiyama, Y., and Paul, S. (2003) *J. Biol. Chem.* 278, 20436-20443
12. Tramontano, A., Janda, K. D., and Lerner, R. A. (1986) *Science* 234, 1366-1570
13. Melchers, F., ten Boekel, E., Seidl, T., Kong, X. C., Yamagami, T., Onishi, K., Shimizu, T., Rolink, A. G., and Andersson, J. (2000) *Immunol. Rev.* 175, 33-46
14. Prak, E. L., and Weigert, M. (1995) *J. Exp. Med.* 182, 541-548
15. Papavasiliou, F., Casellas, R., Suh, H., Qin, X. F., Besmer, E., Pelanda, R., Nemazee, D., Rajewsky, K., and Nussenzweig, M. C. (1997) *Science* 278, 298-301
16. Xu, J. L., and Davis, M. M. (2000) *Immunity* 13, 37-45
17. Dunn-Walters, D. K., Hackett, M., Boursier, L., Ciclitira, P. J., Morgan, P., Challacombe, S. J., and Spencer, J. (2000) *J. Immunol.* 164, 1595-1601
18. Nishiyama, Y., Taguchi, H., Luo, J., Zhou, Y.-Z., Burr, G., Karle, S., and Paul, S. (2002) *Arch. Biochem. Biophys.* 402, 281-288
19. Poindexter, B. J., Pereira-Smith, O., Wadhwa, R., Buja, L. M., and Bick, R. J. (2002) *Microscopy & Analysis* 89, 21-23
20. Shaw, D. C., Shultz, B. B., Ramsland, P. A. and Edmundson, A. B. (2002) *J. Mol. Recog.* 15, 341-348

21. Kalaga, R., Li, L., O'Dell, J., and Paul, S. (1995) *J. Immunol.* 155, 2695-2702
22. Marks, R., and Bosma, M. J. (1985) *J. Exp. Med.* 162, 1862-1877
23. Li, L., Sun, M., Gao, Q. S., and Paul, S. (1996) *Mol. Immunol.* 33, 593-600
24. Malynn, B. A., Shaw, A. C., Young, F., Stewart, V., and Alt, F. W. (2002) *Mol. Immunol.* 38, 547-556
25. Ozato, K., Mayer, N. M., and Sachs, D. H. (1982) *Transplantation* 34, 113-120
26. Marangoni, A. G. (2003) *Enzyme Kinetics: A Modern Approach*, pp. 70-79, John Wiley and Sons, Hoboken, N.J.
27. Paul, S., Li, L., Kalaga, R., Wilkins-Stevens, P., Stevens, F. J., and Solomon, A. (1995) *J. Biol. Chem.* 270, 15257-15261
28. Cornish-Bowden, A., and Knowles, J. (1969) *Biochem. J.* 113, 353-362
29. Paul, S., Tramontano, A., Gololobov, G., Zhou, Y.-X, Taguchi, H., Karle, S., Nishiyama, Y., Planque, S., and George, S. (2001) *J. Biol. Chem.* 276, 28314-28320
30. Sato, S., Ono, N., Steeber, D. A., Pisetsky, D. S., and Tedder, T. F. (1996) *J. Immunol.* 157, 4371-4378
31. Gao, Q.-S., Sun, M., Rees, A., and Paul, S. (1995) Site-directed mutagenesis of proteolytic antibody light chain. *J. Mol. Biol.* 253, 658-664
32. Hatiuchi, K., Hifumi, E., Mitsuda, Y., and Uda, T. (2003) *Immunol. Lett.* 86, 249-257
33. Kolesnikov, A. V., Kozyr, A. V., Alexandrova, E. S., Koralewski, F., Demin, A. V., Titov, M. I., Avalle, B., Tramontano, A., Paul, S., Thomas, D., Gabibov, A. G., and Friboulet, A. (2000) *Proc. Natl. Acad. Sci U.S.A.* 97, 13526-13531
34. Ku, G. S., Quigley, J. P., and Sultzer, B. M. (1981) *J. Immunol.* 126, 2209
35. Jeannin, P., Lecoanet-Henchoz, S., Delneste, Y., Gauchat, J. F., and Bonnefoy, J. Y. (1998) *Eur. J Immunol.* 28, 1815-1822
36. Ku, G. S., Quigley, J. P., and Sultzer, B. M. (1983) *J. Immunol.* 131, 2494-2499
37. Mizuguchi, J., Utsunomiya, N., Nakanishi, M., Arata, Y., and Fukazawa, H. (1989) *Biochem. J.* 263, 641-646
38. Biro, A., Sarmay, G., Rozsnyay, Z., Klein, E., and Gergely, J. (1992) *Eur. J. Immunol.* 22, 2547-2553
39. Crabb, J. W., O'Neil, J., Miyagi, M., West, K., and Hoff, H. F. (2002) *Protein Sci.* 11, 831-840
40. MacKenzie, M. R., Gutman, G. A., and Warner, N. L. (1978) *Scand. J. Immunol.* 7, 367-370
41. Roux, K. H., Strelets, L., Brekke, O. H., Sandlie, I., Micbaelsen, T. E. (1998) *J Immunol.* 161, 4083-4090
42. Morelock, M. M., Rothlein, R., Bright, S. M., Robinson, M. K., Graham, E. T., Sabo, J. P., Owens, R., King, D. J., Norris, S. H., Scher, D. S., Wright, J. L., and Adair, J. R. (1994) *J. Biol. Chem.* 269, 13048-13055
43. van Erp, R., Gribnau, T. C., van Sommeren, A. P., and Bloemers, H. P. (1991) *J. Immunol. Methods* 140, 235-241
44. Chavin, S. I., and Franklin, E. C. (1969) *J. Biol. Chem.* 244, 1345-1352
45. Chen, T. Y., Huang, C. C., and Tsao, C. J. (1993) *Am. J. Hematol.* 44, 276-279
46. Rohen, P. W., Salem, A. N., and Silverman, G. J. (1995) *J. Immunol.* 154, 6437-6445
47. Berberian, L., Goodglick, L., Kipps, T. J., and Braun, J. (1998) *Science* 261, 1588-1591
48. Ballard, D. W., Kranz, D. M., Voss, E. W., Jr. (1983) *Proc. Natl. Acad. Sci. U.S.A.* 80, 5071-5074
49. Saveliev, A. N., Ivanen, D. R., Kulminskaya, A. A., Ershova, N. A., Kanyshkova, T. G., Buneva, V. N., Mogelnitskii, A. S., Doronin, B. M., Favorova, O. O., Nevinsky, G. A., and Neustroev, K. N. (2003) *Immunol. Lett.* 86, 291-297
50. Tawfik, D., Chap, R., Green, B., Sela, M., and Eshhar, Z. (1995) *Proc. Natl. Acad. Sci. U.S.A.* 92, 2145-2149
51. Li, L., Kaveri, S., Tyutyulkova, S., Kazatchkine, M., and Paul, S. (1995) *J. Immunol.* 154, 3328-3332
52. Matsuura, K., Ikoma, S., Sugiyama, M., Funauchi, M., and Sinohara, H. (1998) *Immunol.* 95, 26-30
53. Bangale, Y., Karle, S., Zhou, Y.-X., Lan, L., Kalaga, R., and Paul, S. (2003) *FASEB J.* 17, 628-635
54. Berisha, H. I., Bratut, M., Bangale, Y., Colasurdo, G., Paul, S., and Said, S. I. (2002) *Pulm. Phamacol. Ther.* 15, 121-127

Footnotes

[1] Abbreviations: AAU, arbitrary area unit; Ab, antibody; AMC, 7-amino-4-methylcoumarin; BCR, B cell receptor; CDRs, complementary determining regions; CHAPS, 3-[(3-cholamidopropyl)dimethylammonio]-1-propanesulfonic acid; CRA, covalently reactive analog; DFP, diisopropyl fluorophosphate; EAR-MCA, Boc-Glu(OBzl)-Ala-Arg-MCA; IEGR-MCA, Boc-Ile-Glu-Gly-Arg-MCA, Fab, fragment antigen binding; FITC, fluorescein isothiocyanate; FRs, Framework regions; Ig, immunoglobulin; PE, phycoerythrin; SDS, sodium dodecylsulfate; VL and VH, light and heavy chain variable domains; VIP, vasoactive intestinal peptide.

[2] However, all 10 IgM valencies are usually not filled (e.g., ref 44).

[3] If $k_2$, the rate constant for dissociation of the antibody-antigen noncovalent complex, is $\gg k_{cat}$, the rate constant for chemical transformation of the noncovalent complex.

[4] Certain IgM Abs cleave gp120 at rates exceeding other polypeptides (S. Karle, S. Planque and S. Paul; unpublished observations).

EXAMPLE V

Selective IgM-Catalyzed Hydrolysis of HIV gp120: An Innate Defense Against gp120?

Hapten-like covalently reactive antigen analogs (CRAs) containing an electrophilic phosphonate diester group are reported to bind irreversibly to the variable (V) domains of IgG antibodies (Abs) suggesting the presence of enzyme-like nucleophilic sites (Planque et al., 2003). Noncovalent Ab-antigen interactions guide the nucleophilic reactivity to individual polypeptide antigens, as judged from the specific reactivity of polypeptide CRAs with Abs directed to the polypeptide component (Planque et al., 2003). Despite these properties, IgG Abs only express low-level proteolytic activities. This may be due to physiological barriers resulting from the opposing events occurring in Ab catalysis and the later stages of B cell differentiation. Occupancy of the B cell receptor complex (BCR; membrane bound Ig subunits together with noncovalently associated signal transducing proteins) by the antigen drives cell division. Efficient catalysis, on the other hand, entails rapid release of antigen fragments, which could result in cessation of antigen-driven clonal selection.

The human immunodeficiency virus (HIV) coat protein gp 120 initiates viral infection by binding host cell CD4 receptors. In addition, monomer gp120 is shed from the viral and infected cell surfaces in soluble form. Free gp120 may be important in the pathogenesis of AIDS. Binding of the protein to infected CD+ cells has been implicated in depletion of T cells (Siciliano, 1996), and free gp120 also induces neuronal damage (Kaul and Lipton, 1999). Presently, no effective immunotherapeutic or vaccination strategies against HIV infection or soluble gp120 are available. The humoral IgG responses to HIV infection are generally dominated by Abs to the mutable regions of gp120. These Abs are ineffective against viral escape mutants appearing over the course of infection. Abs to the CD4 receptor binding site of gp120, developed by experimental immunization (He et al., 2002) and phage library protocols (Burton et al., 1994), have been proposed as immunotherapy candidates. Recently, immunization with the CRA derivative of gp120 was shown to induce the synthesis of specific IgG Abs that cleave gp120 (Paul et al., 2003). Proteolytic Abs with the appropriate gp120 recognition specificity are advantageous for the purpose of permanent inactivation of the protein. Moreover, repeated reaction cycles should result in the fragmentation of multiple gp120 molecules by a single catalyst molecule. Conventional Abs bind gp120 stoichiometrically, and dissociation of the Ab-antigen complex releases the biologically active protein.

IgG Abs from healthy humans and immunologically naive mice are reported to cleave short peptide substrates promiscuously (Kalaga et al., 1995). Reactions like esterolysis and hydrogen peroxide synthesis are also catalyzed by certain Abs regardless of the adaptive maturational status of the V domains (Wentworth et al., 2000; Patten et al., 1996). As the first class of Abs synthesized in B cell development, IgM Abs usually contain V domains with lower levels of adaptive sequence diversification than IgG V domains produced by differentiated B cells. In the course of studies on Ab-catalyzed gp120 cleavage (Paul et al., 2003), we discovered the phenomenon of selective and efficient gp120 cleavage by IgM from the preimmune repertoire. The IgM Abs recognize a peptide determinant reported to contribute contact sites for CD4, i.e., gp120 residues 421-433 (Goodglick et al., 1995; Karray and Zouali, 1997). This determinant is also implicated in gp120 recognition as a superantigen by the conserved V domain regions of certain Abs (Neshat et al., 2000; Karray et al., 1998).

Results

Catalytic Activity of Polyclonal IgM Abs.

Biotinylated gp120 (Bt-gp120) was cleaved byIgM from all 5 human sera (FIG. 32A), assessed by depletion of the parent gp120 bandand appearance offragments with lower-mass in electrophoresis gels (FIG. 32B; the recombinant protein migrates with Mr ~94 kD, presumably because of incomplete glycosylation in the baculovirus expression system). None of the IgG samples from the 5 human sera cleaved gp 120 detectably. The data in FIG. 32A are expressed per equivalent combining sites of IgM and IgG (10 and 2, respectively; note, however, that all 10 IgM valencies are usually not filled (Chavin and Franklin, 1969). Superior IgM catalysis, therefore, can not be ascribed to the greater number of IgM combining sites. Essentially identical results were obtained using IgM and IgG Abs prepared from the pooled sera of immunologically unstimulated BALB/c mice (87.9% cleavage/20 hours/150 nM IgM combining sites; undetectable gp120 cleavage at equivalent IgG combining site concentration; reaction conditions as in FIG. 32A).

Affinity-purified IgM was subjected to two cycles of gel filtration in the denaturing solvent, 6 M guanidine hydrochloride (FIG. 33). Abs recovered from this procedure were renatured by dialysis and the catalytic activity was measured. IgM subjected to denaturing gel filtration displayed near-equivalent Bt-gp120 cleaving activity as the starting IgM fraction (82.2±9.2 and 78.8±1.0% cleavage, respectively), indicating the absence of noncovalently-associated contaminating proteases.

Catalytic Activity of Monoclonal IgM Abs.

Each of six monoclonal IgM Abs studied (5 murine; 1 human) displayed gp120 cleaving activity (FIG. 34A). IgM Yvo purified by repetitive warming and cooling was analyzed for catalytic activity prior to and after further affinity chromatography on an anti-IgM column. The levels of gp120 cleavage before and after the final purification step were essentially identical (46.4±0.6% (s.d.) and 44.3±4.9% Bt-gp120 cleaved/50 nM IgM/6 hours, respectively; reactions as in FIG. 32B). This fulfils the criterion of purification to constant specific activity required for assignment of enzymatic activity to IgM.

Identically-purified murine IgM Abs expressed differing levels of catalytic activity varying over a 27.5-fold range; FIG. 34A). As the constant domain architecture of the Abs is identical, the results suggest that the catalytic activity is a V domain property. This is supported by observation of gp120 cleaving activity in the Fab fragment of IgM Yvo prepared by digestion with immobilized pepsin and gel filtration (FIG. 34B). Under the neutral pH conditions employed, pepsin is inactivated irreversibly (Cornish-Bowden et al., 1969). Treatment of Bt-gp120 with purified pepsin (1.2 μM) did not cleave the protein detectably (not shown; reaction conditions as in FIG. 34C), confirming that the observed gp120 cleaving activity of Fab is not due to pepsin contamination.

Treatment of Bt-gp120 with IgM Yvo generated an 80 kD biotin-containing fragment, the intensity of which changed only marginally over the course of the reaction, accompanied by progressive disappearance of the parent band (FIG. 35A). This suggested that the 80 kD band may be susceptible to additional cleavage reactions. Several faint biotin-containing bands appeared at lower Mr values in highly overexposed gels (43, 31, 25 and 17 kD; not shown). Because of the low biotin content of gp120 (1.4 moles/moles), the presence of biotin does not accurately predict the relative abundance of the fragments. Incubation of gp120 devoid of biotin with IgM Yvo generated several compasses blue-stainable bands at 15.4-18.8 kD (FIG. 35B; bands at 25 kD and 70 kD correspond to IgM Yvo light and heavy chains, respectively). The fragments were subjected to N terminal amino acid sequencing (Table 8). The 80 kD gel region yielded a sequence corresponding to the N terminus of gp120. As no internal gp120 peptide sequence was detected, the cleavage site was not identifiable, but it was concluded that the fragment is produced by cleavage at a site located in the C terminal half of gp120. Peptide sequences corresponding to gp120 residues 433-442 were identified in fragments corresponding to 15.4-16.4 kD and 17.6 kD gel regions, permitting unambiguous identification of the 432-433 peptide bond as one of the cleavage site. Two peptide sequences corresponding to gp120 residues 1-10 were present in the 15.4-16.4 kD and 18.8 kD gel regions. These gp120 fragments indicate the existence of two additional cleavage sites located in the N terminal half of the protein.

Kinetics and Selectivity.

Treatment of biotinylated bovine serum albumin (Bt-BSA), biotinylated soluble CD4 (Bt-sCD4) or biotinylated soluble epidermal growth factor receptor (Bt-sEGFR) with polyclonal human IgM did not result in noticeable depletion of the electrophoresis bands corresponding to full-length form of these proteins (FIG. 36). Under these conditions, readily detectable Bt-gp120 cleavage was observed. Similarly, there was no detectable depletion of full-length Bt-sCD4, Bt-sEGFR and Bt-BSA bands treated with IgM Yvo and polyclonal murine IgM (reaction conditions as in FIG. 36; cleavage of Bt-gp120 by these Abs, 69.1% and 97.4% respectively).

The kinetic parameters for three IgM preparations were determined by fitting the observed initial rates at increasing concentrations of gp120 to the general quadratic equation predicting the concentration of the catalyst-substrate complex (Table 9). The method is is applicable to the study of the reaction kinetics when the gp120 concentrations are lower than the $K_d$. The apparent $K_d$ is the value yielding the best fit between observed velocity and [IgM-gp120], and apparent $k_{cat}$ is the slope of the velocity versus [IgM-gp120] plot. Correlation coefficients for the 3 plots corresponding to the data reported in Table 9 were >0.9. Observed $k_{cat}$ values for polyclonal human IgM, monoclonal human IgM Yvo and monoclonal murine IgM 8704 varied over a 52.5-fold range, and the $K_d$ values, over a 23.8-fold range.

Nucleophilic Reactivity.

The phosphonate diester-containing analog of gp120 residues 421-432 (gp120pep-CRA; FIG. 37A) has been developed as a covalent probe for nucleophilic anti-gp120 Abs. Abs raised by immunization with the peptide component bind irreversibly and rapidly with gp120pep-CRA due to the facilitatory effects of noncovalent antigen-Ab binding interactions (Planque et al., 2003). In the present study, progressive inhibition of the cleavage of Bt-gp120 by IgM Yvo was observed at increasing gp120pep-CRA concentrations (FIG. 37B). Covalent gp120pep-CRA binding was measured by estimating the biotin content in protein adduct bands on electophoresis gels. All 5 IgM Ab preparations studied (3 monoclonal IgMs, murine polyclonal IgM and human polyclonal IgM) formed covalent adducts with the gp120pep-CRA at rates exceeding adduct formation with hapten CRA I (FIG. 38A; mean rate, 41-fold greater for the former compound; P<0.002, Student's t test, 2 tailed). The μ chain subunit accounted for the majority of covalent gp120pep-CRA binding except in the case of monoclonal IgM Yvo (FIG. 38B; rates in arbitrary area units (AAU)/h/μM Ab subunit: H chain, 41.5-257.5; L chain, 22.3-247.7). The CRA adducts accumulated linearly as a function of time (e.g., IgM Yvo L chain adducts shown in FIG. 38C). Inclusion of excess synthetic gp120(421-436) in the reaction mixture (500 μM) inhibited the formation of gp120pep-CRA adducts by each of the 5 IgM preparations by ≥68%, regardless of the subunit at which the reaction occurred (e.g., FIG. 38D).

Discussion

These studies indicate the selective ability of IgM Abs to catalyze the cleavage of the HIV coat protein gp120. The Abs were from uninfected humans and immunologically naïve mice. IgG Abs, products of B cells at more advanced stages of differentiation, did not cleave gp120 appreciably. The observed selectivity of IgM catalyzed gp120 hydrolysis, therefore, must reflect the intrinsic properties of the preimmune Ab repertoire. Assignment of the catalytic activity to IgM V domains is supported by these observations: (a) IgM Abs differing only by virtue of their V domains displayed divergent levels of catalytic activity; (b) The Fab fragment expressed the activity; and (c) Formation of covalent IgM adducts with the gp120 pep-CRA probe proceeded more rapidly than the hapten CRA; different Abs formed the adducts at varying levels; the reaction for different Abs displayed distinct subunit preferences; and, the reaction was inhibited by a synthetic peptide spanning the peptide determinant located in gp120pep-CRA. The CRA phosphonate diester group inhibits serine proteases by covalent binding at the activated Ser nucleophile (Oleksyszyn and Powers, 1994; Sampson and Barton, 1991). A germline configuration light chain has been described to express serine protease-like proteolytic activity (Gololobov et al., 1999) and IgG Abs in the preimmune murine and human repertoires are also reported to express proteolytic activities (Kalaga et al., 1995; Matsuura et al., 1998). The reactivities of proteolytic IgMs described here are consistent with the germline origin of the catalytic activity.

Avidity effects due to the decavalent character of IgM can strengthen the binding to antigens with repeat epitopes even if the intrinsic affinity of the individual combining sites is small. Superior catalysis by IgM compared to IgG can not be attributed to this factor, however, as gp120 does not contain repeat epitopes. Furthermore, catalysis assays conducted in solution using monoclonal Abs do not favor multivalent IgM binding to the same gp120 molecule. The following explanations can be presented for the superior catalytic activity of IgM Abs. First, loss of catalytic activity may be attendant to V domain somatic diversification after isotype switching from IgM to IgG.

Second, distinctive IgM constant domain characteristics may be important in maintaining the integrity of the catalytic site, in which case isotype switching itself may result in reduced catalytic activity. These explanations are not mutually exclusive. Both explanations are consistent with the argument that catalysis is a disfavored phenomenon in the advanced stages of B cell development, as efficient BCR catalysis is predicted to result in reduced BCR occupancy. We did not attempt to address these points experimentally in the present study. However, the monovalent Fab studies suggested that disruption of the constant domain architecture of IgM is deleterious for catalysis. The Fab preparations displayed ~100-fold lower activity than computed for the individual combining sites of pentameric IgM. Pepsin employed to prepare Fab cleaves tt chains on the C terminal side of the CH2 domain (MacKenzie et al., 1978), which is distinguished by its conformational flexibility (Roux et al., 1998). Alterations of antigen binding activity when the same V domains are expressed as full-length IgG Abs belonging to different isotypes are described (e.g., Morelock et al., 1994), but we are not aware of IgM-IgG V domain swapping experiments in the literature. Positive cooperativity effects such as those described for antigen binding by the two IgG combining sites (van Erp et al., 1991), could theoretically furnish favorable contributions in catalysis. The sequence of events as individual IgM combining sites bind antigen has not been elucidated, but the hypothesis of positive cooperativity is not supported by findings that only 5 of the 10 IgM combining sites are filled at excess antigen concentration (e.g., Chavin and Franklin, 1969).

Selective gp120 recognition by IgM proteases can not be understood from the local chemical interactions confined to recognition of the dipeptide cleavage site, as the same dipeptide units are present in other poorly cleaved proteins. The selectivity probably arises from noncovalent gp120 recognition by Abs. This may be deduced from the comparatively small $K_d$ values for catalytic IgM recognition of gp120, 1.3-30.0 μM. These values are about 2 orders of magnitude smaller than the apparent $K_d$ for promiscuous proteolytic reactions catalyzed by IgMAbs (S. Planque and S. Paul, unpublished observations) and IgG Abs isolated from the sera of preimmune mice and healthy humans (Kalaga et al., 1995). Further support for the importance of noncovalent interactions can be drawn from observations that the covalent reaction of gp120pep-CRA with IgM Abs is guided by noncovalent recognition of its peptide component. Precedents for Ab catalytic selectivity derived from noncovalent recognition are available. Noncovalent paratope-epitope binding coordinated with nucleophilic attack on the scissile bond is the basis for selective cleavage of individual polypeptide antigens by adaptively matured proteolytic Abs obtained by experimental immunization (Paul et al., 2003; Sun et al., 1997).

Selective cleavage of gp120 by IgM from subjects not infected with HIV may be traced to the superantigenic character of gp120 (Berberian et al., 1993). IgM Abs are described to bind gp120 as a superantigen (Townsley-Fuchs et al., 1996; Juompan et al., 1998) by contacts at conserved Ab V domain regions (Neshat et al., 2000; Karray et al., 1998). The superantigenic site of gp120 consists of discontinuous peptide segments, one of which spans residues 421-433 (Goodglick et al., 1995; Karray and Zouali, 1997). An IgM Ab studied here cleaved the peptide bond linking residues 432 and 433. All of the catalytic IgM Abs displayed selective covalent binding of gp120pep-CRA, which contains residues 421-431 and an amidino phosphonate mnimetic of residues 432 and 433. This supports a model entailing noncovalent gp120 binding that is functionally coordinated with the nucleophilic reactivity of the catalytic site. The proposed mechanism is identical to that utilized by catalytic IgG Abs induced by experimental immunization (Paul et al., 2003; Sun et al., 1997), except that the noncovalent binding takes place at conserved V domain regions instead of the adaptively matured hypervariable loops. However, certain aspects of the model remain to be explored. For instance, the covalent gp120pep-CRA data suggest the extent to which the nucleophilic reactivity is coordinated with noncovalent peptide epitope recognition, but they do not establish the subunit location of the catalytic nucleophile. Adducts of gp120pep-CRA were formed mainly by the heavy chain of four IgM preparations and the light chain of one IgM preparation. Previous reports indicate that the light and heavy chains can each express catalytic nucleophiles (Gao et al., 1995; Matsuura and Sinohara, 1996; Hatiuchi et al., 2003). Another interesting aspect is the cleavage of nmultiple peptide bonds in gp120, analogous to the complex cleavage profiles reported for monoclonal Ab L chain catalyzed fragmentation of gp41 (Hifumi et al., 2002) and vasoactive intestinal peptide (VIP) (Sun et al., 1997). The fragmentation profiles maybe explained by the formation of alternate Ab-gp120 ground state complexes with different peptide bonds positioned in register with the nucleophilic residue (Paul et al., 2003). When the Ab recognizes a conformational epitope, the alternate cleavage sites must be spatially adjacent but they can be distant in the linear sequence, producing complex cleavage pattern.

Noncovalent IgM-gp120 complexes reported previously contain Abs with VH domains belonging to the VH3 family (Goodglick et al., 1995; Karray and Zouali, 1997; Berberian et al., 1993). The VH domain of IgM Yvo belongs to the VH2 family (VH2-5 germline gene; deduced from Shaw et al., 2002; VH sequences of remaining IgM Abs studied here are not available). This discrepancy maybe explained as follows. First, proteolysis of gp120 entails rapid product release. Efficient catalysts will be detected poorly by binding assays because of the small concentration of stable immune complexes. Second, the turnover capability allows more sensitive detection of catalysts than noncatalytic Abs. At the IgM (15 nM) and gp120 concentrations (100 nM) in FIG. 32A, a noncatalytic Ab with $K_d$ 31 μM will bind only 0.5 nM gp120 at equilibrium [computed from the equation $[Ab-Ag]^2-[Ab-Ag]([Ab_0]+[Ag_0]+K_d)+[Ab_0][Ag_0]=0$, where $[Ab_0]$ and $[Ag_0]$ are Ab and antigen concentrations at time 0]. In comparison, 70 nM gp120 will be cleaved over 20 hours under similar conditions by a catalytic IgM preparation with $k_{cat}$ 2.1/min and $K_d$ equivalent to the noncatalytic Ab (computed as $P_t=Ag_0[1-e^{(-k[Ab]_0)t}]$, where $P_t$ is product concentration at time t and k is $k_{cat}/K_m$; Marangoni, 2003).

Catalytic Abs produced spontaneously by the immune system have been viewed until now primarily as pathogenic effector molecules, e.g., autoantibodies to VIP (Paul et al., 1989), nucleic acids (Shuster et al., 1992) and Factor VIII (Lacroix-Desmazes et al., 1999). The present study suggests that IgM catalysis may be relevant to the pathogenesis of HIV infection. Free gp120 shed from HIV is thought to exert deleterious effects on several cell types. The neurotoxic effect of free gp120 has been implicated in AIDS dementia (Kaul and Lipton, 1999) and its ability to induce apoptosis may contribute to the decline of CD4+ T cells, regardless of whether the cells are infected (Siliciano, 1996). A caveat in assessing the functional potency of Ig Abs is the possibility of inhibition by naturally occurring serine protease inhibitors in blood and other anatomic locations relevant to HIV infection. In the absence of inhibitors, circulating human IgM at 2 mg/ml in blood may be computed to hydrolyze 50% and 90% of gp120 present at concentrations<<$K_d$ in 4.6 min and 15.5 min, respectively (assuming $K_d$ 31 μM, $k_{cat}$ 2.1/min, Table 9). Similarly, if cleavage of trimeric gp120 on the viral surface proceeds at the rate observed for the free protein, only short time periods are needed to hydrolyze the majority of viral gp120 (gp120 concentrations in infection remain <<observed $K_d$; e.g., $10^6$ HIV copies/ml with 100 gp120 molecules/virion correspond to ~$2 \times 10^{-13}$ M gp120; Richieri et al., 1998). Support for a protective role for IgM Abs can be drawn from their ability to recognize gp120 residues 421-433. These residues contribute contact sites in the binding of gp120 by host cell CD4 receptors (Olshevesky et al., 1990; Kwong et al., 1998). Fragments generated by cleavage at the IgM-sensitive Lys432-Ala433 bond are reportedly devoid of CD4 binding activity (Pollard et al., 1991). IgG Abs that bind the gp120 superantigenic site noncovalently are described as resistance factors in progression of HIV infection (Townsley-Fuchs et al., 1996; Juompan et al., 1998). Initial studies conducted as in Karle et al., In press suggest that polyclonal human IgM can neutralize the infection of peripheral blood mononuclear cells by primary HIV-1 isolates under low serum conditions (Hanson, Karle and Paul, to be published elsewhere). Berberian et al., 1993 have previously cited their unpublished data suggesting that HIV neutralization in the absence of serumby IgM antibodies that bind the superantigenic site gp120 (citation 11 in Berberian et al., 1993).

These studies may also be relevant to HIV vaccine design. Synthetic peptides containing gp120 residues 421-433 have been advanced as vaccine candidates (Morrow et al., 1992; Karle et al., 2003), inpart because these residues are comparatively conserved in diverse HIV strains. The gp120 peptidyl CRA described here is a potential immunogen for induction of Abs with strengthened recognition of the gp120 superantigenic site. A CRA derivative of full-length gp120 induces the synthesis of catalytic Abs (Paul et al., 2003), but Abs to irrelevant epitopes probably dominate the response to this imnmunogen.

Experimental Procudures

Antibodies.

Human serum Abs were isolated from subjects without evidence of infection or immunological disease (2 females, 3 males; age 23-45 yrs). Murine serum Abs were from BALB/c mice (Harlan, Indianapolis, Ind.; pooled from 150 mice; age 8-12 weeks). Murine monoclonal IgM Abs used here are directed against certain major histocompatibility antigens (clones corresponding to catalog nos. 8702, 8704, 9008, 9010 and 9020; cell-free ascites; Cedarlane, Ontario, Canada). Monoclonal IgM Yvo was obtained by plasmapheresis of a patient with Waldenstrom's macroglobulinemia (Shaw et al., 2002). All monoclonal IgM Abs contained κ chains. Serum or ascites (1 ml) was mixed for 1 h with 1 ml Sepharose 4B conjugated rat anti-mouse IgM Abs (settled gel; Zymed, San Francisco, Calif.) or agarose conjugated goat anti-human IgM Abs (Sigma, St. Louis, Mo.) with IgM binding capacities 0.8 and 3 mg, respectively, in 50 mM Tris-HCl, pH 7.5, 0.1 mM CHAPS (3-[(3-cholamidopropyl)dimethylammonio]-1-propanesulfonic acid) (buffer A). The unbound fraction was recovered and the gel washed with 20 buffer A volumes, taking care that protein in the effluent had returned to undetectable levels prior to elution ($A_{280}$<0.001). Elution was with 100 mM glycine pH 2.7 (0.5 ml/fraction into 25 µl 1M Tris-HCl, pH 9.0). Further purification was on a Superose-6 FPLC gel filtration column (1×30 cm; 0.25 ml/min; Pharmacia) in twvo different solvents: 50 mM Tris-HCl, pH 7.7, 0.1 M glycine, 0.15 M NaCl, 0.025% Tween-20 (buffer B) or 6 M guanidine hydrochloride in buffer B adjusted to pH 6.5 with HCl (buffer C). Prior to column fractionation, the affinity purified IgM was dialyzed against buffer C. Column calibration was with thyroglobulin (660 kD), IgG (150 kD) and albumin (67 kD). The IgM eluted with apparent Mr 900 kD close to the void volume of the column. IgM was renatured following buffer C chromatography by dialysis against buffer B (Kalaga et al., 1995). IgMYvo, a cryoglobulin, was purified from serum by repetitive warming (37° C.) and cooling (4° C.; 3 cycles; Shaw et al., 2002) followed by affinity chromatography on the anti-human IgM column. IgG was purified on Protein G-Sepharose columns (Kalaga et al., 1995) using as starting material the unbound fraction from the anti-IgM columns or cell-free ascites. Fab fragments were prepared by digesting IgM (300 µl, 1 mg/ml) with agarose conjugated pepsin (0.6 ml gel, 30 min, 37° C.) in 100 mM sodium acetate, pH 4.5, 150 mM NaCl, 0.05% $NaN_3$, 0.1 mM CHAPS) as recommended by the manufacturer (Pierce). The unbound fraction was dialyzed against buffer B, purified by FPLC gel filtration on a Superose 12 column and dialyzed against 50 mM Tris-HCl, pH 7.7, 0.1 M glycine, 0.1 mM CHAPS. Total protein was determined by the bicinchoninic acid method (Pierce). SDS-polyacrylamide gel electrophoresis (4-20% gels) was conducted under reducing conditions (2-mercaptoethanol). Blots of the gels were stained with peroxidase conjugated goat anti-human µ, γ, κ and λ Abs (1:1000; Sigma) or goat anti-mouse µ, γ, κ and λ Abs followed byperoxidase conjugated rabbit anti-goat IgG (Fc specific, 1:1000; Pierce; Kalaga et al., 1995). Nominal Mr values were computed by comparison with standard proteins (14 kDa-94 kDa; Pharmacia).

Proteolysis Assays.

gp120, the soluble extracellular domain of the epidermal growth factor receptor (sEGFR) and bovine serum albumin were labeled with biotin (Bt) at Lys residues has been described (1-2 mol Bt/mol protein) as described in Planque et al., 2003. Soluble CD4 (sCD4; residues 1-183; NIH AIDS Reagent Program) was biotinylated and purified by similar methods (1.3 mol Bt/mol sCD4). The gp120 (strain MN) is a recombinant protein expressed in the baculovirus system (Immunodiagnostics, Woburn, Mass.). Synthesis of gp120pep-CRA (Bt-KQIINMWQEVGN with the amidino phosphonate diester group at the C terminus) is described in Taguchi et al., 2002. Catalysis assays (Paul et al., 2003) were performed by incubating Bt-proteins with the Abs in 50 mM Tris-HCl, 100 mM glycine, pH 7.7, 1 mM CHAPS at 37° C. The samples were boiled in buffer containing SDS and 2-mercaptoethanol, electrophoresed on SDS-gels. Cleavage was determined by densitometry of electroblots stained with streptavidin peroxidase. Assays for inhibition of catalysis by the gp120pep-CRA were performed in 6% ethanol. Purified porcine pepsin used as control in Fab cleavage studies was from Sigma N terminal sequencing of gp120 fragments electroblotted from electrophoresis gels was performed as in Sun et al., 1997 (Applied Biosystems Model 492 Procise cLC sequencer). Kinetic parameters were determined by fitting rate data at varying Bt-gp120 concentrations to the quadratic equation (Sun et al., 1997): $[CS]^2-[CS]([C_t]+[S_t]+K_d)+[C_t][S_t]=0$, where $[C_t]$ and $[S_t]$ are the total concentrations of catalyst and substrate, and [CS] is the concentration of the catalyst-substrate complex.

Irreversible CRA Binding.

Synthesis of the biotin-containing hapten phosphonate CRA, its irreversible reaction with proteases and Abs, and the irreversible binding of gp120pep-CRA with specific Abs to the synthetic peptide composed of gp120 residues 421-436 have been described (Planque et al., 2003; Taguchi et al., 2002; Nishiyama et al., 2002). Formation of CRA-IgM adducts was measured by reducing SDS-electrophoresis, electroblotting and densitometry using a streptavidin-peroxidase conjugate (Planque et al., 2003). Band intensities are expressed in arbitrary area units. Initial velocities were computed as slopes of progress curves (incubation for 20, 40, 60, 120 and 220 min; $r^2$>0.9 for all data reported here).

REFERENCES

Berberian, L., Goodglick, L., Kipps, T. J., and Braun, J. (1993). Immunoglobulin VH3 gene products: natural ligands for HIV gp120. Science 261, 1588-1591.

Burton, D. R., Pyati, J., Koduri, R., Sharp, S. J., Thornton, G. B., Parren, P. W., Sawyer, L. S., Hendry, R. M., Dunlop, N., and Nara, P. L. (1994). Efficient neutralization of primary isolates of HIV-1 by a recombinant human monoclonal antibody. Science 266, 1024-1027.

Chavin, S. I., and Franklin, E. C. (1969). Studies on antigen-binding activity of macroglobulin antibody subunits and their enzymatic fragments. J. Biol. Chem. 244, 1345-1352.

Cornish-Bowden, A., and Knowles, J. (1969). The pH dependence of pepsin-catalyzed reactions. Biochem. J. 113, 353-362.

Gao, Q.-S., Sun, M., Rees, A., and Paul, S. (1995). Site-directed mutagenesis of proteolytic antibody light chain. J. Mol. Biol. 253, 658-664.

Gololobov, G., Sun, M., and Paul, S. (1999). Innate antibody catalysis. Mol. Immunol. 36, 1215-1222.

Goodglick, L., Zevit, N., Neshat, M. S., and Braun, J. (1995). Mapping the Ig superantigen-binding site of HIV-1 gp120. J. Immunol. 155, 5151-5159.

Hatiuchi, K., Hifumi, E., Mitsuda, Y., and Uda, T. (2003). Endopeptidase character of monoclonal antibody i41-7 subunits. Immunol. Lett. 86, 249-257.

He, Y., Honnen, W. J., Krachmarov, C. P., Burkhart, M., Kayman, S. C., Corvalan, J., and Pinter, A. (2002). Efficient isolation of novel human monoclonal antibodies with neutralizing activity against HIV-1 from transonic mice expressing human Ig loci. J. Immunol. 169, 595-605.

Hifumi, E., Mitsuda, Y., Ohara, K., and Uda, T. (2002). Targeted destruction of the HIV-1 coat protein gp41 by a catalytic antibody light chain. J. Immunol. Methods. 269, 283-298.

Juompan, L., Lambin, P., and Zouali, M. (1998). Selective deficit in antibodies specific for the superantigen binding site of gp120 in HIV infection. FASEB J. 12, 1473-1480.

Kalaga, R., Li, L., O'Dell, J., and Paul, S. (1995). Unexpected presence of polyreactive catalytic antibodies in IgG from unimmunized donors and decreased levels in rheumatoid arthritis. J. Immunol. 155, 2695-2702.

Karle, S., Nishiyama, Y., Zhou, Y.-X., Luo, J., Planque, S., Hanson, C., and Paul, S. (2003). Carrier-dependent specificity of antibodies to a conserved peptide determinant of gp120. Vaccine 21, 1213-1218.

Karle, S., Planque, S., Nishiyama, Y., Taguchi, H., Zhou, Y.-X., Salas, M., Lake, D., Thiagarajan, P., Arnett, F., Hanson, C. V., and Paul, S. (2003). Cross-clade HIV-1 neutralization by an antibody fragment from a lupus phage display library. AIDS. In press.

Karray, S., Juompan, L., Maroun, R. C., Isenberg, D., Silverman, G. J., and Zouali, M. (1998). Structural basis of the gp120 superantigen-binding site on human immunoglobulins. J. Immunol. 161, 6681-6688.

Karray, S., and Zouali M. (1997). Identification of the B cell superantigen-binding site of HIV-1 gp120. Proc. Natl. Acad. Sci. USA 94, 1356-1360.

Kaul, M., and Lipton, S. A. (1999). Chemokines and activated macrophages in HIV gp120-induced neuronal apoptosis. Proc. Natl. Acad. Sci. USA 96, 8212-8216.

Kwong, P. D., Wyatt, R., Robinson. J., Sweet, R. W., Sodroski, J., and Hendrickson, W. A. (1998). Structure of an HIV gp120 envelope glycoprotein in complex with the CD4 receptor and a neutralizing human antibody. Nature 393, 648-659.

Lacroix-Desmazes, S., Moreau, A., Sooryanarayana, B. C., Stieltjes, N., Pashov, A., Sultan, Y., Hoebeke, J., Kazatchkine, M. D. and Kaveri, S. V. (1999). Catalytic activity of antibodies against factor VIII in patients with hemophilia A. Nat. Med. 5, 1044-1047.

MacKenzie, M. R., Gutman, G. A., and Warner, N. L. (1978). The binding of murine IgM to staphylococcal A protein. Scand. J. Immunol. 7, 367-370.

Marangoni, A. G. (2003). Enzyme kinetics: A modern approach. (New Jersey: John Wiley and Sons), pp. 50-52.

Matsuura, K., Ikoma, S., Sugiyama, M., Funauchi, M., and Sinohara, H. (1998). Amidolytic and peptidolytic activities of inmmunoglobulin G present in sera from patients with rheumatoid arthritis, Sjogren's syndrome and systemic lupus erytlematosus. Immunol. 95, 26-30.

Matsuura, K., and Sinohara, H. (1996). Catalytic cleavage of vasopressin by human Bence Jones proteins at the arginylglycinamide bond. Biol. Chem. 377, 587-589.

Morelock, M. M., Rothlein, R., Bright, S. M., Robinson, M. K., Graham, E. T., Sabo, J. P., Owens, R., King, D. J., Norris, S. H., Scher, D. S., Wright, J. L., and Adair, J. R. (1994). Isotype choice for chimeric antibodies affects binding properties. J. Biol. Chem. 269, 13048-13055.

Morrow, W. J., Williams, W. M., Whalley, A. S., Ryskamp, T., Newman, R., kang, C. Y., Chamat, S., Kohler, H., and Kieber-Emmons, T. (1992). Synthetic peptides from a conserved region of gp120 induce broadly reactive anti-HIV responses. Immunol. 75, 557-564.

Neshat, M. N., Goodglick, L., Lim, K., and Braun, J. (2000). Mapping the B cell superantigen binding site for HIV-1 gp120 on a VH3 Ig. International. Immunology 12, 305-312.

Nishiyama, Y., Taguchi, H., Luo, J., Zhou, Y.-Z., Burr, G., Karle, S., and Paul, S. (2002). Covalent reactivity of a phosphonate monophenyl ester with serine proteinases: An overlooked feature of oxyanionic transition state analogs. Arch. Biochem. Biophys. 402, 281-288.

Oleksyszyn, J., and Powers, J. C. (1994). Proteolytic enzymes: Serine and cysteine peptidases. In Methods in Enzymology. (New York: Academic Press), pp. 423-441.

Olshevesky, T. J., Helseth, E., Furman, C., Li, J., Haseltine, W., and Sodroski, J. (1990). Identification of individual human inumunodeficiency virus type 1 gp120 amino acids important for CD4 receptor binding. J. Virol. 64, 5701-5707.

Patten, P. A., Gray, N. S., Yang, P. L., Marks, C. B., Wedemayer, G. J., Boniface, J. J., Stevens, R. C., and Schultz, P. G. (1996). The immunological evolution of catalysis. Science 271, 1086-1091.

Paul, S., Planque, S., Zhou, Y.-X., Taguchi, H., Bhatia, G., Karle, S., Hanson, C., and Nishiyama, Y. (2003). Specific HIV gp120 cleaving antibodies induced by covalently reactive analog of gp120. J. Biol. Chem. 278, 20429-20435.

Paul, S., Volle, D. J., Beach, C. M., Johnson, D. R., Powell, M. J., and Massey, R. J. (1989). Catalytic hydrolysis of vasoactive intestinal peptide by human autoantibody. Science 244, 1158-1162.

Planque, S., Taguchi, H., Burr, G., Bhatia, G., Karle, S., Zhou, Y.-X., Nishiyama, Y., and Paul, S. (2003). Broadly distributed chemical reactivity of natural antibodies expressed in coordination with specific antigen binding activity. J. Biol. Chem. 278, 20436-20443.

Pollard, S., Meier, W., Chow, P., Rosa, J., and Wiley, D. (1991). CD4-binding regions of human immunodeficiency virus envelope glycoprotein gp120 defined by proteolytic digestion. Proc. Natl. Acad. Sci. USA. 88, 11320-11324.

Richieri, S. P., Bartholomew, R., Aloia, R. C., Savary, J., Gore, R., Holt, J., Ferre, F., Musil, R., Tian, H. R., Trauger, R., Lowry, P., Jensen, F., Carlo, D. J., Maigetter, R. Z., and Prior, C. P. (1998). Characterization of highly purified, inactivated HIV-1 particles isolated by anion exchange chromatography. Vaccine 16, 119-129.

Roux, K. H., Strelets, L., Brekke, O. H., Sandlie, I., and Michaelsen, T. E. (1998). Comparisons of the ability of human IgG3 hinge mutants, IgM, IgE, and IgA2, to form small immune complexes: a role for flexibility and geometry. J. Immunol. 161, 4083-4090.

Sampson, N. S., and Barton, P. A. (1991). Peptidic phophonylating agents as irreversible inhibitors of serine proteases and models of the tetrahedral intermediates. Biochemistry 30, 22255-22263.

Shaw, D. C., Shultz, B. B., Ramsland, P. A., and Edmundson, A. B. (2002). Dealing with intractable protein cores: protein sequencing of the Mcg IgG and the Yvo IgM heavy chain variable domains. J. Mol. Recog. 15, 341-348.

Shuster, A. M., Gololobov, G. V., Kvashuk, O. A., Bogomolova, A. E., Smirnov, I. V., and Gabibov, A. G. (1992). DNA hydrolyzing autoantibodies. Science 256, 665-667.

Siliciano, R. F. (1996). The role of CD4 in HIV envelope-mediated pathogenesis. Curr. Top. Microbiol. Immunol. 205, 159-179.

Sun, M., Gao, Q.-S., Kimarskiy, L., Rees, A., and Paul, S. (1997). Cleavage specificity of aproteolytic antibody light chain and effects of the heavy chain variable domain. J. Mol. Biol. 271, 374-385.

Taguchi, H., Burr, G., Karle, S., Planque, S., Zhou, Y.-X., Paul, S., and Nishiyama, Y. (2002). A mechanism-based probe for gp120-hydrolyzing antibodies. Bioorg. Med. Chem. Lett. 12, 3167-3170.

Townsley-Fuchs, J., Kam, L., Fairhurst, R., Gange, S. J., Goodglick, L., Giorgi, J. V., Sidell, N., Detels, R., and Braun, J. (1996). Human immunodeficiency virus-1 (HIV-1) gp120 superantigen-binding serum antibodies. J. Clin. Invest. 98, 1794-1801.

van Erp, R., Gribnau, T. C., van Sommeren, A. P., and Bloemers, H. P. (1991). Affinity of monoclonal antibodies.

Interpretation of the positive cooperative nature of anti-hCG/hCG interactions. J. Immunol. Methods. 140, 235-241.

Wentworth, A. D., Jones, L. H., Wentworth, P., Jr, Janda, K. D., and Lerner, R. A. (2000). Antibodies have the intrinsic capacity to destroy antigens. Proc. Natl. Acad. Sci. USA 97, 10930-10935.

EXAMPLE VI

Additional Evidence and Methods for Specific Covalent and Catalytic Antibody Responses Induced by pCRA Immunization In Example II are disclosed data concerning IgG Abs raised by immunization of autoimmune mice (MRL/lpr strain) with the gp120-CRA immunogen. The gp120-CRA has also been used as the immunogen in non-autommune BALB/c mice. In the present Example, Abs from the latter immunization were raised essentially as in Example II. gp120 devoid of phosphonate diester groups served as the control immunogen. The immunizations were conducted in standard adjuvant without or with simultaneous coimmunization with Protein A, a B cell superantigen thought to skew the repertoire away from utilization of VH3+ family Abs (1). In addition to IgG Abs, IgM Abs were also examined in the present example. Measurement of specific Abs to gp120 in sera from mice obtained over the course of immunization suggested that accumulation of anti-gp120 Abs of the IgM class in response to gp120-CRA was greater than in response to control gp120 (FIG. 39). Coimmunization with protein A enhanced the accumulation of anti-gp120 IgM Abs further.

Monoclonal IgM and IgG Abs from one of the gp120-CRA immunized mice were prepared as in Example II. Screening of the monoclonal IgM secreting hybridomas for cleavage of Bt-gp120 was done essentially as described in Example II. For this purpose, the hybridoma culture supernatants were subjected to high throughput affinity purification in 96 well plates using anti-mouse IgM Abs immobilized on Sepharose (see Example V for details of the affinity gel). Several IgM clones were identified that cleaved Bt-gp120 at levels considerably greater than IgM Abs from unimmunized mice (for example, clones F223-3E7 and F223-6H1 shown in FIG. 40).

IgG secreting wells from the hybridomas described in the preceding paragraph were screened for covalent binding to Bt-gp120 by denaturing electrophoresis on reducing SDS-gels (N=117). The antigen in this screen is devoid of phosphonate groups. Any binding detected on the SDS-gels may be interpreted to reflect unusually stable interactions involving bonds with covalent characteristics. A Bt-gp120 band with nominal mass 154 kD was observed for incubations conducted using 4 clones, an example of which is shown in FIG. 41. This band was also stainable with Abs to mouse IgG in immunoblots, confirming that it represents stable complexes of gp120 with the subunits of the IgG (as the SDS-electrophoresis is conducted under reducing conditions, the S-S bonded structure of the IgG is destroyed and covalent gp120-IgG complexes migrate with the characteristics of gp120-H chain complexes and gp120-L chain complexes.

These results are consistent with additional studied perfomed on the YZ series IgG Abs described in Example II. As noted therein, seven monoclonal IgGs from mice immunized with gp120-CRA were identified to bind the immobilized gp120-CRA covalently, evaluated by the resisatance of the complexes to 2% SDS treatment in our covalent ELISA protocol. In our more recent studies, we observed that all seven of these monoclonal IgGs also display SDS-resistant binding to gp120 devoid of phosphonate moieties (data for 3 of the MAbs are shown in FIG. 42). The SDS-resistant binding was observed using purified IgG (by protein G-Sepharose chromatography) as well as tissue culture supernatants. Identical SDS treatments resulted in near complete removal of conventional anti-gp120 Abs bound to the immobilized gp120 (clones 1121, 257-D IV and 268-D IV directed to gp120 V3 domain; courtesy NIH AIDS Research and Reference Reagent Program and Dr. S. Zolla-Pazner; refs 2-3). These results indicate unusually stable gp120 binding by Abs raised to the gp120-CRA. We concluded that covalent immunization is a viable means to strengthen the covalent reactivity of anti-HIV Abs.

We also conducted new studies involving immunization of mice with the VIP-CRA described in Example III. Immunization with the VIP-CRA resulted in progressively increasing levels nucleophilic reactivity of polyclonal IgG over the course of immunization, determined by the appearance of CRA adducts on denaturing electrophoresis gels (FIG. 43). The level of VIP-CRA covalent binding was superior to that of the hapten CRA devoid of the VIP sequence, suggesting a specific nucleophilic antibody response. These studies confirm that immunization with pCRAs induced the synthesis of Abs with enhanced nucleophilic reactivity coordinated with the traditional noncovalent binding forces responsible for specificity.

REFERENCE

1. Berberian L, Goodglick L, Kipps T J, Braun J. Immunoglobulin VH3 gene products: natural ligands for HIV gp120. Science 1993 Sep. 17; 261(5128):1588-91.
2. Gomy M K, Xu J Y, Gianakakos V, Karwowska S, Williams C, Sheppard H W, Hanson C V, Zolla-Pazner S. Production of site-selected neutralizing human monoclonal antibodies against the third variable domain of the human immunodeficiency virus type 1 envelope glycoprotein. Proc Natl Acad Sci USA 1991 Apr. 15; 88(8):3238-42
3. Gorny M K, Xu J Y, Karwowska S, Buchbinder A, Zolla-Pazner S. Repertoire of neutralizing human monoclonal antibodies specific for the V3 domain of HIV-1 gp120. J Immunol 1993 Jan. 15; 150(2):635-43.

EXAMPLE VII

Evidence for HIV Neutralization by Anti-gp120-CRA Antibodies

Infection of peripheral blood mononuclear cells from normal donors by primary isolates of HIV-1 was measured using a p24 enzymeimmunoassay (methodology details can be found in ref 1). The HIV-1 isolates studied included R5- and X4-dependent strains (strains ZA009, BR004 and SF-162). Controls included the appropriate irrelevant Abs (isotype-matched monoclonal IgG). A positive control included monoclonal Ab b12 directed to the CD4bs of gp120 (2). The test Ab samples did not exert a cytotoxic effect on PBMC, as no loss of cell viability was observed following incubation of the Abs in the absence of HIV (determined by staining cells with acridine orange/ethidium bromide; Sigma; viability ~80-85% in cells treated with diluent and the Ab preparations). Results are as follows: Monoclonal IgG YZ18, YZ22 and YZ23 raised by immunization with the gp120-CRA neutralized the R5-dependent clade C strain ZA009 reproducibly and in a dose-dependent manner (FIG. 44). The positive control (clone b12 kindly provided by Dr. Dennis Burton) displayed limited ability to neutralize this HIV-1 strain. No neutralization of HIV-1 was observed in the presence of an equivalently purified irrelevant monoclonal IgG, clone CRL169. It may concluded that the Abs raised by gp120-CRA recognize native gp120 expressed on the surface of HIV-1 and can be useful for passive immunotherapy of HIV-1 infection.

REFERENCES

1. Karle S, Planque S, Nishiyama Y, Taguchi H, Zhou Y X, Salas M, Lake D, Thiagarajan P, Arnett F, Hanson C V, Paul S. Cross-clade HIV-1 neutralization by an antibody fragment from a lupus phage display library. AIDS 2004, 18(2): 329-331.
2. Burton D R, Pyati J, Koduri R, Sharp S J, Thornton G B, Parren P W, Sawyer L S, Hendry R M, Dunlop N, Nara P L, et al. Efficient neutralization of primary isolates of HIV-1 by a recombinant human monoclonal antibody. Science 1994 Nov. 11; 266(5187):1024-7.

EXAMPLE VIII

Isolation of Catalytic Anti-HIV Ab Fragments from Lupus Libraries

Lupus patients synthesize Abs that bind the HIV gp120 determinant composed of residues 421-436 of this protein (1). As noted previously, catalytic Ab synthesis occurs at enhanced levels in lupus patients (2). Therefore, we turned to the CRAs for identification of catalytic Abs specific for gp120. We previously reported that hapten CRAs are useful to isolate non-specific catalysts by virtue of covalent bonding between the electrophilic phosphorus and activated nucleophiles (3). Essentially, phages expressing the lupus Ab repertoire on their surface are allowed to bind the CRAs and Ab cDNA recovered from the covalently bonded phages is expressed in soluble form, purified by metal affinity chromatography by means of the his6 tag in the recombinant Abs and then analyzed for antigen binding and cleaving activities. Ref 3 describes preparation and characterization of the phage libraeies expressing single chain Fv (scFv) and light chain subunits (L chains) from the lupus patients. scFv constructs are composed of the VL and VH domains of Abs linked by a short and flexible peptide linker. The VL domain of the L chains has previously been demonstrated to express catalytic activity independent of the VH domain located in the heavy chain subunit (4,5). Like noncatalytic Abs, peptidase Abs are capable of binding antigens with high specificity mediated by contacts at residues from the VL and VH domains (6). The precise contribution of the two V domains varies in individual Ab-antigen complexes, but the VH domain may contribute at a somewhat greater level, because CDRH3 tends to be longer and more variable in sequence compared to CDRL3. The VH domain can nevertheless influence the peptidase activity by "remote control", because in binding to VIP remote from the cleavage site, it can influence the conformation of the binding site as shown by the peptidase activity of $F_v$ constructs composed of the catalytic anti-VIP VL domain linked to its VH domain. The anti-VIP VH domain exerted beneficial effects and an irrelevant VH domain exerted detrimental effects on the catalytic activity, as evaluated by the values of VIP binding affinity and catalytic efficiency (6).

To isolate gp120 specific catalysts, we utilized the peptidyl-CRA and full-length gp120-CRA shown in FIG. 7C and FIG. 14, respectively. These CRAs capture specific catalysts by combining the covalent bonding reaction with traditional noncovalent bonding occurring at the epitope-paratope interface. Using the gp120(421-431)-CRA, we isolated a specific gp120-cleaving L chain from our lupus phage library (FIG. 45). Phage-CRA complexes were trapped on a streptavidin column and then eluted by cleaving the S-S bond located between the biotin and the phosphonate moieties. Highly purified preparations of the L chain were obtained by metal-affinity chromatography. Catalysis assays utilized the substrate gp120(421-432)-methylcoumarinamide [MCA; the targeted bond is Lys432-MCA, located at the position of the phosphonate moiety in gp120(421-431)-CRA]. Aminomethylcoumarin release was measured fluorimetrically (7). One L chain expressed the catalytic activity. Electrophoretic catalysis assays using biotinylated gp120 showed that this L chain also cleaved full-length gp120 (FIG. 45). Specificity was indicated by lack of cleavage of irrelevant polypeptides studied in parallel (albumin, extracellular domain of EGFR). As expected, the L chain displayed the ability to bind the gp120-(421-431)-CRA covalently. Synthetic gp120(421-436) devoid of the CRA moiety inhibited the covalent binding of the peptidyl CRA, suggesting that the activated nucleophile is located close to the site responsible for noncovalent recognition.

Attribution of the proteolytic activity to the L chain (as opposed to trace contaminants) is supported by the absence of nonspecific proteolytic activity, expression of correct epitope specificity predicted from the CRA structure employed for phage selection, and expression of specific covalent binding to the gp120(421-431)-CRA. Previously, we validated the catalytic activity of similarly purified catalytic scFv and L chain clones directed to a different antigen (VIP) by mutagenesis (8) and immunochemical tests (9).

Similar studies were conducted using full-length gp120-CRA to isolate lupus scFv fragments with some modifications in the phage selection procedure, i.e., use of immobilized anti-biotin Ab to capture phages complexed with gp120-CRA, followed by a low pH elution step to elute the phages. Twenty four purified scFv fragments obtained from the bound phage fraction were screened for cleavage of biotinylated gp120 by electrophoresis. Eight catalytic scFv clones were identified (FIG. 46 shows gp120 cleavage by 2 scFv clones). Several identically prepared scFv clones screened in parallel were devoid of gp120 cleaving activity.

These scFv and L chain clones are potential reagents for immunotherapy of HIV-1 infection.

REFERENCES

1. Bermas B L, Petri M, Berzofsky J A, Waisman A, Shearer G M, Mozes E. Binding of glycoprotein 120 and peptides from the HIV-1 envelope by autoantibodies in mice with experimentally induced systemic lupus erythematosus and in patients with the disease. AIDS Res Hum Retroviruses 1994 September; 10(9): 1071-7.
2. Bangale Y, Karle S, Planque S, Zhou Y X, Taguchi H, Nishiyama Y, Li L, Kalaga R, Paul S. VIPase autoantibodies in Fas-defective mice and patients with autoimmune disease. FASEB J 2003 April; 17(6):628-35.
3. Paul S, Tramontano A, Gololobov G, Zhou Y X, Taguchi H, Karle S, Nishiyama Y, Planque S, George S. Phosphonate ester probes for proteolytic antibodies. J Biol Chem 2001 Jul. 27; 276(30):28314-20.
4. Paul S, Li L, Kalaga R, Wilkins-Stevens P, Stevens F J, Solomon A. Natural catalytic antibodies: peptide-hydrolyzing activities of Bence Jones proteins and V L fragment. J Biol Chem 1995 Jun. 23; 270(25): 15257-61.

5. Matsuura K, Sinohara H. Catalytic cleavage of vasopressin by human Bence Jones proteins at the arginylglycinamide bond. Biol Chem 1996 September; 377(9):587-9.
6. Sun M, Gao Q S, Kirnarskiy L, Rees A, Paul S. Cleavage specificity of a proteolytic antibody light chain and effects of the heavy chain variable domain. J Mol Biol 1997 Aug. 22; 271(3):374-85.
7. Kalaga R, Li L, O'Dell J R, Paul S. Unexpected presence of polyreactive catalytic antibodies in IgG from unimmunized donors and decreased levels in rheumatoid arthritis. J Immunol 1995 Sep. 1; 155(5):2695-702.
8. Gao Q S, Sun M, Rees A R, Paul S. Site-directed mutagenesis of proteolytic antibody light chain. J Mol Biol 1995 Nov. 10; 253(5):658-64.
9. Paul S, Mei S, Mody B, Eklund S H, Beach C M, Massey R J, Hamel F. Cleavage of vasoactive intestinal peptide at multiple sites by autoantibodies. J Biol Chem 1991 Aug. 25; 266(24):16128-34.

EXAMPLE IX

Engineering Improved Anti-HIV-1 RAbs

Once anti-HIV Ab fragments with the desired catalytic activity are obtained, they can be improved by standard antibody engineering methods. The feasibility of engineering therapeutic grade Abs is supported by the development of a human scFv construct against tumor necrosis factor using a phage library prepared from unimmunized human subjects. Recloned as full-length IgG, this construct has been recently approved for the treatment of rheumatoid athritis (1).

Monitoring the level of gp120 cleavage as described above is a useful way to determine improvements in the activity of the engineered antibody fragments. In addition, HIV neutralization tests are performed to confirm that the activity of the clones has been improved.

Domain Linkage and Expansion:

A gain in potency is realized by recloning the monovalent scFv clones as bivalent IgG. The IgG version of a monovalent Fab has previously been reported to displays 400-fold increased neutralized potency due to enhanced binding avidity (2). Decavalent expression of the monovalent scFv as IgM Abs will increase the HIV-1 binding avidity further. An important factor is the pharmacokinetics of full-length antibodies versus scFv and Fab fragments. Half-lives for scFv constructs are usually on the order of hours, whereas IgG and IgM Abs display half-lives ranging from weeks to days, respectively. Therefore, to achieve persistent neutralization of the antigen, the preferred reagents are the full-length Abs. On the other hand, the smaller scFv constructs may offer tissue penetration capabilities superior to full-length Abs. For example, scFv constructs intended for HIV immunotherapy will permeate tissue viral reservoirs more efficiently than the full-length antibodies.

The constant domains bring to Abs certain effector functions, for example, the ability to fix complement, mediate Ab-dependent cellular cytotoxicity and bind Fc receptors expressed on antigen presenting cells. Moreover, recloning of the scFv as IgA antibodies permits protection against HIV-1 in mucosal fluids, as IgA antibodies can cross epithelial surfaces.

Full-length antibodies are obtained from scFv constructs by recloning into mammalian cell expression vectors. The vectors contain cDNA encoding the constant domains of the desired antibody class and subclass (3). scFv recloning as IgG1 and IgM constructs will be accomplished by standard methodology (4). The vectors are available commercially, for example, from Lonza. The vectors contain human Ab constant domains flanked by restriction sites for insertion of foreign V domains. $V_L$ and $V_H$ domain cDNA are amplified from pHEN2 plasmid DNA using back/forward primers containing appropriate restriction sites present in the vectors. The $V_L$ domain of the scFv is cloned into the vectors on the 5' side of the κ constant region, and the $V_H$ domain on the 5' side of the appropriate heavy chain domain (e.g., γ1, α and μ constant regions). The vectors contain have antibiotic resistance genes for selection. Stable transfectants are prepared in CHO cells or another mammalian cell line (Ab yield, 5-30 μg/ml). Purification of IgG, IgA and IgM will be done using immobilized protein G, anti-IgA and anti-IgM Ab.

Increased avidity of HIV-1 recognition can also be obtained by forming multimers of the scFv For example, tetravalent antibody fragments are generated by placing a 33-amino acid self-aggregating peptide derived from the GNC4 protein at the C terminus of an scFv construct (5). The peptide associates noncovalently into a 4-helix bundle, permitting expression of multiple valencies by the homotetramer. As the overall binding strength for multivalent binding (binding avidity) is substantially greater than the sum of the binding strength for the individual combining sites, virtually irreversible binding can be obtained by these means. The linker methodology can also be applied to generate bispecific antibodies, i.e., antibodies comprised of two scFv components with differing antigenic specificity. In this instance, the goal is to target two distinct antigens, e.g., a bispecific construct directed to the transferrin receptor and CD3 is shown to direct CD3+ T cells to lyse cells expressing the transferrin receptor.

Affinity maturation in vitro. To obtain Ab fragments with improved catalytic activity, mutations are introduced into the CDRs using mutagenic primers, the mutant molecules are expressed on the surface of phages, and the phages are allowed to bind covalently to the CRAs as described in Example VIII. The process is repeated several times, with additional mutations introduced at each cycle followed by the phage separation by antigen binding. Antigen-specific scFv clones with binding affinity as great as $10^{10}$-$10^{11}$ $M^{-1}$ ($K_a$) have been obtained using as starting material the scFv repertoire expressed by unimmunized human donors. The 6 CDRs of the VL and VH domains contain about 100 amino acids. Study of antibodies that are comprehensively mutated at these residues with each of the 20 natural amino acids is impractical because of the large size of the resultant mutant library (~$100^{20}$ clones). CDR3 of the VH domain is often chosen for introducing mutations, as antigen contacts at CDRH3 are thought to impart specificity to antigen-antibody interactions. Several groups have reported that optimizing the structure of the $V_H$ CDR3 improves the antigen binding properties (6-9)]. An example of improved HIV-1 recognition by this strategy follows.

CDR walking mutagenesis procedures are employed to produce mutants in the desired CDRs as described previously by other groups (6,7). As it is impractical to use phage libraries larger than ~$10^8$ clones (due to constraints imposed by phage solubility and transfection), mutagenesis is done in a stepwise fashion. For example, the 5 N-terminal CDR residues are initially randomized and the resultant phage library (library 1) is selected for binding to gp120 (or whole HIV) as described above. Then the next 5 residues is randomized (library 2), followed again by antigen binding selection. This process is repeated until the entire CDR has been spanned. By this process, optimization of the gp120 cleaving and HIV-1 neutralizing properties are achieved. The $V_L$ and $V_H$ domains of the resultant scFv constructs are sequenced and the sequences compared with the parental scFv clone to identify the V domain mutations associated with the improved biological activity of the engineered clones.

In addition to the strategy described above, favorable mutations can also be introduced in the V domains on a rational basis to improve the binding affinity (recent example, ref 10), particularly if structural information is available about the antigen-antibody complex. For instance, candidate amino acids suitable for mutagenesis can be identified by molecular modeling or X-ray crystallography information. Molecular modeling of antibody V domains is carried out using combined homology and ab initio algorithms. Computer programs with strong predictive value for tracing peptide backbone topography have been developed, but side chain positions are more difficult to predict. Modeling is initiated by identifying the database Fab/Fv structure with the greatest sequence homology. Canonical structures for the FRs, VL CDR1-3 and VH CDR1-2 are available. Regions of greatest variability (particularly VH CDR3 loop structure) are iteratively energy minimized under a suitable force field. The ligand can be positioned in the hypothetical binding site to identify candidate residues suitable for rational mutagenesis. For instance, replacement of a small neutral amino acid with a similarly sized charged residue can be attempted as a means to introduce an additional electrostatic stabilizing interaction.

$V_L$-$V_H$ Hybridization.

In addition to scFv clones, L chain clones from lupus libraries displaying catalytic activity are available for improvement by engineering methods. Ab V domains can recognize antigens independently of each other, albeit with reduced binding affinity compared to the native combining site formed by the VL and VH domains. The binding activity of the individual VL domains comprising the anti-HIV L chains is improved by searching for compatible VH domains from suitable VH libraries. The feasibility of this approach is suggested by the following considerations: (a) The $V_L$ and the $V_H$ domains are independently capable of binding antigens (11,12), with the $V_H$ domain providing the major contribution to overall antigen binding specificity (13). An example of this is the improved recognition of the antigen VIP by pairing of a VIP recognizing L chain with its partner $V_H$ domain (14).

Individual VH domains from Abs with established gp120-recognizing activity, e.g., antibody clones S1-1 (15) or b12 (16) can be employed as the lupus VL domains partners. Alternatively a library of VH domains is employed to increase the probability of finding appropriate VH domains capable of forming a compatible $V_L$-$V_H$ molecular interface (i.e., an interface that brings the CDRs into sufficient spatial proximity to form a functional catalytic site). The most favorably paired $V_L$-$V_H$ domains are then identified by phage selection methods even if they constitute a minority of the overall combinations. Suitable $V_H$ domain sources are the HIV-1 infected individuals, who produce large amounts of specific anti-gp120 antibodies. Another suitable source of VH domains is transonic mice expressinghuman antibodies that are immunizedwith gp120 or synthetic gp120(421-436), e.g., Xenomouse™ mice produced by Abgenix Inc. Methods for immunization of these mice are as described by us previously (17), by administration of gp120 or synthetic gp120(421-436) conjugated to carrier proteins. Preparation of scFv libraries from the HIV-infected individuals and the transonic mice is essentially as described previously (18). Phages expressing scFv are subjected to selection by binding to gp120 or synthetic gp120(421-436) as before, allowing recovery of scFv clones as the source of VH domains. A large proportion of $V_H$ domains from these scFv clones can be anticipated to independently recognize gp120, as suggested by studies that the $V_H$ domain provides a dominant contribution in noncovalent antigen recognition. Such VH domains are suitable as partners for the anti-HIV L chains isolated from lupus patients.

Methods to generate the hybrid scFvs are in place in our lab (18). Essentially, the cDNA of the $V_L$ cDNA is amplified from the vector using primers containing the appropriate restriction sites necessary for cloning into pHEN2 vector containing the scFv contructs. The linker sequence is contained within the vector. Following removal of the endogenous $V_L$ domain cDNA by restriction digestion, the desired $V_L$ domain is ligated into the vector. VH domains from phage DNA selected as in the preceding paragraph (from HIV-1 infected individuals and transonic mice) are then ligated into the vector, and hybrid scFv phages will be packaged. The hybrid phages expressing hybrid scFv are subjected to CRA selection and screening for cleavage of the appropriate gp120 antigenic preparation. The success of this strategy is reflected by increased gp120 cleavaing activity and HIV-1 neutralizing activity of the scFv clones compared to the parental L chain.

VL-VH Orientations:

If needed the orientation of the V domains in the scFv is changed. Some groups investigating scFv binding have not found a significant difference in the ability of scFv to bind antigen in either orientation (VH-VL or VL-VH)[19,20]. Briefly, oligonucleotide primers are synthesized to PCR-amplify the VH with SfiI and Xho I restriction sites such that it can be ligated into the 5' position. Likewise, are synthesized to amplify the VL for ligation 3' of the linker into Apa LI and Not I sites. The scFv in both its orientations is purified and tested for cleavage of gp120 and neutralization of HIV.

Linker Effects:

As noted previously, scFv constructs can undergo intermolecular aggregation (21-23). To determine such effects, the scFv is analyzed by gel filtration columns. Peaks corresponding to each multimeric species are identified by comparison with retention times of standard proteins, and the proportion of scFv existing in monomeric and aggregate state is computed. ELISA studies are conducted as a function of soluble scFv concentration and these results are compared with the concentration dependence of the aggregation phenomenon.

The length and constitution of the linker peptide can exert important effects. Optimization of the linker can be done, for example, by randomization of the linker sequence, followed by identification of the variants showing the desired behavior. An example of one of a preferred strategy for this purpose follows. As retention of linker flexibility is necessary, glycines in the linker are maintained and serines at linker positions 2, 7, 12 and 15 are substituted with all 20 amino acids using a modification of the randomization method of Tang et al. (24). This has the effect of offering a variety of VL-VH interfacial interactions, some of which alleviate aggregation effects and improve functional behavior. Briefly, an oligonucleotide with an Nco I restriction site at the 5' end of the oligo and an Xho I site at the 3' end is synthesized such that the codons corresponding to serines 2, 7, 12 and 15 are randomized and allow incorporation of all 20 amino acids. The diversity of this linker library is $3.2 \times 10^6$. A complementary antisense 15-mer hybridizing with the 3' end of the primer containing an Xho I site is used to generate double stranded linker. This mutagenized linker library is ligated into pHEN2 containing S1-1 VL and VH and used to transform TG-1 cells followed by phage production. The linker library is subjected to selection for covalent binding to a suitable gp120 or synthetic gp120 CRA. Screening for HIV neutralization is done as before to identify the best variant.

REFERENCES 1. van de Putte L B, Rau R, Breedveld F C, Kalden J R, Malaise M G, van Riel P L, Schattenkirchner M, Emery P. Bunmester G R, Zeidler H, Moutsopoulos H M, Beck K, Kupper H. Efficacy and safety of the fully human anti-tumour necrosis factor alpha monoclonal antibody adalimumab (D2E7) in DMARD refractory patients with rheumatoid arthritis: a 12 week, phase II study. Ann Rheum Dis. 2003 December; 62(12): 1168-77.
2. Kessler J A 2nd, McKenna P M, Emini E A, Chan C P, Patel M D, Gupta S K, Mark G E 3rd, Barbas C F 3rd, Burton D R, Conley A J. Recombinant human monoclonal antibody IgG1b12 neutralizes diverse human immunodeficiency virus type 1 primary isolates. AIDS Res Hum Retroviruses 1997 May 1; 13(7):575-82.
3. Coloma M J, Hastings A, Wims L A, Morrison S L. Novel vectors for the expression of antibody molecules using variable regions generated by polymerase chain reaction. J Immunol Methods. 1992 Jul. 31; 152(1):89-104.
4. Shin S U, Morrison S L. Production and properties of chimeric antibody molecules. Methods Enzymol. 1989; 178:459-76.
5. Paul S (1998) Protein engineering. In Walker J (ed) Molecular Biotechniques, pp. 547-566. Totowa: Humana Press.
6. Yang W P, Green K, Pinz-Sweeney S, Briones A T, Burton D R, Barbas C F 3rd. CDR walking mutagenesis for the affinity maturation of a potent human anti-HIV-1 antibody into the picomolar range. J Mol Biol. 1995 Dec. 1; 254(3): 392-403.
7. Barbas C F 3rd, Bain J D, Hoekstra D M, Lemer R A. Semisynthetic combinatorial antibody libraries: a chemical solution to the diversity problem. Proc Natl Acad Sci USA. 1992 May 15; 89(10):4457-61.
8. Hoogenboom H R, Winter G. By-passing immunisation. Human antibodies from synthetic repertoires of germline V H gene segments rearranged in vitro. J Mol Biol. 1992 Sep. 20; 227(2):381-8.
9. Barbas C F 3rd, Hu D, Dunlop N, Sawyer L, Cababa D, Hendry R M, Nara P L, Burton D R. In vitro evolution of a neutralizing human antibody to human immunodeficiency virus type 1 to enhance affinity and broaden strain cross-reactivity. Proc Natl Acad Sci USA. 1994 Apr. 26; 91(9): 3809-13.
10. Luo G X, Kohlstaedt L A, Charles C H, Gorfain E, Morantte I, Williams J H, Fang F. Humanization of an anti-ICAM-1 antibody with over 50-fold affinity and functional improvement. J Immunol Methods. 2003 Apr. 1; 275(1-2):31-40.
11. Ward E S, Gussow D, Griffiths A D, Jones P T, Winter G. Binding activities of a repertoire of single immunoglobulin variable domains secreted from *Escherichia coli*. Nature. 1989 Oct. 12; 341(6242):544-6.
12. Sun M, Li L, Gao Q S, Paul S. Antigen recognition by an antibody light chain. J Biol Chem 1994 Jan. 7; 269(1):734-8.
13. Davies, D. R. and Chacko, S. Antibody structure. Acc Chem Res. 1993; 26:421-427.
14. Sun M, Gao Q S, Kirnarskiy L, Rees A, Paul S. Cleavage specificity of a proteolytic antibody light chain and effects of the heavy chain variable domain. J Mol Biol 1997 Aug. 22; 271(3):374-85.
15. Lake D F, Kawamura T, Tomiyama T, Robinson W E Jr, Matsumoto Y, Masuho Y, Hersh E M. Generation and characterization of a human monoclonal antibody that neutralizes diverse HIV-1 isolates in vitro. AIDS 1992 January; 6(1):17-24.
16. Burton D R, Pyati J, Koduri R, Sharp S J, Thornton G B, Parren P W, Sawyer L S, Hendry R M, Dunlop N, Nara P L, et al. Efficient neutralization of primary isolates of HIV-1 by a recombinant human monoclonal antibody. Science 1994 Nov. 11; 266(5187):1024-7.
17. Paul S, Planque S, Zhou Y X, Taguchi H, Bhatia G, Karle S, Hanson C, Nishiyama Y. Specific HIV gp120-cleaving Antibodies Induced by Covalently Reactive Analog of gp120. J Biol Chem 2003 May 30; 278(22):20429-20435.
18. Paul S, Tramontano A, Gololobov G, Zhou Y X, Taguchi H, Karle S, Nishiyama Y, Planque S, George S. Phosphonate ester probes for proteolytic antibodies. J Biol Chem 2001 Jul. 27; 276(30):28314-20.
19. Hamilton S, Odili J, Gundogdu O, Wilson G D, Kupsch J M. Improved production by domain inversion of single-chain Fv antibody fragment against high molecular weight proteoglycan for the radioimmunotargeting of melanoma. Hybrid Hybridomics 2001; 20(5-6):351-60.
20. Lawrence L J, Kortt A A, Iliades P, Tulloch P A, Hudson P J. Orientation of antigen binding sites in dimeric and trimeric single chain Fv antibody fragments. FEBS Lett. 1998 Apr. 3; 425(3):479-84.
21. Pluckthun A, Skerra A. Expression of functional antibody Fv and Fab fragments in *Escherichia coli*. Methods Enzymol. 1989; 178:497-515.
22. Skerra A, Pluckthun A. Assembly of a functional immunoglobulin Fv fragment in *Escherichia coli. Science.* 1988 May 20; 240(4855):1038-41.
23. Worn A, Pluckthun A. Stability engineering of antibody single-chain Fv fragments. J Mol Biol. 2001 Feb. 2; 305 (5):989-1010.
24. Tang Y, Jiang N, Parakh C, Hilvert D. Selection of linkers for a catalytic single-chain antibody using phage display technology. J Biol Chem. 1996 Jun. 28; 271(26):15682-6.

EXAMPLE X

β-Amyloid-CRAs and β-Amyloid-CRAWs for Covalent and Catalytic Production

We recently published our studies describing well-characterized catalytic Ab light chains (IgL) that cleave amyloid-beta peptide 1-40 (Aβ1-40; ref 1). One of these IgLs (murine clone c23.5) cleaved Aβ1-40 at a single peptide bond, Lys16-Leu17, consistent with its previously described preference for cleavage on the C-terminal side of basic residues (2). Another IgL (human clone hk14) displayed more complex cleavage patterns with apparent dependence on the aggregation state of Aβ1-40. At a large concentration of Aβ1-40 (1 mM), several peptide fragments with length differing only by a single residue each were generated, suggesting a sequential, exopeptidase-like reaction resulting in cleavage at several peptide bonds. At a lower Aβ1-40 concentration (100 μM), IgL hk14 cleaved a single peptide bond, the His14-Gln15 bond (FIG. 47), evident by the detection of the two peptide fragments corresponding to residues 1-14 and 15-40 (determined by ESI-mass spectroscopy). No background cleavage of Aβ1-40 was detected in the absence of the IgL. The difference in cleavage specificity is attributable to the differing confirmation adopted by the peptide in its various conformational states at different concentrations.

Aβ1-42 aggregates more readily and is more cytotoxic than Aβ1-40. Following Aβ1-42 (100 μM) incubation with IgL hk14 (24 h), analysis by HPLC as in FIG. 47 revealed the appearance of an Aβ1-14 fragment (11.8 min), suggesting cleavage of the Aβ1-42 peptide.

The IgLs were bound covalently by a hapten CRA, which is a mechanism-based probe for serine proteases (3). These observations indicate that promiscuous Aβ peptide cleaving Abs are found in the natural immune repertoire. Specific Aβ peptide cleaving Abs are candidate reagents for the immunotherapy of Alzheimer's disease. Abs with improved specificity, improved covalent reactivity and improved catalytic activity can be obtained by immunization with Aβ1-42-CRA. Examples of CRAs and CRAWs useful for this purpose are shown in FIG. 48 (Aβ1-42-CRA 1-3, Aβ1-42-CRAW 4). The rationale for immunization with Aβ1-42-CRA 1-3 is described under Detailed Description of the Invention. Our previous studies suggest that the magnitude of nucleophilic reactivity correlates with proteolytic activity but rate-limitations are also imposed by slow processing of the acyl-Ab intermediate formed by nucleophilic attack on the antigen. Accordingly, a new feature is incorporated in Aβ1-42-CRAW 4 designed to facilitate water attack on the acyl-Ab intermediate. This CRA contains a metal-water complex, with the goal that it will induce Ab active sites that can accommodate a water molecule close to the nucleophilic site. [Note that nucleophilic activation of water molecules analogous to the mechanism of metalloproteases is not required, as the Ab nucleophiles are available for the reaction. Rather, our goal is to induce serine protease Abs that allow water to diffuse into the active site]. Previous crystallography studies suggest the possible paucity of water molecules in the Ab active site, justifying purposeful design of water containing Abs]. Water binding by Aβ1-42-CRAW 4 is accomplished by initial treatment in a metal solution, i.e., salts of $Cu^{2+}$, $Ni^{2+}$, $Mn^{2+}$, $Zn^{2+}$, $Mg^{2+}$ or $Ca^{2+}$. $His_4$ in the CRA is designed to chelate a metal ion with certain coordinate valencies still available for water binding [reviewed in Ref 4]. Metal binding by Aβ1-42-CRAW 4 is measured experimentally by atomic absorption spectrometry, and the water content of the complexes is determined by elemental analysis. X-ray crystallography is an alternative way to determine the water content.

To maximize the immune response, the CRA/CRAW is conjugated to a carrier protein (KLH) via Cys residues at the N-terminus (which serves as a source of T cell epitopes). Standard immunization methods are applied to induce Ab synthesis. Blood from mice hyperimmunized with the CRA/CRAW is collected to assay the anti-AβAb response. Spleens are harvested to prepare MAbs. IgG and IgM are purified to electrophoretic homogeneity from the sera using Protein G-Sepharose and anti-IgM-Sepharose, respectively. The following assays are conducted:

(a) Total and covalent binding of the immunogen (Aβ1-42-CRA 1-3) by ELISA and SDS-electrophoresis, respectively;
(b) Cleavage of Aβ1-42 by RP-HPLC; and
(c) Neutralization of Aβ1-42 toxic effects on cultured N2a cells.

The purpose of the covalent binding studies is to establish the induction of a specific, nucleophilic Ab response (indicated by superior covalent binding of Aβ1-42-CRA compared to the hapten CRA). Catalysis studies identify Abs that not only have nucleophilic activity and specificity for Aβ1-42, but can also facilitate the next step of the reaction, that is, hydrolysis of the acyl-Ab intermediate and release of products. Initial studies are done with pooled IgG from immunized mice. Once the activity level is known, repeat experiments are conducted using IgG from individual mice to ensure the reproducibility of the response. Yields of IgG/IgM from 100 μl serum are sufficient to conduct ~100 reactions at 0.2 μM Ab. Controls include preimmune IgG; measurement of covalent binding by an irrelevant peptide-CRA (e.g., VIP-CRA); inhibition of Aβ1-42-CRA binding by Aβ1-42 devoid of phosphonate groups; and, inhibition of Aβ1-42 cleavage by Aβ1-42-CRA. Ab proteolytic activities are confirmed by assay of Fab activity and immunoadsorbed Abs. Controls for neurotoxicity assays include the preimmune IgG.

In addition, the Ab:Aβ1-42-CRA reaction mixtures are dialyzed to remove free CRA and then studied for ability to neutralize Aβ1-42 mediated toxic effects on N2A cells. This helps show that the Ab neutralizing activity is mediated by Ab combining sites.

It is possible that improvements in Ab nucleophilicity do not follow the same kinetics observed for maturation of non-covalent Ab responses. This can result from B cell down-regulation at later points in the immunization schedule due to covalent BCR-immunogen binding or changes in T cell responses. It is important, therefore, to carefully determine the appearance of catalytic Abs as a function of time over the course of the immunization schedule. Consequently, the timing of inimunogen administration can be varied to optimize the Ab response (e.g., 4 wks instead of 2 wks). Also, Aβ1-42-CRA can be administered alternately with ordinary Aβ1-42 devoid of electrophilic groups, or a conventional immune response to the Aβ1-42 can be established first, followed by administrations of the Aβ1-42-CRA to induce adaptive maturation of the nucleophiles.

Standard methods are employed to prepare hybridomas as in our previous studies (5,6). The primary screen of hybridoma supernatants is the assay of Aβ1-42 cleavage. Direct screening for proteolysis is important to detect proteolytic Abs. The purification of such proteolytic antibodies that bind the Aβ with high affinity and have high turnover will not be detected because they will destroy the Aβ1-42 immobilized substrate. To enable direct screening for catalysis, we have developed high throughput method for rapid capture and elution of IgG and IgM Abs in hybridoma supernatants in 96 well plates. Protein G and anti-IgM beads are used to capture IgG and IgM, respectively; low pH eluates are collected in 96 well assay and then incubated with the substrate. About 50 samples/day can be screened for Aβ1-42 cleavage by the HPLC method using an autosampler. A secondary screen is the covalent binding of Aβ1-42 by electrophoresis. Again, comparatively high throughput methods for this are in place (using an electrophoresis apparatus that accommodates 12 gels/run; 24 wells/gel). This screen identifies Abs with the greatest nucleophilicity, which is a predictor of catalytic activity. However, some Abs may express phosphonatase activity, as has been described for some conventional enzymes (7). If so, the covalent complex will be hydrolyzed, and binding may not be detected. Thus, reliance on the APβ1-42 cleavage assay is advisable as the primary screen. Anti-Aβ Abs displaying the greatest proteolytic activity for Aβ will be tested for their ability to inhibit the toxic effects of Aβ1-41 on N2A. Controls for these assays will include culture supernatants from the non-cross-reacting anti-VIP hybridoma.

Important properties of the Abs that are determined experimentally are:
(a) Cleavage site specificity, determined by HPLC and mass spectroscopy/N terminal sequencing;
(b) Antigenic specificity, determined by studying hydrolysis of Aβ oligomers, monomers and fibrils along with a panel of unrelated polypeptide substrates;

(c) Kinetic parameters ($k_{cat}$; $K_m$) determined at varying reactant concentrations;

(d) Aβ peptide neutralizing activity of proteolytic and control non-proteolytic Abs, determined using wildtype N2A cells and amyloid precursor protein expressing transfectants.

CRA immunogen are designed to bypass physiological restrictions on proteolytic Ab synthesis. The nucleophilic and specificity features in this approach are programmed into the Ab active site by the structural components of the CRAs. Sufficient water exists in the active sites of conventional serine proteases, but tight packing of antigen within the Ab combining site could result in water exclusion, resulting in constrained hydrolysis of the acyl-Ab intermediate (deacylation step). We have therefore included a water-binding site in the CRA to induce Abs capable of accommodating a water molecule. If needed, the CRA structure can be optimized further by varying the linker length and flexibility) and including an oxyanion (phosphonate monoester instead of diester, see ref 48 for details), which may help improve Ab catalytic rate constant further. Perturbations in the antigenic structure of Aβ1-42 due to various substituents can be alleviated by changing their location, e.g., acidic side chains instead of Lys NH2 groups. No increase was evident in mortality or morbidity in CRA-imnmunized mice in our previous studies, nor are signs of local reactions seen at the administration sites. Generalized CRA inhibition of serine protease and serine esterases could be deleterious, but this concern is largely alleviated because only small amounts of peptide CRAs are needed, as Abs at concentrations 4-6 log orders lower than conventional enzymes are shown to bind the peptide CRAs.

Neutralization of Aβ toxic effects is the desired property of the Abs. This capability is more likely ifthe cleavage reaction occurs towards the C terminal region of the peptide or if Aβ1-42 is cleaved at multiple peptide bonds, e.g., the exopeptidase-like reaction observed using IgL clone hk14. Previously, we also observed cleavage of gp120 and VIP at multiple peptide bonds by MAbs (5,8). Provided that the cleavage reaction releases fragments that are not themselves neurotoxic, proteolytic Ab-mediated protection against Aβ toxicity may be achieved even if the Ab epitope specificity differs from that of conventional MAbs. As long as antigenic specificity is maintained, affinity is lesser concern for proteolytic Abs, as neutralization depends on the catalytic reaction. At excess Aβ concentration (concentration $>>K_m$), the neutralizing potency of a proteolytic IgG molecule with a turnover of 1.0/min may be computed to be 28,800 fold greater than of an IgG molecule that binds Aβ stoichiometrically (assuming t½ 20 days in vivo; 1×60×24×20). For an IgM Ab, t½ in circulation is ~3 days, but our preliminary studies suggest that the constant domain structure of IgM Abs may support catalysis better than IgG (9). Generation of specific IgM Abs is not a problem, as this Ab class can undergo affinity maturation leading to specific antigen recognition. IgMs are larger than IgGs, but Ab entry into the CNS may not be necessary to reduce the Aβ burden in the brain, as reduction of peripheral Aβ could lead to Aβ egress from the brain.

An alternative way to identify high turnover catalysts is by flow cytometric sorting of nucleophilic B cells labeled with Aβ-CRAs, followed by application of the hybridoma methods Murine MAbs are not ideal for passive immunotherapy (because of possible anti-Ab responses). However, the methods developed in the present aim are readily applicable to obtain human Abs from transonic mice expressing the human Ab locus (10). These mice are shown to mount robust and high affinity human Ab responses to a variety of antigens. Similarly, SCID mice reconstituted with human lymphocytes can mount human Ab responses. Finally, molecular engineering techniques are available to humanize murine Abs, consisting of grafting the murine V domains into the constant domain scaffold of a human Ab, followed by replacements in the murine V domains that reduce human anti-mouse Ig responses. Guided by molecular modeling or crystal structures, the antigen contacting residues are maintained. Thus, there is no insurmountable difficulty in obtaining human and humanized proteolytic Abs to Aβ peptide.

REFERENCE

1. Rangan S K, Liu R, Brune D, Planque S, Paul S, Sierks M R. Degradation of beta-Amyloid by proteolytic antibody light chains. Biochemistry 2003 Dec. 9; 42(48):14328-14334.
2. Gao Q S, Sun M, Rees A R, Paul S. Site-directed mutagenesis of proteolytic antibody light chain. J Mol Biol 1995 Nov. 10; 253(5):658-64.
3. Oleksyszyn S, Powers J C. Amino acid and peptide phosphonate derivatives as specific inhibitors of serine peptidases. Methods Enzymol 1994; 244:423-41.
4. Glusker, J. P., Katz, A. K. and Bock, C. W. Metal ions in biological systems. The Rigaku Journal. 16:8-16, 1999.
5. Paul S, Planque S, Zhou Y X, Taguchi H, Bhatia G, Karle S, Hanson C, Nishiyama Y. Specific HIV gp120-cleaving Antibodies Induced by Covalently Reactive Analog of gp120. J Biol Chem 2003 May 30; 278(22):20429-20435.
6. Paul S, Sun M, Mody R, Tewary H K, Stemmer P, Massey R J, Gianferrara T, Mehrotra S, Dreyer T, Meldal M, and Tramontano, A. Peptidolytic monoclonal antibody elicited by a neuropeptide. J Biol Chem 1992 Jul. 5; 267(19):13142-5.
7. Dotson S B, Smith C E, Ling C S, Barry G F, Kishore G M. Identification, characterization, and cloning of a phosphonate monoester hydrolase from Burkholderia caryophilli PG2982. J Biol Chem. 1996 Oct. 18; 271(42):25754-61.
8. Paul S, Mei S, Mody B, Eklund S H, Beach C M, Massey R J, Hamel F. Cleavage of vasoactive intestinal peptide at multiple sites by autoantibodies. J Biol Chem 1991 Aug. 25; 266(24):16128-34.
9. Planque S, Bangale Y, Song X T, Karle S, Taguchi H, Poindexter B, Bick R, Edmundson A, Nishiyama Y, Paul S. Ontogeny of proteolytic immunity: IgM serine proteases. J Biol Chem in press (published on line ahead of print on Jan. 15, 2004, 10.1074/jbc.M312152200).
10. Mendez M J, Green L L, Corvalan J R, Jia X C, Maynard-Currie C E, Yang X D, Gallo M L, Louie D M, Lee D V, Erickson K L, Luna J, Roy C M, Abderrahim H, Kirschenbaum F, Noguchi M, Smith D H, Fukushima A, Hales J F, Klapholz S, Finer M H, Davis C G, Zsebo K M, Jakobovits A. Functional transplant of megabase human immunoglobulin loci recapitulates human antibody response in mice. Nat Genet. 1997 February; 15(2):146-56.

EXAMPLE XI

Use of Variant VIP-CRA Structures and B Cell Defective Hosts for Catalytic Antibody Generation VIP-CR structures. The synthesis and characterization of a VIP-CRA is described in Example III. In addition to phosphonate ester VIP-CRAs shown in FIG. 49, carbonyl pCRAs are useful because of their longer half-life and superior simulation of the carbonyl reaction center in the cleavage of peptide bonds by Abs. An example of a carbonyl VIP-CRA is shown in FIG. 49. The structure of this compound is based on reports that amidinophenyl pyruvate forms covalent complexes with serine proteases (1,2) similar to those of phosphonate CRAs. The amidino moiety is a Lys/Arg mimetic, corresponding to the cleavage specificity of many catalytic Abs.

Key elements of phosphonate VIP-CRA are: (a) the peptidic structure, allowing noncovalent binding to the Ab paratope; (b) one (monoester) or 2 leaving groups (diester) that determine the level of chemical reactivity of the phosphorus, and in the case of the monoester, allow expression of a negative charge on the unesterified oxygen; and (c) the positively charged amidino group Biotin and amino acids for conjugation to carrier proteins are incorporated at the N terminus. The rate constant $k_3$ (FIG. 7) depends on the covalent reactivity of the phosphorus atom. CRAs with different $k_3$ values are useful for different purposes. Rapid and complete inhibition of Abs is achieved by highly reactive CRAs with large $k_3$ values. Weakly covalent CRAs (low $k_3$) react with strong Ab nucleophiles without reacting at weak nucleophiles. The weak covalency may also promote catalytic Ab synthesis, as it limits the possibility of B cell tolerization by permanent BCR engagement. In the reaction scheme of FIG. 7, a VIP-CRA that fully mimics the reversible binding of VIP with the Ab will possess an equilibrium constant $K_i$ ($k_2/k_1$) equivalent to $K_d$ of VIP. Additionally, as the negatively charged monoester CRA mimic the noncovalent reactivity of the transition state, the Ki will reflect some component of transition state binding energy.

VIP-CRA 4 was observed to bind anti-VIP Abs selectively (see Example III). Synthesis of VIP-CRAs 3 and 5 is done essentially as for 4. For synthesis of VIP-CRAs 1, the protected peptide VIP 1-19 with C-terminal phosphonate diester residue is treated with aqueous sodium bicarbonate to give the monoester. This peptidyl phosphonate monoester is coupled to the C-terminal peptide fragment with an N-terminal glycolate residue (3), and the product is treated with anhydrous TFA. VIP-CRA 2 is prepared by an analogous strategy using the peptide fragment with the C-terminal phosphonate monomethyl ester. The product is HPLC purified and characterized by mass spectroscopy. Preparation and Ab reactivity of a peptidyl CRA analogous to VIP-CRAs 1 and 2 has been documented by our group (4). VIP-CRAs 3-5 contain the phosphonate diester located on NH2 side chains of the three Lys residues of VIP. The pyridyl VIP-CRA is structurally similar to 3. VIP-CRAs 1-3 structures depart from traditional strategies, in that the covalently reactive group is out of register with peptide backbone. The main pitfall in the syntheses is of side reactions at unintended groups. This is minimized by utilizing appropriate protecting groups. Preparation of the pyridyl VIP-CRA does present difficulties as the necessary reaction between the pyruvate carboxyl and side chain amine of Lys should proceed much like the analogous reaction for VIP-CRA 4.

Study of these pCRAs allows examination of the flexibility enjoyed by Ab nucleophiles. VIP-CRAs 1 and 2 contain the full sequence of VIP with the phosphonate group located within the backbone in place of Lys20. The presence ofpeptides on both flanks of the phosphonate maybe desirable to capture noncovalent paratope-epitope interactions and mimic the extended transition state, which may involve structural elements remote from the covalent reaction site (5; remote structural changes in the transition state are possible because of free rotation around the C—N bond as it develops single bond character in the transition state, allowing movement of distant structural elements). The region of VIP on the C terminal side of the phosphonate (residues 22-28) is suggested to furnish an important energetic contribution in Ab-VIP recognition (6).

Available VIP-specific Abs are used to confirm that the VIP-CRAs express Ab-recognizable epitopes. Noncovalent binding at the peptidyl epitopes allows superior VIP-CRA binding by specific Abs compared to other proteins (nonspecific Abs, serine proteases, serine esterases). All VIP-CRAs are studied for covalent binding to: (a) a panel of catalytic Abs with specific VIPase activity (MAbs c23.5 and c23.4 IgG; lupus single chain Fv clone DM506; polyclonal serum IgG codes 39, 80 and 5960; ref 7); (b) Nonimmune Abs, isotype matched-where possible (MAbs UPC 10, RPC5; lupus Fv clone DM302; polyclonal human IgG without VIPase or VIP binding activity); and (c) commercially available serine proteases (trypsin, thrombin, subtilisin). The assay consists of incubating suitable concentrations of purified Abs with the VIP-CRAs followed by SDS-electrophoresis, blotting of the gels and visualization of biotin-containing bands (~153 kD for IgG; ~30 kD for Fv) using streptavidin-peroxidase and a chemiluminescent substrate. Controls include reactions in the presence of excess DFP (competes for binding at the nucleophile) or excess VIP (noncovalent competitor).

Catalytic Ab Generation.

Dysfunctional B cell signaling is likely an underlying reason for amplified catalytic Ab production observed in autoimmune disease. Thus, transgenic mice expressing certain defects in B cell transmembrane signaling will yield high turnover catalytic Abs. In particular, mice expressing accelerated signaling are useful for this purpose, for example, CD19 transgenic mice. CD19 transduces BCR signaling through the Tyr kinase mediated pathway. Accelerated and decelerated BCR signaling in the CD19-overexpressing and CD19-knockout mice has been reported (8). These mice display attenuated and amplified responses to antigen stimulation, respectively, and changes in autoantibody levels are also apparent (8). Mice with the appropriate genetic background serve as controls (CD95-deficient mice and C3H/++ controls from Jackson Labs). B cells from homozygous mice with a disrupted CD19 gene are generally immunocompetent, but B-1 cell number is reduced and responsiveness to T-dependent antigens is somewhat variable (9). This is due to intrinsic defects in BCR signal transduction, rather than defective T-B cell interactions (10). Lyn- and CD22-deficient mice are also available if needed, e.g., [Lyn: a Src tyrosine kinase activated by BCR crosslinking with anti-IgM Ab; CD22, an adaptor protein in signal transduction].

Following hyperimmunization with the VIP-CRAs, the proteolytic activities of polyclonal Abs from CD19-overexpressing mice, CD19-deficient mice [C57B1/6 background] and their wildtype controls (n=10 each) is studied as described in Examples III, including determination of kinetic parameters from rate data fitted to the equation [$V=k_{cat}[Ag]/K_m+[Ag]$; v, velocity; $K_m \sim K_d$; $k_{cat}$, maximum velocity] and covalent binding to the VIP-CRAs It may be necessary to repeat immunizations at various immunogen doses, as the response in these mice is highly dose-dependent (9). MAbs will be produced as in the preceding section from mouse strains displaying large differences in VIP cleaving Ab responses compared to the wildtype controls.

The VIP-CRA immunizations are expected to yield low $K_m$, high $k_{cat}$ Abs. Monoester VIP-CRA immunization is of interest because this peptide may stimulate synthesis of Abs that combine nucleophilic reactivity with oxyanion stabilization. The weaker covalent reactivity of the monoester may also be beneficial in avoiding permanent BCR engagement, which could drive the cells into apoptosis. Abs to VIP-CRAs 1 and 2 should cleave VIP at Lys20-Lys21. The phosphonate moiety in VIP-CRAs 3-5 is located on Lys side chains, as opposed to the backbone of the peptide. Immunization experiments with such CRAs serve as a test for the flexibility of the active site, because a rigid Ab nucleophile developed to recognize the side chain group cannot move into register with the peptide backbone. The carbonyl VIP-CRA should elicit high kcat, specific Abs, supporting the hypothesis that endogenous CRAs can be the stimulating immunogen for proteolytic Ab production in autoimmune disease. [Reactive carbonyl compounds are produced at higher levels in autoimmune disease (protein glycation products, lipid peroxidation products]. As CD19-overexpressing B cells transmit antigen-stimulated BCR signals more efficiently than normal B cells, they should develop Abs with superior catalytic activity without risking clonal abortion.

REFERENCES

1. Walter J, Bode W. The X-ray crystal structure analysis of the refined complex formed by bovine trypsin and p-amidinophenylpyruvate at 1.4 A resolution. Hoppe Seylers Z Physiol Chem. 1983 August; 364(8):949-59.
2. Chen Z, Li Y, Mulichak A M, Lewis S D, Shafer J A. Crystal structure of human alpha-thrombin complexed with hirugen and p-amidinophenylpyruvate at 1.6 A resolution. Arch Biochem Biophys. 1995 Sep. 10; 322(1):198-203.
3. Campagne J M, Coste J, Jouin P. Synthesis of mixed phosphonate diester analogues of dipeptides using BOP or PyBOP reagents. Tetrahedron Lett 1993 Oct. 15; 34(42): 6743-4.
4. Nishiyama Y, Bhatia G, Bangale Y, Planque S, Mitsuda Y, Taguchi H, Karle S, Paul S. Toward selective covalent inactivation of pathogenic antibodies: a phosphate diester analog of vasoactive intestinal peptide that inactivates catalytic autoantibodies. J Biol Chem 2004 Feb. 27; 279(9): 7877-83. Epub 2003 Dec. 15.
5. Paul S. Natural catalytic antibodies. Mol Biotechnol 1996 June; 5(3):197-207.
6. Paul S, Volle D J, Powell M J, Massey R J. Site specificity of a catalytic vasoactive intestinal peptide antibody. An inhibitory vasoactive intestinal peptide subsequence distant from the scission peptide bond. J Biol Chem 1990 Jul. 15; 265(20):11910-3.
7. Paul S, Mei S, Mody B, Eklund S H, Beach C M, Massey R J, Hamel F. Cleavage of vasoactive intestinal peptide at multiple sites by autoantibodies. J Biol Chem 1991 Aug. 25; 266(24):16128-34.
8. Hasegawa M, Fujimoto M, Poe J C, Steeber D A, Tedder T F. CD19 can regulate B lymphocyte signal transduction independent of complement activation. J Immunol 2001 Sep. 15; 167(6):3190-200.
9. Felr T, Rickert R C, Odermatt B, Roes J. Rajewsky K, Hengartner H, Zinkemagel R M. Antiviral protection and germinal center formation, but impaired B cell memory in the absence of CD19. J Exp Med. 1998 Jul. 6; 188(1):145-55.
10. Sato S, Steeber D A, Tedder T F. The CD19 signal transduction molecule is a response regulator of B-lymphocyte differentiation. Proc Natl Acad Sci USA. 1995 Dec. 5; 92(25): 11558-62.

TABLE 1

Comparative features of natural and designer of transacylase Abs.

| | Natural | Designer |
|---|---|---|
| Activity | Peptidase | Esterase |
| Mechanism | Covalent + Noncovalent | Noncovalent |
| Origin | Germline, natural | De novo, adaptive |
| Target | Ground/transition state | Transition state |
| Target conc | Physiological | Excess |
| Optimal pH | Physiological | Alkaline |

TABLE 2

Examples of polypeptides suitable for targeting by covalent and catalytic Abs

| Target Antigen | Disease Indications |
|---|---|
| CD4 | Rheumatoid Arthritis, Asthma, Transplantation, Autoimmune Disease |
| HER 2 | Various Tumors |
| EGFR | Various Tumors |
| CTLA-4 | Various Tumors, Microbial Disease |
| Macrophage Inhibitory Factor | Inflammatory and Autoimmune Disease |
| CD80 (B7-1) | Inflammatory and Autoimmune Disease, Atherosclerosis |
| CD86 (B7-2) | Inflammatory and Autoimmune Disease, Atherosclerosis |
| CD28 | Inflammatory and Autoimmune Disease, Atherosclerosis |
| CD70 | Inflammatory and Autoimmune Disease, Atherosclerosis |
| CD11b/CD18 | Arthritis, Inflammatory and Autoimmune Disease |
| CD23 | Arthritis, Inflammatory and Autoimmune Disease |
| ICAM-1 | Inflammatory and Autoimmune Disease, Rheumatoid Arthritis, Inflammatory Bowel Disease, Organ Transplant Rejection, Psoriasis, Atherosclerosis |
| VLA-4 Integrin Receptor | Inflammatory and Autoimmune Disease |
| TNF-alpha | Rheumatoid Arthritis, Autoimmune Disease, Neurotropic Pain, Ischemia-reperfusion Injury, Septic Shock, SIRS, ARDS, Multiple Sclerosis, AIDS |
| Complement Component C5 | Autoimmune Disease, Immunosuppression |
| IL-1 beta Receptor | Rheumatoid Arthritis, Autoimmune Disease, Neurotropic Pain, Ischemia-reperfusion Injury, Septic Shock, SIRS, ARDS |
| IL-1 beta | Rheumatoid Arthritis, Autoimmune Disease, Neurotropic Pain, Ischemia-reperfusion Injury, Septic Shock, SIRS, ARDS |
| GPIIb/IIIa Receptor | Anti-thrombotic, Use in combination with Angioplasty, Percutaneous Coronaryr Intervention, Unstable Angina, Stroke |
| Plasminogen Activator Inhibitor (PAI-1) | Anti-coagulant |
| IL-4 | Thrombolytic |
| IL-4 Receptor | Asthma |
| IL-5 | Asthma |
| IL-5 Receptor | Allergy |
| IgE | Allergy |
| Eotaxin | Allergic Asthma and Allergic Rhinitis |
| Eotaxin Receptor | Allergic Inflammatory Disease, Allergic Asthma |
| PDGF | Allergic Inflammatory Disease, Allergic Asthma |
| PDGF beta Receptor | Vascular Disease, Restinosis |
| Alpha.v.beta.3 Integrin | Vascular Disease, Restenosis, Inhibit Pathogenic Bone Resorption |
| Beta-amyloid peptide | Alzheimer's Disease |

TABLE 3

Broad distribution of hapten I irreversible binding by antibodies.

| Antibody | Hapten I irreversible binding, AAU × 10³/μM protein | | | |
|---|---|---|---|---|
| | Mean ± S.D | Median | Range | N |
| Human serum IgG | 33.7 ± 20.4 | 30.1 | 12.4–67.1 | 5 |
| scFv | 928 ± 688 | 1050 | 55–1900 | 16 |

N: number of IgG donors (healthy individuals without evident immunological abnormalities); individual scFv clones from a human library, randomly picked.

Hapten CRA I, 10 μM (IgG) and 200 μM (scFv); 60 min incubation.

Values (in arbitrary area units, AAU) correspond to the intensities of IgG-I adducts (150 kD band) and scFv-I adducts (27 kD band along with scFv-containing aggregate bands observed in some clones).

TABLE 5

Initial velocities ($V_{app}$) for formation of VIP-CRA 3 and hapten-CRA 1 Ab adducts.

| Ab | Subunit | $V_{app}$ ± S.D., AAU min$^{-1}$ | |
|---|---|---|---|
| | | VIP-CRA 3 | Hapten CRA 1 |
| Anti-VIP IgG, c23.5 | Light | 19.8 ± 0.4 | 3.3 ± 0.4 |
| Anti-VIP IgG, c23.5 | Heavy | 3.0 ± 0.3 | 5.3 ± 0.7 |
| Control IgG, UPC10 | Light | 0.3 ± 0.1 | ND$^a$ |
| Control IgG, UPC10 | Heavy | 2.0 ± 0.3 | ND$^a$ |

$V_{app}$ values determined as in FIG. 2 legend.

$^a$ND, not determined.

TABLE 6

Cleavage preference of IgM Abs. Designations 8702, 8704, 9008, 9010 and 9020 refer to murine monoclonal IgM Abs. Yvo is a human monoclonal IgM. Reaction conditions: IgM, 5 nM; peptide-AMC substrates, 200 μM, except for polyclonal murine IgM (400 μM); 37° C. Blocking groups at the N termini of the substrates were: succinyl, AE-AMC, AAA-AMC, AAPF-AMC, IIW-AMC; t-butyloxycarbonyl, EKK-AMC, VLK-AMC, IEGR-AMC, EAR-AMC. Values (means of 3 replicates ± S.D.) are the slopes of progress curves monitored for 24 h.

| Substrate | μM AMC/h/μM Ab | | | | | | | |
|---|---|---|---|---|---|---|---|---|
| | Polyclonal, human | Polyclonal, murine | Yvo | 8702 | 8704 | 9008 | 9010 | 9020 |
| AE-AMC | ND | N.D. | N.D. | N.D. | N.D. | N.D. | N.D. | N.D. |
| AA-AMC | ND | N.D. | N.D. | N.D | N.D. | N.D. | N.D. | N.D. |
| IW-AMC | ND | N.D. | N.D. | N.D. | N.D. | N.D. | N.D. | N.D. |
| APF-AMC | ND | N.D. | N.D. | N.D. | N.D. | N.D. | N.D. | N.D. |
| KK-AMC | ND | N.D. | N.D. | 0.7 ± 0.2 | 6.6 ± 0.3 | 10.7 ± 0.8 | 13.1 ± 1.4 | 4.2 ± 0.5 |
| LK-AMC | 1.6 ± 0.1 | N.D. | 2.6 ± 0.2 | N.D. | 8.0 ± 0.1 | 7.4 ± 0.8 | 6.9 ± 0.4 | 3.0 ± 1.7 |
| AR-AMC | 35.4 ± 0.7 | 86.4 ± 12.2 | 7.4 ± 0.3 | 2.6 ± 0.3 | 18.6 ± 1.8 | 15.7 ± 0.6 | 61.6 ± 6.9 | 24.7 ± 1.4 |
| GR-AMC | 0.8 ± 0.1 | N.D. | N.D. | 0.8 ± 0.2 | 1.1 ± 0.4 | 17.5 ± 3.2 | 2.0 ± 0.7 | 4.1 ± 0.6 |
| FR-AMC | 5.6 ± 0.2 | 20.5 ± 4.4 | N.D. | N.D. | 2.2 ± 0.1 | 6.0 ± 0.3 | 37.4 ± 0.7 | 13.0 ± 1.2 |
| FP-AMC | ND | NT | N.D. | N.D. | N.D. | N.D. | N.D. | N.D. |

ND, not detectable (<0.125 μM AMC/h/μM Ab);
NT, not tested.

TABLE 4

Kinetic parameters for cleavage of Bt-gp120 and Boc-E-A-R-MCA by MAb YZ20.

| Antigen | $K_m$, M | $k_{cat}$, min-1 | $k_{cat}/K_m$, M$^{-1}$ min$^{-1}$ |
|---|---|---|---|
| Bt-gp120 | $2.0 \times 10^{-6}$ | $3.4 \pm 0.1 \times 10^{-3}$ | $1.7 \times 10^3$ |
| E-A-R-MCA | $4.0 \pm 1.2 \times 10^{-4}$ | $3.3 \pm 0.4 \times 10^{-2}$ | $8.4 \times 10^1$ |

IgG (1 μM) was incubated with Bt-gp120 (0.14–2.2 μM; 13 h) or Boc-E-A-R-MCA 31–1000 μM, 6 h).

Cleavage of Bt-gp120 was determined by measuring depletion of the 120 kD intact protein band on SDS-gels run in duplicate, and of E-A-R-MCA, by fluorimetry in triplicate. Kinetic parameters for Bt-gp120 cleavage were computed using the general quadratic equation describing a one site binding interaction and for, E-A-R-MCA, by fitting the data to the Michaelis-Menten equation (see text).

TABLE 7

Apparent kinetic parameters for IgM catalysis.

| Antibody | $K_m$, M | $k_{cat}$, mol/mol Ab/min |
|---|---|---|
| IgM, murine serum | $120 \pm 22 \times 10^{-6}$ | 2.1 ± 0.1 |
| IgM 9010 | $144 \pm 15 \times 10^{-6}$ | 1.9 ± 0.1 |
| IgM 9020 | $154 \pm 28 \times 10^{-6}$ | 0.9 ± 0.1 |
| IgM, human serum | $120 \pm 11 \times 10^{-6}$ | 2.8 ± 0.1 |
| IgG c23.5* | $0.34 \times 10^{-9}$ | $8 \times 10^{-4}$ |

*Substrate, VIP

Substrate, Glu-Ala-Arg-AMC (25–600 μM); IgM, 5 nM.

Correlation coefficients for fits to the Michaelis-Menten equation were ≥0.96 in every case.

TABLE 8

N terminal sequences (10 residues) of gp120 fragments generated by IgM Yvo.

| Product, kD | Amino acid sequence[a] | Cleavage site |
|---|---|---|
| 80 | I(2.3), P(1.7), G(1.2), E(1.9), K(0.8), L(1.5), X, V(1.4), T(1.2), V(1.4) | N.I. |
| 18.8 | I(8.4), P(6.3), G(3.7), E(5.7), K(4.0), L(5.1), W(0.4), V(4.8), T(3.0), V(4.8) | N.I. |
| 17.6 | A(1.7), M(0.6), Y(0.8), A(0.9), P(0.5), P(0.5), I(0.4), E(0.4), G(0.4), Q(0.3) | $K^{432}$–$A^{433}$ |
| 15.4–16.4 | A(9.4), M(5.3), Y(6.7), A(8.7), P(6.3), P(4.6), I(4.8), E(3.8), G(2.4), Q(3.5) | $K^{432}$–$A^{433}$ |
|  | I(1.7), P(0.8), G(1.6), E(1.3), K(0.4), L(1.1), W(0.1), V(1.1), T(1.0), V(1.2) | N.I. |

Reaction conditions: gp120 8.5 μM, IgM 50 nM, 46 h.
N.I., not identifiable; however, identification of the 15.4–16.4 and 18.8 kD fragments with N-termini corresponding to gp120 residues 1–10 indicates two cleavage sites located in the N-terminal half of the protein. X, unidentified amino acid.
[a] Values in parentheses indicate recovery of the amino acids in pmol.

TABLE 9

Apparent kinetic parameters for IgM catalyzed biotinylated gp120 cleavage. Increasing gp120 concentrations (2, 1, 0.5, 0.25, 0.125 μM) treated in duplicate with IgM (50 nM) for a sufficient length of time to yield gp120 cleavage levels in the measurable, linear phase of the reaction. See text for method of $k_{cat}$ and $K_d$ computation.

| Antibody | $K_d$, M | $k_{cat}$, min$^{-1}$ | $k_{cat}/K_d$, M$^{-1}$ min$^{-1}$ |
|---|---|---|---|
| IgM Yvo | $1.3 \times 10^{-6}$ | $0.04 \pm 0.002$ | $2.8 \times 10^4$ |
| IgM polyclonal human | $31.0 \times 10^{-6}$ | $2.14 \pm 0.03$ | $6.8 \times 10^4$ |
| IgM 8704 | $7.4 \times 10^{-6}$ | $0.12 \pm 0.05$ | $1.6 \times 10^4$ |

The invention claimed is:

1. A method of obtaining covalent or catalytic antibodies from an organism, comprising identifying and isolating said covalent or catalytic antibodies by contacting antibodies from the organism with a covalently reactive polypeptide antigen analog (pCRA) of formula (I)

$$L-E \quad\quad (I)$$

wherein L is a polypeptide comprising an antigenic epitope recognized by said covalent or catalytic antibodies, wherein said antigenic epitope is linear or discontinuous wherein E is an electrophilic group conjugated to an amino acid side chain functional group of L having the formula

Y-Y'-Y"- wherein

Y" is an atom, covalent bond or linker,

Y' is an atom, bond or chemical group that connects Y and L or Y",

Y is a covalently reactive electrophilic group which forms a covalent bond with a nucleophilic group of said covalent or catalytic antibody;

wherein said organism is optionally immunized with said pCRA.

2. The method according to claim 1, in which anyone of Y, Y', or Y" contains a water-binding group as a terminal or internal component (pCRAW).

3. The method according to claim 1, wherein said organism is immunized with said covalently reactive polypeptide antigen analog.

4. The method according to claim 1, in which Y", Y' or Y contains a water binding group as a terminal or internal component that is composed of a site that binds a zinc, copper, nickel, cobalt, calcium or magnesium ion which chelates one or more water molecules in which the metal binding site is -(His)n wherein n=2 or more, -Cys-X-Cys-Cys- or -Cys-X-Cys- peptide regions wherein X is an amino acid residue, ethylene diamine tetraacetic acid or diaminomethyl pyridine.

5. The method according to claim 1, wherein L represents an antigenic determinant or polypeptide from a microbial protein, a human, animal or plant protein, an antigen that is over-expressed on cancer cells, Factor VIII, epidermal growth factor receptor, CD4, beta-amyloid peptide 1-40 or beta-amyloid peptide 1-42 or the epidermal growth factor receptor derivatized at one or more Lys side chain amino group with

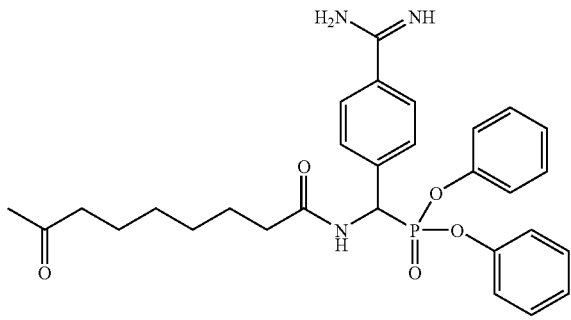 [SMILES: CC(=O)CCCCCCC(=O)NC(c1ccc(C(=N)N)cc1)P(=O)(Oc1ccccc1)Oc1ccccc1]

or, is vasoactive intestinal peptide derivatized at the Lys20 side chain with

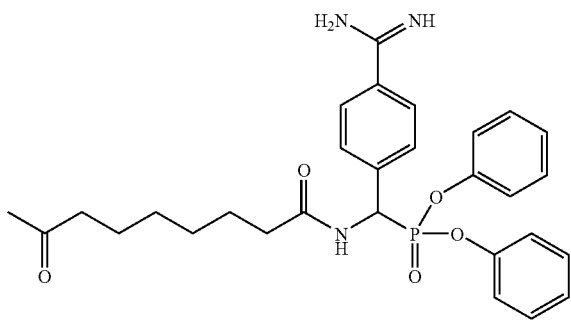 [SMILES: CC(=O)CCCCCCC(=O)NC(c1ccc(C(=N)N)cc1)P(=O)(Oc1ccccc1)Oc1ccccc1]

or, is the HIV-I protein gp120 derivatized at Lys side chain amino group at a density of 23 moles/mole protein with

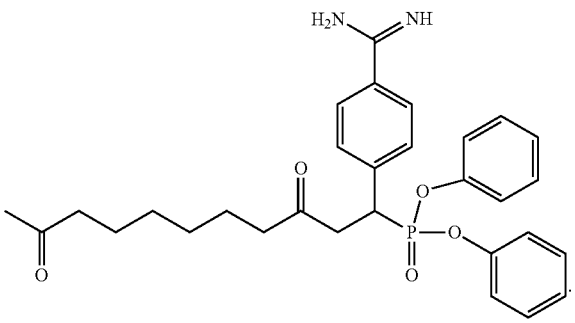 [SMILES: CC(=O)CCCCCCC(=O)CC(c1ccc(C(=N)N)cc1)P(=O)(Oc1ccccc1)Oc1ccccc1]

6. The method according to claim 1, wherein the antibodies are:
polyclonal antibodies identified in the serum of the organism by steps comprising:
a) screening and selection for covalent antibodies by binding to the antigenic pCRA or a polypeptide, wherein the binding is optionally determined in sodium dodecyl sulfate; and
b) screening and selection for catalytic hydrolysis of a suitable substrate;
or,
monoclonal antibodies or antibody fragments obtained from lymphocytes of the organism by steps comprising:
i) preparing from the lymphocytes a library of hybridoma cell lines, virus-transformed cell lines or immunoglobulin fragment genes cloned in and expressed from a vector, wherein the lymphocytes are optionally contacted with the pCRA or a polypeptide, and lymphocytes that bind the pCRA or polypeptide are separated from lymphocytes that do not bind the pCRA or polypeptide;
ii) screening and selecting for covalent antibodies or antibody fragments by binding to the antigenic pCRA or a polypeptide;
iii) screening and selecting for catalytic hydrolysis of a suitable substrate; and
iv) purifying the antibodies or the antibody fragments.

7. The method according to claim 6, wherein the antibody fragments are single chain Fv fragments containing the VL and VH domains or light chains expressing covalent or catalytic activity isolated by steps comprising:
a) preparing the immunoglobulin VL cDNA, VH cDNA and light chain cDNA by reverse-transcriptase polymerase chain reaction using as template the RNA from lymphocytes;
b) cloning the VL and VH cDNA in a form enabling their expression as single chain Fv fragments expressed on the surface of a display vector;
c) cloning the light chain cDNA in a vector in a form enabling their expression as light chains expressed on the surface of a display vector;
d) contacting the vector particles with immobilized pCRA or polypeptide, removing unbound vector particles by washing, and expressing the Fv cDNA or light chain cDNA from the pCRA-bound vector particles in soluble form in prokaryotic or eukaryotic cells;
e) screening the soluble Fv or light chain constructs for covalent antigen binding activity; and
f) screening the soluble Fv or light chain constructs for catalytic activity.

8. The method according to claim 7, further comprising improving the covalent or catalytic activity of the antibody fragments by the further steps of:
a) introducing mutations in the VL or VH domains or both;
b) displaying the resultant antibody fragments on the surface of a display vector;
c) contacting the vector particles with the pCRA or polypeptide and removing the unbound vector particles;
d) expressing the antibody fragments in soluble form in prokaryotic or eukaryotic cells;
e) screening the antibody fragments for covalent antigen binding activity;
f) screening the antibody fragments for catalytic activity.

9. The method according to claim 7 further comprising preparing full-length IgG, IgA, IgM, IgD or IgE antibodies from the Fv fragments by steps comprising:
a) insertion of the VL and VH domain DNA at the 5' side of Ig constant domains contained in an expression vector by nucleic acid digestion and ligation procedures;

b) growth of the vectors in a prokaryotic or eukaryotic host cell, extraction of the full-length antibodies from the culture medium or the cellular contents and purification of said antibodies.

10. The method according to claim 7 further comprising preparing full length IgG, IgA, IgM, IgD or IgE antibodies from the light chain fragments by steps comprising:

a) insertion of the cDNA encoding the VL domain with covalent or catalytic activity into an expression vector containing the constant domain of the light chain by nucleic acid digestion and ligation procedures;

b) insertion of the cDNA encoding the VH domain with noncovalent antigen binding activity into an expression vector containing the constant domains of the heavy chain by nucleic acid digestion and ligation procedures;

c) growth of the vectors in a prokaryotic or eukaryotic host cell, extraction of the full-length antibodies from the culture medium or the cellular contents and purification of said antibodies.

11. The method according to claim 1, wherein L represents an antigenic determinant or polypeptide from gp120 or is gp120 derivatized at the Lys side chain amino group at a density of 23 moles/mole protein with:

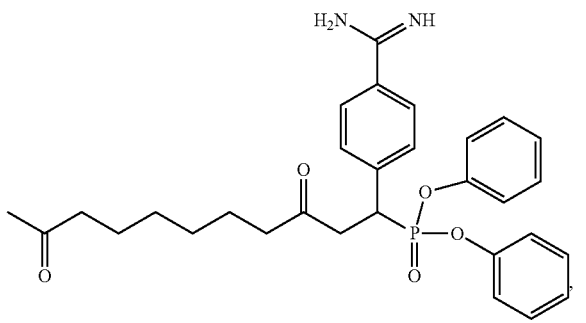 [SMILES: CC(=O)CCCCCCC(=O)CC(c1ccc(C(=N)N)cc1)P(=O)(Oc1ccccc1)Oc1ccccc1]

and wherein said antibody and said pCRA form a complex that is resistant to dissociation with 2% SDS.

12. The method according to claim 11 further comprising preparing a composition comprising the covalent or catalytic antibodies or antibody fragments and a biologically acceptable medium.

13. The method according to claim 1, further comprising preparing a composition comprising said covalent or catalytic antibodies and a biologically acceptable medium.

14. The method according to claim 1, further comprising preparing a composition comprising the covalent or catalytic antibodies or antibody fragments and a biologically acceptable medium, wherein L represents an antigenic determinant or polypeptide from amyloid β.

15. A water-binding, covalently reactive polypeptide antigen analogue (pCRAW) of formula (I):

L-E (I)

wherein L is a polypeptide comprising an antigenic epitope recognized by an antibody, wherein said antigenic epitope is linear or discontinuous;

wherein E is an electrophilic group conjugated to an amino acid side chain functional group of L having the formula

Y-Y'-Y"- wherein

Y" is an atom, covalent bond or linker,

Y' is an atom, bond or chemical group that connects Y and L or Y",

Y is a covalently reactive electrophilic group which forms a covalent bond with a nucleophilic group of said antibody, Y", Y' or Y contains a water-binding group as a terminal or internal component with a site that binds a zinc, copper, nickel, cobalt, calcium or magnesium ion which chelates one or more water molecules in which the metal binding site is -(His)n- where n=2 or more, or Cys-X-Cys-Cys or -Cys-X-Cys- wherein X is an amino acid residue, ethylene diamine tetraacetic acid or diaminomethyl pyridine.

* * * * *